US007521190B2

(12) United States Patent
Jones et al.

(10) Patent No.: US 7,521,190 B2
(45) Date of Patent: Apr. 21, 2009

(54) COMPOSITIONS AND METHODS FOR GENETIC ANALYSIS OF POLYCYSTIC KIDNEY DISEASE

(75) Inventors: Jeffrey G. Jones, Wilbraham, MA (US); Aidan N. Hennigan, Millbury, MA (US); John A. Curran, Worcester, MA (US); Susan K. Allen, Worcester, MA (US); Normand J. Robichaud, Leominster, MA (US); Jing Wang, Worcester, MA (US); Kerry E. Flynn, Grafton, MA (US); Jorge A. Garcés, Dudley, MA (US); Christopher M. Palatucci, Shrewsbury, MA (US); William K. Seltzer, Holden, MA (US)

(73) Assignee: Athena Diagnostics, Inc., Worcester, MA (US)

( * ) Notice: Subject to any disclaimer, the term of this patent is extended or adjusted under 35 U.S.C. 154(b) by 0 days.

(21) Appl. No.: 11/713,772

(22) Filed: Mar. 2, 2007

(65) Prior Publication Data

US 2007/0166755 A1 Jul. 19, 2007

Related U.S. Application Data

(60) Division of application No. 10/411,915, filed on Apr. 11, 2003, now Pat. No. 7,273,701, which is a continuation-in-part of application No. 10/083,246, filed on Feb. 26, 2002, now Pat. No. 6,916,619.

(60) Provisional application No. 60/328,739, filed on Oct. 12, 2001.

(51) Int. Cl.
*C12Q 1/68* (2006.01)
*C12P 19/34* (2006.01)

(52) U.S. Cl. .......................................... 435/6; 435/91.2
(58) Field of Classification Search .................. 435/6, 435/91.2
See application file for complete search history.

(56) References Cited

U.S. PATENT DOCUMENTS

| 5,891,628 | A | 4/1999 | Reeders et al. |
| 6,031,088 | A | 2/2000 | Somlo et al. |
| 6,071,717 | A | 6/2000 | Klinger et al. |
| 6,228,591 | B1 | 5/2001 | Somlo et al. |
| 6,485,960 | B1 | 11/2002 | Harris et al. |
| 6,656,681 | B1 | 12/2003 | Harris et al. |
| 6,916,619 | B2 | 7/2005 | Jones et al. |
| 7,273,701 | B2 | 9/2007 | Jones et al. |
| 2003/0008288 | A1 | 1/2003 | Germino et al. |

FOREIGN PATENT DOCUMENTS

WO  WO 02/06529 A2  1/2002

OTHER PUBLICATIONS

Phakdeekitcharoen, B., et al. "Mutation Analysis of the Entire Replicated Portion of *PKD1* Using Genomic DNA Samples," *J. Am. Soc. Nephrol.*, 12: 955-963 (2001).

Perrichot, R.A., et al., "DGGE Screening of *PKD1* Gene Reveals Novel Mutations in a Large Cohort of 146 Unrelated Patients," *Hum. Genet.*, 105: 231-239 (1999).

Thomas, R., et al., "Identification of Mutations in the Repeated Part of the Autosomal Dominant Polycystic Kidney Disease Type 1 Gene, PKD1, by Long-Range PCR," *Am. J. Hum. Genet.*, 65: 39-49 (1999).

Watnick, T., et al., "Mutation Detection of *PKD1* Identifies a Novel Mutation Common to Three Families with Aneurysms and/or Very-Early-Onset Disease," *Am. J. Hum. Genet.*, 65: 1561-1571 (1999).

Watnick, T.J., et al., "Somatic Mutation in Individual Liver Cysts Supports a Two-Hit Model of Cystogenesis in Autosomal Dominant Polycystic Kidney Disease," *Molecular Cell*, 2: 247-251 (1998).

Roelfsema, J.H., et al., "Mutation Detection in the Repeated Part of the PKD1 Gene," *Am. J. Hum. Genet.*, 61: 1044-1052 (1997).

Watnick, T.J., et al., "An Unusual Pattern of Mutation in the Duplicated Portion of *PKD1* is Revealed by Use of a Novel Strategy for Mutation Detection," *Human Molecular Genetics*, 6(9): 1473-1481 (1997).

Neophytou, P., et al., "Detection of a Novel Nonsense Mutation and an Intragenic Polymorphism in the *PKD1* Gene of a Cypriot Family with Autosomal Dominant Polycystic Kidney Disease," *Hum. Genet.*, 98: 437-442 (1996).

Peral, B., et al., "Screening the 3' Region of the Polycystic Kidney Disease 1 (*PKD1*) Gene Reveals Six Novel Mutations," *Am. J. Hum. Genet.*, 58: 86-96 (1996).

Turco, A.E., et al., "A Novel Nonsense Mutation in the PKD1 Gene (C3817T) is Associated with Autosomal Dominant Polycystic Kidney Disease (ADPKD) in a Large Three-Generation Italian Family," *Human Molecular Genetics*, 4(8): 1331-1335 (1995).

Ward, C.J. et al., "*Homo Sapiens* Polycystic Kidney Disease-Associated Protein (PKD1) Gene, Complete CDS," Database *EMBL* Online, Database Accession No. L39891:1-20.

International Search Report of International Application No. PCT/US01/22035.

Rossetti, et al., Mutation Analysis of the Entire PKD1 Gene: Genetic and Diagnostic Implications, *Am. J. Hum. Genet.*, 68: 46-63 (2000).

Underhill, et al., "Detection of Numerous Y Chromosome Biallelic Polymorphisms by Denaturing High Performance Liquid Chromatography," *Genome Research*, 7: 9961005 (1997).

Liu, et al., "Denaturing High Performance Liquid Chromotograph (DHPLC) Used in the Detection of Germline and Somatic Mutations," *Nucleic Acids Research*, 26(6): 1396-1400 (1998).

(Continued)

*Primary Examiner*—Kenneth R. Horlick
(74) *Attorney, Agent, or Firm*—Hamilton, Brook, Smith & Reynolds, P.C.

(57) ABSTRACT

The subject invention relates to nucleic acid sequences for detection of mutations in a PKD-1 or PKD-2 gene, as well as biomarkers for ADPKD. The invention further relates to methods for diagnosing ADPKD in an individual, and kits for performing the methods of the invention. The invention also provides a method for determining in an individual the presence or absence of a mutant PKD gene.

14 Claims, 108 Drawing Sheets

OTHER PUBLICATIONS

Inoue, S., et al., "Mutation Analysis in *PKD1* of Japanese Autosomal Dominant Polycystic Kidney Disease Patients," *Human Mutation* 19: 622-628 (2002).

Aguiari, G., et al., "Mutations in Autosomal Dominant Polycystic Kidney Disease 2 Gene: Reduced Expression of PKD2 Protein in Lymphoblastoid Cells," *American Journal of Kidney Disease* 33(5): 880-885 (1999).

Garcia-Gonzalez, et al., "Evaluating the Clinical Utility of a Molecular Genetic Test for Polycystic Kidney Disease," *Mol. Genet. Metab.*, 92:160-167 (2007).

Reiterova, J., et al., "Four Novel Mutations of the PKD2 Gene in Czech Families with Autosomal Dominant Polycystic Kidney Disease," *Human Mutation*, # 506 (2002) online.

Reynolds, D.M., et al., "Aberrant Splicing in the *PKD2* Gene as a Cause of Polycystic Kidney Disease," *J. Am. Soc. Nephrol.*, 10:2342-2351 (1999).

Rossetti, S., et al., "A Complete Mutation Screen of the ADPKD Genes by DHPLC," *Kidney International*, 61: 1588-1599 (2002).

Harris, P.G., "Autosomal Dominant Polycystic Kidney Disease: Clues to Pathogenesis," *Hum. Mol. Genet.*, 8:1861-1866 (1999).

Xiao, W. and P.J. Oefner, "Denaturing High-Performance Liquid Chromatography: A Review," *Hum. Mut.*, 17:439-474 (2001).

| Codon Number | | |
|---|---|---|
| | | Exon 1 |
| 1 | 212 | atgccgccgccagcgcccgcccgcctgcgcctggccctggcgctg |
| | | M P P A A P A R L A L A L G |
| 16 | 257 | tgcctgtggctcggggcgctggcgggaggccccggcgcggctgc |
| | | C L W L G A L A G G P G R G C |
| 31 | 302 | tgccctgcgagcccccctgcctctgtggcccagcgccggcgcc |
| | | P C E P P C L C G P A P G A |
| 46 | 347 | tcctgccgcgtcaactgctcggggcgcaggctgcggacgctcggt |
| | | Y C R V N C S G K G L R T L |
| | | Exon 2 |
| 61 | 392 | cccgcgctgcgcatcccacggacgccacagcgct[...] |
| | | P A L R I P A D A T A L [...] |
| 76 | 437 | [...] |
| | | [...] |
| | | Exon 3 |
| 91 | 482 | [...]gatataagcaacaacaagatttctacc |
| | | [...] D I S N N K I S T |
| | | Exon 4 |
| 106 | 527 | tagaagaaggaatatttgctaatttatttaatttaagtgaaatc |
| | | E E G I F A N L F N L S E I |
| 121 | 572 | [...] |
| | | [...] |
| 136 | 617 | [...] |
| | | [...] |
| 151 | 662 | [...] |
| | | [...] |
| | | Exon 5-A |
| 166 | 707 | [...]gtgaggagtat |
| | | [...] G E E Y |
| 181 | 752 | gtcgcctgcctccctgacaacagctcaggtcaccgtggcagcagtc |
| | | V A C L P D N S S G T V A A V |
| 196 | 797 | ccctttcagctgcccacgaaggcctgcttcagccagaggcctgc |
| | | S F S A A H E G L L Q P E A |

FIG. 1A

Figure 1 con.

```
 797 tcctttctcagctgcccacgaaggcctgcttcagccagaggcctgc
196      S  F  S  A  A  H  E  G  L  L  Q  P  E  A  C 842 agcgccttctgcttctccaccggccagggcctcgcagccctctcg
211      S  A  F  C  F  S  T  G  Q  L  A  A  L  S
                                    → 5-B
 887 gagcagggctggtgcctgtgtggggcgcccagccctccagtgcc
226      E  Q  G  W  C  L  C  G  A  A  Q  P  S  S  A
                 ← 5-A
 932 tcctttgcctgcctgtccctctgctccggcccccgccacctcct
241      S  F  A  C  L  S  L  C  S  G  P  P  P  P 977 gccccacctgtaggggccccaccctcctccagcacgtcttccct
256      A  P  T  C  R  G  P  T  L  L  Q  H  V  F 1022 gcctccccaggggccaccctggtggggccccacggacctctggcc
271      A  S  P  G  A  T  L  V  G  P  H  G  P  L  A 1067 tctggccagctagcagccttccacatcgctgccccgctccctgtc
286      S  G  Q  L  A  A  F  H  I  A  A  P  L  P  V
                                    → 5-C
1112 actgccacacgctgggacttcggagacggctccgccgaggtggat
301      T  A  T  R  W  D  F  G  D  G  S  A  E  V  D
                                    ← 5-B
1157 gccgctgggccggctgcctcgcatcgctatgtgctgcctgggcgc
316      A  A  G  P  A  A  S  H  R  Y  V  L  P  G  R 1202 tatcacgtgacggccgtgctggccctgggggccggctcagccctg
331      Y  H  V  T  A  V  L  A  L  G  A  G  S  A  L 1247 ctggggacagacgtgcaggtggaagcggcacctgccgccctggag
346      L  G  T  D  V  Q  V  E  A  A  P  A  A  L  E 1292 ctcgtgtgcccgtcctcggtgcagagtgacgagagccttgacctc
361      L  V  C  P  S  S  V  Q  S  D  E  S  L  D  L 1337 agcatccagaaccgcggtggttcaggcctggaggccgcctacagc
376      S  I  Q  N  R  G  G  S  G  L  E  A  A  Y  S
                                         Exon 6
1382 atcgtggccctgggcgaggagccggcccgacgtgtcaccgcctc
391      I  V  A  L  G  E  E  P  A  R
```

FIG. 1B

Figure 1 con.

```
1427  cgccgctcgacagcagatcctggcagcggtgctgctac
406   G  P  S  D  ...  ...  D  G  ...  ...  ...  Y 1472  ggcctggcgtggagagcaggtggctgcaggcgcaggagg
421   R  ...  V  E  K  A  ...  W  L  Q  A  Q  ...  ...

1517  cgtcaggcctggacgcggccgcctcaaggtcgacgctcc
436   ...  Q  ...  W  ...  ...  ...  ...  ...  ...  M  V  ...  S  ...
                                                           Exon 7
1562  gccatgcagcgctcctgtctcccgggtcaccaggagcctagac
451   A  ...  Q  R  ...  ...  V  S  R  ...  T  ...  S  L  D 1607  gtgtggatcggcttctcgactgtgcaggggtggaggtgggccca
466   V  W  I  G  F  S  T  V  Q  G  V  E  V  G  P 1652  gcgccgcagggcgaggccttcagcctggagagctgccagaactgg
481   A  P  Q  G  E  A  F  S  L  E  S  C  Q  N  W 1697  ctgcccggggagccacacccagccacagccgagcactgcgtccgg
496   L  P  G  E  P  H  P  A  T  A  E  H  C  V  R 1742  ctcgggcccaccgggtggtgtaacaccgacctgtgctcagcgccg
511   L  G  P  T  G  W  C  N  T  D  L  C  S  A  P
                                                   Exon 8
1787  cacagctacgtctgcgagctgcagcccggagcccgactggcaggat
526   H  S  Y  V  C  E  L  Q  P  G  ...  P  ...  W  ...  ...

1832  gcggagaaccctcctggggaggcctcagtgcggacctgcaggga
541   A  E  N  P  ...  V  G  A  ...  P  S  ...  D  L  Q  G 1877  cccgtgacgcctggcacgccggagaccggcgcccaccgccccac
556   P  ...  ...  P  L  A  ...  P  ...  D  G  ...  ...  S  A  P  H
                           Exon 9
1922  gagcccgtggaggtcatggtattcccggcctgcgtctgagccgt
571   E  P  V  E  V  M  V  F  P  G  L  R  L  S  R 1967  gaagccttcctcaccacggccgaatttgggacccaggagctccgg
586   E  A  F  L  T  T  A  E  F  G  T  Q  E  L  R 2012  cggcccgccagctgcggctgcaggtgtaccggctcctcagcaca
601   R  P  A  Q  L  R  L  Q  V  Y  R  L  L  S  T
           Exon 10
2057  gcaggaacccggagaacggcagcgagctgagtcaggcccg
616   A  G  T  P  E  N  G  S  E  P  E  S  R  S  P
```

FIG. 1C

Figure 1 con.

```
       2102 gacaacaggagccagctggccgcggggcgtgccaggcggtacgc
631         D  N  R  Q  L  A  A  G  V  P  G  G  T
       2147 tggcagcctggagcaagatctgtccgaccctgacgccgcttcg
646         W  Q  P  G  A  N  I  C  P  D  L  T  A  A  S
       2192 caccccgcactcggggccaacagcaactgcagctgcatccgct
661         H  P  A  L  G  A  N  S  N  C  S  C  I  R
       2237 ccggcgccccctatgcggctgtggaacacgcggcttcccgagt
676         P  G  A  P  Y  A  A  V  N  R  L  P  E  S  V
                                              Exo. 11-A
       2282 gccgcggggccccccgccagtacgggtcaccctccacggccag
691         A  A  G  P  P  A  Q  Y  G  V  T  L  H  G  Q
       2327 gatgtcctcatgctccctggtgacctcgttggcttgcagcacgac
706         D  V  L  M  L  P  G  D  L  V  G  L  Q  H  D
       2372 gctggccctggcgccctcctgcactgctcgccggctcccggccac
721         A  G  P  G  A  L  L  H  C  S  P  A  P  G  H
       2417 cctggtccccaggccccgtacctctccgccaacgcctcgtcatgg
736         P  G  P  Q  A  P  Y  L  S  A  N  A  S  S  W
                                              → 11-B
       2462 ctgccccacttgccagcccagctggagggcacttgggcctgccct
751         L  P  H  L  P  A  Q  L  E  G  T  W  A  C  P
       2507 gcctgtgccctgcggctgcttgcagccacggaacagctcaccgtg
766         A  C  A  L  R  L  L  A  A  T  E  Q  L  T  V
            ←     11-A
       2552 ctgctgggcttgaggcccaaccctggactgcggatgcctgggcgc
781         L  L  G  L  R  P  N  P  G  L  R  M  P  G  R
       2597 tatgaggtccgggcagaggtgggcaatggcgtgtccaggcacaac
796         Y  E  V  R  A  E  V  G  N  G  V  S  R  H  N
       2642 ctctcctgcagctttgacgtggtctccccagtggctgggctgcgg
811         L  S  C  S  F  D  V  V  S  P  V  A  G  L  R
       2687 gtcatctaccctgcccccgcgacggccgcctctacgtgcccacc
826         V  I  Y  P  A  P  R  D  G  R  L  Y  V  P  T
       2732 aacggctcagccttggtgctccaggtggactctggtgccaacgcc
841         N  G  S  A  L  V  L  Q  V  D  S  G  A  N  A
```

FIG. 1D

Figure 1 con.

```
2777 acggccacggctcgctggcctggggcagtgtcagcgcccgcttt
 856      T  A  T  A  R  W  P  G  G  S  V  S  A  R  F
                                              →  11-C
2822 gagaatgtctgccctgccctggtggccaccttcgtgcccggctgc
 871      E  N  V  C  P  A  L  V  A  T  F  V  P  G  C 2867 ccctggggagaccaacgatacccctgttctcagtggtagcactgccg
 886      P  W  E  T  N  D  T  L  F  S  V  V  A  L  P
                                        ←  11-B
2912 tggctcagtgagggggagcacgtggtggacgtggtggtggaaaac
 901      W  L  S  E  G  E  H  V  V  D  V  V  V  E  N 2957 agcgccagccgggccaacctcagcctgcgggtgacggcggaggag
 916      S  A  S  R  A  N  L  S  L  R  V  T  A  E  E 3002 cccatctgtggcctccgcgccacgccagccccgaggcccgtgta
 931      P  I  C  G  L  R  A  T  P  S  P  E  A  R  V
                                Exon 12
3047 ctgcagggagtcctagtgaggaagcgcggcgcgtcggcggca
 946      L  Q  G  V  L  V  R  K  R  G  A  S  A  A 3092 tggagatggtcttccggtcgaccagcacgacagcgtgccct
 961      S  D  M  V  F  R  S  T  T  T  T  A  V  P  S 3137 acgttcgagaacgtggtcatccagttctgcagcagcgtggcc
 976      V  F  E  N  V  V  I  Q  F  C  S  S  G  A
                                Exon 13
3182 gtccgcaagctctcactgacggcctccaaccacgtgagcaacgtc
 991      V  K  K  L  S  L  T  A  S  N  H  V  S  N  V 3227 accgtgaactacaacgtaaccgtggagcggatgaacaggatgcag
1006      T  V  N  Y  N  V  T  V  E  R  M  N  R  M  Q 3272 ggtctgcaggtctccacagtgccggccgtgctgtccccaatgcc
1021      G  L  Q  V  S  T  V  P  A  V  L  S  P  N  A 3317 acgctagcactgacggcgggcgtgctggtggactcggccgtggag
1036      T  L  A  L  T  A  G  V  L  V  D  S  A  V  E
                                Exon 14
3362 gtggccttcctggaactgggagggaccgggccctccac
1051      V  A  F  L  W  N  W  G  G  T  G  P  S  H 3407 cagtcccggccctccgacaacgtcctccggctggagaccc
1066
```

FIG. 1E

Figure 1 con.

```
      3452 tcgctgcggcgaggcgggccacaactctatgtgcacccac
1081       R L R R G G P Q L Y V H P
                        Exon 15-A
      3497 gctgcaccaggtgagtacctcctgaccgtgctggcatctaatgcc
1096       A A P  G  E  Y  L  L  T  V  L  A  S  N  A 3542 ttcgagaacctgacgcagcaggtgcctgtgagcgtgcgcgcctcc
1111       F  E  N  L  T  Q  Q  V  P  V  S  V  R  A  S 3587 ctgccctccgtggctgtgggtgtgagtgacggcgtcctggtggcc
1126       L  P  S  V  A  V  G  V  S  D  G  V  L  V  A
                                                → 15-B
      3632 ggccgcccgtcaccttctacccgcacccgctgccctcgcctggg
1141       G  R  P  V  T  F  Y  P  H  P  L  P  S  P  G 3677 ggtgttctttacacgtgggacttcggggacggctcccctgtcctg
1156       G  V  L  Y  T  W  D  F  G  D  G  S  P  V  L
       ←        15-A
      3722 acccagagccagccggctgccaaccacacctatgcctcgaggggc
1171       T  Q  S  Q  P  A  A  N  H  T  Y  A  S  R  G 3767 acctaccacgtgcgcctggaggtcaacaacacggtgagcggtgcg
1186       T  Y  H  V  R  L  E  V  N  N  T  V  S  G  A 3812 gcggcccaggcggatgtgcgcgtctttgaggagctccgcggactc
1201       A  A  Q  A  D  V  R  V  F  E  E  L  R  G  L
                                    → 15-C
      3857 agcgtggacatgagcctggccgtggagcagggcgcccccgtggtg
1216       S  V  D  M  S  L  A  V  E  Q  G  A  P  V  V
                                  ←         15-B
      3902 gtcagcgccgcggtgcagacgggcgacaacatcacgtggaccttc
1231       V  S  A  A  V  Q  T  G  D  N  I  T  W  T  F 3947 gacatgggggacggcaccgtgctgtcgggcccggaggcaacagtg
1246       D  M  G  D  G  T  V  L  S  G  P  E  A  T  V 3992 gagcatgtgtacctgcgggcacagaactgcacagtgaccgtgggt
1261       E  H  V  Y  L  R  A  Q  N  C  T  V  T  V  G 4037 gcggccagccccgccggccacctggcccggagcctgcacgtgctg
1276       A  A  S  P  A  G  H  L  A  R  S  L  H  V  L
                    → 15-D
      4082 gtcttcgtcctggaggtgctgcgcgttgaacccgccgcctgcatc
1291       V  F  V  L  E  V  L  R  V  E  P  A  A  C  I
             ←            15-C
```

FIG. 1F

Figure 1 con.

```
       4127 cccacgcagcctgacgcgcggctcacggcctacgtcaccgggaac
1306        P  T  Q  P  D  A  R  L  T  A  Y  V  T  G  N 4172 ccggcccactacctcttcgactggaccttcggggatggctcctcc
1321        P  A  H  Y  L  F  D  W  T  F  G  D  G  S  S 4217 aacacgaccgtgcgggggtgcccgacggtgacacacaacttcacg
1336        N  T  T  V  R  G  C  P  T  V  T  H  N  F  T
                                                    →15-E 4262 cggagcggcacgttcccctggcgctggtgctgtccagccgcgtg
1351        R  S  G  T  F  P  L  A  L  V  L  S  S  R  V
                                        ←      15-D 4307 aacagggcgcattacttcaccagcatctgcgtggagccagaggtg
1366        N  R  A  H  Y  F  T  S  I  C  V  E  P  E  V 4352 ggcaacgtcaccctgcagccagagaggcagtttgtgcagctcggg
1381        G  N  V  T  L  Q  P  E  R  Q  F  V  Q  L  G 4397 gacgaggcctggctggtggcatgtgcctggcccccgttcccctac
1396        D  E  A  W  L  V  A  C  A  W  P  P  F  P  Y 4442 cgctacacctgggactttggcaccgaggaagccgcccccacccgt
1411        R  Y  T  W  D  F  G  T  E  E  A  A  P  T  R
                                                 →15-F 4487 gccaggggccctgaggtgacgttcatctaccgagacccaggctcc
1426        A  R  G  P  E  V  T  F  I  Y  R  D  P  G  S
                                        ←      15-E 4532 tatcttgtgacagtcaccgcgtccaacaacatctctgctgccaat
1441        Y  L  V  T  V  T  A  S  N  N  I  S  A  A  N 4577 gactcagccctggtggaggtgcaggagcccgtgctggtcaccagc
1456        D  S  A  L  V  E  V  Q  E  P  V  L  V  T  S 4622 atcaaggtcaatggctcccttgggctggagctgcagcagccgtac
1471        I  K  V  N  G  S  L  G  L  E  L  Q  Q  P  Y
                                           →15-G 4667 ctgttctctgctgtgggccgtgggcgccccgccagctacctgtgg
1486        L  F  S  A  V  G  R  G  R  P  A  S  Y  L  W 4712 gatctggggacggtgggtggctcgagggtccggaggtcacccac
1501        D  L  G  D  G  G  W  L  E  G  P  E  V  T  H
                              ←     15-F 4757 gcttacaacagcacaggtgacttcaccgttagggtggccggctgg
1516        A  Y  N  S  T  G  D  F  T  V  R  V  A  G  W
```

FIG. 1G

Figure 1 con.

```
     4802 aatgaggtgagccgcagcgaggcctggctcaatgtgacggtgaag
1531      N  E  V  S  R  S  E  A  W  L  N  V  T  V  K
                        →  15-H
     4847 cggcgcgtgcgggggctcgtcgtcaatgcaagccgcacggtggtg
1546      R  R  V  R  G  L  V  V  N  A  S  R  T  V  V
                  ←              15-G
     4892 cccctgaatgggagcgtgagcttcagcacgtcgctggaggccggc
1561      P  L  N  G  S  V  S  F  S  T  S  L  E  A  G 4937 agtgatgtgcgctattcctgggtgctctgtgaccgctgcacgccc
1576      S  D  V  R  Y  S  W  V  L  C  D  R  C  T  P 4982 atccctgggggtcctaccatctcttacaccttccgctccgtgggc
1591      I  P  G  G  P  T  I  S  Y  T  F  R  S  V  G
                                               →  15-I
     5027 accttcaatatcatcgtcacggctgagaacgaggtgggctccgcc
1606      T  F  N  I  I  V  T  A  E  N  E  V  G  S  A 5072 caggacagcatcttcgtctatgtcctgcagctcatagagggggctg
1621      Q  D  S  I  F  V  Y  V  L  Q  L  I  E  G  L
       ←           15-H
     5117 caggtggtgggcggtggccgctacttccccaccaaccacacggta
1636      Q  V  V  G  G  G  R  Y  F  P  T  N  H  T  V 5162 cagctgcaggccgtggttagggatggcaccaacgtctcctacagc
1651      Q  L  Q  A  V  V  R  D  G  T  N  V  S  Y  S
                                                  →  15-J
     5207 tggactgcctggagggacagggggcccggccctggccggcagcggc
1666      W  T  A  W  R  D  R  G  P  A  L  A  G  S  G 5252 aaaggcttctcgctcaccgtgctcgaggccggcacctaccatgtc
1681      K  G  F  S  L  T  V  L  E  A  G  T  Y  H  V
                              ←             15-I
     5297 cagctgcggccaccaacatgctgggcagcgcctgggccgactgc
1696      Q  L  R  A  T  N  M  L  G  S  A  W  A  D  C 5342 accatggacttcgtggagcctgtgggggtggctgatggtgaccgcc
1711      T  M  D  F  V  E  P  V  G  W  L  M  V  T  A 5387 tcccccgaacccagctgccgtcaacacaagcgtcaccctcagtgcc
1726      S  P  N  P  A  A  V  N  T  S  V  T  L  S  A 5432 gagctggctggtggcagtggtgtcgtatacacttggtccttggag
1741      E  L  A  G  G  S  G  V  V  Y  T  W  S  L  E
```

FIG. 1H

Figure 1 con.

```
                                            →  15-K
      5477 gaggggctgagctgggagacctccgagccatttaccacccatagc
1756       E  G  L  S  W  E  T  S  E  P  F  T  T  H  S 5522 ttccccacacccggcctgcacttggtcaccatgacggcagggaac
1771       F  P  T  P  G  L  H  L  V  T  M  T  A  G  N 5567 ccgctgggctcagccaacgccaccgtggaagtggatgtgcaggtg
1786       P  L  G  S  A  N  A  T  V  E  V  D  V  Q  V 5612 cctgtgagtggcctcagcatcagggccagcgagcccggaggcagc
1801       P  V  S  G  L  S  I  R  A  S  E  P  G  G  S 5657 ttcgtggcggccgggtcctctgtgcccttttggggggcagctggcc
1816       F  V  A  A  G  S  S  V  P  F  W  G  Q  L  A
                                  ←        15-J
      5702 acgggcaccaatgtgagctggtgctgggctgtgcccggcggcagc
1831       T  G  T  N  V  S  W  C  W  A  V  P  G  G  S 5747 agcaagcgtggccctcatgtcaccatggtcttcccggatgctggc
1846       S  K  R  G  P  H  V  T  M  V  F  P  D  A  G 5792 accttctccatccggctcaatgcctccaacgcagtcagctgggtc
1861       T  F  S  I  R  L  N  A  S  N  A  V  S  W  V 5837 tcagccacgtacaacctcacggcggaggagcccatcgtgggcctg
1876       S  A  T  Y  N  L  T  A  E  E  P  I  V  G  L
                 →  15-L
      5882 gtgctgtgggccagcagcaaggtggtggcgcccggcagctggtc
1891       V  L  W  A  S  S  K  V  V  A  P  G  Q  L  V
                                  ←        15-K
      5927 cattttcagatcctgctggctgccggctcagctgtcaccttccgc
1906       H  F  Q  I  L  L  A  A  G  S  A  V  T  F  R 5972 ctgcaggtcggcggggccaaccccgaggtgctcccggggccccgt
1921       L  Q  V  G  G  A  N  P  E  V  L  P  G  P  R 6017 ttctcccacagcttcccccgcgtcggagaccacgtggtgagcgtg
1936       F  S  H  S  F  P  R  V  G  D  H  V  V  S  V 6062 cggggcaaaaaccacgtgagctgggcccaggcgcaggtgcgcatc
1951       R  G  K  N  H  V  S  W  A  Q  A  Q  V  R  I 6107 gtggtgctggaggccgtgagtgggctgcagatgcccaactgctgc
1966       V  V  L  E  A  V  S  G  L  Q  M  P  N  C  C
```

FIG. 1I

Figure 1 con.

```
      6152 gagcctggcatcgccacgggcactgagaggaacttcacagcccgc
1981       E  P  G  I  A  T  G  T  E  R  N  F  T  A  R 6197 gtgcagcgcggctctcgggtcgcctacgcctggtacttctcgctg
1996       V  Q  R  G  S  R  V  A  Y  A  W  Y  F  S  L
                      → 15-M 6242 cagaaggtccagggcgactcgctggtcatcctgtcgggccgcgac
2011       Q  K  V  Q  G  D  S  L  V  I  L  S  G  R  D 6287 gtcacctacacgcccgtggccgcggggctgttggagatccaggtg
2026       V  T  Y  T  P  V  A  A  G  L  L  E  I  Q  V
                                        ←    15-L 6332 cgcgccttcaacgccctgggcagtgagaaccgcacgctggtgctg
2041       R  A  F  N  A  L  G  S  E  N  R  T  L  V  L 6377 gaggttcaggacgccgtccagtatgtggccctgcagagcggcccc
2056       E  V  Q  D  A  V  Q  Y  V  A  L  Q  S  G  P 6422 tgcttcaccaaccgctcggcgcagtttgaggccgccaccagcccc
2071       C  F  T  N  R  S  A  Q  F  E  A  A  T  S  P 6467 agccccggcgtgtggcctaccactgggactttggggatgggtcg
2086       S  P  R  R  V  A  Y  H  W  D  F  G  D  G  S 6512 ccagggcaggacacagatgagcccagggccgagcactcctacctg
2101       P  G  Q  D  T  D  E  P  R  A  E  H  S  Y  L 6557 aggcctggggactaccgcgtgcaggtgaacgcctccaacctggtg
2116       R  P  G  D  Y  R  V  Q  V  N  A  S  N  L  V 6602 agcttcttcgtggcgcaggccacggtgaccgtccaggtgctggcc
2131       S  F  F  V  A  Q  A  T  V  T  V  Q  V  L  A 6647 tgccgggagccggaggtggacgtggtcctgcccctgcaggtgctg
2146       C  R  E  P  E  V  D  V  V  L  P  L  Q  V  L
                                        → 15-N 6692 atgcggcgatcacagcgcaactacttggaggcccacgttgacctg
2161       M  R  R  S  Q  R  N  Y  L  E  A  H  V  D  L 6737 cgcgactgcgtcacctaccagactgagtaccgctgggaggtgtat
2176       R  D  C  V  T  Y  Q  T  E  Y  R  W  E  V  Y 6782 cgcaccgccagctgccagcggccggggcgcccagcgcgtgtggcc
2191       R  T  A  S  C  Q  R  P  G  R  P  A  R  V  A
```

FIG. 1J

Figure 1 con.

← 15-M

```
     6827 ctgcccggcgtggacgtgagccggcctcggctggtgctgccgcgg
2206      L  P  G  V  D  V  S  R  P  R  L  V  L  P  R 6872 ctggcgctgcctgtggggcactactgctttgtgtttgtcgtgtca
2221      L  A  L  P  V  G  H  Y  C  F  V  F  V  V  S 6917 tttggggacacgccactgacacagagcatccaggccaatgtgacg
2236      F  G  D  T  P  L  T  Q  S  I  Q  A  N  V  T 6962 gtggcccccgagcgcctggtgcccatcattgagggtggctcatac
2251      V  A  P  E  R  L  V  P  I  I  E  G  G  S  Y 7007 cgcgtgtggtcagacacacgggacctggtgctggatgggagcgag
2266      R  V  W  S  D  T  R  D  L  V  L  D  G  S  E 7052 tcctacgaccccaacctggaggacggcgaccagacgccgctcagt
2281      S  Y  D  P  N  L  E  D  G  D  Q  T  P  L  S
```
Exon 16
```
     7097 ttccactgggcctgtgtggcttcgacacaggggagccggcgcgg
2296      F  H  W  A  C  V  A  S  T  Q  R  E  A  G  G 7142 cgtcgctgtactgttggcccggcgcagaagacggtcaccatt
2311      C  A  S  T  N  R  G  P  R  R  W  S  P  V  T  I 7187 ccacgggagctacgtggaggccgtggaggagagccgaagcctg
2326      P  R  E  L  R  G  G  R  G  V  A  E  S  E  A  L 7232 accgtgtggaagaccggccgcaaggaggaggccagcaaccagac
2341      T  V  W  K  T  G  R  K  E  E  A  S  N  Q  T
```
Exon 17
```
     7277 gtgctgatccggagtggccgggtgcccattgtgtccttggagtgt
2356      V  L  I  R  S  G  R  V  P  I  V  S  L  E  C 7322 gtgtcctgcaaggcacaggccgtgtacgaagtgagccgcagctcc
2371      V  S  C  K  A  Q  A  V  Y  E  V  S  R  S  S 7367 tacgtgtacttggagggccgctgcctcaattgcagcagcggctcc
2386      Y  V  Y  L  E  G  R  C  L  N  C  S  S  G  S
```
Exon 18
```
     7412 aagcgagggcggcggctgcacgtacgttcagcaacaagacgctg
2401      K  R  G  R  R  W  A  R  T  F  S  N  K  T  L 7457 gtgctggatgagaccaccatcacgggagtgcagccatcga
2416      V  L  D  E  T  T  N  L  T  S  T  G  S  A  G  M  R
```

FIG. 1K

Figure 1 con.

```
      7502 ctggtgctgcgcaggcgtgctgcgagacggcgaggatacgcc
2431       L  V  L  R  R  G  V  L  R  D  G  E  G  Y  T 7547 tccacgctcacgtgctggaccgctgctgcgaggacgacgctgc
2446       S  T  L  T  V  L  D  R  C  C  E  D  D  A  A 7592 ggctccatccgcctgtccccaaccgccgccgcctgggggctc
2461       A  S  I  R  L  S  P  N  R  R  P  L  G  G  S 7637 tgccggctctgtccactggcgcgtgtcacgccctcaccaccaag
2476       C  R  L  C  P  L  A  R  V  T  P  S  P  P  S
                                          Exon 19
      7682 ctgccctggatgcacggctggcatgacgcggaggatgctggc
2491       L  P  W  M  H  G  W  H  D  A  E  D  A  G 7727 gccccgctggtgtacgccctgctgctgcggcgctgtcgccagggc
2506       A  P  L  V  Y  A  L  L  L  R  R  C  R  Q  G 7772 cactgcgaggagttctgtgtctacaagggcagcctctccagctac
2521       H  C  E  E  F  C  V  Y  K  G  S  L  S  S  Y 7817 ggagccgtgctgccccggggtttcaggccacacttcgaggtgggc
2536       G  A  V  L  P  G  F  R  P  H  F  E  V  G 7862 ctggccgtggtggtgcaggaccagctgggagccgctgtggtcgcc
2551       L  A  V  V  V  Q  D  Q  L  G  A  A  V  V  A
                Exon 20
      7907 ctcaacaggtccgtggccatgaccgcccagatgccaacggcagc
2566       L  N  R  S  V  A  M  T  A  Q  M  P  N  G  S 7952 gcaaggggactcacagtcgtggatcacgctcacggctagtgtg
2581       A  R  G  L  T  V  V  D  H  A  G  L  T  A  S  V 7997 ctgccacggcgacgcagcaggcgaagcccagcacgtcatcgag
2596       L  P  G  D  A  A  G  E  A  Q  H  V  I  E
                                          Exon 21
      8042 tactctgtggctgtggtcacggtgctgaacgag tacgagcgggcc
2611       Y  S  V  A  V  V  T  V  L  N  E  Y  E  R  A 8087 ctggacgtggcggcagagcccaagcacgagcggcagcaccgagcc
2626       L  D  V  A  A  E  P  K  H  E  R  Q  H  R  A 8132 cagatacgcaagaacatcacggagactctggtgtccctgagggtc
2641       Q  I  R  K  N  I  T  E  T  L  V  S  L  R  V
```

FIG. 1L

Figure 1 con.

```
         8177 cacactgtggatgacatccagcagatcgctgctgcgctggcccag
2656          H  T  V  D  D  I  Q  Q  I  A  A  A  L  Q
                            Exon 22
         8222 tgcatgggggccaccagggagtcgatgccgcctgcctgaag
2671          C  M  G  A  T  R  E  S  M  P  P  A  C  L  K 8267 cagacggctgcacaagctgatgcccatgatgctcatcctgcaggca
2686          Q  T  A  A  Q  A  D  A  H  D  A  H  P  A  A 8312 gagaccacggcggcacggacgcccacggcatggagacag
2701          E  T  T  G  T  D  V  T  P  T  A  W  R  D  S
                              Exon 23-A
         8357 atcctcaacatcacaggagacctcatccacctggccagctcggac
2716          I  L  N  I  T  G  D  L  I  H  L  A  S  S  D 8402 gtgcgggcaccacagccctcagagctgggagccgagtcaccatct
2731          V  R  A  P  Q  P  S  E  L  G  A  E  S  P  S 8447 cggatggtggcgtcccaggcctacaacctgacctctgccctcatg
2746          R  M  V  A  S  Q  A  Y  N  L  T  S  A  L  M 8492 cgcatcctcatgcgctcccgcgtgctcaacgaggagcccctgacg
2761          R  I  L  M  R  S  R  V  L  N  E  E  P  L  T
                                                    → 23-B
         8537 ctggcgggcgaggagatcgtggcccagggcaagcgctcggacccg
2776          L  A  G  E  E  I  V  A  Q  G  K  R  S  D  P 8582 cggagcctgctgtgctatggcggcgccccagggcctggctgccac
2791          R  S  L  L  C  Y  G  G  A  P  G  P  G  C  H 8627 ttctccatccccgaggctttcagcggggccctggccaacctcagt
2806          F  S  I  P  E  A  F  S  G  A  L  A  N  L  S
                              → 23-C
         8672 gacgtggtgcagctcatctttctggtggactccaatccctttccc
2821          D  V  Q  L  I  F  L  V  D  S  N  P  F  P
           ← 23-A              ← 23-B
         8717 tttggctatatcagcaactacaccgtctccaccaaggtggcctcg
2836          F  G  Y  I  S  N  Y  T  V  S  T  K  V  A  S 8762 atggcattccagacacaggccggcgcccagatccccatcgagcgg
2851          M  A  F  Q  T  Q  A  G  A  Q  I  P  I  E  R 8807 ctggcctcagagcgcgccatcaccgtgaaggtgcccaacaactcg
2866          L  A  S  E  R  A  I  T  V  K  V  P  N  N  S
```

FIG. 1M

Figure 1 con.

```
      8852 gactgggctgcccggggccaccgcagctccgccaactccgccaac
2881       D  W  A  A  R  G  H  R  S  S  A  N  S  A  N 8897 tccgttgtggtccagcccaggcctccgtcggtgctgtggtcacc
2896       S  V  V  V  Q  P  Q  A  S  V  G  A  V  V  T 8942 ctggacagcagcaaccctgcggccgggctgcatctgcagctcaac
2911       L  D  S  S  N  P  A  A  G  L  H  L  Q  L  N
                                              Exon 24
      8987 tatacgctgctggacggccacgtaccgtctgaggacctgaggcc
2926       Y  T  L  L  D  G  H  V  P  S  E  D  L  R  P 9032 taactggcactgtactacactcggagccccggccaatgagcac
2941       E  L  A  V  Y  Y  T  R  S  P  R  P  N  E  H 9077 aactgctccgctagcaggacgatccgccagactcactccagggt
2956       N  C  S  A  S  R  R  T  R  P  E  S  L  Q  G
                                                  Exon 25
      9122 gctgacaccagcctaaccatctcattcccaggagcaga
2971       A  D  H  R  P  T  Y  T  F  H  S  R  G  S  R 9167 gacccagcggggagttaccatctgaacctctccagccacttccgc
2986       D  P  A  G  S  Y  H  L  N  L  S  S  H  F  R 9212 tggtcggcgctgcaggtgtccgtgggcctgtacacgtccctgtgc
3001       W  S  A  L  Q  V  S  V  G  L  Y  T  S  L  C 9257 cagtacttcagcgaggaggacatggtgtggcggacagaggggctg
3016       Q  Y  F  S  E  E  D  M  V  W  R  T  E  G  L 9302 ctgcccctggaggagacctcgccccgccaggccgtctgcctcacc
3031       L  P  L  E  E  T  S  P  R  Q  A  V  C  L  T 9347 cgccacctcaccgccttcggcgccagcctcttcgtgcccccaagc
3046       R  H  L  T  A  F  G  A  S  L  F  V  P  P  S
                                              Exon 26
      9392 catgtccgctttgtgtttcctgagccgacagcggatgtaaactac
3061       H  V  R  F  V  F  P  E  P  T  A  D  V  N  Y 9437 ctcgtcatgctgacatgtgctgagtgcttcggtgacctacatggtc
3076       L  V  M  L  T  C  F  G  D  L  V  T  Y  E  V 9482 atggccgccatcctgcacaaggtggaccagttggatgccagccgg
3091       M  A  A  I  L  H  K  V  D  Q  L  D  A  S  R
```

FIG. 1N

Figure 1 con.

```
        9527 ggccggccatggctttctgtggcagcggccgtgtcagtac
3106         G  R  A  M  A  F  C  G  S  G  R  V  S  R  T
                                                    Exon 27
        9572 gagatcctcgtcaagacaggctgggcgggcctggtaccacg
3121         E  I  L  V  K  T  G  W  A  G  L  G  T  T 9617 gcccacgtgggcatcatgctgtatggggtggacagccggagcggc
3136         A  H  V  G  I  M  L  Y  G  V  D  S  R  S  G 9662 caccggcacctggacggcgacagagccttccaccgcaacagcctg
3151         H  R  H  L  D  G  D  R  A  F  H  R  N  S  L 9707 gacatcttccggatcgccaccccgcacagcctgggtagcgtgtgg
3166         D  I  F  R  I  A  T  P  H  S  L  G  S  V  W
                                                    Exon 28
        9752 aagatccgagtgtggcacgacaacaaaggcctcagccctgcctgg
3181         K  I  R  V  W  H  D  N  K  G  L  S  P  A  W 9797 ttcctgcagacccttcatcgtcaggggaccgcagacggcacgagc
3196         F  L  Q  T  L  H  R  V  R  D  R  R  T  A  R  S 9842 aagttcgagctggtcaatgatgggctttcggtggagacggacgcc
3211         K  F  E  L  V  N  D  G  L  S  V  E  T  D  A
                                                    Exon 29
        9887 aacggggcatggtggacaaggagctgtggcgcgagtcgacgca
3226         N  G  A  W  W  T  R  S  C  G  A  S  D  A 9932 gcccttttgcgcttccggcgcctgctggtggctgagctgcagcgt
3241         A  L  L  R  F  R  R  L  L  V  A  E  L  Q  R 9977 ggcttctttgacaagcacatctggctctccatatgggaccggccg
3256         G  F  F  D  K  H  I  W  L  S  I  W  D  R  P 10022 cctcgtagccgtttcactcgcatccagagggccacctgctgcgtt
3271         P  R  S  R  F  T  R  I  Q  R  A  T  C  C  V 10067 ctcctcatctgcctcttcctgggcgccaacgccgtgtggtacggg
3286         L  L  I  C  L  F  L  G  A  N  A  V  W  Y  G
                                                    Exon 30
        10112 gctgttggcgactctgcctacagcacgggcatgtgcagcgc
3301         A  V  G  D  S  A  Y  S  T  G  M  C  S  R 10157 agccgctgagcgtcgacacagtcgctgtgggcctgtggtccagc
3316         S  P  L  S  V  D  T  V  A  V  G  L  V  S  S
```

FIG. 1O

Figure 1 con.

```
      10202 gtggttgtctatcccgtctacctggccatcctrctgctcggg
3331        V V V Y P V Y L A I L L L L G
                                       Exon 31
      10247 atgtcccgaagcaagGTGGCTGGGAGCCCGAGCCCCACACCTGCC
3346        M S R S K  V A G S P S P T P A 10292 GGGCAGCAGGTGCTGGACATCGACAGCTGCCTGGACTCGTCCGTG
3361        G Q Q V L D I D S C L D S S V
                                                 Exon 32
      10337 CTGGACAGCTCCTTCCTCACGTTCTCAGGCCTCCACGCTGAGgcc
3376        L D S S F L T F S G L H A E A 10382 ctggtggacagatgaagagtgactgtttcagatgattctagc
3391        P V D R M K S D C F R D D S K
            Exon 33
      10427 agTCTGGTGTGCTGGCCCTCCGGCGAGGGAACGCTCAGTTGGCCG
3406        S L V C W P S G E G T L S W P 10472 GACCTGCTCAGTGACCCGTCCATTGTGGGTAGCAATCTGCGGCAG
3421        D L L S D P S I V G S N L R Q 10517 CTGGCACGGGGCCAGGCGGGCCATGGGCTGGGCCCAGAGGAGGAC
3436        L A R G Q A G H G L G P E E D 10562 GGCTTCTCCCTGGCCAGCCCCTACTCGCCTGCCAAATCCTTCTCA
3451        G F S L A S P Y S P A K S F S
                  Exon 34
      10607 gcatcagatgaagaccgatcagcagtcgttgccgacgggctc
3466        A S D E D R S A V V A D G L 10652 agcagcccagccctagcgaagcacccatggaagaggactg
3481        S S P A L A K H P W K R T Exon 35
      10697 ctcagcagctGTCCAGCACTCCTGGGGAGAAGACAGAGACGCTG
3496        L S S S  S T P G E K T E T L 10742 GCGCTGCAGAGGCTGGGGGAGCTGGGGCCACCCAGCCCAGGCCTG
3511        A L Q R L G E L G P P S P G L
                                                 Exon 36
      10787 AACTGGGAACAGCCCCAGGCAGCGAGGCTGTCCAGGACAGgactg
3526        N W E Q P Q A A R L S R T G L 10832 gtggacggtctacggaagcggcctgctgccggctggtgcctcc
3541        V D G L R K R L L P A W C A S
```

FIG. 1P

Figure 1 con.

```
      10877 ctggcccacggggctgagcctgctggctggctgtggctgcagct
 3556       L A H G L S L L A G W L Q L 10922 ggctcagggtcgttggtgcgagcgtccggcgggcctgagtgtt
 3571       G S G S W V R A S G G P E C 10967 gcgtggctcctgcccagcggccagctcctgtcctcattcctg
 3586       A W L L P S G Q L L S S F L
                                          Exon 37
      11012 ggctgggagccactgaaggtcttgctggaagccctgtacttctca
 3601       G W E P L K  V  L  L  E  A  L  Y  F  S 11057 ctggtggccaagcggctgcacccggatgaagatgacaccctggta
 3616        L  V  A  K  R  L  H  P  D  E  D  D  T  L  V 11102 gagagcccggctgtgacgcctgtgagcgcacgtgtgccccgcgta
 3631        E  S  P  A  V  T  P  V  S  A  R  V  P  R  V 11147 cggccaccccacggctttgcactcttcctggccaaggaagaagcc
 3646        R  P  P  H  G  F  A  L  F  L  A  K  E  E  A
                                                    Exon 38
      11192 cgcaaggtcaagagctacatggcatgctgcggagctcctcctgtg
 3661        R  K  V  K  R  L  H  G  M  L  R 11237 tacatgctgcctgctggtgaccctgtgccagcatgtggat
 3676

11282 gcctcatgccatgggcacggctaccatctgcaaagcgccatgaag
 3691

Exon 39
      11327 caggagctgcacagccgggccttcctggccatcacccggtctgag
 3706                                              S  E 11372 gagctctggccatggatggcccacgtgctgctgccctacgtccac
 3721        E  L  W  P  W  M  A  H  V  L  L  P  Y  V  H 11417 gggaaccagtccagcccagagctggggccccacggctgcggcag
 3736        G  N  Q  S  S  P  E  L  G  P  P  R  L  R  Q
                                                Exon 40
      11462 gtgcggctgcaggaagactctaccagacctcccggcccagg
 3751        V  R  L  Q  E 11507
 3766
```

FIG. 1Q

Figure 1 con.

```
         11552 gacgttggctgggacagtcctcacattgtcggggacgtggccg
3781           D  V  G  W  D  S  P  H  I  V  G  D  V  A
                                            Exon 41
         11597 tagtcagcgccggatctccggc ggcatggtcctggggctcctgt
3796           V  S  A  G  S  P  G    A  W  S  W  G  S  C 11642 gccgtgtatgacagcgggggctacgtgcaggagctgggcctgagc
3811           A  V  Y  D  S  G  G  Y  V  Q  E  L  G  L  S 11687 ctggaggagagccgcgaccggctgcgcttcctgcagctgcacaac
3826           L  E  E  S  R  D  R  L  R  F  L  Q  L  H  N
                                    Exon 42
         11732 tggctggacaacaggagccgggctgtgttcctggagctgacgcgc
3841           W  L  D  N  R  S  R  A  V  F  L  E  L  T  R 11777 tacagcccgcccgtgggcctgcacgccgcgctcacgcctgccctc
3856           Y  S  P  P  V  G  L  H  A  A  L  T  P  A  L 11822 gagttccggccggcgccggccgcgccctggcgccctcagcgccgc
3871           E  F  R  P  A  P  A  A  P  W  R  P  Q  R  R 11867 ccgttgcgctggcccggctgagcgcgggcctcgctgcgcct
3886           P  L  A  L  A  R  L  S  A  G  L  S  C  A  P
                                      Exon 43
         11912 ctcacctcc gtgtgcctgctgctgttcgccgtgcacttcgccgtg
3901           L  T  S    V  C  L  L  L  F  A  V  H  F  A  V 11957 gccgaggcccgtacttggcacagggaagggcgctggcgcgtgctg
3916           A  E  A  R  T  W  H  R  E  G  R  W  R  V  L 12002 cggctcggagcctgggcgcggtggctgctggtggcgctgacggcg
3931           R  L  G  A  W  A  R  W  L  L  V  A  L  T  A 12047 gccacggcactggtacgcctcgcccagctgggtgccgctgaccgc
3946           A  T  A  L  V  R  L  A  Q  L  G  A  A  D  R 12092 cagtggacccgtttcgtgcgcggccgcccgcgccgcttcactagc
3961           Q  W  T  R  F  V  R  G  R  P  R  R  F  T  S 12137 ttcgaccaggtggcgcagctgagctccgcagcccgtggcctggcg
3976           F  D  Q  V  A  Q  L  S  S  A  A  R  G  L  A
                                              Exon 44
         12182 gcctcgctgctcttcctgctttttggtcaaggcggcggcagcggc
3991           A  S  L  L  F  L  L  L  V  K  A  A  A  A  A
```

FIG. 1R

Figure 1 con.

```
     12227 cggttcctgcgccagtggtccaccctggcagcacatatgccga
4006       R  F  L  R  Q  W  S  T  L  A  A  H  M  P  R 12272 gctgtggcagagctcctgggactgccccttggacctgtaggcctc
4021       A  V  A  E  L  L  G  L  P  L  G  P  V  G  L Exon 45
     12317 gggtagcctaccccagctggccgctcgctcgtgtcttcctgt
4036       G  V  A  Y  P  S  W  P  L  A        L  V  S  S  C 12362 gtggactccctctggagcgtggcccaggccctgttggtgctgtgc
4051       V  D  S  L  W  S  V  A  Q  A  L  L  V  L  C 12407 cctgggactgggctctctaccctgtgtcctgccgagtcctggcac
4066       P  G  T  G  L  S  T  L  C  P  A  E  S  W  H 12452 ctgtcacccctgctgtgtgtggggctctgggcactgcggctgtgg
4081       L  S  P  L  L  C  V  G  L  W  A  L  R  L  W 12497 ggcgccctacggctggggctgttattctccgctggcgctaccac
4096       G  A  L  R  L  G  A  V  I  L  R  W  R  Y  H 12542 gccttgcgtggagagctgtaccggccggcctgggagccccaggac
4111       A  L  R  G  E  L  Y  R  P  A  W  E  P  Q  D 12587 tacgagatggtggagttgttcctgcgcaggctgcgcctctggatg
4126       Y  E  M  V  E  L  F  L  R  R  L  R  L  W  M Exon 46
     12632 ggcctcagcaaggtcaaggag cccccagaagagcggcttgat
4141       G  L  S  K  V  K  E     R  P  L  W  R  A  E 12677 gggctggagccgcctgcctgcgctttccaggggctcaaggta
4156       G  M  E  P  P  L  C  S  R  S  S  R  G  S  K  V 12722 tcccgggatgtacccccatccagcgctggctcgatgctcgcac
4171       S  R  D  V  P  P  S  S  A  G  S  D  A  R  H 12767 cccttcagctcctcaggcagctggataggctgaggtggccctg
4186       P  S  S  S  S  Q  L  D  G  L  S  V  T  S 12812 ggccggcctgaggacaagcctgagccctgagccctccgcctcca
4201       G  R  P  E  D  K  P  E  P  E  P  S  R  L  Q 12857 gccgtcttccaggccctgctcacccagttgaccaccaaccac
4216       A  V  F  Q  A  L  L  T  Q  L  T  T  N  H
```

FIG. 1S

Figure 1 con.

| | | |
|---|---|---|
| 4231 | 12902 | gccacagaggacgctaccagctgcagcagctgcagcagcatc |
| | | A T E D Y Q L Q Q L H S T |
| 4246 | 12947 | caaggcgcaggagcagccaggcggctcggatcttttccgtggc |
| | | Q G R R S S R A R A G S S R G |
| 4261 | 12992 | ccatgccggggctgcgccagcactgccagcgccttgccgcc |
| | | P S P G L R P A L P S R L A R |
| 4276 | 13037 | gccagtcgggggtggacctggccactggcccagcaggacacc |
| | | A S R G V D L A T G P S R T P |
| 4291 | 13082 | cttcgggccaagaacaaggtccatccaggagcacttag 13120 |
| | | L R A K N K V H P S S A L |

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cgggcgggcgtgggcgggttccctggcccgggacgggaagcaggacgcgggccaggacgc  3963
              |||||||||||||| |||||||||||||||||||||||||||||||||||||||||||||
Sbjct: 16646  cgggcgggcgtgggcgcgttccctggcccgggacgggaagcaggacgcgggccaggacgc 16705

Query:  3964  tcccagggg cgaggctccggcgcggcacggcgggccctgctaaataaggaacgcctggag 4023
              ||||||||  ||||||||||||||||||||| |||| |||||||||||||||||||||||
Sbjct: 16706  tcccaggg-cgaggctccggcgcggcacagcgg-ccctgctaaataaggaacgcctggag 16763

Query:  4024  ccgcggttggcacggccccggggagccgaaaaacccgggtctggagacagacgtcccac  4083
              |||||||||||||||||||||||||||||||||||||||||||||||||||||||||||
Sbjct: 16764  ccgcggttggcacggccccggggagccgaaaaacccgggtctggagacagacgtcccac 16823

PstI
Query:  4084  ccgggggctctgcagacgccagcggggcggggcgcggaggccgcgctcagctgggagga  4143
              ||||||||||||  |||||||||||||||||||||||||||||||||||||||||||||
Sbjct: 16824  ccgggggctctgcggacgccagcggggcggggcgcggaggccgcgctcagctgggagga 16883

Query:  4144  caaacagtcgctaattggagaggaattgggatgcggcctggggctgcgggtacccggag  4203
              |||||||||||||||||||||||||||||||||| ||||||||||||||||||||||||
Sbjct: 16884  caaacagtcgctaattggagaggaattgggattcggcctggggctgcgggtacccggag 16943

Query:  4204  aggtggggatggctgtagggggcggcaggaagagttccaggaggtgtctggaaaaggat  4263
              || |||||||||||||||||||||| || ||||||||||||||||||||||| ||||||
Sbjct: 16944  agatggggatggctgtagggggctgcagggaagagttccaggaggtgtctggacaaggat 17003
```

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cggcgggcgtgggcgggttccctggcccgggacgggaagcaggacgcgggccaggacgc  3963
              |||||||||||||| |||||||||||||||||||||||||||||||||||||||||||||
Sbjct: 16646  cgggcgggcgtgggcgcgttccctggcccgggacgggaagcaggacgcgggccaggacgc 16705

Query:  3964  tcccagggg cgaggctccggcgcggcacggcgggccctgctaaataaggaacgcctggag 4023
              ||||||||  ||||||||||||||||||||| |||| |||||||||||||||||||||||
Sbjct: 16705  tcccaggg-cgaggctccggcgcggcacagcgg-ccctgctaaataaggaacgcctggag 16763
```

FIG. 2A

Figure 2 con.

```
                    Stretch of Exon 6-Homolog 1

Query: 21589 tcgttcccaccggtctccagcggtgcacccgctctgccccteggacacggagatcttccc 21648
             ||||||||||||||||||||||||||||||||||||||||||||||||||||||||||| |
Sbjct: 23917 tcgttcccaccggtctccagcggtgcaccegetetgecectcggacacggagatettete 23976

Query: 21649 tggcaacgggcactgctaccgcctggtggtggagaaggcggcctggctgcaggcgcagga 21708
             ||||||  ||||||||||||||||||||||||||||||||||||||||||||||||||||
Sbjct: 23977 tggcaatgggcactgctaccgcctggtggtggagaaggcggcctggctgcaggcgcagga 24036
                            StuI
Query: 21709 gcagtgtcaggcctgggccgggccgccctggcaatggtggacagtcccgccgtgcagcg 21768
             ||||||||  |||||||||||||| ||||||||||||||||||||||||||||||||||
Sbjct: 24037 gcagtgtcgggcctgggccgggccacccctggcaatggtggacagtcccgccgtgcagcg 24096

Stretch of Exon 6-Homolog 2

Query: 21589 tcgttcccaccggtctccagcggtgcaccegetetgceectcggacacggagatettecc 21648
             ||||||||||||||||||||||||||||||||||||||||||||||||||||||||||| |
Sbjct: 63611 tcgttcccaccggtctccagcggtgcaccegetetgcccctcggacacggagatcttctc 63670

Query: 21649 tggcaacgggcactgctaccgcctggtggtggagaaggcggcctggctgcaggcgcagga 21708
             ||||||  ||||||||||||||||||||||||||||||||||||||||||||||||||||
Sbjct: 63671 tggcaacgggcactgctaccgcctggtggtggagaaggcggcctggctgcaggcgcagga 63730

Query: 21709 gcagtgtcaggcctgggccgggccgccctggcaatggtggacagtcccgccgtgcagcg 21768
             ||||||||  |||||||||||||| ||||||||||||||||||||||||||||||||||
Sbjct: 63731 gcagtgtcgggcctgggccgggccacccctggcaatggtggacagtcccgccgtgcagcg 63790
```

FIG. 2B

Figure 2 con.

Stretch of Exon 10—Homolog 1

```
Query: 23622 aaatcagggccccaacaccctccctcctcacagggacccggagaacggcagcgagcct 23681
             ||| ||||||||||||||||||||||||| |||||||||||||||||||||||||||
Sbjct: 25938 gaatgagggcccaacaccctccctcctcgcagggaccccggagaacggcagcgagcct 25997

Query: 23682 gagagcaggtccccggacaacaggacccagctggccccgcgtgcatgccaggggacgc 23741
             |||||||||||||||||||||||||||||||||||||||||||||||||||||||||
Sbjct: 25998 gagagcaggtccccggacaacaggacccagctggccccgcgtgcatgccaggggacgc 26057

Query: 23742 tggtgccctggagccaacatctgcttgccgctggacgcctcctgccaccccaggcctgc 23801
             ||||||||||||||||||||||||||||||||||||| ||||||||||||| |||||||
Sbjct: 26058 tggtgccctggagccaacatctgcttgccgctggacacctcctgccacccc-aggcctgc 26116

XmaI
Query: 23802 gccaatggctgcacgtcaggg-ccagggctacccggggcccctatgcgctatggagaga 23860
             |||||||||||||||||||||  ||||||||| ||||||||||||||||||||||||||
Sbjct: 26117 gccaatggctgcacgtcagggccagggctactcggggcccctatgcgctatggagaga 26176

Query: 23861 gttcctcttctccgttcccgcggggcccccgcgcagtactcggtgtgtggccctgacct 23920
             |||||||||||||||||||||||||||||||||||||||||||||||||||||||||
Sbjct: 26177 gttcctcttctccgttcccgcggggcccccgcgcagtactcggtgtgtggccctgacct 26236

Query: 23921 gggtctgttccctgcatctcctcaggccaccttcctgtctgctgcccagggtctgggtct 23980
             ||||||||||||||||||||||||||||||||||||||||||||||||||||||||||||
Sbjct: 26237 gggtctgttccctgcatctcctcaggccaccttcctgtctgctgcccagggtctgggtct 26296
```

Stretch of Exon 10—Homolog 2

```
Query: 23622 aaatcagggccccaacaccctccctcctcacagggacccggagaacggcagcgagcct 23681
             ||| ||||||||||||||||||||||||| |||||||||||||||||||||||||||
Sbjct: 65628 gaatgagggcccaacaccctccctcctcgcagggaccccggagaacggcagcgagcct 65687

Query: 23682 gagagcaggtccccggacaacaggacccagctggccccgcgtgcatgccaggggacgc 23741
             |||||||||||||||||||||||||||||||||||||||||||||||||||||||||
Sbjct: 65688 gagagcaggtccccggacaacaggacccagctggccccgcgtgcatgccaggggacgc 65747

Query: 23742 tggtgccctggagccaacatctgcttgccgctggacgcctcctgccaccccaggcctgc 23801
             |||||||||||||||||||||||||||||||||||||||||||||||||| |||||||
Sbjct: 65748 tggtgccctggagccaacatctgcttgccgctggacgcctcctgccacccc-aggcctgc 65806

Query: 23802 gccaatggctgcacgtcaggg-ccagggctacccggggcccctatgcgctatggagaga 23860
             |||||||||||||||||||||  ||||||||| ||||||||||||||||||||||||||
Sbjct: 65807 gccaatggctgcacgtcagggccagggctactcggggcccctatgcgctatggagaga 65866

Query: 23861 gttcctcttctccgttcccgcggggcccccgcgcagtactcggtgtgtggccctgacct 23920
             |||||||||||||||||||||||||||||||||||||||||||||||||||||||||
Sbjct: 65867 gttcctcttctccgttcccgcggggcccccgcgcagtactcggtgtgtggccctgacct 65926

Query: 23921 gggtctgttccctgcatctcctcaggccaccttcctgtctgctgcccagggtctgggtct 23980
             ||||||||||||||||||||||||||||||||||||||||||||||||||||||||||||
Sbjct: 65927 gggtctgttccctgcatctcctcaggccaccttcctgtctgctgcccagggtctgggtct 65986
```

FIG. 2C

Figure 2 con.

Exon 11—Homolog 1

```
Query:  24267  agccctgcgtgtccaccctcatccgtcgtgcggggtccacgggccatgaccgtgaggac  24326
               ||||||||||||||||||||||||||||||||| |||||||||||||||||||||||||
Sbjct:  26604  agccctgcgtgtccaccctcatccgtcgtgcaggggtccacgggccatgaccgtgaggac  26663

Query:  24327  gtgatgcagccctgcctccctctccacaggtcaccctccacggccaggatgtcctcatgc  24386
               ||||||||||||||||||||||||||||||||||||||||||| ||||||||||||||||
Sbjct:  26664  gtgatgcagccctgcctccctctccacaggtcaccctccacagccaggatgtcctcatgc  26723

Query:  24387  tccctggtgacctcgttggcttgcagcacgacgctggccctggcgccctcctgcactgct  24446
               ||||||||||||| ||||||||||||||||||||||||||||||||||||||||||||||
Sbjct:  26724  tccctggtgacctcgttggcttgcagcacgacgctggccctggcgccctcctgcactgct  26783

XmaI
Query:  24447  cgccggctccggccaccctggtccccgggccccgtacctctccgccaacgcctcgtcat  24506
               |||||||||||||||||||||||||||| |||||||||||||||||||||||||||||||
Sbjct:  26784  cgccggctccggccaccctggtcccccaggcccgtacctctccgccaacgcctcgtcat  26843

Query:  24507  ggctgcccacttgccagcccagctggagggcacttgggcctgccctgcctgtgccctgc  24566
               ||||||||||||||||||||||||||||||||||||||||||||||||||||||||||||
Sbjct:  26844  ggctgcccacttgccagcccagctggagggcacttgggcctgccctgcctgtgccctgc  26903

Query:  24567  ggctgcttgcagccacggaacagctcaccgtgctgctgggcttgaggcccaaccctggac  24626
               ||||||||||||||||||||||||||||||||||||||||||| ||||||||||||| |
Sbjct:  26904  ggctgcttgcagccacggaacagctcaccgtgctgctgggcctgaggcccaaccctggc  26963

Query:  24627  tgccggctgcctgggcgctatgaggtccgggcagaggtgggcaatggcgtgtccaggcaca  24686
               |||||||||||||||||||||||||||||||||||||||||||||||||||||||||||
Sbjct:  26964  tgcggctgcctgggcgctatgaggtccgggcagaggtgggcaatggcgtgtccaggcaca  27023

Query:  24687  acctctcctgcagctttgacgtggtctcccagtggctgggctgcgggtcatctaccctg  24746
               ||||  ||||||||||||||||||||||||||||||||||||||||||||||||||||
Sbjct:  27024  acctgtcctgcagctttgacgtggtctcccagtggctgggctgcgggtcatctaccctg  27083

Query:  24747  cccccgcgacggccgcctctacgtgcccaccaacggctcagccttggtgctccaggtgg  24806
               ||||||||||||||||||||||||||||||||||||||||||| |||||||||||||
Sbjct:  27084  cccccgcgacggccgcctctacgtgcccaccaacggctcagcctcggtgctccaggtgg  27143

Query:  24807  actctggtgccaacgccacggccacggctcgctggcctgggggcagtgtcagcgcccgct  24866
               |||||||||| ||||||||||||||||||||||||||||||||||||||||||||||||
Sbjct:  27144  actctggtgccagcgccacggccacggctcgctggcctgggggcagtgtcagcgcccgct  27203

Query:  24967  ttgagaatgtctgccctgccctggtggccaccttcgtgcccggctgccctgggagacca  24926
               |||||||  ||||||||||||||||||||||||||||||| ||||||||||||||||||
Sbjct:  27204  ttgagaatgcctgccctgccctggtggccaccttcgtgcccagctgccctgggagacca  27263

Query:  24927  acgataccctgttctcagtggtagcactgccgtggctcagtgaggggagcacgtggtgg  24986
               | |||||||||||||||||||||||||||||||||||| |||| ||||||||||| |||
Sbjct:  27264  atgataccctgttctcagtggtagcactgccgtggctcggtgaggggagcacgtgatgg  27323

Query:  24987  acgtggtggtggaaaacagcgccagccgggccaacctcagcctgcgggtgacggcggagg  25046
               |||  |||||||||||||||||||||||||||||||||||||||||||||||||||||
Sbjct:  27324  acgttgtggtggaaaacagcgccagccgggccaacctcagcctgcgggtgacggcggagg  27383

Query:  25047  agcccatctgtggcctccgcgccacgcccagccccgaggcccgtgtactgcagggagtcc  25106
               ||||||||||||||||||||||||||||||||||||||||||||||||||||||||||
Sbjct:  27384  agcccatctgtggcctccgcgccacgcccagccccgaggcccgtgtactgcagggagtcc  27443
```

FIG. 2D

Figure 2 con.

```
Query: 25107 tagtggtgagtatggccgaggctccaccaccagccccaggcaggtgcctgcagacaggg 25166
              |   ||||||||||||||||||||||||||||||||||||||||||||||||||||||
Sbjct: 27444 ca---gtgagtatggccgaggctccaccaccagccccaggcaggtgcctgcagacaggg 27500

Query: 25167 tgctcacacagggcgtgaggcctggcttcccagtgagggcagcagcccagttactgggga 25226
              ||||||||||||| ||||||||||||||||||||||||||||||||||||||||||||
Sbjct: 27501 tgctcacacagggcttgaggcctggcttcccagtgagggcagcagcccagttactgggga 27560
```

Exon 11—Homolog 2

```
Query: 24267 agccctgcgtgtccaccctcatccgtcgtgcggggtccacgggccatgaccgtgaggac 24326
              ||||||||||||||||||||||||||||||| |||||||||||||||||||||||||
Sbjct: 66294 agccctgcgtgtccaccctcatccgtcgtgcagggtccacgggccatgaccgtgaggac 66353

Query: 24327 gtgatgcagccctgcctccctctccacaggtcacctccacggccaggatgtcctcatgc 24386
              |||||||||||||||||||||||||||||||||||||||||||||||||||||||||
Sbjct: 66354 gtgatgcagccctgcctccctctccacaggtcacctccacggccaggatgtcctcatgc 66413

Query: 24387 tccctggtgacctcgttggcttgcagcacgacgctggccctggcgccctcctgcactgct 24446
              |||||||||||||||||||||||||||||||||||||||||||||||||||| |||||
Sbjct: 66414 tccctggtgacctcgttggcttgcagcacgacgctggccctggcgccctccgcactgct 66473

Query: 24447 cgccggctccggccaccctggtccccggccccgtacctctccgccaacgcctcgtcat 24506
              ||||||||||||||||||||||||||  |||||||||||||||||||||||||||||
Sbjct: 66474 cgccggctccggccaccctggtcccaggccccgtacctctccgccaacgcctcgtcat 66533

Query: 24507 ggctgccccacttgccagcccagctggagggcacttggcctgccctgctgtgccctgc 24566
              ||||||||||||||||||||||||||||||||||||||||||||||||||||||||
Sbjct: 66534 ggctgccccacttgccagcccagctggagggcacttggcctgccctgctgtgccctgc 66593

Query: 24567 ggctgcttgcagccacggaacagctcaccgtgctgctgggcttgaggcccaaccctggac 24626
              |||||||||||||||||||||||||||||||||||||||||||| |||||||||||| |
Sbjct: 66594 ggctgcttgcagccacggaacagctcaccgtgctgctgggcctgaggcccaaccctgggc 66653

Query: 24627 tgcggctgcctgggcgctatgaggtccggcagaggtgggcaatggcgtgtccaggcaca 24686
              |||||||||||||||||||||||||||||||||||||||||||||||||||||||||
Sbjct: 66654 tgcggctgcctgggcgctatgaggtccggcagaggtgggcaatggcgtgtccaggcaca 66713

Query: 24687 acctctcctgcagctttgacgtggtctccccagtggctgggctgcgggtcatctaccctg 24746
              ||||  |||||||||||||||||||||||||||||||||||||||||||||||||||||
Sbjct: 66714 acctgtcctgcagctttgacgtggtctccccagtggctgggctgcgggtcatctaccctg 66773

Query: 24747 cccccgcgacggccgcctctacgtgcccaccaacggctcagccttggtgctccaggtgg 24806
              ||||||||||||||||||||||||||||||||||||||||||||  |||||||||||
Sbjct: 66774 cccccgcgacggccgcctctacgtgcccaccaacggctcagcctcggtgctccaggtgg 66833

Query: 24807 actctggtgccaacgccacggccacggctcgctggcctgggggcagtgtcagcgcccgct 24866
              ||||||||||||   |||||||||||||||||||||||||||||||||||||||||||
Sbjct: 66834 actctggtgccagcgccacggccacggctcgctggcctgggggcagtgtcagcgcccgct 66893

Query: 24867 ttgagaatgtctgccctgccctggtggccaccttcgtgcccggctgccctgggagacca 24926
              ||||||||  |||||||||||||||||||||||||||||||||||||||||||||||
Sbjct: 66894 ttgagaatgcctgccctgccctggtggccaccttcgtgcccggctgccctgggagacca 66953
```

FIG. 2E

Figure 2 con.

```
Query: 24927 acgatacoctgttctcagtggtagcactgccgtggctcagtgagggggagcacgtggtgg 24986
              | |||||||||||||||||||||||||||||||||||||| |||||||||||||||| |||
Sbjct: 66954 atgatacoctgttctcagtggtagcactgccgtggctcggtgagggggagcacgtgatgg 67013

Query: 24987 acgtggtggtggaaaaacagcgccagccgggccaacctcagcctgcgggtgacggcggagg 25046
              |||| |||||||||||||||||||||||||||||||||||||||||||||||||||||||
Sbjct: 67014 acgttgtggtggaaaaacagcgccagccgggccaacctcagcctgcgggtgacggcggagg 67073

Query: 25047 agcccatctgtggcctccgcgccacgcccagccccgaggcccgtgtactgcagggagtcc 25106
              ||||||||||||||||||||||||||||||||||||||||||||||||||||||||||||
Sbjct: 67074 agcccatctgtggcctccgcgccacgcccagccccgaggcccgtgtactgcagggagtcc 67133

Query: 25107 tagtggtgagtatggccgaggctccaccaccagccccaggcaggtgcctgcagacaggg 25166
              ||||||||||||||||||||||||||||||||||||||||||||||||||||||||||||
Sbjct: 67134 cagtggtgagtatggccgaggctccaccaccagccccaggcaggtgcctgcagacaggg 67193

Query: 25167 tgctcacacagggcgtgaggcctggcttcccagtgagggcagcagcccagttactgggga 25226
              ||||||||||||||||||||||||||||||||||||||||||||||||||||||||||||
Sbjct: 67194 tgctcacacagggcgtgaggcctggcttcccagtgagggcagcagcccagttactgggga 67253
```

FIG. 2F

Figure 2 con.

Exon 15—Homolog 1

```
Query: 27279 tgggaccettaaggctgggccgcaggtgcagccgttcaccccgggctcctcaggcggggg 27338
              |||||||||||||||||||||||||||||||||||||||||||||||||||||||||||
Sbjct: 29661 tgggaccettaaggctgggccgcaggtgcagccgttcaccccgggctcctcaggcggggg 29720

Query: 27339 gcttctgcegagcgggtggggagcaggtgggggtgccgcggctgccccactcgggcctgt 27398
              ||||||| |||||||||||||||||||||||||||||||||||||| ||||||||
Sbjct: 29721 gcttctgctgagcgggtggggagcaggtgggggtgccgcggctgccccacttgggcctgt 29780

Query: 27399 ccccacaggtgagtacctcctgaccgtgctggcatctaatgccttcgagaaccggacgca 27458
              ||||||||||||||| |||||||||||||||||||||||||||||||||||||||||||
Sbjct: 29781 ccccacaggtgagtacgtcctgaccgtgctggcatctaatgccttcgagaaccggacgca 29840

Query: 27459 gcaggtgcctgtgagcgtgcgcgcctccctgccctccgtg 27498
              |||||||||||||||||||| ||||||||||||||| |||
Sbjct: 29841 gcaggtgcctgtgagcgtgtgcgcctccctgccctctgtg 29880
```

Exon 15—Homolog 2

```
Query: 27279 tgggaccettaaggctgggccgcaggtgcagccgttcaccccgggctcctcaggcggggg 27338
              |||||||||||||||||||||||||||||||||||||||||||||||||||||||||||
Sbjct: 69326 tgggaccettaaggctgggccgcaggtgcagccgttcaccccgggctcctcaggcggggg 69385

Query: 27339 gcttctgccgagcgggtggggagcaggtgggggtgccgcggctgccccactcgggcctgt 27398
              |||||||||||||||||||||||||||||||||||||||||||||||||| ||||||||
Sbjct: 69386 gcttctgccgagcgggtggggagcaggtgggggtgccgcggctgccccacttgggcctgt 69445

Query: 27399 ccccacaggtgagtacctcctgaccgtgctggcatctaatgccttcgagaaccggacgca 27458
              ||||||||||||||| |||||||||||||||||||||||||||||||||||||||||||
Sbjct: 69446 ccccacaggtgagtacgtcctgaccgtgctggcatctaatgccttcgagaaccggacgca 69505

Query: 27459 gcaggtgcctgtgagcgtgcgcgcctccctgccctccgtggctgtgggtgtgagtgacgg 27518
              |||||||||||||||||||||||||||||||||||||||  |||||||||||||||||
Sbjct: 69506 gcaggtgcctgtgagcgtgcgcgcctccctgccctccgaggctgtgggtgtgagtgacgg 69565

Query: 27519 cgtcctggtggccggccggcccgtcaccttctaccgcacccgctgccctcgcctggggg 27578
              ||||||||||||||||||||||||||||||||||||||| | ||||||||||||||||
Sbjct: 69566 cgtcctggtggccggccggcccgtcaccttctaccgcatctgctgccctcgcctggggg 69625

Query: 27579 tgttctttacacgtgggacttcggggacggctccctgtcctgacccagagccagccggc 27638
              |||||||||||||||||||||||||||||||||||||||||||||||||||||||||||
Sbjct: 69626 tgttctttacacgtgggacttcggggacggctccctgtcctgacccagagccagccggc 69685

Query: 27639 tgccaaccacacctatgcctcgaggggcacctaccacgtgcgcctggaggtcaacaacac 27698
              ||||||||||||||| ||||||||| ||||||||||||||||||||||||||||||||||
Sbjct: 69686 tgccaaccacacctatccctcgaggggcatctaccacgtgcgcctggaggtcaacaacac 69745

Query: 27699 ggtgagcggtgcggcggcccaggcggatgtgcgcgtctttgaggagctccgcggactcag 27758
              |||||||||||||||||||||||||||||||||||||||||||||||||||  |||||
Sbjct: 69746 ggtgagcggtgcggcggcccaggcggatgtgcgcgtctttgaggagctccgcgggctcag 69805

Query: 27759 cgtggacatgagcctggccgtggagcagggcgccccgtggtggtcagcgccgcggtgca 27818
```

FIG. 2G

Figure 2 con.

```
                 |||||||||||||||||||||||||||||||||||||||||||||||  |||||||||||
Sbjct:  69806 cgtggacatgagcctggccgtggagcagggcgcccccgtggtggtcagtgccgcggtgca 69865

Query:  27819 gacgggcgacaacatcacgtggaccttcgacatggggggacggcaccgtgctgtcgggccc 27878
              ||||||||||||||||||||||||||||||||||||||||||||||||||||||||||||
Sbjct:  69866 gacgggcgacaacatcacgtggaccttcgacatggggggacggcaccgtgctgtcgggccc 69925

Query:  27879 ggaggcaacagtggagcatgtgtacctgcgggcacagaactgcacagtgaccgtgggtgc 27938
              ||||| |||||||||||||||||||||||||||||||||||||||||||||||||||||
Sbjct:  69926 agaggccacagtggagcatgtgtacctgcgggcacagaactgcacagtgaccgtgggtgc 69985

Query:  27939 ggccagcccgccggccacctggcccggagcctgcacgtgctggtcttcgtcctggaggt 27998
              |||||||||||||||||||||||||||||||||||||||||||||||||||||||||||
Sbjct:  69986 ggccagcccgccggccacctggcccggagcctgcacgtgctggtcttcgtcctggaggt 70045

Query:  27999 gctgcgcgttgaacccgccgcctgcatccccacgcagcctgacgcgcggctcacggccta 28058
              ||||||||  || |||||||||||||||||||| ||||||||||||||||||||||||||
Sbjct:  70046 gctgcgcgtcgagcccgccgcctgcatccccactcagcctgacgcgcggctcacggccta 70105

Query:  28059 cgtcaccgggaacccggcccactacctcttcgactggaccttcggggatggctcctccaa 28118
              ||||||||||||||||||||  ||||||||||||||||||||| ||||||||||||||||
Sbjct:  70106 cgtcaccgggaacccggcccgctacctcttcgactggacctttggggatggctcctccaa 70165
                                                                     MluI
Query:  28119 cacgaccgtgcggggtgcccgacggtgacacacaacttcacgcggagcggcacgttccc 28178
              |||||||  ||||||||||||||||||||||||||||||||||||| ||||||||||||
Sbjct:  70166 cacgaccatgcggggtgcccgacggtgacacacaacttcacgcgtagcggcacgttccc 70225

Query:  28179 cctggcgctggtgctgtccagccgcgtgaacagggcgcattacttcaccagcatctgcgt 28238
              |||||||||||||||||||||||||||||||||||||| |||||||||||||||||||||
Sbjct:  70226 cctggcgctggtgctgtccagccgcgtgaacagggcgcgttacttcaccagcatctgcgt 70285

Query:  28239 ggagccagaggtgggcaacgtcaccctgcagccagagaggcagtttgtgcagctcgggga 28298
              ||||||||||||||||||||||||||||||||||||||||||||||||||||||||||||
Sbjct:  70286 ggagccagaggtgggcaacgtcaccctgcagccagagaggcagtttgtgcagctcgggga 70345

Query:  28299 cgaggcctggctggtggcatgtgcctggccccgttcccctaccgctacacctgggactt 28358
              ||||||| ||||||||||||||||||||||||||||||||||||||||||||||||||||
Sbjct:  70346 cgaggccaggctggtggcatgtgcctggccccgttcccctaccgctacacctgggactt 70405

Query:  28359 tggcaccgaggaagccgcccccacccgtgccagggggccctgaggtgacgttcatctaccg 28418
              ||||||||| |||||| |||| ||||||   |||||||||||||||||||||||||||||
Sbjct:  70406 tggcaccgaagaagccgtccccgccgtgtcgggggccctgaggtgacgttcatctaccg 70465

Query:  28419 agaccaggctcctatcttgtgacagtcaccgcgtccaacaacatctctgctgccaatga 28478
              ||||||||||||||||||||||||||||||||||||||||||||||||||| ||||||||
Sbjct:  70466 agaccaggctcctatcttgtgacagtcaccgcgtccaacaacatctccgctgccaatga 70525

Query:  28479 ctcagccctggtggaggtgcaggagcccgtgctggtcaccagcatcaaggtcaatggctc 28538
              |||||||||||||||||||||||||||| |||||||||||||||||||||||||||||||
Sbjct:  70526 ctcagccctggtggaggtgcaggagcccatgctggtcaccagcatcaaggtcaatggctc 70585

Query:  28539 ccttggctggagctgcagcagccgtacctgttctctgctgtgggccgtgggcgccccgc 28598
              |||||||||||||||||  |||||||||||||||||||||||||||||||||||||||||
Sbjct:  70586 ccttggctggagctgcagtagccgtacctgttctctgctgtgggccgtgggcgccccgc 70645

Query:  28599 cagctacctgtgggatctggggacggtgggtggctcgaggtgcggaggtcacccacgc 28658
              ||||||||||||||||||||||||||||| ||||||||||||||||||||||||||||||
```

FIG. 2H

Figure 2 con.

```
Sbjct: 70646 cagctacctgtgggatctgggggacggtgggcggctcgagggtccggaggtcacccacgc 70705

Query: 28659 ttacaacagcacaggtgacttcaccgttagg-tggccggctggaatgaggtgagccgcag 28717
              |||||||||||||||||||||||||||||||| |||||||||| |||||||||||||||
Sbjct: 70705 ttacaacagcacaggtgacttcaccgttagggtggccggctgcaatgaggtgagccgcag 70765

Query: 28718 cgaggcctggctcaatgtgacggtgaagcggcgcgtgcgggggctcgtcgtcaatgcaag 28777
              ||||||||||||||||||||||||||||||||||||||||||||| ||||||||| ||
Sbjct: 70766 cgaggcctggctcaatgtgacggtgaagcggcgcgtgcgggggctcatcgtcaatgccag 70825

Query: 28778 ccccacggtggtgccctgaatgggagcgtgagcttcagcacgtcgctggaggccggcag 28837
              |   ||||||||||||||||||||||||||| ||||||||| ||||||||||||||||
Sbjct: 70826 ctgcacggtggtgccctgaatgggagcatgagcttcagcacctcgctggaggccggcag 70885

Query: 28838 tgatgtgcgctattcctgggtgctctgtgaccgctgcacgcccatcctgggggtcctac 28897
              |||||||||||||||||||||||||||||||||||||||||||||| |||||||||| |
Sbjct: 70886 tgatgtgcgctattcctgggtgctctgtgaccgctgcacgcccatctctgggggtcctgc 70945

Query: 28898 catctctt-acaccttccgctccgtgggcaccttcaatatcatcgtcacggctgagaacg 28956
              ||||||||  |||||||||||||||||||||||||||||||||||||| |||||||||
Sbjct: 70946 catctctttacaccttccgctccgtgggcaccttcaatatcatcgtcacagctgagaacg 71005

Query: 28957 aggtgggctccgcccaggacagcatcttcgtctatgtcctgcagctcatagagggggctgc 29016
              |||||||||||||||||||||||||||||||||||||||||||||||||||||||||||
Sbjct: 71006 aggtgggctccgcccaggacagcatcttcgtctatgtcctgcagctcatagagggggctgc 71065

Query: 29017 aggtggtgggcggtggccgctacttcccaccaaccacacggtacagctgcaggccgtgg 29076
              |||||||||||||||||||||||||||||||||||||||||||||||||||||||||||
Sbjct: 71066 aggtggtgggcggtggccgctacttcccaccaaccacacggtacagctgcaggccgtgg 71125

Query: 29077 tcagggatggcaccaacgtctcctacagctggactgcctggagggacaggggccggccc 29136
              | ||||||||||||||| |||   |||||||||||||||||||||||||||||||||||
Sbjct: 71126 tcaggatggcaccaacatct---acagctggactgcctggagggacaggggccggccc 71182

Query: 29137 tggccggcagcggcaaaggcttctcgctcacgt-ctcgaggccggcacctaccatgtgc 29195
              |||||||||||||||||||||||||||||||| | ||||||||||||||||||||||
Sbjct: 71183 tggccggcagcggcaaaggcttctcgctcactgcgctcgaggccggcacctaccatgtgc 71242

Query: 29196 agctgcgggccaccaacatgctgggcagcgcctgggccgactgcaccatggacttcgtgg 29255
              ||||||||||||||||||||||||||||||||||||| |||||||| |||||||||||
Sbjct: 71243 agctgcgggccaccaacatgctgggcagcgcctgggctgactgcaccgtggacttcgtgg 71302

Query: 29256 agcctgtgggtggctgatggtggccgcctcccgaacccagctgccgtcaacaaaagcg 29315
              ||||||||||||||||||||||||||||||||||||||||||||||||||||| ||| |
Sbjct: 71303 agcctgtgggtggctgatggtggccgcctcccgaacccagctgccgtcaacacaagtg 71362

Query: 29316 tcaccctcagtgccgagctggctggtggcagtggtgtcgtatacacttggtccttggagg 29375
              |||||||||||||||||||||||||||||||||||||||||||||||||||||||||||
Sbjct: 71363 tcaccctcagtgccgagctggctggtggcagtggtgtcgtatacacttggtccttggagg 71422

Query: 29376 aggggctgagctgggagacctccgagccatttaccacccatagcttcccacacccggcc 29435
              ||||||||||||||||||||||||||| |||||||||||| |||||||||| ||||||
Sbjct: 71423 aggggctgagctgggagacccccgagccatttaccacccacagcttcccacacccggcc 71482

Query: 29436 tgcacttggtcaccatgacggcagggaaccgctgggctcagccaacgccaccgtggaag 29495
              |||||||||||||||||||||||||||||||||||||||||||||||||||||||||
Sbjct: 71483 tgcacttggtcaccatgacggcagggaacccgctgggctcagccaacgccaccgtggaag 71542
```

FIG. 2I

Figure 2 con.

```
Query: 29496 tggatgtgcaggtgcctgtgagtggcctcagcatcagggccagcgagcccggaggcagct 29555
              ||||||||||||||||||||||||||||||||||||||||||||||| |||||||||||
Sbjct: 71543 tggatgtgcaggtgcctgtgagtggcctcagcatcagggccagcgagccggaggcagct 71602

Query: 29556 tcgtggcggccgggtcctctgtgccctttt gggggcagctggccacgggcaccaatgtga 29615
              ||||||||||||||||||||||||||||||||||||||||||||||||||||||||||
Sbjct: 71603 tcgtggcggccgggtcctctgtgccctttt gggggcagctggccacgggcaccaatgtga 71662

Query: 29616 gctggtgctgggctgtgcccggcggcagcagcaagcgtggccctcatgtcaccatggtct 29675
              ||||||||||||||||||||||||||||||||||||||||||||||||||||||||||
Sbjct: 71663 gctggtgctgggctgtgcccggcggcagcagcaagcgtggccctcatgtcaccatggtct 71722

Query: 29676 tcccggatgctggcaccttctccatccggctcaatgcctccaacgcagtcagctgggtct 29735
              |||||||||||||||||||   |||||||||||||||||||||||||||||||||||||
Sbjct: 71723 tcccggatgctggcaccttcaacatccggctcaatgcctccaacgcagtcagctgggtct 71782

Query: 29736 cagccacgtacaacctcacggcggaggagcccatcgtgggcctggtgctgtgggccagca 29795
              ||||||||||||||||||||   ||||||||||||||||||||||||||||||||||||
Sbjct: 71783 cagccacgtacaacctcacggtggaggagcccatcgtgggcctggtgctgtgggccagca 71842

Query: 29796 gcaaggtggtggcgcccgggcagctggtccatttt cagatcctgctggctgccggctcag 29855
              |||||||||||||||||||||||  |||||||||||||||||||||||||||||||||
Sbjct: 71843 gcaaggtggtggcgcccgggcagcttgtccatttt cagatcctgctggctgccggctcag 71902

PstI                 XmaI
Query: 29856 ctgtcaccttccgcctgcaggtcggcggggccaacccgaggtgctccccgggcccgtt 29915
              |||||||||||| ||||||||||||||||||   ||||| ||||||| |||||||||||
Sbjct: 71903 ctgtcaccttccgccggcaggtcggcggggccagcccgaagtgctccctgggcccgtt 71962

Query: 29916 tctcccacagcttcccccgcgtcggagaccacgtggtgagcgtgcgggcaaaaaccacg 29975
              ||||||||||||||||||| |||||||||||||||||||||||||| | |||||||||
Sbjct: 71963 tctcccacagcttcccccgcatcggagaccacgtggtgagcgtgcagagcaaaaaccacg 72022

Query: 29976 tgagctgggcccaggcgcaggtgcgcatcgtggtgctggaggccgtgagtgggctgcagg 30035
              |||||||||||||||||||||||||||||||||||||||||||||||| |||||||||
Sbjct: 72023 tgagctgggcccaggcgcaggtgcgcatcgtggtgctggaggccgtgagcgggctgcagg 72082

Query: 30036 tgcccaactgctgcgagcctggcatcgccacgggcactgagaggaacttcacagcccgcg 30095
              ||||||||||| |||||||||||||||||  ||||||||||||||||||||| ||||||
Sbjct: 72083 tgcccaactgctgtgagcctggcatcgccatgggcactgagaggaacttcacagcccgcg 72142

Query: 30096 tgcagcgcggctctcgggtcgcctacgcctggtacttctcgctgcagaaggtccagggcg 30155
              ||| ||||||||||||||||||||||||||||| ||||||||||||||||||| |||||
Sbjct: 72143 tgcagcgcggctctcgggtcgcctacgcctggtatttctcgctgcagaaggtccgggg cg 72202

Query: 30156 actcgctggtcatcctgtcgggccgcgacgtcacctacacgccgtggccgcggggctgt 30215
              |||| || ||||||||||||||||||||||||||||||||||||| ||||||||||||
Sbjct: 72203 actctctgttcatcctgtcgggccgcgacgtcacctacacgcc-gtggccgcggggctgt 72261

BssHII
Query: 30216 tggagatccaggtgcgcgccttcaacgccctgggcagtgagaaccgcacgctggtgctgg 30275
              |||||||||||||||   ||||||||||||||||||||||||||||| |||||||||||
Sbjct: 72262 tggagatccaggtgcgtgccttcaacgccctgggcagtgagaaccgcacgctggtgctgg 72321

PstI
Query: 30276 aggttcaggacgccgtccagtatgtggccctgcagagcggcccctgcttcaccaaccgct 30335
              ||||||||||||||||||||||||||||||||  ||||||||||||||||||||||||
Sbjct: 72322 aggttcaggacgccgtccagtatgtggccctgcggagcggcccctgcttcaccaaccgct 72381
```

FIG. 2J

Figure 2 con.

```
Query: 30336 cggcgcagtttgaggccgccaccagccccagccccggcgtgtggcctaccactgggact 30395
              ||||||||||||||||||||||||||||||||||||||| |||||||||||||||||||
Sbjct: 72382 tggcgcagtttgaggccgccaccagccccagccccggcgcgtggcctaccactgggact 72441

Query: 30396 ttggggatgggtcgccaggggcaggacacagatgagcccagggccgagcactcctacctga 30455
              ||||||||||||| |||||||||||||||||||| |||||||||||||||||||||||||
Sbjct: 72442 ttggggatgggtccccagggcaggacacagataagcccagggccgagcactcctacctga 72501

Query: 30456 ggcctggggactaccgcgtgcaggtgaacgcctccaacctggtgagcttcttcgtggcgc 30515
              |||||||||||||||||||||||||||||||||||||||||||||||||||||||||||
Sbjct: 72502 ggcctggggactaccgcgtgcaggtgaacgcctccaacctggtgagcttcttcgtggcgc 72561

Query: 30516 aggccacggtgaccgtccaggtgctggcctgccgggagccggaggtggacgtggtcctgc 30575
              |||||||||||||||||||||||||||||||||||||||||||||||||||||||||||
Sbjct: 72562 aggccacggtgaccgtccaggtgctggcctgccgggagccggaggtggacgtggtcctgc 72621

Query: 30576 ccctgcaggtgctgatgcggcgatcacagcgcaactacttggaggccacgttgacctgc 30635
              |||||||||||||||||| |||||||||||||||||| |||| ||| ||||||||||||
Sbjct: 72622 ccctgcaggtgctgatgcgacgatcacagcgcaactgcctggatgcctacgttgacctgc 72681

Query: 30636 gcgactgcgtcacctaccagactgagtaccgctgggaggtgtatcgcaccgccagctgcc 30695
              ||||||| |||||||||||||||||||||||||||||||||| ||||||||||||||||
Sbjct: 72682 gcgactgtgtcacctaccagactgagtaccgctgggaggtgtaccgcaccgccagctgcc 72741

Query: 30696 agcggccggggcgcccagcgcgtgtggccctgcccggcgtggacgtgagccggcctcggc 30755
              |||||||||| |||| |||||||||||||||||||||||||||||||||||||||| ||
Sbjct: 72742 agcggccggggtgcccggcgcgtgtggccctgcccggcgtggacgtgagccggcctcagc 72801

Query: 30756 tggtgctgccgcggctggcgctgcctgtggggcactactgctttgtgtttgtcgtgtcat 30815
              ||||||||||||||||||||||||||||||||||||||||||||||||||||||||||||
Sbjct: 72802 tggtgctgccgcggctggcgctgcctgtggggcactactgctttgtgtttgtcgtgtcat 72861

Query: 30816 ttggggacacgccactgacacagagcatccaggccaatgtgacggtggccccgagcgcc 30875
              ||||||||||||||| ||| |||||||||||||||||||||||||||||||||||||||
Sbjct: 72862 ttggggacacgccactggcacggagcatccaggccaatgtgacggtggccccgagcgcc 72921

Query: 30876 tggtgcccatcattgagggtggctcataccgcgtgtggtcagacacacgggacctggtgc 30935
              ||||||||||| |||||||||||| |||||||||||||||||||||||| |||||||||
Sbjct: 72922 tggtgcccatcactgagggtggctcctaccgcgtgtggtcagacacacaggacctggtgc 72981

Query: 30936 tggatggagcgagtcctacgaccccaacctggaggacggcgaccagacgccgctcagtt 30995
              |||||||||||||||||||||||||||||||||||||||||||||||||||||||||||
Sbjct: 72982 tggatggagcgagtcctacgaccccaacctggaggacggcgaccagacgccgctcagtt 73041

Query: 30996 tccactgggcctgtgtggcttcgacacaggtcagtgcgtggcagggccgtcctccatgcc 31055
              |||| |||||||||||||||||||||||||||||||||||||||||||||||||| |||
Sbjct: 73042 tccagtgggcctgtgtggcttcgacacaggtcagtgcgtggcagggccgtcctcctgcc 73101

Query: 31056 cctcaccgtccacacccatgagcccagagaacacccagcttgccaccagggctggccg 31115
              |||||||||||||||||||||||||||||||||||||||||||||||||||||||||||
Sbjct: 73102 cctcacccgtccacacccatgagcccagagaacacccagcttgccaccagggctggccg 73161
```

FIG. 2K

Figure 2 con.

Exon 16-Homolog 2

```
Query: 31176 gggccgggctctgctttaaaactggatggggctctcaggccacgtcgcccttgttctcg 31235
              ||||||||||||||||||||||||||||||| ||||  |||||||||||||||||||||
Sbjct: 73222 gggccgggctctgctttaaaactggatggggttctcgggccacgtcgcccttgttctcg 73281

Query: 31236 gcctgcagagggaggctggcgggtgtgcgctgaactttgggccccgcgggagcagcacgg 31295
              ||||||||||||||||||||||||||||||||||||||||||||||||||||||||||
Sbjct: 73282 gcctgcagagggaggctggcgggtgtgcgctgaactttgggccccgcgggagcagcacgg 73341

Query: 31296 tcaccattccacgggagcggctggcggctggcgtggagtacaccttcagcctgaccgtgt 31355
              ||||||||||||||| ||||||| |||||||||||||||||||||||||  ||||||||
Sbjct: 73342 tcaccattccacgggaacggctggcagctggcgtggagtacaccttcagcctcaccgtgt 73401
                                           PvuII Query: 31356 ggaaggccggccgcaaggaggaggccaccaaccagacggtgggtgccgcccgcccctcgg 31415
              ||||||||||||||||||||||||||||||||||||||||||||||||||||||||||
Sbjct: 73402 ggaaggccggccgcaaggaggaggccaccaaccagacggtgggtgccgccgccccctcgg 73461
```

FIG. 2L

Figure 2 con.

Exon 20-Homolog 1

```
Query:  33189 agccaggccgtgggagggcgccccgagactgccacctgctcaccacccc-ctctgctcg 33247
              ||||||||||||||||||||||||||||||||||||||||||||||||| ||||||||
Sbjct:  31282 agccaggccgtgggagggcgccccgagactgccacctgctcaccacccgctctgctcg 31341

Query:  33248 taggtctttggccatcaccctcccagagcccaacggcagcgcaacggggctcacagtctg 33307
              |||||| |||||||||||||||||||||||||||||||||||||| ||||||||||||
Sbjct:  31342 taggtctctggccatcaccctcccagagcccaacggcagcgcaatggggctcacagtctg 31401

Query:  33308 gctgcacgggctcaccgctagtgtgctcccagggctgctgcggcaggccgatcccagca 33367
              ||||| ||||||||||||||||||||||  |||||||||||||||||||||||||||
Sbjct:  31402 gctgcagggctcaccgctagtgtgctcccggggctgctgcggcaggccgatcccagct 31461
                                                XmaI Query:  33368 cgtcatcgagtactcgttggccctggtcaccgtgctgaacgaggtgagtgcagcctggga 33427
              |||||||||||||||| ||||||||||||| |||||||||||||||||||||||||||
Sbjct:  31462 cgtcatcgagtactcgctggccctggtcactgtgctgaacgaggtgagtgcagcctggg 31521
                 AatII
Query:  33428 ggggacgtcacatctgctgcatgcgtgcttgggaccaagacctgtacccctgcctggagc 33487
              |||||| ||||||||||||||||||||| |||||||||||||| |||||||||||||
Sbjct:  31522 ggggatctcacatctgctgcatgcgtgctggggaccaagacctgttcccctgcctggagc 31581
```

Exon 20-Homolog 2

```
Query:  33215 gactgccacctgctcacca-ccccctctgctcgtaggtctttggccatcaccctcccaga 33274
              ||||||||||||||||||| ||||||||||||||||| ||||||||||||||||||||
Sbjct:  75262 gactgccacctgctcaccaccccctctgctcgtaggtctctggccatcaccctcccaga 75321

Query:  33275 gcccaacggcagcgcaacggggctcacagtctggctgcacgggctcaccgctagtgtgct 33334
              |||||||||||||||| ||||||||||||||||||||| ||||||||||||||||||
Sbjct:  75322 gcccaacggcagcgcaatggggctcacagtctggctgcacgggctcaccgctagtgtgct 75381

Query:  33335 cccagggctgctgcggcaggccgatcccagcacgtcatcgagtactcgttggccctggt 33394
              ||| |||||||||||||||||||||||||||||||||||||||||||| |||||||||
Sbjct:  75382 cccggggctgctgcggcaggccgatcccagcacgtcatcgagtactcgctggccctggt 75441

Query:  33395 caccgtgctgaacgaggtgagtgcagcctgggagggacgtcacatctgctgcatgcgtg 33454
              ||| |||||||||||||||||||||||||||||||| ||||||||||||||||||||
Sbjct:  75442 cactgtgctgaacgaggtgagtgcagcctgggagggacctcacatctgctgcatgcgtg 75501
```

FIG. 2M

Figure 2 con.

Exon 22-Homolog 1

```
Query:  36719  atgtcaagaggtgccttgtgtggtcggtgggctgcatcacgtggtcccaggtggaggcc  36778
               ||||||||||||||||||||||||||||||||||||||||||||||||||| ||||||||
Sbjct:  32576  atgtgaagaggtgccttgtgtggtcggtgggctgcatcacgtggtcccaagtggaggcc  32635

Query:  36779  ctggtcatgcagagccacagaaaatgcttagtgaggaggctgtgggggtccagtcaagt  36838
               || ||||||||||||||||||||||||||||||||||||||||| |||||||||||||||
Sbjct:  32636  ctcggtcatgcagagccacagaaaatgcttagtgaggagactgtgggggtccagtcaagt  32695

Query:  36839  gggctctccagctgcagggctggggtgggagccaggtgaggaccgtgtagagaggagg  36898
               |||||||||||||||||||||||  |||||||||||||||||||||||||||||||||||
Sbjct:  32696  gggctctccagctgcagggctggaggtgggagccaggtgaggaccgtgtagagaggagg  32755

Query:  36899  gcgtgtgcaaggagtggggccaggagcggggctggacactgctggctccacacaggggcc  36958
               |||||||||| ||||||||||||||||||||||||||||||||||||||||||||||||
Sbjct:  32756  gcgtgtgcaaggagtggggccaggagcggggctggacactgctggctccacacaggggcc  32815

Query:  36959  cagcagggagctcgtatgccgctcgtgcctgaagcagacgctgcacaagctggaggccat  37018
               ||||||||||||||||||||||||||||||||||||||||||||||||||||||||||||
Sbjct:  32816  cagcagggagctcgtatgccgctcgtgcctgaagcagacgctgcacaagctggaggccat  32875

Query:  37019  gatgctcatcctgcaggcagagaccaccgcgggcaccgtgacgcccaccgccatcggaga  37078
               ||||| ||||||||||||||||||||||||||||||||||||||||||||||||||||||
Sbjct:  32876  gatgcgcatcctgcaggcagagaccaccgcgggcaccgtgacgcccaccgccatcggaga  32935
                        FspI
                                                          NlaIII
Query:  37079  cagcatcctcaacatcacaggtgccgcggcccgtgcccatgccaccgcccgcccc  37135
               |||||||||||||||||||||||||||||||||||||||| |||||||||||||||
Sbjct:  32936  cagcatcctcaacatcacaggtgccgcggcccgtgcccacgccaccgcccgcccc  32992
```

FIG. 2N

Figure 2 con.

```
                               Exon 22-Homolog 2

Query: 36719 atgtgaagaggtgccttgtgtggtcggtgggctgcatcacgtggtccccaggtggaggcc 36778
              ||||||||||||||||||||||||| ||||||||||||||||| ||||||||||||||||
Sbjct: 75778 atgtgaagaggtgccttgtgtggtcagtgggctgcatcacgtgttcccaggtggaggcc 75837

Query: 36779 ctgggtcatgcagagccacagaacatgcttagtgaggaggctgtgggggtccagtcaagt 36838
              |||||||||||||||||||||||| |||||||||||||||||||||||||||||||||||
Sbjct: 75838 ctgggtcatgcagagccacaaaaaatgcttagtgaggaggctgtgggggtccagtcaagt 75897

Query: 36839 gggctctccagctgcagggctgggggtgggagccaggtgaggacccgtgtagagaggagg 36898
              ||||||||||||||||||||||||| ||||||||||||||||||||||||||||||||||
Sbjct: 75898 gggctctccagctgcagggctgggggtgggagccaggtgaggacccgtgtagagaggagg 75957

Query: 36899 gcgtgtgcaaggagtggggccaggagcggggctggacactgctggctccacacagggcc 36958
              ||||||||||||||||||||||||||||||||||||||||||||||||||||||||||||
Sbjct: 75958 gcgtgtgcaaggagtggggccaggagcggggctggacactgctggctccacacagggcc 76017

Query: 36959 cagcagggagctcgtatgccgctcgtgcctgaagcagacgctgcacaagctggaggccat 37018
              ||||||||||||||||||||||| |||||||||||||||||||||||||||||||||||
Sbjct: 76018 cagcagggagctcgtatgccgctcgtgcctgaagcagacgctgcacaagctggaggccat 76077

Query: 37019 gatgctcatcctgcaggcagagaccaccgcgggcaccgtgacgccaccgccatcggaga 37078
              ||||| |||||||||||||||||||||||||||||||||||||||||||||||||||||
Sbjct: 76078 gatgcgcatcctgcaggcagagaccaccgcgggcaccgtgacgccaccgccatcggaga 76137

Query: 37079 cagcatcctcaacatcacaggtgccgcggcccgtgcccatgccaccgctcgcccc 37135
              ||||||||||||||||||||||||||||||||||||||||| ||||||||||||||||
Sbjct: 76138 cagcatcctcaacatcacaggtgccgcggcccgtgcccacgccacccgcccgcccc 76194
```

FIG. 2O

Figure 2 con.

Exon 23-Homolog 1

```
Query: 37663 cctccctgtctctgcactgacctcacgcatgtctgcaggagacctcatccacctggccag 37722
              |||||||||||||||||||||||||||||| ||||||||||||||||||||||||||||
Sbjct: 33404 cctccctgtctctgcactgacctcacgcctgtctgcaggagacctcatccacctggccag 33463

Query: 37723 ctcggacgtgcgggcaccacagcctcagagctgggagccgagtcaccatctcggatggt 37782
              ||| |||||||||||||||||||||| |||||||||||||||||| ||||| ||||||
Sbjct: 33464 ctcagacgtgcgggcaccacagcgctcagagctgggagccgagtcaccatcgcggatggt 33523

Query: 37783 ggcgtcccaggcctacaacctgacctctgccctcatgcgcatcctcatgcgctcccgcgt 37842
              |||||||||||||||||||||||||||||||||| |  ||| ||| ||||||||||||
Sbjct: 33524 ggcgtcccaggcctacaacctgacctctgccctcacgcctatcgtcacgcgctcccgcgt 33583

Query: 37843 gctcaacgaggagcccctgacgctggcggccgaggagatcgtggcccagggcaacgcctc 37902
              |||||||||||||||||||||||||||| || ||||||||||||||||||| ||||||
Sbjct: 33584 gctcaacgaggagcccctgacgctggcggtgaggagatcgtggcccagggcaacgcctc 33643

Query: 37903 ggacccgcggagcctgctgtgctatggcggcgcccagggcctggctgccacttctccat 37962
              |||||||||||||||||||||||||||||||||||||||||||||||||||||||||||
Sbjct: 33644 ggacccgcggagcctgctgtgctatggcggcgcccagggcctggctgccacttctccat 33703

MscI
Query: 37963 ccccgaggctttcagcggggccctggccaacctcagtgacgtggtgcagctcatctttct 38022
              |||| ||||||||| |||| |||||||||||||||||||||||||||||||||||||||
Sbjct: 33704 cccctaggctttcagcagggcccggccaacctcagtgacgtggtgcagctcatctttct 33763

Query: 38023 ggtggactccaatcccttcccctttggctatatcagcaactacaccgtctccaccaaggt 38082
              |||||||||||||||||||||||||||||||||||||||||||||||||||||||||||
Sbjct: 33764 ggtggactccaatcccttcccctttggctatatcagcaactacaccgtctccaccaaggt 33823

Query: 38083 ggcctcgatggcattccagacacaggccggcgcccagatccccatcgagcggctggcctc 38142
              |||||||||| ||||||||||||||||||||||||||||||||||||||||||||||||
Sbjct: 33824 ggcctcgatggcgttccagacacaggccggcgcccagatccccatcgagcggctggcctc 33883

Query: 38143 agagcgcgccatcaccgtgaaggtgcccaacaactcggactgggctgcccggggccaccg 38202
              |||||||||| |||||||||||||||||||||||||||||||||||||||||||||||
Sbjct: 33884 agagcgcgcc-tcaccgtgaaggtgcccaacaactcggactgggctgcccggggccaccg 33942

Query: 38203 cagctccgccaactccgccaactccgttgtggtccagcccaggcctccgtcggtgctgt 38262
              |||||||||||||||           |||||||||||||||||||||||||||||||
Sbjct: 33943 cagctccgccaact---------ccgttgtggtccagcccaggcctccgtcggtgctgt 33993

Query: 38263 ggtcaccctggacagcagcaaccctgcggccggcgtgcatctgcagctcaactatacgct 38322
              |||||||||||||||||||||||||||||| |||| ||||||||||||||||||||||
Sbjct: 33994 ggtcaccctggacagcagcaaccctgcggccgtgctgcatctgcagctcaactatacgct 34053

Query: 38323 gctggacggtgcgtgcagcgggtggggcacacgcggccccctggccttgttcttggggg 38382
              ||||||||||| |||| |||| |||||||||||||||||||||||||||||||| |||
Sbjct: 34054 gctggacggtgcatgcagcggttggggcacacgcggccccctggccttgttcttggggg 34113
                                                                   SphI
```

FIG. 2P

Figure 2 con.

```
                              Exon 23-Homolog 2

Query: 37663 cctccctgtctctgcactgacctcacgcatgtctgcaggagacctcatccacctggccag 37722
              ||||||||||||||||||||||||||||||  ||||||||||||||||||||||||||||
Sbjct: 76762 cctccctgtctctgcactgacctcacgcctgtctgcaggagacctcatccacctggccag 76821

Query: 37723 ctcggacgtgcgggcaccacagccctcagagctgggagccgagtcaccatctcggatggt 37782
              ||| |||||||||||||||  |||| |||||||||||||||||||||||| |||||||||
Sbjct: 76822 ctcagacgtgcgggcaccgcagcgctcagagctgggagccgagtcaccattgcggatggt 76881

Query: 37783 ggcgtcccaggcctacaacctgacctctgccctcatgcgcatcctcatgcgctcccgcgt 37842
              ||||||||||||||||||||||||||||||||||||||||||||||||| ||||||||||
Sbjct: 76882 ggcgtcccaggcctacaacctgacctctgccctcatgcgcatcctcacgcgctcccgcgt 76941

Query: 37843 gctcaacgaggagcccctgacgctggcgggcgaggagatcgtgcccagggcaagcgctc 37902
              |||||||||||||||||| |||||||||||||||||||||| ||||||||||||||||||
Sbjct: 76942 gctcaacgaggagcccgtgacgctggcgggcgaggagatcatgcccagggcaagcgctc 77001

Query: 37903 ggacccgcggagcctgctgtgctatggcggcgccccagggcctggctgccacttctccat 37962
              |||||||||||||||||||||||||||||||||||||||||||||||||||| |||||||
Sbjct: 77002 ggacccgcggagcctgctgtgctatggcggcgccccagggcctggctgccacctctccat 77061

Query: 37963 ccccgaggctttcagcgggcccctggccaacctcagtgacgtggtgcagctcatctttct 38022
              ||||  |||||||||||| ||||||  ||||||||||||||||||||||||||| ||||||
Sbjct: 77062 ccctaggctttcagcagggcccggccaacctcagtgacgtggtgcagctcgtctttct 77121

Query: 38023 ggtggactccaatcccttctctttggctatatcagcaactacaccgtctccaccaaggt 38082
              |||||||||||||||||||  ||||||||||||||||||||||||||||||||||||||
Sbjct: 77122 ggtggactccaatcccttctctttggctatatcagcaactacaccgtctccaccaaggt 77181

Query: 38083 ggcctcgatggcattccagacacaggccggcgcccagatccccatcgagcggctggcctc 38142
              |||||||||||| |||||||||||||||||||||||||||||||||||||||||||||||
Sbjct: 77182 ggcctcgatggcgttccagacacaggccggcgcccagatccccatcgagcggctggcctc 77241

Query: 38143 agagcgcgccatcaccgtgaaggtgcccaacaactcggactgggctgcccggggccaccg 38202
              ||||||||||||||||||||||||||||||||||||||||||||||||||||||||||||
Sbjct: 77242 agagcgcgccatcaccgtgaaggtgcccaacaactcggactgggctgcccggggccaccg 77301

Query: 38203 cagctccgccaactccgccaactccgttgtggtccagcccaggcctccgtcggtgctgt 38262
              ||||||         |||||||||||||||||||||||||||||||||||||||||||||
Sbjct: 77302 cagctc---------cgccaactccgttgtggtccagcccaggcctccgtcggtgctgt 77352

Query: 38263 ggtcaccctggacagcagcaaccctgcgggccggctgcatctgcagctcaactatacgct 38322
              |||||||||||||||||| |||| |||||  |||||||||||||||||| |||||| |||
Sbjct: 77353 ggtcaccctggacagcagcaaccctgtggccgtgctgcatctgcagctcaactatacgct 77412

Query: 38323 gctggacggtgcgtgcagcgggtgggcacacgcggcccctggccttgttcttgggggg 38382
              ||||||||||| | ||||||||||||||||||||||||||||||||||||||||||||||
Sbjct: 77413 gctggacggtgtgtgcagcgggtgggcacacgcggcccctggccttgttcttgggggg 77472
```

FIG. 2Q

Figure 2 con.

Exon 29 and 30—Homolog 1

```
Query: 41535 ttttgcgcttccggcgcctgctggtggctgagctgcagcgtggcttctttgacaagcaca 41594
              | |||||||||!!||||||||||||||||||| |||||||||||||||||||||||||||
Sbjct: 37269 tgttgcgcttccggcgcctgctggtggctg-gctgcagcgtggcttctttgacaagcaca 37327

Query: 41595 tctggctctccatatgggaccggccgcctcgtagccgtttcactcgcatccagagggcca 41654
              |||||||||||||||||||||||||||||||| ||| |||||||||||||||||||||||
Sbjct: 37328 tctggctctccatatgggaccggccgcctcggagctgtttcactcgcatccagagggcca 37387

Query: 41655 cctgctgcgttctcctcatctgcctcttcctgggcgccaacgccgtgtggtacggggctg 41714
              |||||||||||||||||||||| |||||||||||||||||||||||||||||||||||||
Sbjct: 37388 cctgctgcgttctcctcatctgtctcttcctgggcgccaacgccgtgtggtacggggctg 37447

Query: 41715 ttggcgactctgcctacaggtgggtgccgtaggggtcggggcagcctcttcctgcccagc 41774
              |||| |||||||||||||||||||||||||||||||||||||| |||| |||||||||||
Sbjct: 37448 ttggagactctgcctacaggtgggtgccgtaggggtcgggacagcctcttcctgcccagc 37507

Query: 41775 ccttcctgcccctcagcctcacctgtgtggcctcctctcctccacacagcacgggcatg 41834
              ||||||||||||||||||||||||||||||||||||||||||||||||||||||||| ||
Sbjct: 37508 ccttcctgcccctcagcctcacctgtgtggcctcctctcctccacacagcacgggcgtg 37567

Query: 41835 tgtccaggctgagcccgctgagcgtcgacacagtcgctgttggcctggtgtccagcgtgg 41894
              |||||||||||| ||||||||||||||||||||||||||||||||||||||||||||||
Sbjct: 37568 tgtccaggctgaacccgctgagcgtcgacacagtcgctgttggcctggtgtccagcgtgg 37627

Query: 41895 ttgtctatcccgtctacctggccatccttttctcttccggatgtcccggagcaaggtgg 41954
              ||||||||||||||||||||||||||||| ||||||||||||||||||||||||||||||
Sbjct: 37628 ttgtctatcccgtctacctggccatcctcttctcttccggatgtcccggagcaaggtgg 37687
                                                                                       AvrII or BlnI
Query: 41955 gctgggctggggaccgggagtactgggaatggagcctgggcctcggcaccatgcctag 42014
              |||||||||||||||||||||||||||||||||||||||||||||||||||||||| ||
Sbjct: 37688 gctgggctggggaccgggagtactgggaatggagcctgggcctcggcaccatgcccag 37747

Query: 42015 ggccgccactttccagtgctgcagccagagggaaaggcgtccaccaaaggctgctcggga 42074
              ||||||||||||||||||||||||||||||||||||||||||||||||||||||||||||
Sbjct: 37748 ggccgccactttccagtgctgcagccagagggaaaggcgtccaccaaaggctgctcggga 37807
```

FIG. 2R

Figure 2 con.

```
                    Exon 29 and 30-Homolog 2

Query: 41535  ttttgcgcttccggcgcctgctggtggctgagctgcagcgtggcttctttgacaagcaca  41594
              | |||||||.||||||||||||||||||||||||||||||||||||||||||||||||||
Sbjct: 80620  tgttgcgcttccggcgcctgctggtggctgagctgcagcgtggcttctttgacaagcaca  80679

Query: 41595  tctggctctccatatgggaccggccgcctcgtagccgtttcactcgcatccagagggcca  41654
              ||||||||||||||||||||||||| ||||||||| |||||||||||||||||||||||
Sbjct: 80680  tctggctctccatatgggaccggccacctcgtagctgtttcactcgcatccagagggcca  80739

Query: 41655  cctgctgcgttctcctcatctgcctcttcctgggcgccaacgccgtgtggtacggggctg  41714
              |||||||||||||| ||||||||||||||||||||||||||||||||||||||||||||
Sbjct: 80740  cctgctgcgttctcctcatctgcctcttcctgggcgccaacgccgtgtggtacggggctg  80799

Query: 41715  ttggcgactctgcctacaggtgggtgccgtaggggtcggggcagcctcttcctgcccagc  41774
              ||||  |||||||||||||||||||||||||||||||||  |||||||||||||||||
Sbjct: 80800  ttggtgactctgcctacaggtgggtgccgtaggggtcgggacagcctcttcctgcccagc  80859

Query: 41775  ccttcctgcccctcagcctcacctgtgtggcctcctctcctccacacagcacgggcatg  41834
              |||||||||||||||||||||| |||||||||||||||||||||||||||||||||||
Sbjct: 80860  ccttcctgcccctcagcctcacctgtgtggcctcctctcctccacacagcacgggcatg  80919

Query: 41835  tgtccaggctgagcccgctgagcgtcgacacagtcgctgttggcctggtgtccagcgtgg  41894
              ||||||||||||||||||||||||||||||||||||||||||||||||||||||||||||
Sbjct: 80920  tgtccaggctgagcccgctgagcgtcgacacagtcgctgttggcctggtgtccagcgtgg  80979

Query: 41895  ttgtctatcccgtctacctggccatcctttttctcttccggatgtcccggagcaaggtgg  41954
              |||||||||||||||||||||||||||     |||||||||||||||||||||||||||
Sbjct: 80980  ttgtctatcccgtctacctggccatcctctttctcttccggatgtcccggagcaaggtgg  81039

Query: 41955  gctggggctggggacccgggagtactgggaatggagcctggcctcggcaccatgcctag  42014
              |||||||||||||||||| |||||||||||||||||||||||||||||||||||||| |
Sbjct: 81040  gctggggctggggacccgggagtactgggaatggagcctggcctcggcaccatgcccag  81099

Query: 42015  ggccgccactttccagtgctgcagccagagggaaaggcgtccaccaaaggctgctcggga  42074
              |||||||||||||||||||||||||||||||||||||||||||||||||||||||||||
Sbjct: 81100  ggccgccactttccagtgctgcagccagagggaaaggcgtccaccaaaggctgctcggga  81159
```

FIG. 2S

| | Polymorph | Probable | Missense | Frame Shi | Indeterminate | |
|---|---|---|---|---|---|---|
| 1 | 13 | 8 | 1 | 0 | 0 | 22 |
| 2 | 13 | 8 | 1 | 0 | 0 | 22 |
| 3 | 14 | 6 | 0 | 0 | 0 | 20 |
| 4 | 14 | 6 | 0 | 0 | 0 | 20 |
| 5 | 1 | 1 | 1 | 0 | 0 | 3 |
| 6 | 1 | 2 | 0 | 0 | 0 | 3 |
| 7 | 4 | 0 | 0 | 1 | 0 | 5 |
| 8 | 0 | 0 | 2 | 0 | 0 | 2 |
| 9 | 13 | 4 | 0 | 0 | 1 | 18 |
| 10 | 4 | 0 | 1 | 1 | 0 | 6 |
| 11 | 16 | 5 | 0 | 0 | 0 | 21 |
| 12 | 0 | 1 | 0 | 0 | 0 | 1 |
| 13 | 13 | 9 | 2 | 1 | 0 | 25 |
| 14 | 1 | 0 | 1 | 1 | 0 | 3 |
| 15 | 1 | 1 | 1 | 0 | 0 | 3 |
| 16 | 2 | 1 | 0 | 0 | 0 | 3 |
| 17 | 13 | 12 | 2 | 1 | 0 | 28 |
| 18 | 16 | 6 | 0 | 0 | 0 | 22 |
| 19 | 4 | 3 | 0 | 0 | 0 | 7 |
| 20 | 0 | 0 | 0 | 0 | 0 | 0 |

| Gene | | Exon | Ampli-con | Temp | PC Ret Time | PC Height | NC Ret Time | NC Height |
|---|---|---|---|---|---|---|---|---|
| 1 | x | 1 | | | | | | |
| 1 | x | 2 | | 66 | 2.25-6.5 | 0.8-3.2 | 2-6.5 | 0.9-3.6 |
| 1 | x | 2 | | 67 | 0.7-5.8 | 0.8-3.2 | 0.7-5.8 | 1-4 |
| 1 | x | 3 | | 56 | 4.2-6.8 | 1-4 | 4-6.75 | 1.1-4.4 |
| 1 | x | 3 | | 57 | 3.5-6.5 | 0.7-2.8 | 4-6.5 | 1-4 |
| 1 | x | 4 | | 66 | 2-6.8 | 1-4 | 2-6.8 | 0.8-3.2 |
| 1 | x | 4 | | 67 | 1.5-6 | 0.5-2.0 | 1.5-6 | 1.1-4.4 |
| 1 | x | 5 | A | 66 | 2.6-4.6 | 1.3-5.4 | 2.7-4.7 | 1.3-5.2 |
| 1 | x | 5 | B | 67 | 2-6.5 | 0.4-7.0 | 3-6.5 | 0.5-4.6 |
| 1 | x | 5 | C | 67 | 3-6.5 | 1-4 | 3-6.5 | 1.2-4.8 |
| 1 | x | 5 | C | 68 | 1.7-5.8 | 0.7-2.8 | 2.5-5.8 | 1-4 |
| 1 | x | 6 | | 66 | 3.5-5.9 | 0.3-1.5 | 3.9-5.9 | 1.0-4.2 |
| 1 | x | 6 | | 67 | 2.5-5.4 | 0.5-2.0 | 3.4-5.4 | 1-4.2 |
| 1 | x | 6 | | 68 | 2.2-4.8 | 0.3-1.4 | 2.8-4.8 | 0.7-3.0 |
| 1 | x | 7 | | 66 | 2.7-6.25 | 0.5-2.0 | 3-6.25 | 0.6-2.4 |
| 1 | x | 7 | | 68 | 1.5-5 | 0.9-3.6 | 1.5-5 | 0.6-2.4 |
| 1 | x | 8 | | 68 | 1.5-5 | 1.3-5.2 | 1.7-5 | 1-4 |
| 1 | x | 9 | | 67 | 3.5-6.5 | 0.5-2.0 | 3.5-6.8 | 0.25-2.0 |
| 1 | x | 10 | | 65 | 2.5-6.5 | 0.9-3.6 | 3-6.5 | 1.9-7.6 |
| 1 | x | 10 | | 67 | 1.5-5 | 1.5-6 | 1.5-5 | 2-8 |
| 1 | x | 11 | A | 67 | 1.5-6.5 | 0.7-2.8 | 2-6.5 | 2-8 |
| 1 | x | 11 | A | 68 | 1.5-5.5 | 0.8-3.2 | 2-5.8 | 1.3-5.2 |
| 1 | x | 11 | B | 66 | 3-6.8 | 1-4 | 3-6.8 | 1-4 |
| 1 | x | 11 | B | 67 | 2-6 | 1.5-6 | 2-6 | 1.2-4.8 |
| 1 | x | 11 | C | 66 | 4.2-6.2 | 1.5-6 | 4.2-6.2 | 2.5-10.2 |
| 1 | x | 11 | C | 67 | 3.6-5.6 | 1.7-7 | 3.6-5.6 | 2.3-9.2 |
| 1 | x | 11 | C | 68 | 2.9-4.9 | 1.1-4.6 | 2.8-4.8 | 1.7-6.8 |
| 1 | x | 12 | | 63 | 4.4-6.6 | 0.6-2.4 | 4.7-6.7 | 1-4 |
| 1 | x | 12 | | 65 | 2.8-4.8 | 0.4-1.6 | 2.6-5.4 | 0.4-1.8 |
| 1 | x | 13 | | | | | | |
| 1 | x | 14 | | 66 | 1.5-5.5 | 0.6-2.4 | 0.7-5.5 | 0.6-2.4 |
| 1 | x | 15 | A | 67 | 2.5-6.5 | 0.8-3.2 | 2.5-6.5 | 1-4 |
| 1 | x | 15 | A | 68 | 1.5-5.75 | 1-4 | 1.5-5.75 | 1.2-4.8 |
| 1 | x | 15 | B | 67 | 2-5.75 | 0.5-2.0 | 2.75-5.75 | 1-4 |
| 1 | x | 15 | B | 68 | 1.5-5.25 | 0.6-2.4 | 2.5-5.5 | 0.9-3.6 |
| 1 | x | 15 | C | 68 | 2-6.5 | 0.4-1.6 | 2-6.5 | 0.8-3.2 |
| 1 | x | 15 | C | 69 | 1.5-6 | 0.5-2.0 | 1.5-6 | 0.75-3.0 |
| 1 | x | 15 | D | 67 | 3.75-7.25 | 1.5-6 | 3.75 | 7.25 |
| 1 | x | 15 | D | 68 | 3-6.5 | 1-4 | 3-6.5 | 1.2-4.8 |
| 1 | x | 15 | E | 65 | 3-6.5 | 1-4 | 3-6.5 | 1.5-6 |
| 1 | x | 15 | E | 66 | 2-6 | 0.8-3.2 | 2-6 | 1.3-5.2 |
| 1 | x | 15 | F | 65 | 4-7 | 1.4-5.6 | 3.75-7 | 1.2-4.8 |
| 1 | x | 15 | F | 66 | 3-6.5 | 1-4 | 3-6.5 | 1-4 |
| 1 | x | 15 | F | 67 | 1.5-5.75 | 1.3-5.2 | 1.5-5.75 | 1-4 |
| 1 | x | 15 | G | 66 | 3-6 | 0.8-3.2 | 3-6 | 1.1-4.4 |
| 1 | x | 15 | G | 68 | 1.5-4.5 | 1-4 | 1.5-4.5 | 1.5-6 |

FIG. 11A

Figure 11 con

| 1 | x | 15 | H | 65 | 2-6.5 | 1.5-6 | 2-6.5 | 1.5-6 |
|---|---|---|---|---|---|---|---|---|
| 1 | x | 15 | H | 66 | 1.5-5.5 | 1-4 | 1.5-5.75 | 1-4 |
| 1 | x | 15 | I | 66 | 3-7 | 2-8 | 3-7 | 1.8-7.2 |
| 1 | x | 15 | I | 67 | 2.5-6.5 | 1.5-6 | 2.5-6.5 | 1.5-6 |
| 1 | x | 15 | J | 64 | 4-7.5 | 2.2-8.8 | 4-7.5 | 2-8 |
| 1 | x | 15 | J | 65 | 4-7 | 2-8 | 4-7 | 1.5-6 |
| 1 | x | 15 | J | 66 | 3-6.5 | 1.5-6 | 2-6.5 | 1.1-4.4 |
| 1 | x | 15 | K | 65 | 3.5-6.5 | 1-4 | 3.75-6.5 | 0.8-3.2 |
| 1 | x | 15 | K | 66 | 3-6.5 | 0.7-2.8 | 3.5-6.5 | 0.6-3.2 |
| 1 | x | 15 | K | 67 | 2-6 | 0.6-2.4 | 2-5.5 | 0.5-2.0 |
| 1 | x | 15 | L | | | | | |
| 1 | x | 15 | M | 66 | 4.5-7 | 1-4 | 4.5-7 | 1.5-6 |
| 1 | x | 15 | M | 67 | 4-6.75 | 1-4 | 4-6.75 | 1.3-5.2 |
| 1 | x | 15 | N | | | | | |
| 1 | x | 16 | | 67 | 1.5-5.5 | 2.25-9 | 2.0-5.5 | 3-13 |
| 1 | x | 17 | | 65 | 2.5-6 | 1.5-6 | 2.5-6 | 1.75-7 |
| 1 | x | 17 | | 66 | 1.5-5 | 1.25-5 | 1.5-5 | 1.75-7 |
| 1 | x | 18 | | 66 | 3-6.5 | 2-8 | 3-6.5 | 3.25-13 |
| 1 | x | 18 | | 67 | 4-6.4 | 3.8-16 | 4.25-6.25 | 6.2-24.8 |
| 1 | x | 18 | | 68 | 1.5-5 | 2.5-10 | 1.5-5 | 2.75-11 |
| 1 | x | 19 | | 67 | 3-6.5 | 1.5-6 | 3-6.5 | 3-12 |
| 1 | x | 19 | | 68 | 3.0-6.5 | 1.5-6 | 3-6.5 | 3-12 |
| 1 | x | 20 | | 65 | 3.5-6.5 | 2-8 | 3.5-6.5 | 2.25-9 |
| 1 | x | 20 | | 66 | 2.5-6 | 1.25-5 | 2.5-6 | 1.75-7 |
| 1 | x | 20 | | 67 | 1.5-5.5 | 1.25-5 | 1.5-5.5 | 1.75-7 |
| 1 | x | 21 | | 65 | 3-7 | 1.5-6 | 3-7 | 4-16 |
| 1 | x | 21 | | 67 | 1.5-5.5 | 2.25-9 | 1.5-5.5 | 4.5-18 |
| 1 | x | 22 | | 66 | 4-7.5 | 2-8 | 4-7 | 2-8 |
| 1 | x | 22 | | 67 | 3-7.25 | 1.5-6 | 3.5-6.5 | 1.5-6 |
| 1 | x | 23 | A | 65 | 3.5-6.5 | 0.75-3.0 | 3.5-6.5 | 1.5-6.0 |
| 1 | x | 23 | A | 66 | 2.5-6.0 | 0.5-2.0 | 2.5-6.0 | 1.25-5.0 |
| 1 | x | 23 | A | 68 | 1.5-4.5 | 2.5-10.0 | 1.5-4.5 | 2.5-10.0 |
| 1 | x | 23 | B | 63 | 3.5-7.25 | 1.5-6 | 3.5-7.25 | 1.5-6 |
| 1 | x | 23 | B | 66 | 1.5-6.5 | 0.9-3.5 | 1.5-6.5 | 1-4 |
| 1 | x | 23 | B | 67 | 1.25-5.5 | 1-4 | 1.25-5.5 | 1-4 |
| 1 | x | 23 | C | 61 | 3-6.25 | 1.5-6 | 3-6.25 | 3.25-13 |
| 1 | x | 23 | C | 66 | 1.5-5 | 2.25-9 | 2.5-5 | 4.25-17 |
| 1 | x | 23 | C | 67 | 1.5-5 | 2.75-11 | 2-5 | 5.5-22 |
| 1 | x | 24 | | 65 | 2.5-6.0 | 0.5-2.0 | 2.5-6.0 | 0.6-3.0 |
| 1 | x | 25 | | 65 | 2-6 | 0.7-4 | 2-6 | 0.7-4 |
| 1 | x | 25 | | 67 | 1.5-4.5 | 2-8 | 1.5-4.5 | 2-8 |
| 1 | x | 26 | | 64 | 2.5-6 | 0.9-3.6 | 2.5-6 | 0.9-3.6 |
| 1 | x | 26 | | 66 | 1.5-4.5 | 1.75-7 | 1.5-4.5 | 1.75-7 |
| 1 | x | 27 | | 65 | 3.5-6.7 | 1.5-6 | 3.5-6.7 | 1.5-6 |
| 1 | x | 27 | | 66 | 2.5-6 | 2-8 | 2-5.7 | 1.25-5 |
| 1 | x | 28 | | 66 | 1.5-5.75 | 1-4 | 1.5-5.75 | 1-4 |
| 1 | x | 29 | | 65 | 1.5-6.25 | 1.5-6 | 1.5-6.25 | 3-12 |
| 1 | x | 29 | | 66 | 1.5-5.25 | 1.5-6 | 1.5-5.25 | 2.5-8.5 |
| 1 | x | 30 | | | | | | |

FIG. 11B

Figure 11 con

| | | | | | | | |
|---|---|---|---|---|---|---|---|
| 1 | x | 31 | | 66 | 3-6.5 | 2.5-10 | 3-6.5 | 1-4 |
| 1 | x | 31 | | 68 | 1.5-5.5 | 1.5-6 | 1.5-5.5 | 0.5-2 |
| 1 | x | 32 | | 62 | 2-6.5 | 1.25-5.0 | 2-6.5 | 3.5-14 |
| 1 | x | 33 | | 64 | 4.2-6.2 | 1.4-6 | 4.3-6.3 | 1.5-6 |
| 1 | x | 33 | | 67 | 2.5-4.7 | 0.8-3.5 | 2.7-4.7 | 1.2-4.8 |
| 1 | x | 34 | | | | | | |
| 1 | x | 34 | | | | | | |
| 1 | x | 35 | | 64 | 4.3-6.5 | 1.4-5.5 | 4.5-6.5 | 2.4-9.5 |
| 1 | x | 35 | | 66 | 2.6-5.1 | 1.1-4.4 | 3.1-5.1 | 1.75-7 |
| 1 | x | 36 | | 66 | 3.3-5.7 | 0.5-2.0 | 3.6-5.6 | 1-4 |
| 1 | x | 36 | | 67 | 2.7-5.1 | 0.6-2.5 | 3.1-5.1 | 1.1-4.4 |
| 1 | x | 37 | | 64 | 3-5.75 | 0.65-2.6 | 3.7-5.7 | 1.1-4.5 |
| 1 | x | 37 | | 66 | 2-4.75 | 0.9-3.6 | 2.7-4.7 | 1-4 |
| 1 | x | 38 | | 65 | 3.5-6.5 | 1.1-4.5 | 4.3-6.3 | 1.6-6.5 |
| 1 | x | 38 | | 66 | 3-5.75 | 0.7-3.0 | 3.5-5.5 | 1-4 |
| 1 | x | 39 | | 66 | 1.5-4.5 | 1.1-4.6 | 2-4.6 | 1.25-3.0 |
| 1 | x | 39 | | 67 | 1.5-4 | 1.25-3.0 | 1.5-4 | 0.7-3.0 |
| 1 | x | 40 | | 66 | 1.5-5.5 | 0.6-2.5 | 3.25-5.25 | 0.7-3.0 |
| 1 | x | 41 | | 67 | 2.5-5.75 | 0.9-3.6 | 3.75-5.75 | 1.1-4.4 |
| 1 | x | 42 | | 70 | 2.75-5.75 | 0.5-2.0 | 3-5.8 | 0.3-1.2 |
| 1 | x | 42 | | 71 | 2.5-4.5 | 0.7-3.0 | 2.6-4.6 | 0.6-2.4 |
| 1 | x | 43 | | 67 | 4-6.75 | 0.4-1.6 | 4-6.75 | 0.6-2.4 |
| 1 | x | 43 | | 68 | 3.75-6.5 | 0.4-1.6 | 3.75-6.5 | 0.6-2.4 |
| 1 | x | 43 | | 70 | 2.25-5.25 | 0.25-2 | 2.25-5.25 | 0.6-2.4 |
| 1 | x | 44 | | 66 | 3.25-5.75 | 0.5-2.0 | 3.7-5.7 | 0.8-3.2 |
| 1 | x | 45 | | 65 | 3.5-6.25 | 0.4-1.6 | 4.1-6.1 | 0.9-3.6 |
| 1 | x | 45 | | 66 | 2.5-5.5 | 0.4-1.6 | 3.5-5.5 | 0.8-3.2 |
| 1 | x | 46 | A | 66 | 4.25-6.5 | 0.4-1.6 | 4.4-6.4 | 0.8-3.2 |
| 1 | x | 46 | A | 67 | 3.25-5.25 | 0.3-1.2 | 3.5-5.5 | 0.5-2.0 |
| 1 | x | 46 | B | 65 | 4-6.75 | 1-4 | 4-6.75 | 1.2-4.8 |
| 1 | x | 46 | B | 68 | 1.75-4.75 | 1.3-5.2 | 1.75-4.75 | 1.5-6 |
| 2 | x | 1 | A | 70 | 3-6 | 1.5-6 | 3-6 | 1-4 |
| 2 | x | 1 | A | 71 | 2-5.75 | 0.6-2.4 | 2-5.75 | 0.9-3.6 |
| 2 | x | 1 | A | 72 | 1.5-5.25 | 0.5-3.0 | 1.5-5.25 | 0.5-2 |
| 2 | x | 1 | B | 67 | 2.5-6.5 | 0.6-2.5 | 2.5-6.5 | 0.6-2.5 |
| 2 | x | 1 | B | 70 | 1.5-4.5 | 0.7-3 | 1.5-4.5 | 1-4 |
| 2 | x | 1 | B | 71 | 1-4 | 0.5-2 | 1-4 | 0.7-3 |
| 2 | x | 1 | C | 69 | 2.5-6.5 | 1.25-5 | 2.5-6.5 | 1-4 |
| 2 | x | 1 | C | 70 | 1.5-6.5 | 0.8-2.5 | 1.5-6.5 | 0.8-3.5 |
| 2 | x | 1 | C | 71 | 1.5-5.75 | 0.8-3.5 | 1.5-5.75 | 0.8-3.5 |
| 2 | x | 2 | | 58 | 2.5-4.5 | 1.2-5.0 | 3.2-5.2 | 1.4-5.6 |
| 2 | x | 3 | | 58 | 4.7-6.9 | 2.9-11.6 | 4.9-6.9 | 3.5-14 |
| 2 | x | 3 | | 59 | 4.4-6.9 | 2.1-8.4 | 4.7-6.7 | 2.0-8.0 |
| 2 | x | 3 | | 60 | 3.5-6.1 | 1.3-5.2 | 3.9-5.9 | 1.6-6.4 |
| 2 | x | 4 | | 60 | 3.4-6.1 | 1.7-7.0 | 4.1-6.1 | 0.9-3.8 |
| 2 | x | 5 | | 58 | 4.5-6.5 | 2.3-9.2 | 4.6-6.6 | 2.3-9.4 |
| 2 | x | 5 | | 59 | 3.9-6.2 | 1.6-6.6 | 4.3-6.3 | 1.7-6.8 |
| 2 | x | 6 | | 57 | 1.5-6.25 | 1.5-6 | 1.5-6.25 | 2-8 |
| 2 | x | 7 | | 53 | 3.4-6.6 | 1.2-5.0 | 3.3-6.6 | 1.0-4.0 |

FIG. 11C

Figure 11 con

| 2 | x | 7 | | 56 | 2.5-4.5 | 2.5-10.2 | 2.6-5.2 | 1.1-4.4 |
|---|---|---|---|---|---|---|---|---|
| 2 | x | 8 | | 54 | 3.7-6.2 | 1.5-6 | 3.7-6.2 | 5.5-22 |
| 2 | x | 8 | | 58 | 3-6 | 0.8-3.2 | 2.5-6 | 4-16 |
| 2 | x | 9 | | 54 | 3-6.5 | 0.5-2.0 | 3.5-6.5 | 1-4 |
| 2 | x | 9 | | 57 | 1.5-4.75 | 0.5-2 | 1.5-4.75 | 0.5-2.0 |
| 2 | x | 10 | | | | | | |
| 2 | x | 10 | | | | | | |
| 2 | x | 11 | | 58 | 2.5-6.75 | 2.3-9.2 | 2.5-6.75 | 2-8 |
| 2 | x | 11 | | 59 | 1.75-6.5 | 1.5-6 | 1.5-6.5 | 1-4 |
| 2 | x | 12 | | 60 | 1.5-5.75 | 0.7-2.8 | 1.5-5.5 | 0.8-3.2 |
| 2 | x | 13 | | 60 | 3-6.2 | 1.2-4.8 | 4.2-6.2 | 1.2-5 |
| 2 | x | 13 | | 61 | 2.5-5.5 | 1.2-5 | 2.5-5.5 | 0.9-4.0 |
| 2 | x | 14 | | 63 | 2.5-4.5 | 1.1-4.4 | 3.2-5.2 | 2.5-10.0 |
| 2 | x | 15 | | 60 | 2-6.5 | 0.9-3.6 | 2-6.5 | 1-4 |
| 2 | x | 15 | | 61 | 1.5-6 | 1.3-5.2 | 1.5-6 | 1.5-6 |

Figure 14. Identified ADPKD associated alterations. Novel alterations are indicated by bold text.

PKD Accessions with UPD variants.

```
                nt
           Position    Codon #      Alteration Type
A.
    Variant  PKD1X1 - 1:     UAA    Transversion C > A
              318        36         proline ---> histidine Variant  PKD1X36 - 1:    KP     Transition C > T
             10976      3589        none Variant  PKD1X40 - 1:    UPD    19bp insertion
             11606      3799        frameshift Variant  PKD1X43 - 1:    KP     Transition C > T
             12124      3971        none Variant  PKD1X44 - 1:    KP     Sequence alteration detected: 1bp deletion
             IVS 44+19delG Variant  PKD2X15 - 1:    KP     Transition G > A
              486        140        none B
    Variant  PKD1X15A - 1:   UAA    Transition C > T
             3591       1127        proline ---> leucine Variant  PKD1X16 - 1:    KP     Transition C > T
             7138       2309        none Variant  PKD1X18 - 1:    UPD    1bp insertion of C
             7518       2436        Frame Shift Variant  PKD1X23A - 1:   KP     Transition G > A
```

FIG. 14A

```
              8555     2782      valine --> methionine
     Variant  PKD1X5C - 1:       KP   Transition T > C   Homozygous
              1330     373       none
     Variant  PKD2X1A - 1:       KP   Transversion G > C
              149      28        arginine ---> proline

C.

Variant  PKD1X10 - 1:       UP   Transition A > G
              IVS9-4

Variant  PKD1X11C - 1:      KP   Transition G > A
              2911     900       none Variant  PKD1X11C - 2:      KP   Transition C > T
              2941     910       none Variant  PKD1X15B - 1:      UAA  Transition C > T
              3713     1168      proline ---> serine Variant  PKD1X15G - 1:      KP   Transversion A > C
              4876     1555      none Variant  PKD1X15J - 1:      UP   Transition C > T
              5383     1724      none Variant  PKD1X15L - 1:      UP   Transition G > A
              5974     1921      none Variant  PKD1X15L - 2:      UAA  Transition G > A
              6218     2003      alanine ---> threonine Variant  PKD1X17 - 1:       KP   Transition T > C
              7376     2389      none Variant  PKD1X18 - 1:       KP   Transition C > T
              7652     2481      none Variant  PKD1X25 - 1:       KP   Transition A > G
```

FIG. 14B

```
              IVS24-17
Variant  PKD1X25 - 2:     KP    Transversion G > C
         9406      3065         none
Variant  PKD1X25 - 3:     KP    Transition T > C
         9407      3066         phenylalanine ---> leucine
Variant  PKD1X26 - 1:     KP    Transition T > C
         9541      3110         none
Variant  PKD1X28 - 1:     UP    Transition T > C
              IVS27-13
Variant  PKD1X30 - 1:     UP    Transition A > G
              IVS30+54
Variant  PKD1X35 - 1:     KP    Transition C > T
         10743     3511         alanine ---> valine
Variant  PKD1X44 - 1:     KP    Transition A > G
         12341     4044         isoleucine ---> valine
Variant  PKD1X45 - 1:     KP    Transition C > T
         12384     4058         alanine ---> valine
Variant  PKD1X45 - 2:     KP    Transition A > G
         12484     4091         none
Variant  PKD1X45 - 3:     KP    Transition C > T
         12617     4136         none
Variant  PKD1X46A - 1:    UP    Transition T > C
         12838     4209         none
Variant  PKD1X6 - 1:      UPD   1bp insertion of G
         1502      431          Frame Shift
Variant  PKD1X9 - 1:      UP    7 bp deletion
              IVS9+28del7
              HOMOZYGOUS
```

FIG. 14C

```
Variant  PKD2X1A - 1:     KP    Transversion G > C
         149       28     arginine ---> proline
```

D.
```
Variant  PKD1X15B - 1:    UAA   Transition C > T
         3713      1168   proline ---> serine
Variant  PKD1X6 - 1:      UPD   1bp insertion of G
         1502      431    Frame Shift
Variant  PKD2X1A - 1:     KP    Transversion G > C
         149       28     arginine ---> proline
```

E.
```
Variant  PKD1X10 - 1:     UP    Transition A > G
         IVS9-4
Variant  PKD1X11C - 1:    KP    Transition G > A
         2911      900    none
Variant  PKD1X11C - 2:    KP    Transition C > T
         2941      910    none
Variant  PKD1X13 - 1:     UP    Transition C > T
         IVS12-15
Variant  PKD1X15A - 1:    UAA   Transversion C > G
         3527      1106   leucine ---> valine
Variant  PKD1X15B - 1:    UP    Transversion C > G
         3724      1171   none
Variant  PKD1X15G - 1:    KP    Transversion A > C
         4876      1555   none
Variant  PKD1X15J - 1:    UP    Transition C > T
         5383      1724   none
```

FIG. 14D

```
Variant PKD1X15L - 1:    UP   Transition G > A
        5974   1921      none
Variant PKD1X17 - 1:     KP   Transition T > C
        7376   2389      none
Variant PKD1X18 - 1:     KP   Transition C > T
        7652   2481      none
Variant PKD1X20 - 1:     UAA  Transition C > T
        8024   2605      proline ---> serine
Variant PKD1X23A - 1:    UP   Transition G > A
        8575   2788      none
Variant PKD1X25 - 1:     KP   Transition A > G
        IVS24-17
Variant PKD1X25 - 2:     KP   Transversion G > C
        9406   3065      none
Variant PKD1X25 - 3:     KP   Transition T > C
        9407   3066      phenylalanine ---> leucine
Variant PKD1X25 - 4:     UPD  2bp deletion of AG
        9294 & 92953028  Frame Shift
Variant PKD1X26 - 1:     UP   Transition C > T
        9481   3090      none
Variant PKD1X26 - 2:     KP   Transition T > C
        9541   3110      none
Variant PKD1X28 - 1:     UP   Transition T > C
        IVS27-13
Variant PKD1X30 - 1:     UP   Transition A > G
        IVS30+54
Variant PKD1X35 - 1:     KP   Transition C > T
        10743  3511      alanine ---> valine
```

FIG. 14E

```
Variant  PKD1X44 - 1:     KP    Transition A > G
    12341      4044       isoleucine ---> valine
Variant  PKD1X45 - 1:     KP    Transition C > T
    12384      4058       alanine ---> valine
Variant  PKD1X45 - 2:     KP    Transition A > G
    12484      4091       none
Variant  PKD1X45 - 3:     KP    Transition C > T
    12617      4136       none
Variant  PKD1X46A - 1:    UP    Transition T > C
    12836      4209       none
Variant  PKD1X9 - 1:      UP    deletion of TGGTGGG
    IVS9+28del7
    Possible homozygous
Variant  PKD2X1A - 1:     KP    Transversion G > C
    149        28         arginine ---> proline
```

F.

```
Variant  PKD1X1 - 1:      UAA   Transversion C > A
    318        36         proline ---> histidine
Variant  PKD1X5C - 1:     KP    Transition C > T
    1234       341        none
Variant  PKD2X5 - 1:      UPD   Transversion T > G
    1224       386        tyrosine ---> stop codon (AMB)
```

G.

```
Variant  PKD1X15G - 1:    KP    Transition G > A
    4885       1558       none
Variant  PKD1X15H - 1:    KP    Transition G > A
```

FIG. 14F

```
            4885        1558        none
    Variant PKD1X19 - 1:    UPD    Transition C > T
            7877        2556        glutamine --> stop codon
    Variant PKD1X5C - 1:    KP     Transition C > T
            1234        341         none
```

H.

```
    Variant PKD1X2 - 1:     UPD    2bp deletion of TC
            482-483     91          Frame Shift
    Variant PKD1X22 - 1:    UP     Transversion G > C
            IVS21-44
    Variant PKD1X41 - 1:    UP     3bp insertion of GGG
            IVS41+5ins3
    Variant PKD1X6 - 1:     UP     Transition C > T
            IVS6+26
    Variant PKD2X1A - 1:    KP     Transversion G > C
            149         28          arginine ---> proline
    Variant PKD2X1B - 1:    KP     Transition G > A
            486         140         none
```

I.

```
    Variant PKD1X15N - 1:   UAA    Transition C > T
            6809        2200        arginine --> cysteine
    Variant PKD1X17 - 1:    KP     Transition T > C
            7376        2389        none
    Variant PKD1X3 - 1:     UPD    5bp deletion of TTTAA
            559-563     116-118     Frame Shift
            STOP CODON CREATED AT CODON 117
```

FIG. 14G

```
Variant  PKD1X5C - 1:     KP    Transition T > C
       1330      373         none
Variant  PKD2X8 - 1:      UAA   Transition G > A
       1815      583         methionine ---> isoleucine
```

J.

```
Variant  PKD1X15F - 1:    UP    Transition C > T
       4706      1499        none
Variant  PKD1X23A - 1:    UPD   Transversion G > T
       8639      2810        glutamic acid --> stop codon
Variant  PKD1X23A - 2:    KP    Transition G > A
       8651      2814        glycine --> arginine
Variant  PKD1X23A - 3:    UAA   Transition T > C
       8658      2816        leucine --> proline
Variant  PKD1X23A - 4:    UP    Transition C > T
       8662      2817        none
Variant  PKD1X23B - 1:    UPD   Transversion G > T
       8639      2810        glutamic acid --> stop codon
Variant  PKD1X23B - 2:    KP    Transition G > A
       8651      2814        glycine --> arginine
Variant  PKD1X23B - 3:    UAA   Transition T > C
       8658      2816        leucine --> proline
Variant  PKD1X23B - 4:    UP    Transition C > T
       8662      2817        none
Variant  PKD1X23C - 1:    UAA   Transition G > A
       8900      2897        valine --> isoleucine
Variant  PKD1X40 - 1:     UP    Transition C > T
       11554     3781        none
```

FIG. 14H

```
Variant  PKD1X41 - 1:    UP   3bp insertion of GGG
    IVS41+5ins3
Variant  PKD1X45 - 1:    UAA  Transition G > A
    12644      4145      valine ---> isoleucine
```

K.

```
Variant  PKD1X10 - 1:    UPD  Transition C > T
    2300       697       glutamine -> stop codon (AMB)
Variant  PKD1X15B - 1:   UAA  Transition C > T
    3713       1168      proline --> serine
Variant  PKD1X44 - 1:    KP   Transition A > G
    12341      4044      isoleucine ---> valine
Variant  PKD1X45 - 1:    KP   Transition C > T
    12384      4058      alanine ---> valine
Variant  PKD1X45 - 2:    KP   Transition A > G
    12484      4091      none
Variant  PKD1X45 - 3:    KP   Transition C > T
    12617      4136      none
Variant  PKD1X46A - 1:   UP   Transition T > C
    12838      4209      none
Variant  PKD1X46B - 1:   UAA  Transition C > T
    13034      4275      arginine ---> tryptophan
Variant  PKD1X5C - 1:    KP   Transition T > C
    1330       373       none
Variant  PKD2X1A - 1:    KP   Transversion G > C
    149        28        arginine ---> proline
```

Variant PKD1X15J - 1:     UPD    1 bp deletion T
     5352     1714         Frame Shift
Variant PKD1X5C - 1:      KP     Transition T > C
     1330     373          none
Variant PKD2X1A - 1        KP     Transversion G > C
     149      28           arginine ---> proline

M.

Variant PKD1X13 - 1:      UP     Transition A > G
     3322     1037         none
Variant PKD1X40 - 1:      UPD    1bp insertion of T
     11558    3783         Frame Shift
Variant PKD2X1A - 1:      KP     Transversion G > C
     149      28           arginine ---> proline

N.

Variant PKD1X29 - 1:      UP     Transition C > T
     10006    3265         none
Variant PKD1X31 - 1:      UPD    1bp deletion of C
     10287    3359         Frame Shift
Variant PKD1X43 - 1:      UP     Transversion C > A
     IVS43+42
Variant PKD1X5C - 1:      KP     Transition T > C
     1330     373          none
Variant PKD2X1A - 1:      KP     Transversion G > C
     149      28           arginine --> proline
Variant PKD2X1B - 1:      KP     Transition G > A
     486      140          none

```
Variant  PKD1X11B - 1:    UP    Transversion A > C
         2905      898          none
Variant  PKD1X11C - 1:    UP    Transversion A > C
         2905      898          none
Variant  PKD1X16 - 1:     KP    Transition C > T
         7138      2309         none
Variant  PKD1X23A - 1:    KP    Transition C > T
         8650      2813         none
Variant  PKD1X23B - 1:    KP    Transition C > T
         8650      2813         none
Variant  PKD1X5C - 1:     KP    Transition T > C
         1330      373          none
Variant  PKD2X1A - 1:     KP    Transversion G > C    Homozygous
         149       28           arginine --> proline
Variant  PKD2X5 - 1:      UPD   Transition G > A
         1308      414          tryptophan --> OPA(stop codon)
```

P.

```
Variant  PKD1X11A - 1:    UAA   Transition A > G
         2427      739          glutamine ---> arginine
Variant  PKD1X5C - 1:     KP    Transition T > C    Homozygous
         1330      373          none
Variant  PKD2X1A - 1:     UPD   52 bp insertion
         139-190   25-42        Frame Shift
Variant  PKD2X1B - 1:     KP    Transition G > A
         486       140          none
```

```
Variant  PKD1X11A - 1:    UAA   Transition A > G
     2427      739        glutamine ---> arginine
Variant  PKD1X19 - 1:     UPD   Transition C > T
     7877     2556        glutamine ---> stop codon(AMB)
Variant  PKD1X5C - 1:     KP    Transition C > T
     1234      341        none
Variant  PKD1X5C - 2:     KP    Transition T > C
     1330      373        none
```

R.

```
Variant  PKD1X15F - 1:
  Variant  PKD1X23A - 1:   UPD   Transversion G > T
       8639     2810       glutamic acid ---> AMB (stop codon)
  Variant  PKD1X23A - 2:   KP    Transition G > A
       8651     2814       glycine ---> arginine
  Variant  PKD1X23A - 3:   UAA   Transition T > C
       8658     2816       leucine ---> proline
  Variant  PKD1X23A - 4:   UP    Transition C > T
       8662     2817       none
  Variant  PKD1X23B - 1:   UPD   Transversion G > T
       8639     2810       glutamic acid ---> AMB (stop codon)
  Variant  PKD1X23B - 2:   KP    Transition G > A
       8651     2814       glycine ---> arginine
  Variant  PKD1X23B - 3:   UAA   Transition T > C
       8658     2816       leucine ---> proline
  Variant  PKD1X23B - 4:   UP    Transition C > T
```

FIG. 14L

```
                8662        2817        none
    Variant   PKD1X23C - 1:     UAA    Transition G > A
                8900        2897        valine ---> isoleucine
    Variant   PKD1X40 - 1:      UP     Transition C > T
                11554       3781        none
    Variant   PKD1X41 - 1:      UP     3bp insertion (GGG)
                IVS41+6ins3
    Variant   PKD1X45 - 1:      UAA    Transition G > A
                12644       4145        valine --> isoleucine s.
    Variant   PKD1X10 - 1:      UP     Transition A > G
                IVS9-4
    Variant   PKD1X11B - 1:     KP     Transition G > A
                2911        900         none
    Variant   PKD1X11B - 2:     KP     Transition C > T
                2941        910         none
    Variant   PKD1X11C - 1:     KP     Transition G > A
                2911        900         none
    Variant   PKD1X11C - 2:     KP     Transition C > T
                2941        910         none
    Variant   PKD1X15G - 1:     KP     Transversion A > C
                4876        1555        none
    Variant   PKD1X15J - 1:     UP     Transition C > T
                5383        1724        none
    Variant   PKD1X17 - 1:      KP     Transition T > C
                7376        2389        none
    Variant   PKD1X18 - 1:      KP     Transition C > T
```

FIG. 14M

```
         7652       2481      none
   Variant  PKD1X25 - 1:     KP    Transition  A > G
         IVS24-17
   Variant  PKD1X25 - 2:     KP    Transversion  G > C
         9406       3065      none
   Variant  PKD1X25 - 3:     KP    Transition  T > C
         9407       3066      phenylalanine --> leucine
   Variant  PKD1X26 - 1:     KP    Transition  T > C
         9541       3110      none
   Variant  PKD1X28 - 1:     UP    Transition  T > C
         IVS27-13
   Variant  PKD1X35 - 1:     KP    Transition  C > T
         10743      3511      alanine --> valine
   Variant  PKD1X36 - 1:     UPD   13bp insertion
         10884      3558      Frame Shift
   Variant  PKD1X42 - 1:     UP    Transversion  C > A   Homozygous
         IVS42+33
   Variant  PKD1X44 - 1:     KP    Transition  A > G
         12341      4044      isoleucine --> valine
   Variant  PKD1X45 - 1:     KP    Transition  C > T
         12384      4058      alanine --> valine
   Variant  PKD1X45 - 2:     KP    Transition  A > G
         12484      4091      none
   Variant  PKD1X45 - 3:     KP    Transition  C > T
         12617      4136      none
   Variant  PKD1X46A - 1:    UP    Transition  T > C
         12838      4209      none
   Variant  PKD1X46B - 1:    UP    Transition  G > A
```

FIG. 14N

```
                    13135       3'UTR

Variant  PKD1X5A - 1:      UP    Transition C > T
                    799         196       none Variant  PKD1X9 - 1:       UP    7bp deletion (TGGTGGG)
                    IVS9+28del7

Variant  PKD2X1B - 1:      KP    Transition G > A
                    486         140       none
```

T.

```
        Variant  PKD1X10 - 1:      UPD   Transition A > G
                    IVS9-2

Variant  PKD1X13 - 1:      UP    Transition A > G
                    3322        1037      none Variant  PKD1X17 - 1:      UAA   Transition C > T
                    7358        2383      arginine ---> cysteine Variant  PKD1X42 - 1:      UP    Transversion C > A
                    IVS42+33

Variant  PKD2X1B - 1:      KP    Transition G > A
                    486         140       none
```

U.

```
        Variant  PKD1X10 - 1:      UP    Transition A > G
                    IVS9-4

Variant  PKD1X11B - 1:     KP    Transition G > A
                    2911        900       none Variant  PKD1X11B - 2:     KP    Transition C > T
                    2941        910       none Variant  PKD1X11C - 1:     KP    Transition G > A
```

FIG. 14O

```
        2911      900           none
    Variant  PKD1X11C - 2:    KP   Transition C > T
        2941      910           none
    Variant  PKD1X13 - 1:     UP   Transition C > T
        IVS12-15
    Variant  PKD1X15G - 1:    KP   Transversion A > C
        4876      1555          none
    Variant  PKD1X15J - 1:    UP   Transition C > T
        5383      1724          none
    Variant  PKD1X15L - 1:    UP   Transition G > A
        5974      1921          none
    Variant  PKD1X17 - 1:     KP   Transition T > C
        7376      2389          none
    Variant  PKD1X18 - 1:     KP   Transition C > T
        7652      2481          none
    Variant  PKD1X26 - 1:     UP   Transition C > T
        9481      3090          none
    Variant  PKD1X46B - 1:    KP   Transition C > T
        12973     4254          none
    Variant  PKD1X9 - 1:      UP   7bp deletion (TGGTGGG)
        IVS9+28del7
Variant  PKD2X1A - 1:     KP   Transversion G > C
        149       28            arginine ---> proline
    Variant  PKD2X4 - 1:      UPD  Transition C > T
        1147      361           arginine ---> OPA (stop codon)

V.
    Variant  PKD1X15M - 1:    UP   Transition C > T
```

FIG. 14P

```
       6415        2068       none
   Variant  PKD2X1C - 1:    UPD   4bp Insertion of CGCC
        596         177      Frame Shift
```

W.

```
   Variant  PKD1X10 - 1:    UP    Transition A > G
        IVS9-4
   Variant  PKD1X11C - 1:   UP    Transition C > T
        IVS11+23
   Variant  PKD1X13 - 1:    UPD   1 bp deletion of C
       3310        1033      Frame Shift
   Variant  PKD1X13 - 2:    KP    Transition T > C
       3274        1021      none
   Variant  PKD1X14 - 1:    KP    Transition T > C
       3486        1092      methionine --> threonine
   Variant  PKD1X15A - 1:   UP    Transition C > T
       3583        1124      none
   Variant  PKD1X15A - 2:   UP    Transition C > T
       3586        1125      none
   Variant  PKD1X15E - 1:   KP    Transition T > C
       4406        1399      tryptophan --> arginine
   Variant  PKD1X15G - 1:   KP    Transversion A > C
       4876        1555      none
   Variant  PKD1X15J - 1:   UP    Transition C > T
       5383        1724      none
   Variant  PKD1X17 - 1:    KP    Transition T > C
       7376        2389      none
   Variant  PKD1X18 - 1:    KP    Transition C > T
```

FIG. 14Q

```
              7652       2481        none
Variant  PKD1X20 - 1:       KP     Transition T > C
              7919       2570        none
Variant  PKD1X21 - 1:       KP     Transition A > G
              8124       2638        histidine --> arginine
Variant  PKD1X25 - 1:       KP     Transition A > G
              IVS24-17
Variant  PKD1X25 - 2:       KP     Transversion G > C
              9406       3065        none
Variant  PKD1X25 - 3:       KP     Transition T > C
              9407       3066        phenylalanine --> leucine
Variant  PKD1X26 - 1:       KP     Transition T > C
              9541       3110        none
Variant  PKD1X44 - 1:       KP     Transition A > G
              12341      4044        isoleucine --> valine
Variant  PKD1X45 - 1:       KP     Transition A > G
              12484      4091        none
Variant  PKD1X46A - 1:      UP     Transition T > C
              12838      4209        none
Variant  PKD2X1A - 1:       KP     Transversion G > C
              149        28          arginine --> proline
Variant  PKD2X1B - 1:       KP     Transition G > A
              486        140         none
```

X.

```
Variant  PKD1X10 - 1:       UP     Transition A > G
              IVS9-4
Variant  PKD1X11C - 1:      UP     Transition C > T
```

FIG. 14R

```
                    IVS11+23
Variant  PKD1X13 - 1:    UPD   1 bp deletion of C
         3310    1033    Frame Shift
Variant  PKD1X13 - 2:    KP    Transition T > C
         3274    1021    none
Variant  PKD1X14 - 1:    KP    Transition T > C
         3486    1092    methionine --> threonine
Variant  PKD1X15A - 1:   UP    Transition C > T
         3583    1124    none
Variant  PKD1X15A - 2:   UP    Transition C > T
         3586    1125    none
Variant  PKD1X15E - 1:   KP    Transition T > C
         4406    1399    tryptophan --> arginine
Variant  PKD1X15G - 1:   KP    Transversion A > C
         4876    1555    none
Variant  PKD1X15J - 1:   UP    Transition C > T
         5383    1724    none
Variant  PKD1X17 - 1:    KP    Transition T > C
         7376    2389    none
Variant  PKD1X18 - 1:    KP    Transition C > T
         7652    2481    none
Variant  PKD1X20 - 1:    KP    Transition T > C
         7919    2570    none
Variant  PKD1X21 - 1:    KP    Transition A > G
         8124    2638    histidine --> arginine
Variant  PKD1X25 - 1:    KP    Transition A > G
         IVS24-17
Variant  PKD1X25 - 2:    KP    Transversion G > C
```

FIG. 14S

```
                9406    3065      none
    Variant  PKD1X25 - 3:    KP    Transition T > C
                9407    3066      phenylalanine --> leucine
    Variant  PKD1X26 - 1:    KP    Transition T > C
                9541    3110      none
    Variant  PKD1X44 - 1:    KP    Transition A > G
               12341    4044      isoleucine --> valine
    Variant  PKD1X45 - 1:    KP    Transition A > G
               12484    4091      none
    Variant  PKD1X46A - 1:   UP    Transition T > C
               12838    4209      none
    Variant  PKD2X1A - 1:    KP    Transversion G > C
                 149      28      arginine --> proline
    Variant  PKD2X1B - 1:    KP    Transition G > A
                 486     140      none
```

Y.

```
    Variant  PKD1X1 - 1:     UPD   1bp deletion of C
                 364      51      Frame Shift
    Variant  PKD1X11A - 1:   UAA   Transition A > G
                2427     739      glutamine --> arginine
    Variant  PKD1X15G - 1:   KP    Transition G > A
                4885    1558      none
    Variant  PKD1X15H - 1:   KP    Transition G > A
                4885    1558      none
    Variant  PKD1X27 - 1:    UAA   Transversion A > T
                9710    3167      isoleucine --> phenylalanine
    Variant  PKD1X42 - 1:
```

FIG. 14T

```
Variant  PKD1X5C - 1:    KP   Transition T > C
    1330      373        none
Variant  PKD2X1A - 1:    KP   Transversion G > C
    149       28         arginine --> proline
```

Z.
```
Variant  PKD1X13 - 1:    UP   Transition C > T
    IVS12-15
Variant  PKD1X15A - 1:   UPD  Transition G > A
    3694      1161       tryptophan --> OPA (stop codon)
Variant  PKD1X15B - 1:   UPD  Transition G > A
    3694      1161       tryptophan --> OPA (stop codon)
Variant  PKD1X5C - 1:    KP   Transition T > C
    1330      373        none
Variant  PKD2X1A - 1:    KP   Transversion G > C
    149       28         arginine --> proline
```

AA.
```
Variant  PKD1X10 - 1:    UPD  1 bp insertion of G
    2291      694        Frame Shift
Variant  PKD1X26 - 1:    UP   Transition C > T
    9475      3088       none
Variant  PKD1X43 - 1:    UP   Transversion C > A
    IVS43+42
Variant  PKD1X5C - 1:    KP   Transition T > C   Homozygous
    1330      373        none
Variant  PKD2X1A - 1:    KP   Transversion G > C
    149       28         arginine --> proline
```

>     Variant  PKD1X23A - 1:    UAA    Transition C > T
>         8516      2769        leucine --> phenylalanine
>     Variant  PKD1X32 - 1:     UP     Transition G > A
>         IVS32+33
>     Variant  PKD1X33 - 1:     UAA    Transversion G > T
>         10441     3410        tryptophan --> cysteine
>     Variant  PKD1X7 - 1:      UP     Transition C > T    Homozygous
>         1750      513         none
>     Variant  PKD2X1B - 1:     UPD    1 bp deletion of G
>         405       113         Frameshift --> stop codon (Amber)

CC.

>     Variant  PKD1X13 - 1:     UAA    Transition A > G
>         3312      1034        asparagine --> serine
>     Variant  PKD1X24 - 1:     UPD    Transversion G > C
>         IVS23-1               splice site mutation
>     Variant  PKD2X1B - 1:     KP     Transition G > A
>         486       140         none

DD.

>     Variant  PKD1X10 - 1:     UP     Transition A > G
>         IVS9-4
>     Variant  PKD1X11A - 1:    UAA    Transition A > G
>         2427      739         glutamine-->arginine
>     Variant  PKD1X11B - 1:    KP     Transition G > A
>         2911      900         none

FIG. 14V

```
Variant  PKD1X11B - 2:    KP    Transition C > T
         2941      910    None
Variant  PKD1X11C - 1:    KP    Transition G > A
         2911      900    none
Variant  PKD1X11C - 2:    KP    Transition C > T
         2941      910    none
Variant  PKD1X15G - 1:    KP    Transversion A > C
         4876     1555    none
Variant  PKD1X15J - 1:    UP    Transition C > T
         5383     1724    none
Variant  PKD1X17 - 1:     KP    Transition T > C
         7376     2389    None
Variant  PKD1X18 - 1:     KP    Transition C > T
         7652     2481    none
Variant  PKD1X19 - 1:     UP    Transversion C > A
         IVS19+24
Variant  PKD1X24 - 1:     UPD   1bp insertion of T
         9134     2975    Frame Shift
Variant  PKD1X25 - 1:     KP    Transition A > G
         IVS24-17
Variant  PKD1X25 - 2:     KP    Transversion G > C
         9406     3065    none
Variant  PKD1X25 - 3:     KP    Transition T > C
         9407     3066    phenylalanine-->leucine
Variant  PKD1X26 - 1:     KP    Transition T > C
         9541     3110    None
Variant  PKD1X28 - 1:     UP    Transition T > C
         IVS27-13
```

FIG. 14W

```
Variant  PKD1X30 - 1:    UP    Transition C > T
    IVS29-11
Variant  PKD1X35 - 1:    KP    Transition C > T
    10743       3511     alanine --> valine
Variant  PKD1X44 - 1:    KP    Transition A > G
    12341       4044     isoleucine --> valine
Variant  PKD1X45 - 1:    KP    Transition C > T
    12384       4058     alanine-->valine
Variant  PKD1X45 - 2:    KP    Transition A > G
    12484       4091     None
Variant  PKD1X45 - 3:    KP    Transition C > T
    12617       4136     None
Variant  PKD1X46A - 1:   UP    Transition T > C
    12838       4209     none
Variant  PKD1X46B - 1:   UP    Transition G > A
    13135       3'UTR    none
Variant  PKD1X5C - 1:    KP    Transition T > C
    1330        373      none
Variant  PKD1X9 - 1:     UP    7bp deletion (Homozygous)
    IVS9+28del7
Variant  PKD2X1A - 1:    KP    Transversion G > C
    149         28       arginine --> proline
Variant  PKD2X1B - 1:    KP    Transition G > A
    486         140      none

EE.

Variant  PKD1X10 - 1:    UP    Transition A > G
    IVS9-4
```

FIG. 14X

```
Variant  PKD1X13 - 1:    KP   Transition T > C
     3274      1021      None
Variant  PKD1X14 - 1:    KP   Transition T > C
     3486      1092      methionine --> threonine
Variant  PKD1X15A - 1:   UP   Transition C > T
     3583      1124      None
Variant  PKD1X15A - 2:   UP   Transition C > T
     3586      1125      None
Variant  PKD1X15E - 1:   KP   Transition T > C
     4406      1399      tryptophan --> arginine
Variant  PKD1X15G - 1:   KP   Transversion A > C
     4876      1555      None
Variant  PKD1X15J - 1:   UP   Transition C > T
     5383      1724      None
Variant  PKD1X16 - 1:    UP   Transition G > A
     IVS16+21
Variant  PKD1X17 - 1:    KP   Transition T > C
     7376      2389      None
Variant  PKD1X18 - 1:    KP   Transition C > T
     7652      2481      None
Variant  PKD1X20 - 1:    KP   Transition T > C
     7919      2570      None
Variant  PKD1X21 - 1:    KP   Transition A > G
     8124      2638      histidine --> arginine
Variant  PKD1X35 - 1:    UPD  2bp deletion of GA
     10735-107363508-3509Frame Shift
Variant  PKD1X35 - 2:    KP   Transition C > T
     10743     3511      alanine --> valine
```

FIG. 14Y

Variant PKD1X42 - 1:

Variant PKD1X44 - 1:   KP   Transition A > G   Homozygous
    12341    4044      isoleucine --> valine Variant PKD1X45 - 1:   KP   Transition C > T
    12384    4058      alanine --> valine Variant PKD1X45 - 2:   KP   Transition A > G   Homozygous
    12484    4091      None Variant PKD1X45 - 3:   KP   Transition C > T
    12617    4136      None Variant PKD1X46A - 1:  UP   Transition T > C   Homozygous
    12838    4209      None Variant PKD1X8 - 1:    KP   Transition C > T
    1921     570       None Variant PKD2X1A - 1:   KP   Transversion G > C
    149      28        arginine --> proline

FF.

Variant PKD1X42 - 1:   UPD  1 bp deletion (Homozygous)
    11836    3875      Frame Shift Variant PKD1X43 - 1:   UP   Transversion C > G
    12184    3991      None Variant PKD2X1A - 1:   KP   Transversion G > C
    149      28        arginine --> proline Variant PKD2X7 - 1:    UAA  Transversion G > C
    1720     552       alanine --> proline

GG.

Variant PKD1X42 - 1:   UPD  1 bp deletion (Homozygous)

FIG. 14Z

```
        11836      3875       Frame Shift

Variant  PKD1X43 - 1:     UP    Transversion C > G 12184      3991       None

Variant  PKD2X1A - 1:     KP    Transversion G > C 149        28         arginine --> proline Variant  PKD2X7 - 1:      UAA   Transversion G > C 1720       552        alanine --> proline

HH.

Variant  PKD1X15F - 1:

Variant  PKD1X23A - 1:    UPD   Transversion G > T 8639       2810       glutamic acid ---> AMB (stop codon)

Variant  PKD1X23A - 2:    KP    Transition G > A 8651       2814       glycine ---> arginine Variant  PKD1X23A - 3:    UAA   Transition T > C 8658       2816       leucine ---> proline Variant  PKD1X23A - 4:    UP    Transition C > T 8662       2817       none Variant  PKD1X23B - 1:    UPD   Transversion G > T 8639       2810       glutamic acid ---> AMB (stop codon)

Variant  PKD1X23B - 2:    KP    Transition G > A 8651       2814       glycine ---> arginine Variant  PKD1X23B - 3:    UAA   Transition T > C 8658       2816       leucine ---> proline Variant  PKD1X23B - 4:    UP    Transition C > T 8662       2817       none Variant  PKD1X23C - 1:    UAA   Transition G > A 8900       2897       valine ---> isoleucine
```

FIG. 14AA

```
Variant  PKD1X40 - 1:     UP   Transition C > T
     11554      3781      none
Variant  PKD1X41 - 1:     UP   3bp insertion (GGG)
     IVS41+6ins3
Variant  PKD1X45 - 1:     UAA  Transition G > A
     12644      4145      valine --> isoleucine

II.

Variant  PKD1X1 - 1:

Variant  PKD1X14 - 1:     UPD  Transition C > T
     3395       1062      Glutamine > AMB (stop codon)

Variant  PKD1X15G - 1:    KP   Transition G > A
     4885       1556      None

Variant  PKD1X15H - 1:    KP   Transition G > A
     4885       1558      None

Variant  PKD1X15K - 1:    UP   Transition C > T
     5893       1894      None

Variant  PKD1X15M - 1:

Variant  PKD1X36 - 1:     KP   Transition C > T
     10976      3589      None

Variant  PKD1X43 - 1:     KP   Transition C > T
     12124      3971      None

Variant  PKD1X44 - 1:     KP   1 bp deletion of G
     IVS44+22delG

Variant  PKD2X1A - 1:     KP   Transversion G > C
     149        28        Arginine > Proline

```
Variant  PKD1X15G - 1:     KP    Transition G > A
     4885      1558      None Variant  PKD1X15H - 1:     KP    Transition G > A
     4885      1558      None Variant  PKD1X2 - 1:

Variant  PKD1X42 - 1:      UP    Transition C > T
     IVS41-11

Variant  PKD1X46B - 1:    UPD   Transversion G > T
     12926     4239      Glutamic acid --> Stop codon (AMB)

Variant  PKD2X1A - 1:      KP    Transversion G > C   Homozygous
     149.      28        Arginine > Proline
```

FIG. 14CC

Figure 15. PKD1 cDNA sequence (GenBank Accesion No. L33243). For a copy of the PKD1 genomic sequence please refer to GenBank (Accesion No. L39891). Exon and PCR product junctions are depicted above the nucleotide sequence. Amino acids are positioned under the center of each codon.

Codon Number

Exon 1
212 atgccgcccgccgcgcccgccgcctggcgctggccctgggcctg
1   M  P  P  A  A  P  A  R  L  A  L  A  L  G  L 257 ggcctgtggctcggggcgctggcgggggcccccgggcgcggctgc
16  G  L  W  L  G  A  L  A  G  G  P  G  R  G  C 302 gggccctgcgagcccccctgcctctgcggcccagcgcccggcgcc
31  G  P  C  E  P  P  C  L  C  G  P  A  P  G  A 347 gcctgccgcgtcaactgctcgggccgcgggctgcggacgctcggt
46  A  C  R  V  N  C  S  G  R  G  L  R  T  L  G

Exon 2
392 cccgcgctgcgcatccccgcggacgccacagcgct
61  P  A  L  R  I  P  A  D  A  T  A  L 437
76

Exon 3
482                              ggatataagcaacaacaagatttctacg
91                               D  I  S  N  N  K  I  S  T

Exon 4
527 ttagaagaaggaatatttgctaatttatttaattaagtgaaat
106 L  E  E  G  I  F  A  N  L  F  N  L  S  E  I 572
121

617
136

662
151

Exon 5-A
707                                          ggtgaggagtat
166                                          G  E  E  Y 752 gtcgcctgcctccctgacaacagctcaggcaccgtggcagcagtg
181 V  A  C  L  P  D  N  S  S  G  T  V  A  A  V

FIG. 15A

Figure 15 con.

```
 797 tcctttcagctgcccacgaaggcctgcttcagccagaggcctgc
196      S  F  S  A  A  H  E  G  L  L  Q  P  E  A  C 842 agcgccttctgcttctccaccggccagggcctcgcagccctctcg
211      S  A  F  C  F  S  T  G  Q  G  L  A  A  L  S
                              → 5-B
 887 gagcagggctggtgcctgtgtggggcggcccagccctccagtgcc
226      E  Q  G  W  C  L  C  G  A  A  Q  P  S  S  A
                        ← 5-A
 932 tcctttgcctgcctgtccctctgctccggccccccgccacctcct
241      S  F  A  C  L  S  L  C  S  G  P  P  P  P  P 977 gcccccacctgtaggggcccacccctcctccagcacgtcttccct
256      A  P  T  C  R  G  P  T  L  L  Q  H  V  F  P 1022 gcctccccaggggccaccctggtggggccccacggacctctggcc
271      A  S  P  G  A  T  L  V  G  P  H  G  P  L  A 1067 tctggccagctagcagccttccacatcgctgcccgctccctgtc
286      S  G  Q  L  A  A  F  H  I  A  A  P  L  P  V
                                          → 5-C
1112 actgccacacgctgggacttcggagacggctccgccgaggtggat
301      T  A  T  R  W  D  F  G  D  G  S  A  E  V  D
                                          ← 5-B
1157 gccgctgggccggctgcctcgcatcgctatgtgctgcctgggcgc
316      A  A  G  P  A  A  S  H  R  Y  V  L  P  G  R 1202 tatcacgtgacggccgtgctggccctgggggccggctcagccctg
331      Y  H  V  T  A  V  L  A  L  G  A  G  S  A  L 1247 ctggggacagacgtgcaggtggaagcggcacctgccgccctggag
346      L  G  T  D  V  Q  V  E  A  A  P  A  A  L  E 1292 ctcgtgtgcccgtcctcggtgcagagtgacgagagccttgacctc
361      L  V  C  P  S  S  V  Q  S  D  E  S  L  D  L 1337 agcatccagaaccgcggtggttcaggcctggaggccgcctacagc
376      S  I  Q  N  R  G  G  S  G  L  E  A  A  Y  S
                                              Exon 6
1382 atcgtggccctgggcgaggagccggcccgagccgtccatccagt
391      I  V  A  L  G  E  E  P  A  R  A  V  H  P  V
```

FIG. 15B

Figure 15 con.

```
     1427 tgccgctcggacacggagatcttcctggcgcacggggactgctac
406       C  P  S  D  T  E  I  F  L  A  H  G  D  C  Y 1472 cgcctggtgtgtgaagaaggcaggtggctgcagggcaggagaac
421       R  L  V  C  E  E  G  R  W  L  Q  G  Q  E  N 1517 cgtgcagcctgggccaggccgccctgtcaatgtggacaattcag
436       R  A  A  W  A  R  P  P  C  Q  C  G  Q  F  S
                                            Exon 7
     1562 gccgtgcagcgtttctggtctcggcgtcaccgagcctagac
451       A  V  Q  R  F  W  S  R  V  T  R  S  L  D 1607 gtgtggatcggcttctcgactgtgcaggggtggaggtgggccca
466       V  W  I  G  F  S  T  V  Q  G  V  E  V  G  P 1652 gcgccgcagggcgaggccttcagcctggagagctgccagaactgg
481       A  P  Q  G  E  A  F  S  L  E  S  C  Q  N  W 1697 ctgcccggggagccacacccagccacagccgagcactgcgtccgg
496       L  P  G  E  P  H  P  A  T  A  E  H  C  V  R 1742 ctcgggcccaccggtggtgtaacaccgacctgtgctcagcgccg
511       L  G  P  T  G  W  C  N  T  D  L  C  S  A  P
                                         Exon 8
     1787 cacagctacgtctgcgagctgcagcccggaggcccagtgcaggat
526       H  S  Y  V  C  E  L  Q  P  G  G  P  V  Q  D 1832 gccggagaacttcatcgtgggagcgcccagtggggacctgcaggg
541       A  P  N  F  I  V  G  A  P  S  G  D  L  Q  G 1877 ccctgacgcctgcacagcaggagggcctcagcgcctgac
556       P  L  T  P  L  A  Q  Q  D  G  L  S  A  L  P
              Exon 9
     1922 gagcccgtggaggtcatggtattcccgggcctgcgtctgagccgt
571       E  P  V  E  V  M  V  F  P  G  L  R  L  S  R 1967 gaagccttcctcaccacggccgaatttgggacccaggagctccgg
586       E  A  F  L  T  T  A  E  F  G  T  Q  E  L  R 2012 cggcccgcccagctgcggctgcaggtgtaccggctcctcagcaca
601       R  P  A  Q  L  R  L  Q  V  Y  R  L  L  S  T
              Exon 10
     2057 gcaggaacccgagaacggcagcgagcctgagagcaggtcccg
616       A  G  T  P  E  N  G  S  E  P  E  S  R  S  P
```

FIG. 15C

Figure 15 con.

```
       2102 gacaacaggaccgagcggcccggcgcatgccacggggacgc
631         D  N  R  D  Q  R  A  A  C  M  P  G  V  G  R 2147 tggtgcctggcgcaacatctgctgccctggacgctctcggc
646         W  C  P  G  A  N  I  C  C  P  L  D  A  S  G 2192 caccccaggctggccaatgctgcactcaggctggcctgcta
661         H  P  Q  A  G  A  N  A  A  L  R  L  A  C  L 2237 cccggggcccctatcgcctatgaggagctcctgctctccgt
676         P  G  A  P  Y  R  Y  E  E  L  L  L  S  V
                                          → Exo. 11-A 2282 ggccggggcccccgcgcagtaccgtcaccctccacggccag
691         A  A  G  P  P  A  Q  Y  R  V  T  L  H  G  Q 2327 gatgtcctcatgctccctggtgacctcgttggcttgcagcacgac
706         D  V  L  M  L  P  G  D  L  V  G  L  Q  H  D 2372 gctggccctggcgcccctcctgcactgctcgccggctcccggccac
721         A  G  P  G  A  L  L  H  C  S  P  A  P  G  H 2417 cctggtccccaggccccgtacctctccgccaacgcctcgtcatgg
736         P  G  P  Q  A  P  Y  L  S  A  N  A  S  S  W
                                                  → 11-B 2462 ctgccccacttgccagcccagctggagggcacttgggcctgccct
751         L  P  H  L  P  A  Q  L  E  G  T  W  A  C  P 2507 gcctgtgccctgcggctgcttgcagccacggaacagctcaccgtg
766         A  C  A  L  R  L  L  A  A  T  E  Q  L  T  V
            ←         11-A 2552 ctgctgggcttgaggcccaaccctggactgcggatgcctgggcgc
781         L  L  G  L  R  P  N  P  G  L  R  M  P  G  R 2597 tatgaggtccgggcagaggtgggcaatggcgtgtccaggcacaac
796         Y  E  V  R  A  E  V  G  N  G  V  S  R  H  N 2642 ctctcctgcagctttgacgtggtctccccagtggctgggctgcgg
811         L  S  C  S  F  D  V  V  S  P  V  A  G  L  R 2687 gtcatctaccctgcccccgcgacggccgcctctacgtgcccacc
826         V  I  Y  P  A  P  R  D  G  R  L  Y  V  P  T 2732 aacggctcagccttggtgctccaggtggactctggtgccaacgcc
841         N  G  S  A  L  V  L  Q  V  D  S  G  A  N  A
```

FIG. 15D

Figure 15 con.

```
       2777 acggccacggctcgctggcctgggggcagtgtcagcgcccgcttt
856         T  A  T  A  R  W  P  G  G  S  V  S  A  R  F
                                                   → 11-C
       2822 gagaatgtctgccctgccctggtggccaccttcgtgcccggctgc
871         E  N  V  C  P  A  L  V  A  T  F  V  P  G  C 2867 ccctgggagaccaacgatacnctgttctcagtggtagcactgccg
886         P  W  E  T  N  D  T  L  F  S  V  V  A  L  P
                                          ←         11-B
       2912 tggctcagtgaggggagcacgtggtggacgtggtggtggaaaac
901         W  L  S  E  G  E  H  V  V  D  V  V  V  E  N 2957 agcgccagccgggccaacctcagcctgcgggtgacggcggaggag
916         S  A  S  R  A  N  L  S  L  R  V  T  A  E  E 3002 cccatctgtggcctccgcgccacgcccagccccgaggccgtgta
931         P  I  C  G  L  R  A  T  P  S  P  E  A  V
                                  Exon 12
       3047 ctgcagggagtcctagtgaggtaaagcccgtggtagcggccggc
946         L  Q  G  V  L  V 3092 tcggacatggtctccggtgaccaccaacgacaagcagtcctc
961

3137 accttccagaacgtggtccaagtgaattacagagcggcc
976
                           Exon 13
       3182 gtcttcaagctctcactgacggcctccaaccacgtgagcaacgtc
991         V  F  K  L  S  L  T  A  S  N  H  V  S  N  V 3227 accgtgaactacaacgtaaccgtggagcggatgaacaggatgcag
1006        T  V  N  Y  N  V  T  V  E  R  M  N  R  M  Q 3272 ggtctgcaggtctccacagtgccggccgtgctgtcccccaatgcc
1021        G  L  Q  V  S  T  V  P  A  V  L  S  P  N  A 3317 acgctagcactgacggcgggcgtgctggtggactcggccgtggag
1036        T  L  A  L  T  A  G  V  L  V  D  S  A  V  E
                               Exon 14
       3362 gtggccttcctgtggaacttggatgggagcaggcctccac
1051        V  A  F  L 3407
1066
```

FIG. 15E

Figure 15 con.

```
       3452 gcggtggccaggtgctggtgacacattcatgcacaccgag
1081        A V A R C W * H I H M H T E
                            Exon 15-A
       3497 gctgcccaggtgagtacctcctgaccgtgctggcatctaatgcc
1096        A A Q G E Y L L T V L A S N A 3542 ttcgagaacctgacgcagcaggtgcctgtgagcgtgcgcgcctcc
1111        F E N L T Q Q V P V S V R A S 3587 ctgccctccgtggctgtgggtgtgagtgacggcgtcctggtggcc
1126        L P S V A V G V S D G V L V A
                                            →15-B
       3632 ggccggcccgtcaccttctacccgcacccgctgccctcgcctggg
1141        G R P V T F Y P H P L P S P G 3677 ggtgttctttacacgtgggacttcggggacggctcccctgtcctg
1156        G V L Y T W D F G D G S P V L
            ←        15-A
       3722 acccagagccagccggctgccaaccacacctatgcctcgagggggc
1171        T Q S Q P A A N H T Y A S R G 3767 acctaccacgtgcgcctggaggtcaacaacacggtgagcggtgcg
1186        T Y H V R L E V N N T V S G A 3812 gcggcccaggcggatgtgcgcgtctttgaggagctccgcggactc
1201        A A Q A D V R V F E E L R G L
                                        →15-C
       3857 agcgtggacatgagcctggccgtggagcagggcgcccccgtggtg
1216        S V D M S L A V E Q G A P V V
                          ←          15-B
       3902 gtcagcgccgcggtgcagacgggcgacaacatcacgtggaccttc
1231        V S A A V Q T G D N I T W T F 3947 gacatgggggacggcaccgtgctgtcgggcccggaggcaacagtg
1246        D M G D G T V L S G P E A T V 3992 gagcatgtgtacctgcgggcacagaactgcacagtgaccgtgggt
1261        E H V Y L R A Q N C T V T V G 4037 gcggccagccccgccggccacctggcccggagcctgcacgtgctg
1276        A A S P A G H L A R S L H V L
                      →15-D
       4082 gtcttcgtcctggaggtgctgcgcgttgaacccgccgcctgcatc
1291        V F V L E V L R V E P A A C I
            ←          15-C
```

FIG. 15F

Figure 15 con.

```
     4127 cccacgcagcctgacgcgcggctcacggcctacgtcaccgggaac
1306      P  T  Q  P  D  A  R  L  T  A  Y  V  T  G  N 4172 ccggcccactacctcttcgactggaccttcggggatggctcctcc
1321      P  A  H  Y  L  F  D  W  T  F  G  D  G  S  S 4217 aacacgaccgtgcgggggtgcccgacggtgacacacaacttcacg
1336      N  T  T  V  R  G  C  P  T  V  T  H  N  F  T
                                                  →15-E
     4262 cggagcggcacgttccccctggcgctggtgctgtccagccgcgtg
1351      R  S  G  T  F  P  L  A  L  V  L  S  S  R  V
                                              ← 15-D 4307 aacagggcgcattacttccagcatctgcgtggagccagaggtg
1366      N  R  A  H  Y  F  T  S  I  C  V  E  P  E  V 4352 ggcaacgtcaccctgcagccagagaggcagtttgtgcagctcggg
1381      G  N  V  T  L  Q  P  E  R  Q  F  V  Q  L  G 4397 gacgaggcctggctggtggcatgtgcctggccccgttcccctac
1396      D  E  A  W  L  V  A  C  A  W  P  P  F  P  Y 4442 cgctacacctgggactttggcaccgaggaagccgcccccacccgt
1411      R  Y  T  W  D  F  G  T  E  E  A  A  P  T  R
                                             →15-F
     4487 gccagggggcctgaggtgacgttcatctaccgagacccaggctcc
1426      A  R  G  P  E  V  T  F  I  Y  R  D  P  G  S
                                              ← 15-E
     4532 tatcttgtgacagtcaccgcgtccaacaacatctctgctgccaat
1441      Y  L  V  T  V  T  A  S  N  N  I  S  A  A  N 4577 gactcagccctggtggaggtgcaggagcccgtgctggtcaccagc
1456      D  S  A  L  V  E  V  Q  E  P  V  L  V  T  S 4622 atcaaggtcaatggctcccttgggctggagctgcagcagccgtac
1471      I  K  V  N  G  S  L  G  L  E  L  Q  Q  P  Y
                                             →15-G
     4667 ctgttctctgctgtgggccgtgggcgccccgccagctacctgtgg
1486      L  F  S  A  V  G  R  G  R  P  A  S  Y  L  W 4712 gatctgggggacggtgggtggctcgagggtccggaggtcacccac
1501      D  L  G  D  G  G  W  L  E  G  P  E  V  T  H
                ← 15-F
     4757 gcttacaacagcacaggtgacttcaccgttagggtggccggctgg
1516      A  Y  N  S  T  G  D  F  T  V  R  V  A  G  W
```

FIG. 15G

Figure 15 con.

```
      4802 aatgaggtgagccgcagcgaggcctggctcaatgtgacggtgaag
1531        N  E  V  S  R  S  E  A  W  L  N  V  T  V  K
                        → 15-H
      4847 cggcgcgtgcgggggctcgtcgtcaatgcaagccgcacggtggtg
1546        R  R  V  R  G  L  V  V  N  A  S  R  T  V  V
                 ←              15-G
      4892 cccctgaatgggagcgtgagcttcagcacgtcgctggaggccggc
1561        P  L  N  G  S  V  S  F  S  T  S  L  E  A  G
      4937 agtgatgtgcgctattcctgggtgctctgtgaccgctgcacgccc
1576        S  D  V  R  Y  S  W  V  L  C  D  R  C  T  P
      4982 atccctgggggtcctaccatctcttacaccttccgctccgtgggc
1591        I  P  G  G  P  T  I  S  Y  T  F  R  S  V  G
                                           → 15-I
      5027 accttcaatatcatcgtcacggctgagaacgaggtgggctccgcc
1606        T  F  N  I  I  V  T  A  E  N  E  V  G  S  A
      5072 caggacagcatcttcgtctatgtcctgcagctcatagaggggctg
1621        Q  D  S  I  F  V  Y  V  L  Q  L  I  E  G  L
           ←        15-H
      5117 caggtggtgggcggtggccgctacttccccaccaaccacacggta
1636        Q  V  V  G  G  G  R  Y  F  P  T  N  H  T  V
      5162 cagctgcaggccgtggttagggatggcaccaacgtctcctacagc
1651        Q  L  Q  A  V  V  R  D  G  T  N  V  S  Y  S
                                              → 15-J
      5207 tggactgcctggagggacaggggcccggccctggccggcagcggc
1666        W  T  A  W  R  D  R  G  P  A  L  A  G  S  G
      5252 aaaggcttctcgctcaccgtgctcgaggccggcacctaccatgtg
1681        K  G  F  S  L  T  V  L  E  A  G  T  Y  H  V
                           ←    15-I
      5297 cagctgcgggccaccaacatgctgggcagcgcctgggccgactgc
1696        Q  L  R  A  T  N  M  L  G  S  A  W  A  D  C
      5342 accatggacttcgtggagcctgtggggtggctgatggtgaccgcc
1711        T  M  D  F  V  E  P  V  G  W  L  M  V  T  A
      5387 tccccgaacccagctgccgtcaacacaagcgtcaccctcagtgcc
1726        S  P  N  P  A  A  V  N  T  S  V  T  L  S  A
      5432 gagctggctggtggcagtggtgtcgtatacacttggtccttggag
1741        E  L  A  G  G  S  G  V  V  Y  T  W  S  L  E
```

FIG. 15H

Figure 15 con.

```
       5477 gaggggctgagctgggagacctccgagccatttaccacccatagc
1756        E  G  L  S  W  E  T  S  E  P  F  T  T  H  S 5522 ttccccacacccggcctgcacttggtcaccatgacggcagggaac
1771        F  P  T  P  G  L  H  L  V  T  M  T  A  G  N 5567 ccgctgggctcagccaacgccaccgtggaagtggatgtgcaggtg
1786        P  L  G  S  A  N  A  T  V  E  V  D  V  Q  V 5612 cctgtgagtggcctcagcatcagggccagcgagcccggaggcagc
1801        P  V  S  G  L  S  I  R  A  S  E  P  G  G  S 5657 ttcgtggcggccgggtcctctgtgccctttgggggcagctggcc
1816        F  V  A  A  G  S  S  V  P  F  W  G  Q  L  A 5702 acgggcaccaatgtgagctggtgctgggctgtgcccggcggcagc
1831        T  G  T  N  V  S  W  C  W  A  V  P  G  G  S 5747 agcaagcgtggccctcatgtcaccatggtcttcccggatgctggc
1846        S  K  R  G  P  H  V  T  M  V  F  P  D  A  G 5792 accttctccatccggctcaatgcctccaacgcagtcagctgggtc
1861        T  F  S  I  R  L  N  A  S  N  A  V  S  W  V 5837 tcagccacgtacaacctcacggcggaggagcccatcgtgggcctg
1876        S  A  T  Y  N  L  T  A  E  E  P  I  V  G  L 5882 gtgctgtgggccagcagcaaggtggtggcgcccgggcagctggtc
1891        V  L  W  A  S  S  K  V  V  A  P  G  Q  L  V 5927 catttcagatcctgctggctgccggctcagctgtcaccttccgc
1906        H  F  Q  I  L  L  A  A  G  S  A  V  T  F  R 5972 ctgcaggtcggcggggccaaccccgaggtgctccccgggccccgt
1921        L  Q  V  G  G  A  N  P  E  V  L  P  G  P  R 6017 ttctcccacagcttctcccgcgtcggagaccacgtggtgagcgtg
1936        F  S  H  S  F  P  R  V  G  D  H  V  V  S  V 6062 cggggcaaaaaccacgtgagctgggcccaggcgcaggtgcgcatc
1951        R  G  K  N  H  V  S  W  A  Q  A  Q  V  R  I 6107 gtggtgctggaggccgtgagtgggctgcagatgcccaactgctgc
1966        V  V  L  E  A  V  S  G  L  Q  M  P  N  C  C
```

FIG. 15I

Figure 15 con.

```
      6152 gagcctggcatcgccacgggcactgagaggaacttcacagcccgc
1981       E  P  G  I  A  T  G  T  E  R  N  F  T  A  R 6197 gtgcagcgcggctctcgggtcgcctacgcctggtacttctcgctg
1996       V  Q  R  G  S  R  V  A  Y  A  W  Y  F  S  L
              →15-M 6242 cagaaggtccagggcgactcgctggtcatcctgtcgggccgcgac
2011       Q  K  V  Q  G  D  S  L  V  I  L  S  G  R  D 6287 gtcacctacacgcccgtggccgcggggctgttggagatccaggtg
2026       V  T  Y  T  P  V  A  A  G  L  L  E  I  Q  V
                                          ←      15-L 6332 cgcgccttcaacgccctgggcagtgagaaccgcacgctggtgctg
2041       R  A  F  N  A  L  G  S  E  N  R  T  L  V  L 6377 gaggttcaggacgccgtccagtatgtggccctgcagagcggcccc
2056       E  V  Q  D  A  V  Q  Y  V  A  L  Q  S  G  P 6422 tgcttcaccaaccgctcggcgcagtttgaggccgccaccagcccc
2071       C  F  T  N  R  S  A  Q  F  E  A  A  T  S  P 6467 agccccggcgtgtggcctaccactgggactttggggatgggtcg
2086       S  P  R  V  W  P  T  T  G  T  L  G  M  G  R 6512 ccagggcaggacacagatgagcccagggccgagcactcctacctg
2101       P  G  Q  D  T  D  E  P  R  A  E  H  S  Y  L 6557 aggcctggggactaccgcgtgcaggtgaacgcctccaacctggtg
2116       R  P  G  D  Y  R  V  Q  V  N  A  S  N  L  V 6602 agcttcttcgtggcgcaggccacggtgaccgtccaggtgctggcc
2131       S  F  F  V  A  Q  A  T  V  T  V  Q  V  L  A 6647 tgccgggagccggaggtggacgtggtcctgcccctgcaggtgctg
2146       C  R  E  P  E  V  D  V  V  L  P  L  Q  V  L
                                           →15-N 6692 atgcggcgatcacagcgcaactacttggaggcccacgttgacctg
2161       M  R  R  S  Q  R  N  Y  L  E  A  H  V  D  L 6737 cgcgactgcgtcacctaccagactgagtaccgctgggaggtgtat
2176       R  D  C  V  T  Y  Q  T  E  Y  R  W  E  V  Y 6782 cgcaccgccagctgccagcggccggggcgcccagcgcgtgtggcc
2191       R  T  A  S  C  Q  R  P  G  R  P  A  R  V  A
```

FIG. 15J

Figure 15 con.

```
       15-M
     6827  ctgcccggcgtggacgtgagccggcctcggctggtgctgccgcgg
2206        L  P  G  V  D  V  S  R  P  R  L  V  L  P  R 6872  ctggcgctgcctgtggggcactactgctttgtgtttgtcgtgtca
2221        L  A  L  P  V  G  H  Y  C  F  V  F  V  V  S 6917  tttggggacacgccactgacacagagcatccaggccaatgtgacg
2236        F  G  D  T  P  L  T  Q  S  I  Q  A  N  V  T 6962  gtggcccccgagcgcctggtgcccatcattgagggtggctcatac
2251        V  A  P  E  R  L  V  P  I  I  E  G  G  S  Y 7007  cgcgtgtggtcagacacgggacctggtgctggatgggagcgag
2266        R  V  W  S  D  T  R  D  L  V  L  D  G  S  E 7052  tcctacgaccccaacctggaggacggcgaccagacgccgctcagt
2281        S  Y  D  P  N  L  E  D  G  D  Q  T  P  L  S
                                                Exon 16
     7097  ttccactgggcctgtgtggcttcgacacag...
2296        F  H  W  A  C  V  A  S  T  Q ...

7142  ...
2311

7187  ...
2326

7232  ...
2341
          Exon 17
     7277  gtgctgatccggagtggccgggtgcccattgtgtccttggagtgt
2356        V  L  I  R  S  G  R  V  P  I  V  S  L  E  C 7322  gtgtcctgcaaggcacaggccgtgtacgaagtgagccgcagctcc
2371        V  S  C  K  A  Q  A  V  Y  E  V  S  R  S  S 7367  tacgtgtacttggagggccgctgcctcaattgcagcagcggctcc
2386        Y  V  Y  L  E  G  R  C  L  N  C  S  S  G  S
                           Exon 18
     7412  aagcgaggg...
2401        K  R  G ...

Figure 15 con.

```
       7502 ctggcgctgcagcaggcgtgcctgcggacggcgaggatacacc
 2431       L  W  R  R  G  V  L  R  D  G  E  G  Y  T 7547 ctcacgctgcaggtgctggccgcgtccgaggaggagacgctgc
 2446       L  T  L  Q  V  L  A  A  S  E  E  E  T  L 7592 gcctccatccgcgtgccaacggcgccctgggcggctc
 2461       A  S  I  R  V  P  N  G  A  L  G  G  S 7637 cgcctgccgcccacgggcgcggtggtccatgcgctcaaccacaag
 2476       R  L  P  P  T  G  A  V  V  H  A  L  N  H  K
                                              Exon 19
       7682 ctgcactccatgcag|gctggcatgacgcggaggatgctggc
 2491       V  H  S  M  Q  G  W  H  D  A  E  D  A  G 7727 gccccgctggtgtacgccctgctgctgcggcgctgtcgccagggc
 2506       A  P  L  V  Y  A  L  L  L  R  R  C  R  Q  G 7772 cactgcgaggagttctgtgtctacaagggcagcctctccagctac
 2521       H  C  E  E  F  C  V  Y  K  G  S  L  S  S  Y 7817 ggagccgtgctgcccccgggtttcaggccacacttcgaggtgggc
 2536       G  A  V  L  P  P  G  F  R  P  H  F  E  V  G 7862 ctggccgtggtggtgcaggaccagctgggagccgctgtggtcgcc
 2551       L  A  V  V  V  Q  D  Q  L  G  A  A  V  V  A
                    Exon 20
       7907 ctcaacag|gtcctggccatcacctcccagagccaactgagc
 2566       L  N  R  S  W  P  S  P  P  E  P  N 7952 gcaaggggcaccagtgtgtggctgcacggggctgcacggctactgg
 2581       A  R  G  T  S  V  W  L  H  G  C  T  A  S  W 7997 ctcccagggctgctgcggcaggcgatccccagcactcatcgag
 2596       P  G  L  L  R  Q  A  D  P  Q  H  V  E
                                                   Exon 21
       8042 tactcgttggccctggtcactgtctgaacgag|tacgagcgggcc
 2611       Y  S  L  A  L  V  T  V  L  N  E  Y  E  R  A 8087 ctggacgtggcggcagagcccaagcacgagcggcagcaccgagcc
 2626       L  D  V  A  A  E  P  K  H  E  R  Q  H  R  A 8132 cagatacgcaagaacatcacggagactctggtgtccctgagggtc
 2641       Q  I  R  K  N  I  T  E  T  L  V  S  L  R  V
```

FIG. 15L

Figure 15 con.

```
        8177 cacactgtggatgacatccagcagatcgctgctgcgctggcccag
2656         H  T  V  D  D  I  Q  Q  I  A  A  A  L  A  Q
                                 Exon 22
        8222 tgcatgggcccaccaggagctgttgtccgctcgtgcctgaag
2671         C  M  G  P  H  Q  E  L  L  S  A  R  S  L  K 8267 cagacgctgcacaagtgtgccatgatgatcctgcaggca
2686         Q  T  L  H  K  C  A  M  M  I  L  Q  A 8312 gagaccacgcgggcacctgacgcccacgcatgggagacagc
2701         E  T  T  R  A  P  D  A  H  A  W  E  T  A
                                   Exon 23-A
        8357 atcctcaacatcacggagacctcatccacctggccagctcggac
2716         I  L  N  I  T  G  D  L  I  H  L  A  S  S  D 8402 gtgcgggcaccacagccctcagagctgggagccgagtcaccatct
2731         V  R  A  P  Q  P  S  E  L  G  A  E  S  P  S 8447 cggatggtggcgtcccaggcctacaacctgacctctgccctcatg
2746         R  M  V  A  S  Q  A  Y  N  L  T  S  A  L  M 8492 cgcatcctcatgcgctcccgcgtgctcaacgaggagcccctgacg
2761         R  I  L  M  R  S  R  V  L  N  E  E  P  L  T
                                                    → 23-B
        8537 ctggcgggcgaggagatcgtggcccagggcaagcgctcggacccg
2776         L  A  G  E  E  I  V  A  Q  G  K  R  S  D  P 8582 cggagcctgctgtgctatggcggcgccccagggcctggctgccac
2791         R  S  L  L  C  Y  G  G  A  P  G  P  G  C  H 8627 ttctccatccccgaggctttcagcggggccctggccaacctcagt
2806         F  S  I  P  E  A  F  S  G  A  L  A  N  L  S
                                        → 23-C
        8672 gacgtggtgcagctcatctttctggtggactccaatcccttttcc
2821         D  V  V  Q  L  I  F  L  V  D  S  N  P  F  P
        ←       23-A       ←       23-B
        8717 tttggctatatcagcaactacaccgtctccaccaaggtggcctcg
2836         F  G  Y  I  S  N  Y  T  V  S  T  K  V  A  S 8762 atggcattccagacacaggccggcgcccagatccccatcgagcgg
2851         M  A  F  Q  T  Q  A  G  A  Q  I  P  I  E  R 8807 ctggcctcagagcgcgccatcaccgtgaaggtgcccaacaactcg
2866         L  A  S  E  R  A  I  T  V  K  V  P  N  N  S
```

FIG. 15M

Figure 15 con.

```
      8852 gactgggctgcccggggccaccgcagctccgccaactccgccaac
2881       D   W   A   A   R   G   H   R   S   S   A   N   S   A   N 8897 tccgttgtggtccagcccaggcctccgtcggtgctgtggtcacc
2896       S   V   V   Q   P   Q   A   S   V   G   A   V   V   T 8942 ctggacagcagcaaccctgcggccgggctgcatctgcagctcaac
2911       L   D   S   S   N   P   A   A   G   L   H   L   Q   L   N
                                              Exon 24
      8987 tatacgctgctggacggccactaccgtctgaggagccgagacc
2926       Y   T   L   L   D   H   Y   S   E   E   P   I   P 9032 tagctggcagtgtacctacactcggagcccggccaatgagcac
2941       Y   L   A   V   Y   T   H   S   E   P   R   E   N   E   H 9077 aactgctcggctagcaggaggatccgccagagtcactccagggt
2956       N   C   S   A   S   R   R   I   R   P   E   S   L   Q   G
                                                          Exon 25
      9122 gctaccaccggccctacaccttcttcattttcccggtgagcaga
2971       A   D   H   R   P   Y   T   F   F   I   S   P   G   S   R 9167 gacccagcggggagttaccatctgaacctctccagccacttccgc
2986       D   P   A   G   S   Y   H   L   N   L   S   S   H   F   R 9212 tggtcggcgctgcaggtgtccgtgggcctgtacacgtccctgtgc
3001       W   S   A   L   Q   V   S   V   G   L   Y   T   S   L   C 9257 cagtacttcagcgaggaggacatggtgtggcggacagagggggctg
3016       Q   Y   F   S   E   E   D   M   V   W   R   T   E   G   L 9302 ctgccctggaggagacctcgccccgccaggccgtctgcctcacc
3031       L   P   L   E   E   T   S   P   R   Q   A   V   C   L   T 9347 cgccacctcaccgccttcggcgccagcctcttcgtgcccccaagc
3046       R   H   L   T   A   F   G   A   S   L   F   V   P   P   S
                                              Exon 26
      9392 catgtccgctttgtgtttcctgagccgacagcggatgtaaactac
3061       H   V   R   F   V   P   E   P   T   A   D   V   N   Y 9437 ctcgtcatgctgacatgtgctggtgcctggcgacctacatggtc
3076       L   V   M   L   T   C   A   W   C   L   V   T   Y   M   V 9482 atggccgccaccctccacaagctggaccagttggatgccagccgg
3091       M   A   A   T   L   H   K   L   D   Q   L   D   A   S   R
```

FIG. 15N

Figure 15 con.

```
     9527 ggcgcggcatccgcttctgcggcagggagcgcttcaatac
3106      G  R  A  I  P  L  L  R  Q  G  A  L  Q  Y
                                              Exon 27
     9572 gagatcctcgtcaagacagcctgggcggggcgcagtaccacg
3121      E  I  L  V  K  T  A  W  A  G  R  S    G  T  T 9617 gcccacgtgggcatcatgctgtatggggtggacagccggagcggc
3136      A  H  V  G  I  M  L  Y  G  V  D  S  R  S  G 9662 caccggcacctggacggcgacagagccttccaccgcaacagcctg
3151      H  R  H  L  D  G  D  R  A  F  H  R  N  S  L 9707 gacatcttccggatcgccacccgcacagcctgggtagcgtgtgg
3166      D  I  F  R  I  A  T  P  H  S  L  G  S  V  W
                                        Exon 28
     9752 aagatccgagtgtggcacgacaacaaagggctgagcctggcctgg
3181      K  I  R  V  W  H  D  N  K  G  L  S  L  A  W 9797 gagctgcagcacgtcatcgtgagggccctgcagacggcacgcagc
3196      E  L  Q  H  V  I  V  R  A  L  Q  T  A  R  S 9842 gccttctcctggtgaatgactggcttcggtgagacacgagcca
3211      A  F  S  W  V  N  D  W  L  R  E  T  R  A
                                              Exon 29
     9887 cacggggcctgtgcagaagcagctgctggccgcagcgacgca
3226      N  G  G  L  V  Q  K  Q  L  L  A  A  S  D  A 9932 gcccttttgcgcttccggcgcctgctggtggctgagctgcagcgt
3241      A  L  L  R  F  R  R  L  L  V  A  E  L  Q  R 9977 ggcttctttgacaagcacatctggctctccatatgggaccggccg
3256      G  F  F  D  K  H  I  W  L  S  I  W  D  R  P 10022 cctcgtagccgtttcactcgcatccagagggccacctgctgcgtt
3271      P  R  S  R  F  T  R  I  Q  R  A  T  C  C  V 10067 ctcctcatctgcctcttcctgggcgccaacgccgtgtggtacggg
3286      L  L  I  C  L  F  L  G  A  N  A  V  W  Y  G
                                        Exon 30
    10112 gctgttggcgactctgcctacagcacgggcatgtggcagcgctg
3301      A  V  G  D  S  A  Y  S  T  G  M  W  S  R  L 10157 agcctgctgagcgtcgacacagtcgctgtggcctggtgtccagc
3316      S  L  L  S  V  D  T  V  A  V  G  L  V  S  S
```

FIG. 15O

Figure 15 con.

```
       10202 gtggttgtctatccgtctaccaggccatgcttctggcttccag
3331         V  V  V  Y  P  V  Y  Q  A  M  L  L  L  P  R
                                              Exon 31
       10247 atgtccgcagcaaggtggctgggagcccgagcccacacctgcc
3346         M  S  R  S  K  V  A  G  S  P  S  P  T  P  A 10292 gggcagcaggtgctggacatcgacagctgcctggactcgtccgtg
3361         G  Q  Q  V  L  D  I  D  S  C  L  D  S  S  V
                                                  Exon 32
       10337 ctggacagctccttcctcacgttctcaggcctccacgctgaggcc
3376         L  D  S  S  F  L  T  F  S  G  L  H  A  E  A 10382 tttgtgtgacagatgaagagtgacttttctgtatgattctaag
3391         F  V  C  Q  M  K  S  D  F  F  V  Y  D  S  K
                Exon 33
       10427 aatctggtgtgctggccctccggcgagggaacgctcagttggccg
3406         S  L  V  C  W  P  S  G  E  G  T  L  S  W  P 10472 gacctgctcagtgacccgtccattgtgggtagcaatctgcggcag
3421         D  L  L  S  D  P  S  I  V  G  S  N  L  R  Q 10517 ctggcacggggccaggcgggccatgggctgggcccagaggaggac
3436         L  A  R  G  Q  A  G  H  G  L  G  P  E  D 10562 ggcttctccctggccagcccctactcgcctgccaaatccttctca
3451         G  F  S  L  A  S  P  Y  S  P  A  K  S  F  S
                 Exon 34
       10607 gcatcagatgaagacctgatccagaggtccttgcgagcggcc
3466         A  S  D  E  D  L  I  Q  R  S  L  R  A  A  V 10652 agcagcccagcccctaccaagacaccacatccacaacggactg
3481         S  S  P  A  P  T  K  T  P  H  P  Q  R  D  L
                          Exon 35
       10697 ctcagcagcctgtccagcactcctggggagaagacagagacgctg
3496         L  S  S  L  S  S  T  P  G  E  K  T  E  T  L 10742 gcgctgcagaggctgggggagctggggccacccagcccaggcctg
3511         A  L  Q  R  L  G  E  L  G  P  P  S  P  G  L
                                                  Exon 36
       10787 aactgggaacagccccaggcagcgaggctgtccaggacagggctg
3526         N  W  E  Q  P  Q  A  A  R  L  S  R  T  G  L 10832 gtggagggtctccggaagaggctgctgccggcctgtgtgcctcc
3541         V  E  G  L  R  K  R  L  L  P  A  W  C  A  S
```

FIG. 15P

Figure 15 con.

```
3556    10877  ctggcccacgggctcagcctgctcctggtggccgtggctggggct
                 A  H  G  L  S  L  L  L  V  A  V  A  G 3571    10922  gtctcagggcggctggtgctgagctccgcccccggcgtgactgtt
                 V  S  G  R  L  V  L  S  S  A  P  G  V  T  V 3586    10967  gcgtggtcctctgccacagcctgcgcatgctactggctcattctc
                 A  W  S  S  A  T  A  C  A  L  L  L  A  H  S
                                          Exon 37
3601    11012  ggctgggagccactgaaggtcttgctggaagccctgtacttctca
                 G  W  E  P  L  K  V  L  L  E  A  L  Y  F  S 3616    11057  ctggtggccaagcggctgcacccggatgaagatgacaccctggta
                 L  V  A  K  R  L  H  P  D  E  D  D  T  L  V 3631    11102  gagagcccggctgtgacgcctgtgagcgcacgtgtgccccgcgta
                 E  S  P  A  V  T  P  V  S  A  R  V  P  R  V 3646    11147  cggccaccccacggctttgcactcttcctggccaaggaagaagcc
                 R  P  P  H  G  F  A  L  F  L  A  K  E  E  A
                                                      Exon 38
3661    11192  cgcaaggtcaagaggctacatggcatgctgcggagcctccgggtg
                 R  K  V  K  R  L  H  G  M  L  R  S  L  R  V 3676    11237  cacatgctttttctggtggacccggctgccagctatgggat
                 H  M  L  F  L  V  D  P  L  A  S  Y  G  D 3691    11282  gcctcatgccatgggcacggctaccgtctgtaaagcgccataaag
                 A  S  C  H  G  H  A  Y  R  L  Q  S  A  I  K
                                                      Exon 39
3706    11327  caggagctgcacagccgggcccttccggccatcacgcggtctgag
                 Q  E  L  H  S  R  A  L  P  A  I  T  R  S  E 3721    11372  gagctctggccatggatggcccacgtgctgctgccctacgtccac
                 E  L  W  P  W  M  A  H  V  L  L  P  Y  V  H 3736    11417  gggaaccagtccagcgcagagctggggcccccacggctgcggcag
                 G  N  Q  S  S  A  E  L  G  P  P  R  L  R  Q
                                          Exon 40
3751    11462  gtgcggctgcaggaagcactctaccccagacctcccggccccgg
                 V  R  L  Q  E  A  L  Y  P  D  P  P  G  P  R 3766    11507  gtccacacgtgctggccgcaggagcgcttcatcaccagcgattac
                 V  H  T  C  W  P  Q  E  R  F  I  T  S  D  Y
```

FIG. 15Q

Figure 15 con.

```
11552 gacgttggctgggagagtcctcacaatggctggggacgtggcc
3781       D  V  G  W  E  S  P  H  N  G  S  G  T  W  A
                                              Exon 41
11597 tattcagcgccggatctgctaggggcatggtcctggggctcctgt
3796       I  S  A  P  D  L  L  G  A  W  S  W  G  S  C 11642 gccgtgtatgacagcgggggctacgtgcaggagctgggcctgagc
3811       A  V  Y  D  S  G  G  Y  V  Q  E  L  G  L  S 11687 ctggaggagagccgcgaccggctgcgcttcctgcagctgcacaac
3826       L  E  E  S  R  D  R  L  R  F  L  Q  L  H  N
                              Exon 42
11732 tggctggacaacaggagccgcgctgtgttcctggagctgacccgc
3841       W  L  D  N  R  S  R  A  V  F  L  E  L  T  R 11777 tacagccgcccgtgggctgcaggcggccctcacgctgcgcctc
3856       Y  S  R  P  W  A  A  G  G  L  H  A  A  P  L 11822 cagttccggcggccggccgcgccctggcggccctcagcgtccgc
3871       Q  F  R  R  P  A  A  G  R  A  L  A  A  L  S  V  R 11867 ccgttcgcgctgcgccgtcagcgcgggctgtcgctgccgctc
3886       P  F  A  L  R  R  H  S  A  L  G  L  S  L  P  L
                                Exon 43
11912 ctcacctcggtgtgcctgctgctgttcgccgtgcacttcgccgtg
3901       L  T  S  V  C  L  L  L  F  A  V  H  F  A  V 11957 gccgaggcccgtacttggcacagggaagggcgctggcgcgtgctg
3916       A  E  A  R  T  W  H  R  E  G  R  W  R  V  L 12002 cggctcggagcctgggcgcggtggctgctggtggcgctgacggcg
3931       R  L  G  A  W  A  R  W  L  L  V  A  L  T  A 12047 gccacggcactggtacgcctcgcccagctgggtgccgctgaccgc
3946       A  T  A  L  V  R  L  A  Q  L  G  A  A  D  R 12092 cagtggacccgtttcgtgcgcggccgcccgcgccgcttcactagc
3961       Q  W  T  R  F  V  R  G  R  P  R  R  F  T  S 12137 ttcgaccaggtggcgcagctgagctccgcagcccgtggcctggcg
3976       F  D  Q  V  A  Q  L  S  S  A  A  R  G  L  A
                                            Exon 44
12182 gcctcgctgctcttcctgcttttggtcaaggctgcacagcagcta
3991       A  S  L  L  F  L  L  L  V  K  A  A  Q  Q  L
```

FIG. 15R

Figure 15 con.

```
        12227  cggcttcatggcgcagtggtccgtcttggcaagacatatggcgg
4006           R  F  V  R  Q  W  S  V  L  G  K  T  Y  G  R 12272  ggctgcagagagctcctggggctgacctggggctggtggctgc
4021           A  A  R  E  L  L  G  V  T  L  G  L  V  V Exon 45
        12317  gggctagcctacgccagctggctatcctctcgtgtcttcctgt
4036           G  V  A  Y  A  S  W  L  S  S  L  V  S  S  C 12362  gtggactccctctggagcgtggcccaggccctgttggtgctgtgc
4051           V  D  S  L  W  S  V  A  Q  A  L  L  V  L  C 12407  cctgggactgggctctctaccctgtgtcctgccgagtcctggcac
4066           P  G  T  G  L  S  T  L  C  P  A  E  S  W  H 12452  ctgtcacccctgctgtgtgtggggctctgggcactgcggctgtgg
4081           L  S  P  L  L  C  V  G  L  W  A  L  R  L  W 12497  ggcgccctacggctgggggctgttattctccgctggcgctaccac
4096           G  A  L  R  L  G  A  V  I  L  R  W  R  Y  H 12542  gccttgcgtggagagctgtaccggccggcctgggagccccaggac
4111           A  L  R  G  E  L  Y  R  P  A  W  E  P  Q  D 12587  tacgagatggtggagttgttcctgcgcaggctgcgcctctggatg
4126           Y  E  M  V  E  L  F  L  R  R  L  R  L  W  M
                                        Exon 46
        12632  ggcctcagcaaggtcaaggagtccgccacaaagctggcttcaa
4141           G  L  S  K  V  K  E  S  R  H  K  W  R  F  E 12677  ggatggagccgctggcctctcgctgttccagggctgcaaggta
4156           G  M  E  P  L  A  S  R  C  S  R  G  C  K  V 12722  tccccgatgtgccgccgacccagcgctggctcccatgcctcgcac
4171           S  P  D  V  P  P  T  Q  R  W  L  P  C  L  A  H 12767  ccctccacctcctcgagccagctggatgggctgagcgtgagcctg
4186           P  S  T  S  S  Q  L  D  G  L  S  V  S  L 12812  ggccggctgtgcacaagcttgcgatgagcactcgggcctccag
4201           G  R  L  C  T  R  C  A  E  P  E  P  S  R  L  Q 12857  gccgtcttcgaggccctgctcacccagttgaccgactcaaccag
4216           A  V  F  E  A  L  L  T  Q  L  T  D  R  L  N  Q
```

FIG. 15S

Figure 15 con.

```
       12902 gccacagaggacgtctaccagctgcaggcgcagtgcacagcctg
4231         A  T  E  D  V  Y  Q  L  Q  A  Q  C  T  A  L 12947 caaggccgcaggagcagccagggcgccccgacggatcttcccgtggc
4246         Q  G  R  R  S  S  R  A  P  T  G  S  S  R  G 12992 ccatcgccggggctgcggcagccagcagtgcccagccggctttccgg
4261         P  S  P  G  L  R  P  A  V  P  S  R  L  A  R 13037 gccgtgagggtgtggacctggccactggcctcagcatgacatcc
4276         A  S  R  G  V  D  L  A  T  G  P  S  R  T  S 13082 cttcgggccaagaacaaggtccatccagcagcacttag 13120  (SEQ ID NO. 169)
4291         L  R  A  K  N  K  V  H  P  S  S  S  *          (SEQ ID NO. 171)
```

FIG. 15T

Figure 16. PKD2 cDNA sequence Exon and PCR product junctions are depicted above the nucleotide sequence. Amino acids are positioned under the center of each codon.

| Codon Number | | |
|---|---|---|
| | | → Exon 1-A |
| 1 | 67 | atggtgaactccagtcgcgtgcagcctcagcagcccggggacgcc |
| | | M V N S S R V Q P Q Q P G D A |
| 16 | 112 | aagcggccgcccgcgccccgcgcgccggacccggggccggctgatg |
| | | K R P P A P R A P D P G R L M |
| 31 | 157 | gctggctgcgcggccgtgggcgccagcctcgccgccccggggcggc |
| | | A G C A A V G A S L A A P G G |
| 46 | 202 | ctctgcgagcagcggggcctggagatcgagatgcagcgcatccgg |
| | | L C E Q R G L E I E M Q R I R |
| | | → 1-B |
| 61 | 247 | caggcggccgcgcgggaccccccggccggagccgcggcctcccct |
| | | Q A A A R D P P A G A A A S P |
| | | ← 1-A |
| 76 | 292 | tctcctccgctctcgtcgtgctcccggcaggcgtggagccgcgat |
| | | S P P L S S C S R Q A W S R D |
| 91 | 337 | aaccccggcttcgaggccgaggaggaggaggaggaggtggaaggg |
| | | N P G F E A E E E E E E V E G |
| 106 | 382 | gaagaaggcggaatggtggtggagatggacgtagagtggcgcccg |
| | | E E G G M V V E M D V E W R P |
| 121 | 427 | ggcagccggaggtcggccgcctcctcggccgtgagctccgtgggc |
| | | G S R R S A A S S A V S S V G |
| | | → 1-C |
| 136 | 472 | gcgcggagccgggggcttggcggctaccacggcgcgggccaccg |
| | | A R S R G L G G Y H G A G H P |
| 151 | 517 | agcggggaggcggcgccggcgagaggaccagggcccgccgtgcccc |
| | | S G R R R R E D Q G P P C P |
| ← | | 1-B |
| 166 | 562 | agcccagtcggcggcggggacccgctgcatcgccacctccccctg |
| | | S P V G G G D P L H R H L P L |
| 181 | 607 | gaagggcagccgccccgagtggcctgggcggagaggctggttcgc |
| | | E G Q P P R V A W A E R L V R |
| | | Exon 2 |
| 196 | 652 | gggctgcgaggtctgaggatcagatcatggagaagcagc |
| | | G L R C ... |
| 211 | 697 | agcaacgagagatacctaaagcgtcttacgggaactggtc |
| | | T N R R Y ... V R |
| | | Exon 3 |
| | 742 | acataccctcc...ggcttgtgcatctgacctacggc |

FIG. 16A

Figure 16 con.

| 226 | | ...L T Y G |
| --- | --- | --- |
| 241 | 787 | atgatgagctccaatgtgtactactacacccggatgatgtcacag<br>M M S S N V Y Y Y T R M M S Q |
| 256 | 832 | ctcttcctagacacccccgtgtccaaaacggagaaaactaacttt<br>L F L D T P V S K T E K T N F |
| 271 | 877 | aaaactctgtcttccatggaagacttctggaag...Exon 4<br>K T L S S M E D F W K... |
| 286 | 922 | |
| 301 | 967 | |
| 316 | 1012 | |
| 331 | 1057 | |
| 346 | 1102 | |
| 361 | 1147 | ...Exon 5 ttggatctacacaagtgaaaagacttgaat<br>...W I Y T S E K D L N |
| 376 | 1192 | ggtagtagccactggggaatcattgcaacttatagtggagctggc<br>G S S H W G I I A T Y S G A G |
| 391 | 1237 | tattatctggatttgtcaagaacaagagaggaaacagctgcacaa<br>Y Y L D L S R T R E E T A A Q |
| 406 | 1282 | gttgctagcctcaagaaaaatgtctggctggaccgaggaaccagg<br>V A S L K K N V W L D R G T R |
| 421 | 1327 | gcaactttttattgacttctcagtgtacaacgccaacattaacctg<br>A T F I D F S V Y N A N I N L |
| 436 | 1372 | ttctgtgtggtcag...Exon 6<br>F C V V R... |
| 451 | 1417 | |
| 466 | 1462 | |
| 481 | 1507 | |

FIG. 16B

Figure 16 con.

```
1552 ggcattcacaaactcacgtattccagaggttggaagctctg
496   R  I  H  K  L  T  Y  S  R  G  W  K  L
                          Exon 7
1597 gaagtcgtcatggtggtggtg ctgtcagtggtagctataggaattaac
511   D  V  V  M  V  V  V   L  S  V  V  A  I  G  I  N 1642 atatacagaacatcaaatgtggaggtgctactacagtttctggaa
526   I  Y  R  T  S  N  V  E  V  L  L  Q  F  L  E 1687 gatcaaaatactttccccaactttgagcatctggcatattggcag
541   D  Q  N  T  F  P  N  F  E  H  L  A  Y  W  Q 1732 atacagttcaacaatatagctgctgtcacagtattttttgtctgg
556   I  Q  F  N  N  I  A  A  V  T  V  F  F  V  W
              Exon 8
1777 attaagctcctcaatcctccgattaacaggacctgacccag
571   I  K  L  L  N  P  P  I  N  R  T  M  S  Q 1822 ctcctcgacaaccatgatccgatgtgccaagaactgcttctctt
586   L  L  D  N  H  D  P  M  C  Q  E  L  L  L 1867 gctaattatgttctgcattatcctagcatgcgaacggca
601   A  I  M  F  C  I  I  L  A  C  E  R  Q 1912 acctgtctgggacactcacgtaatgaactgactacttcgaa
616   T  C  L  G  T  L  T  V  M  N  L  T  T  S
              Exon 9
1957 gagtgtat cttcactcaattccgtatcattttgggcgatatcaac
631   E  C  I  F  T  Q  F  R  I  I  L  G  D  I  N 2002 tttgcagagattgaggaagctaatcgagttttgggaccaatttat
646   F  A  E  I  E  E  A  N  R  V  L  G  P  I  Y
                                      Exon 10
2047 ttcactacatttgtgttctttatgttcttcattcttttggaaatg
661   F  T  T  F  V  F  F  M  F  F  I  L  L  E  M 2092 cgcttggctatcatcaatgtaactactctgaatgaaatcgac
676   R  L  A  I  I  N  V  T  T  L  N  E  I  D 2137 ctggcacagcagaaagctgaaatggaactctcagatctttcaga
691   L  A  Q  Q  K  A  E  M  E  L  S  D  L  S  E
              Exon 11
2182 aaggctaccataaagctttggtcaaactaaaactgaaaaaaaat
706   K  G  Y  H  K  A  L  V  K  L  K  L  K  K  N 2227 accgtggatgacatttcagagagtctgcggcaaggaggaggcaag
721   T  V  D  D  I  S  E  S  L  R  Q  G  G  G  K Exon 12
2272 ttaaactttg            caagatctcaaagggaaggccat
```

FIG. 16C

Figure 16 con.

```
736                 L  N  F  D  E  L  R  Q  D  L  K  G  K  G
     2317   actgatgcagagatcaggcattatcacagaagtacgaccaagat
751         T  D  A  E  I  R  H  Y  H  K  Y  D  Q  D
     2362   ggagacaagactgatccaagatgaagatcatcagattaggaga
766         G  D  K  T  D  P  R  *  R  S  S  D  *  G  E
                                       Exon 13
     2407   gacttggagaaagcgagggaggacctggatttggatcacagttct
781         D  L  E  K  R  E  D  L  D  L  D  H  S  S
     2452   ttaccacgtcccatgagcagccgaagtttccctcgaagcctggat
796         L  P  R  P  M  S  S  R  S  F  P  R  S  L  D
     2497   gactctgaggaggatgacgatgaagatagcggacatagctccaga
811         D  S  E  E  D  D  D  E  D  S  G  H  S  S  R
     2542   aggagggaagcattctagtggcgtttcttacgaagagtttcaa
826         R  R  G  S  I  S  S  G  V  S  Y  E  E  F  Q
                 Exon 14
     2587   gtcctggtgagaccagtggaccgatggagcattccatcggcagc
841         V  L  V  R  P  V  D  R  M  E  H  S  I  G  S
     2632   atagtgtccaagattgaggccgtgatcgtgaagctagacattatg
856         I  V  S  K  I  E  A  V  I  V  K  L  D  I  M
     2677   gagcgagccaaaactgaaaaggatcgaggtgtcgaggatcgtg
871         E  R  A  K  T  E  K  D  R  G  V  E  G  R  V
                                 Exon 15
     2722   gatgggtggccgagatgaaaggctgggtcgtgacagtgaaatc
886         D  G  V  A  E  D  E  R  L  G  R  D  S  E  I
     2767   cataggggaacagatggaacggctagtacgtgaagagttggaacgc
901         H  R  E  Q  M  E  R  L  V  R  E  E  L  E  R
     2812   tgggaatccgatgatgcagcttcccagatcagtcatggtttaggc
916         W  E  S  D  D  A  A  S  Q  I  S  H  G  L  G
     2857   acgccagtgggactaaatggtcaacctcgcccagaagctcccgc
931         T  P  V  G  L  N  G  Q  P  R  P  R  S  S  R
     2902   ccatcttcctcccaatctacagaaggcatggaaggtgcaggtgga
946         P  S  S  S  Q  S  T  E  G  M  E  G  A  G  G
     2947   aatgggagttctaatgtccacgtatga   2973  (SEQ ID NO. 170)
961         N  G  S  S  N  V  H  V  *        (SEQ ID NO. 172)
```

COMPOSITIONS AND METHODS FOR GENETIC ANALYSIS OF POLYCYSTIC KIDNEY DISEASE

RELATED APPLICATIONS

This application is a divisional of U.S. application Ser. No. 10/411,915, filed Apr. 11, 2003, (now U.S. Pat. No. 7,273, 701) which is a continuation-in-part application of U.S. Patent application Ser. 10/083,246, filed Feb. 26, 2002, (now U.S. Pat. No. 6,916,619), which claims benefit to U.S. Provisional Application No. 60/328,739, filed Oct. 12, 2001. The entire teachings of the above applications are incorporated herein by reference.

FIELD OF THE INVENTION

The invention relates to a genetic testing method for identifying alterations or the absence of such alterations in a gene associated with Autosomal Dominant Polycystic Kidney Disease.

BACKGROUND OF THE INVENTION

Autosomal dominant polycystic kidney disease (ADPKD) is an exceptionally common hereditary nephropathology with an incidence of about 1 in 800 live births. The disease is progressive, phenotypically characterized by bilaterally enlarged polycystic kidneys, and typically resulting in end-stage renal disease (ESRD) by the age of 65 years. The more common complications include hypertension, macrohaematuria, urinary-tract infection, cardiac-valve abnormalities, and hernia of the anterior abdominal wall. Cyst formation is also commonly observed in the liver, although the occurrence is not associated with functional impairment of the organ. Although not as frequently reported, additional extrarenal manifestations include pancreatic cysts, connective tissue abnormalities, and cerebral-artery aneurysms.

The typical age of onset is in middle life, but the range is from infancy to 80 years. The clinical presentation of ADPKD differs between and within families as partly explained by the genetically heterogeneous nature of the disorder. Mutations in two genes, PKD-1 and PKD-2, account for nearly all cases of ADPKD (e.g., for reviews, see Arnaout, 2001, Annu Rev. Med. 52:93-123; Koptides and Deltas, 2000, Hum. Genet. 107:115-126). PKD-1 and PKD-2 encode integral membrane proteins whose functions have not been fully elucidated. The major gene responsible for ADPKD, PKD-1, has been fully characterized and shown to encode an integral membrane protein, polycystin 1, which is thought to be involved in cell-cell and cell-matrix interaction. PKD-2 gene encodes polycystin-2 which is a predicted integral membrane protein with non-selective cation channel activity. Based on sequence homology with the alpha 1 subunit component of voltage-activated calcium channels, it has been postulated that polycystin-2 may play a role in ion channeling. The C-terminal cytoplasmic tails of polycystin-1 and polycystin-2 have been shown to interact using in vitro binding assays and in a directed two-hybrid interaction. The interaction occurs via a coiled-coil domain in PKD-1 and a region near R872 in PKD-2. Although the biological relevance of the interaction between the polycystins is not yet understood, it does suggest that PKD-1 and PKD-2 are likely to function along a common pathway.

Both ADPKD type 1 and type 2 share the entire range of renal and extrarenal manifestations, but type 2 appears to have a delayed onset relative to type 1. The common phenotypic complications observed for ADPKD including hypertension, hematuria, and urinary tract infection seem to be clinically milder in type 2 patients. The median age at death or onset of ESRD has been reported as 53 years in individuals with PKD-1 and 69 years in those with PKD-2. Women have been reported to have a significantly longer median survival of 71 years than men (67 years). No sex influence is apparent in PKD-1. Mutations in the PKD-1 gene are the cause of ADPKD in approximately 85% of the cases tested, while those in PKD-2 account for 15%. Although a small subset of families with ADPKD fail to demonstrate genetic linkage to either PKD-1 or PKD-2, raising the possibility of a third gene for ADPKD, the existence of a third disease-associated locus has been strongly challenged.

Despite the discovery of strong links between genetic alterations in PKD genes and the onset of ADPKD, the development of a genetic testing method for ADPKD predisposition for routine clinical use has been hindered by several technical obstacles.

One serious obstacle for developing a DNA-based testing method for ADPKD is that sequences related to the PKD transcript, for example, PKD-1, are duplicated at least three times on chromosome 16 proximal to the PKD-1 locus, forming PKD-1 homologues. Another obstacle is that the PKD-1 genomic interval also contains repeat elements that are present in other genomic regions. In addition, the sequences of PKD genes are extremely GC rich and a large number (15,816 bp) of nucleotides need to be analyzed for a thorough evaluation.

There is a need for the identification of segments of these sequences that are unique to the expressed PKD genes and not are present in the duplicated homologous sequences. There is also a need for developing a sensitive and specific genetic testing method for mutational analysis of PKD genes. The development of such genetic testing method would facilitate the diagnosis and management of ADPKD.

SUMMARY OF THE INVENTION

In one aspect, the present invention provides a method of mutation analysis of a target nucleic acid, the method comprising: incubating a sample comprising the target nucleic acid in a reaction mixture, in the presence of at least one first nucleic acid and at least one second nucleic acid, where the first nucleic acid comprises a primer sequence which anneals to a unique site of a sequence of SEQ ID NO. 1 or 2, and the second nucleic acid has an opposite orientation from the first nucleic acid, and where the incubation produces amplified products; generating duplexes in the amplified products; and detecting the presence or absence of a heteroduplex from the duplexes, where the presence of a heteroduplex indicates the presence of a potential mutation in the target nucleic acid, and where the absence of a heteroduplex indicates the absence of a mutation in the target nucleic acid.

In one embodiment, the method further comprises determining the sequence of a heteroduplex region; and comparing the sequence of the heteroduplex region to SEQ ID NO. 1 or 2; where a sequence difference in the heteroduplex region compared to SEQ ID NO. 1 or 2 resulting in a predicted functional change in the protein encoded by the target nucleic acid is indicative of a mutation in the target nucleic acid.

Preferably, the first or second nucleic acid comprises a sequence selected from the group consisting of SEQ ID NOs. 3-49.

In another embodiment, the method further comprising performing a nested amplification reaction using the amplified products generated by the first and second nucleic acids as templates and generating duplexes in amplified products from the nested amplification.

Preferably, the nested amplification reaction is performed using at least one primer selected from the group consisting of SEQ ID NOs. 3-49 and their complementary sequences.

In a preferred embodiment, the presence or absence of a heteroduplex from the duplexes is identified by DHPLC.

In also a preferred embodiment, the sequence of the heteroduplex region is determined by DNA sequencing.

Preferably, the second nucleic acid of the subject method comprises a primer sequence which anneals to a unique site within a sequence of SEQ ID NO. 1 or 2.

Also preferably, the sample comprising the target template is selected from the group consisting of: genomic DNA, cDNA, total RNA, mRNA, and a cell sample.

In one embodiment, the incubating step comprises an amplification reaction selected from the group consisting of: a polymerase chain reaction, a ligase chain reaction (LCR) and a nucleic acid-specific based amplification.

The subject method of the invention may further comprise confirming the amplified product is a PKD-specific product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In another aspect, the invention provides a diagnosis method for identifying a patient affected with PKD, the method comprising:
(a) obtaining a sample from an individual;
(b) incubating the sample in a reaction mixture, in the presence of at least one first nucleic acid and at least one second nucleic acid, where the first nucleic acid comprises a primer sequence which anneals to a unique site within a sequence of SEQ ID NO. 1 or 2, and the second nucleic acid has an opposite orientation from the first nucleic acid, and where the incubation produces amplified products;
(c) generating duplexes in the amplified products;
(d) detecting the presence or absence of a heteroduplex from the duplexes, and
(e) determining the sequence of the heteroduplex region where the presence of a mutation in the heteroduplex region as compared to SEQ ID No. 1 or 2 is indicative that the individual is affected with PKD.

Preferably, the detection of a hereroduplex is performed by DHPLC.

Also preferably, the sequence is determined by DNA sequencing.

In one embodiment, the second nucleic acid comprises a primer sequence which anneals to a unique site within a sequence of SEQ ID NO. 1 or 2.

In another embodiment, the first or second nucleic acid comprises a primer sequence selected from the group consisting of SEQ ID NOs. 3-49.

The diagnosis method of the invention may further comprise performing a nested amplification reaction using the amplified products generated by the first and second nucleic acids as templates and generating duplexes from the nested amplification.

In one embodiment, the nested amplification reaction is performed using at least one primer selected from the group consisting of SEQ ID NOs. 3-49 and their complementary sequences.

Preferably, the sample in the diagnosis method is selected from the group consisting of: a genomic DNA, cDNA, total RNA, mRNA, and a cell.

Also preferably, the amplification reaction is selected from the group consisting of: a polymerase chain reaction, a ligase chain reaction (LCR) and a nucleic acid-specific based amplification.

The diagnosis method may further comprise verifying the specifically amplified product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In a further aspect, the invention provides one or more nucleic acid primer, where each primer is an isolated nucleic acid selected from the group of SEQ ID NOs 3-49, or the complement thereof.

The invention also provides a pair of nucleic acids, where at least one nucleic acid of the pair is selected from the group of SEQ ID NOs 3-49.

Preferably, the pair of nucleic acids have an opposite orientation and amplify a fragment of a template nucleic acid comprising a sequence of SEQ ID NO. 1 or 2.

In another aspect, the invention provides a composition comprising at least one isolated first nucleic acid and at least one isolated second nucleic acid, where the first nucleic acid is selected from the group of SEQ ID NOs. 3-49 and their complementary sequences, and the second nucleic acid has an opposite orientation from the first nucleic acid, and wherein the first and second nucleic acids amplify a fragment of a template nucleic acid comprising a sequence of SEQ ID NO. 1 or 2.

In one embodiment, the composition of the invention further comprises at least one component selected from the group consisting of: a DNA polymerase, a template nucleic acid, a restriction enzyme, one or more control oligonucleotide primers, ddNTPs, a PCR reaction buffer and their combination thereof.

Preferably, the template nucleic acid in the composition is a genomic DNA or cDNA.

In a further aspect, the invention provides a kit for identifying a PKD patient, the kit comprising at least one isolated first nucleic acid and at least one isolated second nucleic acid, where the first nucleic acid is selected from the group of SEQ ID NOs. 1-49 and their complementary sequences, and the second nucleic acid has an opposite orientation from the first nucleic acid, and where the first and second nucleic acids amplify a fragment of a template nucleic acid comprising a sequence of SEQ ID NO. 1 or 2, and packaging materials therefore.

In one embodiment, the kit of the invention further comprises at least one component selected from the group consisting of: a DNA polymerase, a template nucleic acid, a restriction enzyme, a control oligonucleotide primer, ddNTPs, a PCR reaction buffer and the combination thereof.

Preferably, the template nucleic acid in the kit is a genomic DNA or cDNA molecule.

The invention provides an isolated nucleic acid comprising a sequence selected from the group consisting of SEQ ID NOs. 3-49 and their complementary sequences thereof.

The invention provides a nucleic acid biomarker for ADPKD comprising a PKD-1 or PKD-2 nucleic acid sequence comprising one or more nucleotide alterations as disclosed in FIG. 14A-14CC.

In one embodiment, the at least one of the one or more nucleotide alterations consists of a novel nucleotide alterations as disclosed in FIG. 14A-14CC.

The invention also provides a nucleic acid biomarker for ADPKD comprising a PKD-1 or PKD-2 nucleic acid sequence comprising one or more novel nucleotide alterations as disclosed in FIG. 14A-14CC.

The invention provides a polypeptide biomarker for ADPKD comprising a PKD-1 or PKD-2 polypeptide sequence comprising one or more amino acid alterations as disclosed in FIG. 14A-14CC.

In one embodiment, at least one the one or more amino acid alterations consists of a novel amino acid alteration as disclosed in FIG. 14A-14CC.

The invention provides a polypeptide biomarker for ADPKD comprising a PKD-1 or PKD-2 polypeptide sequence comprising one or more novel amino acid alterations as disclosed in FIG. 14A-14CC.

The present invention further provides a method for diagnosing ADPKD in an individual, comprising identifying nucleotide sequence of PKD-1 or PKD-2 gene of the individual, where the existence of one or more nucleotide sequence alterations in the nucleotide sequence of PKD-1 or PKD-2 gene as disclosed in FIG. 14A-14CC is indicative of ADPKD in the individual.

The present invention further provides a method for determining in an individual the presence or absence of a mutant PKD gene, comprising the steps of a) identifying the nucleotide sequence of a PKD-1 or PKD-2 gene of the individual; b) comparing the nucleotide sequence of step a) to the nucleotide sequence alteration in the nucleotide sequence of a PKD-1 or PKD-2 gene as disclosed in FIG. 14A-14CC; and c) detecting the presence of one or more of the nucleotide sequence alterations disclosed in FIG. 14A-14CC; wherein the presence of at least one of the nucleotide sequence alterations is indicative of ADPKD in the individual; and wherein the absence of any of said nucleotide sequence alterations indicates the absence of a mutant PKD-1 and/or PKD-2 gene.

In one embodiment, the method for diagnosing ADPKD and/or the method for determining the presence or absence of a mutant PKD gene further comprises obtaining a DNA sample from the individual for the identification of nucleotide sequence of PKD-1 or PKD-2 gene.

Preferably the DNA sample obtained is a genomic DNA sample or a cDNA sample.

In another embodiment, the method for diagnosing ADPKD and/or the method for determining the presence or absence of a mutant PKD gene further comprises amplifying a portion of the PKD-1 or PKD-2 gene from the DNA sample before the identification.

Preferably, the portion of the PKD-1 or PKD-2 gene is amplified by a polymerase chain reaction.

Also preferably, the nucleic acid sequence is identified by DNA sequencing.

More preferably, the DNA sequencing is performed using an isolated nucleic acid comprising a sequence selected from the group consisting of SEQ ID NOs. 3-49 and their complementary sequences thereof.

In one embodiment, the at least one or more of the at least one or more nucleotide alterations consists of a novel nucleotide alterations as disclosed in FIG. 14A-14CC.

BRIEF DESCRIPTION OF THE DRAWINGS

The objects and features of the invention can be better understood with reference to the following detailed description and accompanying drawings.

FIG. 1A-1T is a figure showing the PKD1 cDNA sequence (GenBank Accession No. L33243) used in one embodiment of the invention. Exon and PCR product junctions are depicted above the nucleotide sequence. Amino acids are positioned under the center of each codon.

FIG. 2A-2S is a figure showing the comparison of exon sequences of a PKD gene and two homologue sequences according to one embodiment. Restriction enzyme sites which only cleave in either PKD or homologue sequence are indicated.

FIG. 10B is a table showing patient DNA variant genotypes determined in one embodiment of the invention.

FIG. 11A-11D is a table summarizing DHPLC (WAVE) conditions used in some embodiments of the invention.

Figure 12A:
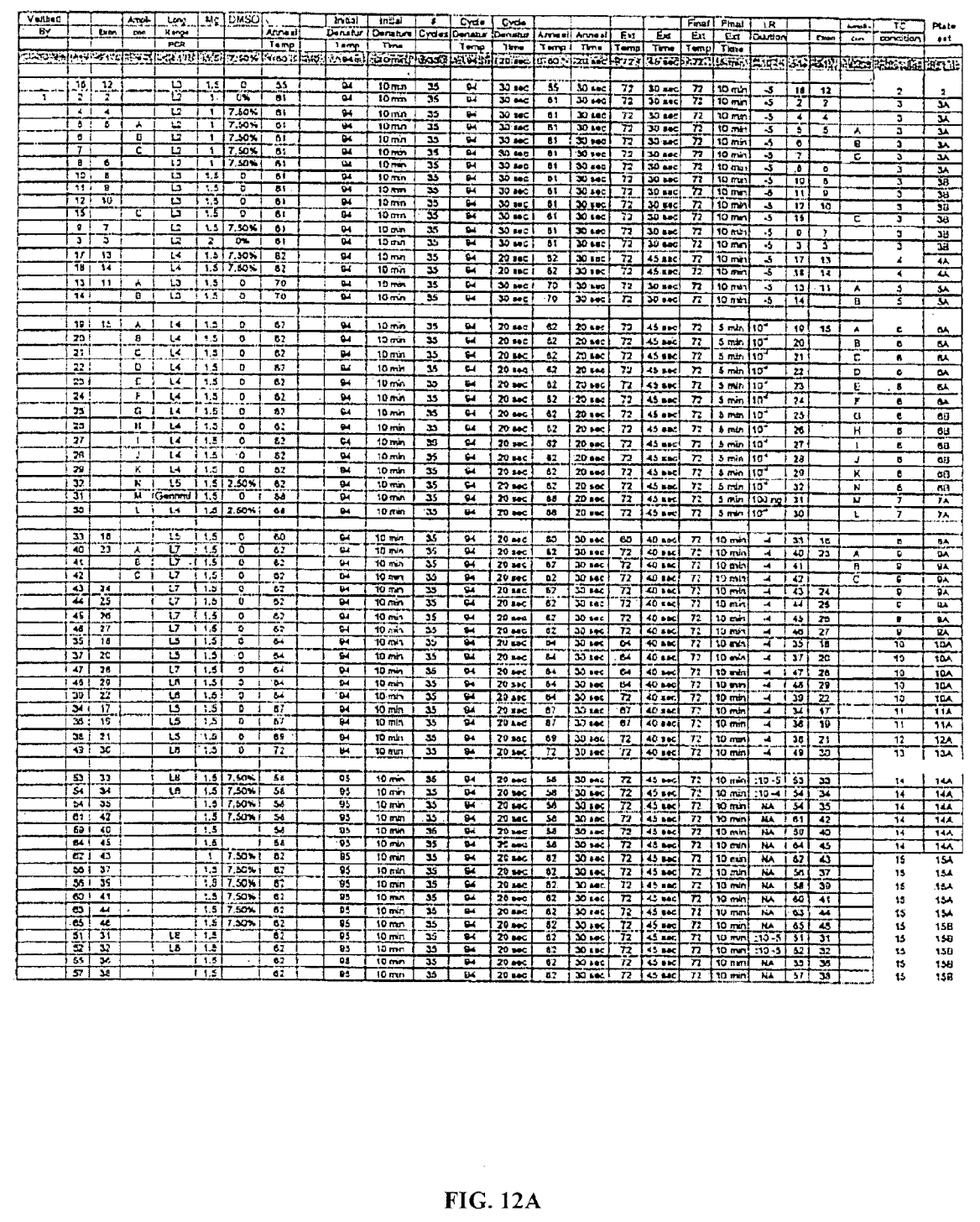
Figure 12B:
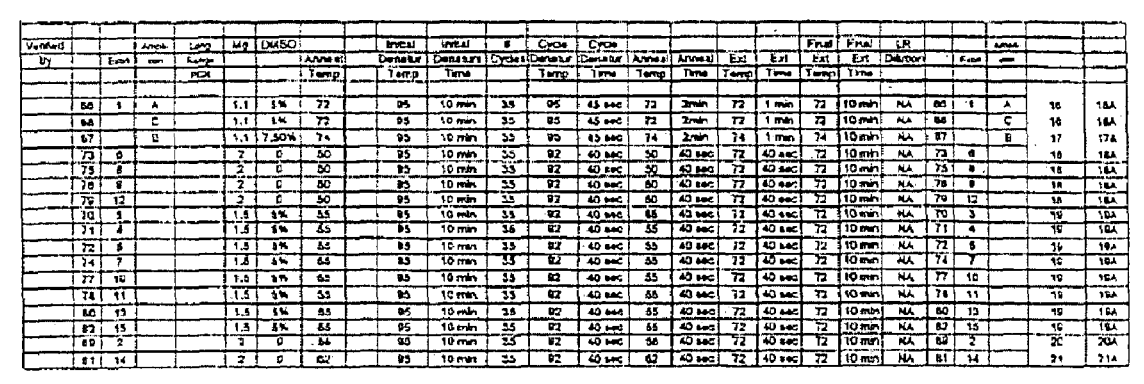

FIG. 12A-12B is a table summarizing PCR conditions used in some embodiments of the invention.

FIG. 14A-14CC is a table showing non-limiting examples of novel and known nucleotide and amino acid alterations identified in PKD-1 and PKD-2 nucleotide and amino acid sequences from ADPKD patients according to one embodiment of the invention. Novel, as used herein, includes the unknown predicted disease causing (UPD) alterations disclosed in bold. X refers to Exon, IVS refers to intervening sequence, KP refers to known polymorphism, UP refers to unknown polymorphism, and UAA refers to unknown amino acid change.

FIG. 15A-15T is a wild-type PKD-1 cDNA sequence according to one embodiment of the invention.

FIG. 16A-16D is a wild-type PKD-2 cDNA sequence according to one embodiment of the invention.

DETAILED DESCRIPTION OF THE INVENTION

Figure 3:
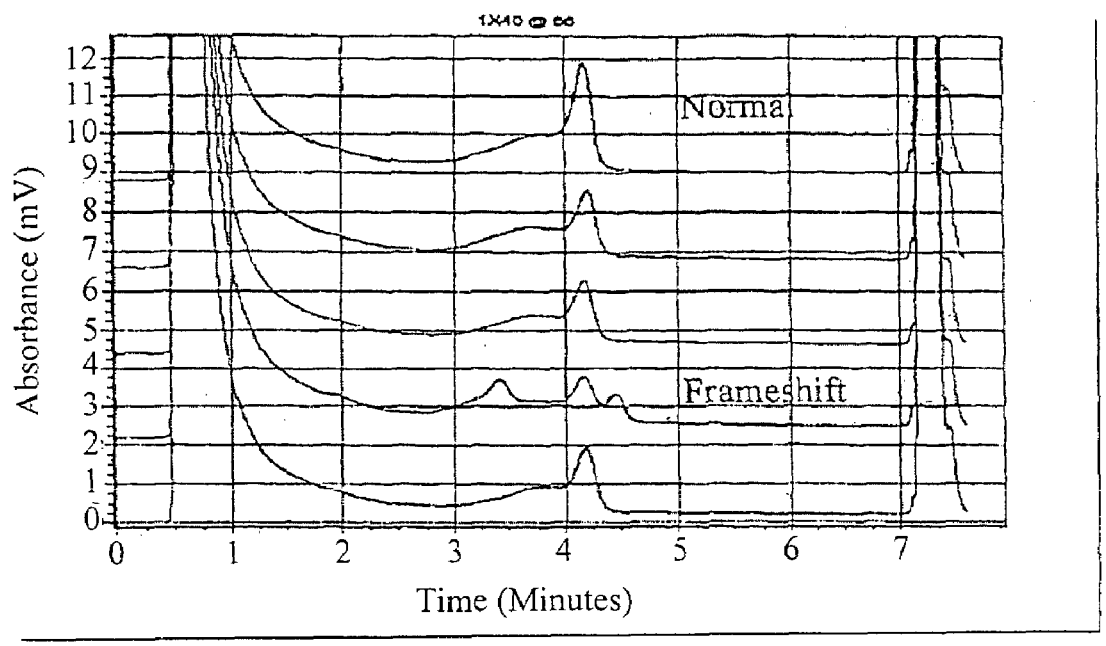
FIG. 3 is a graph showing PKD1 exon 40 DHPLC patterns of 4 normal samples and a 19 bp insertion (duplication) at nucleotide 11606, codon 3799 according to one embodiment.

The subject invention is based on the identification of unique sites within a PKD gene, the design of PKD-specific primers and the DHPLC analysis of PCR products amplified by using these PKD-specific primers.

I. Definitions

As used herein, "ADPKD" refers to autosomal dominant polycystic kidney disease. ADPKD is an exceptionally common hereditary nephropathology and is characterized by the development of renal cysts and, ultimately, renal failure, and may alternatively or in addition involve cysts in other organs including liver and spleen, as well as gastrointestinal, cardiovascular, and musculoskeletal abnormalities.

The term "PKD gene" refers to a genomic DNA sequence which maps to chromosomal position 16p13.3 (i.e., PKD-1) or chromosomal position 4q21-23 (i.e., PKD-2) and gives rise to a messenger RNA molecule encoding a PKD protein. The PKD-1 and PKD-2 genes comprise the sequences of SEQ ID NO. 1 and SEQ ID NO.2, respectively, which include introns and putative regulatory sequences. Like many other genes, PKD-1 and PKD-2 gene sequences, when compared among individuals, show sequence variations. Those genes having polymorphisms which are silent (i.e., with respect to gene expression or function of a gene product) are "normal" genes as defined herein.

A "normal" PKD gene (e.g., PKD-1 or PKD-2) is defined herein as a PKD gene such as described by SEQ ID NO. 1 or 2, respectively, and includes any gene having silent polymorphisms.

A "mutant" PKD gene is defined herein as a PKD gene (e.g., PKD-1 or PKD-2) whose sequence is modified by mutation comprising one or more substitutions (transitions or transversions), deletions (including loss of locus), insertions (including duplications), translocations, and/or other modifications relative to the normal PKD gene. The mutation causes detectable changes in the expression or function of the PKD gene product, and is causative for ADPKD. The mutations may involve from one to as many as several thousand nucleotides, and result in one or more of a variety of changes in PKD gene expression (e.g. decreased or increased rates of expression) or expression of a defective RNA transcript or protein product. Mutant PKD genes encompass those genes whose presence in one or more copies in the genome of a human individual is associated with ADPKD.

As used herein, "biomarker" refers to a biological molecule, e.g., a nucleic acid or polypeptide or peptide etc . . . whose presence or concentration can be detected and correlated with a known condition, such as a disease state, for example polycystic kidney disease, and in particular, ADPKD.

A "nucleotide sequence alteration" or "nucleotide alteration" refers to a nucleotide sequence modification including one or more substitutions (transitions or transversions), deletions (including loss of locus), insertions (including duplications), translocations, and/or other modifications relative to the normal PKD gene.

An "amino acid alteration" refers to an amino acid modification including a substitution, a frameshift, a deletion, a truncation and an insertion, and/or other modifications relative to the normal PKD amino acid sequence.

The term "basepair mismatch" refers to any nucleic acid sequence which is not complementary to the sequence of SEQ ID. NO. 1 or 2. Therefore, basepair mismatch, according to the present invention may be caused by gene alteration or polymorphism of a normal PKD gene; or by any modifications present in a mutant PKD gene. "Basepair mismatch" may be a single nucleotide basepair mismatch or it may include a nucleic acid sequence of 2 or more nucleotides (i.e., 3, or 4, or 5, or 10, or 20, or 100, or 500 more, or up to 1000 nucleotides). The presence or absence of a mismatch, as defined herein, is indicative of the presence or absence of a potential mutation in the target nucleic acid.

The term "authentic" is used herein to denote the genomic sequence of SEQ ID. NO. 1 or 2, as well as sequences derived therefrom, and serves to distinguish these authentic sequences from "PKD homologues" (see below).

A "PKD-1 homologue" is a sequence which is closely related to PKD-1, but which does not encode an expressed PKD-1 gene product. Several examples of such homologues that map to chromosomal location 16p13.1 or 4q21-23 have been identified and sequenced. A PKD-1 homologue may share more than 95% sequence identity to an authentic PKD gene.

As used herein, a "specifically amplified product" is a product amplified from a fragment within an authentic PKD gene (e.g., SEQ ID NO. 1 or 2), but not from a PKD homologue. A "non-specifically amplified product" is a product amplified from a PKD homologue or other sequences due to the annealing of nucleic acid primers to a template sequence which is not completely complementary during the amplification reaction.

As used herein, a "unique site" refers to a stretch of sequence of 10-50 base pairs in length within a PKD gene which comprises at least one nucleotide different form a stretch of sequence in a PKD homologue or other sequences. One exemplary unique site comprises a sequence of 5' AGG TCC AGG GCG ACT CGC TGG 3', or 5' CAG GGC CAC ACG CGC TGG GCG 3', or their complement thereof.

As used herein, a "PKD-specific primer" refers to a nucleic acid sequence which anneals to a sequence within a PKD gene (including introns and exons) under specific stringent conditions. A PKD-specific primer, according to the invention, anneals to a unique site present in the authentic expressed PKD-1 gene or PKD-2 gene, and not to PKD homologues or other sequences under specific stringent conditions. A PKD-specific primer shares more then 95% (e.g., more than 96%, 96%, 97%, 98%, 99%, or up to 100%) sequence identity with a unique site within a PKD gene. A "PKD-specific primer" may be 10 to 60 nucleotides in length, for example, 18-52 nucleotides in length.

As used herein, the term "specific stringent condition" refers to an amplification condition which specifically allows the annealing of a PKD-specific primer to a sequence within a PKD gene. Under a "specific stringent condition", a PKD-specific primer does not anneal to a PKD homologue or other sequences. For example, one specific stringent condition useful to the invention comprises a Taq Precision buffer (TaqPlus Precision buffer, Stratagene, La Jolla, Cat#600210), a dNTP concentration of more than 50 nM, for example, 100 nM, 200 nM, or 300 nM. The annealing temperature in a specific stringent condition may be higher than or less than or equal to 5° C. below the lowest primer annealing temperature (Tm), for example, 1° C., 2° C., 4° C., 5° C., or 10° C. higher than Tm or 4° C., 3° C., 2° C., or 1° C. below Tm.

"Amplification" of DNA as used herein refers to a reaction that serves to increase the concentration of a particular DNA sequence within a mixture of DNA sequences. Amplification may be carried out using polymerase chain reaction (PCR), ligase chain reaction (LCR), nucleic acid-specific based amplification (NSBA), or any other method known in the art.

"RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

A "template nucleic acid" or a "target nucleic acid" (e.g., a genomic DNA or a cDNA), is a normal (e.g., wild type) or a mutant nucleic acid that is or includes a particular sequence (e.g. a PKD-1 or PKD-2 gene sequence). It will be understood that additional nucleotides may be added to the 5' and/or 3' terminus of the disclosed sequence, as part of routine recombinant DNA manipulations. Furthermore, conservative DNA substitutions i.e. changes in the sequence of the protein-coding region that do not change the encoded amino acid sequence, also may be accommodated.

As used herein, "nucleic acid primer" refers to a DNA or RNA molecule capable of annealing to a nucleic acid template and providing a 3' end to produce an extension product which is complementary to the nucleic acid template. The nucleic acid template is catalyzed to produce a primer extension product which is complementary to the target nucleic acid template. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single or double stranded. The primer is single-stranded for maximum efficiency in amplification, and the primer and its complement form a double-stranded nucleic acid. But it may be double stranded. "Primers" useful in the present invention are less than or equal to 100 nucleotides in length, e.g., less than or equal to 90, or 80, or 70, or 60, or 50, or 40, or 30, or 20, or 15, or equal to 10 nucleotides in length.

As used herein, the term "opposite orientation", when referring to primers, means that one primer comprises a nucleotide sequence complementary to the sense strand of a target nucleic acid template, and another primer comprises a nucleotide sequence complementary to the antisense strand of the same target nucleic acid template. Primers with an opposite orientation may generate a PCR amplified product from matched nucleic acid template to which they complement. Two primers with opposite orientation may be referred to as a reverse primer and a forward primer.

As used herein, the term "same orientation", means that primers comprise nucleotide sequences complementary to the same strand of a target nucleic acid template. Primers with same orientation will not generate a PCR amplified product from matched nucleic acid template to which they complement.

Alternatively, primers of the present invention may be labeled with a detectable label such as a radioactive moiety, or a fluorescent label, or alternatively, the amplification reaction may incorporate labeled nucleotides into the reaction product. Thus, the amplification reaction product may be "detected" by "detecting" the fluorescent or radioactive label.

As used herein, a "nucleic acid" generally refers to any polyribonucleotide or poly-deoxyribonucleotide, which may be unmodified RNA or DNA or modified RNA or DNA. "Nucleic acids" include, without limitation, single- and double-stranded nucleic acids. As used herein, the term "nucleic acid(s)" also includes DNAs or RNAs as described above, that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95%, up to 99-100% pure) of non-nucleotide or nucleic acid material naturally associated with it, and thus is distinguished from isolated chromosomes.

As used herein, "genomic DNA" refers to chromosomal DNA, as opposed to complementary DNA copied from an RNA transcript. "Genomic DNA", as used herein, may be all of the DNA present in a single cell, or may be a portion of the DNA in a single cell.

As used herein, "complementary" refers to the ability of a single strand of a nucleic acid (or portion thereof) to hybridize to an anti-parallel nucleic acid strand (or portion thereof) by contiguous base-pairing between the nucleotides (that is not interrupted by any unpaired nucleotides) of the anti-parallel nucleic acid single strands, thereby forming a double-stranded nucleic acid between the complementary strands. A first nucleic acid is said to be "completely complementary" to a second nucleic acid strand if each and every nucleotide of the first nucleic acid forms base-pairing with nucleotides within the complementary region of the second nucleic acid. A first nucleic acid is not completely complementary to the second nucleic acid if one nucleotide in the first nucleic acid does not base pair with the corresponding nucleotide in the second nucleic acid.

As used herein, a "sample" refers to a biological material which is isolated from its natural environment and containing target nucleic acid, and may consist of purified or isolated nucleic acid, or may comprise a biological sample such as a tissue sample, a biological fluid sample, or a cell sample comprising target nucleic acid.

As used herein, a "double stranded DNA" is referred to as a "duplex". When the base sequence of one strand is entirely complementary to base sequence of the other strand, the duplex is called a "homoduplex". When a duplex contains at least one base pair which is not complementary, the duplex is called a "heteroduplex". In the subject invention, the formation of a heteroduplex, when amplified products from a sample taken from an individual are denatured and re-annealed, indicates the presence of a potential mutant PKD gene in that individual.

As used herein, "DHPLC" refers to a separation process called "denaturing high performance liquid chromatography" which has been used to detect sequence variants by separating a heteroduplex (resulting from the presence of a mutation) and a homoduplex having the same bp length. This separation is based on the fact that a heteroduplex has a lower melting temperature (Tm) than a homoduplex. DHPLC can separate heteroduplexes that differ by as little as one base pair under certain conditions. DHPLC can also be used to separate duplexes having different bp in length.

The "heteroduplex site separation temperature" or "midpoint temperature" or "Tm" is defined herein to mean, the temperature at which one or more base pairs denature, i.e., separate, at the site of base pair mismatch in a heteroduplex DNA fragment.

II. General Description of PKD Genes

The PKD-1 gene (e.g., genbank accession number L39891, SEQ ID NO. 1) spans about 54 kb of genomic DNA on chromosome 16 (16p13.3) and contains a 12,906 bp coding sequence divided into 46 exons from which a 14 kb mRNA is transcribed (Mochizuki et al., 1996, Science, 272:1339-1342; Hughes et al., 1995, Nature Genet. 10:151-160). The protein product of PKD-1, Polycystin-1, is a 4303 amino acid protein with a predicted mass of 460 kDa. Until recently, analysis of the PKD-1 gene had not been amenable to genetic analysis largely because of the presence of at least three highly homologous copies of the gene that map proximal to PKD-1 along chromosome 16 (16p13.1). Approximately 75% of the PKD-1 gene is duplicated and shares about 97% identity with its homologous copies. The reiterated region encompasses a 50 kb (5') portion of the gene containing the first 33 exons. Only the most 3', 5.7 kb of the gene, containing exons 34-46, is unique to PKD-1. Another notable feature of the PKD-1 gene is a polypyrimidine tract in intron 21 that is 2.5 kb long, the longest described in the human genome. The PKD-2 gene (e.g., genbank accession number AF004859-004873, SEQ ID NO. 2) spans 68 kb of genomic DNA and is located on chromosome 4 (4q21-23) (Mochizuki et al., 1996, supra). PKD-2 contains 15 exons and encodes a 5.4 kb transcript from which a 968-amino acid protein product of approximately 110 kDa is generated. Mutation analysis of PKD-2 is to a great extent easier than that of PKD-1 because PKD-2 is a single copy gene. See Table 1 for a summary of PKD genes and their protein products.

TABLE 1

PKD gene description

| Gene Description | PKD-1 | PKD-2 |
|---|---|---|
| Chromosome | 16p13.3 | 4q21-23 |
| Genomic length | 54 kb | 68 kb |
| Exons | 46 | 15 |
| Base pairs | 12909 | 2904 |
| Codons | 4303 | 968 |
| Protein | Polycystin-1 | Polycystin-2 |

Based on evidence supporting the occurrence of somatic mutations on the normal allele, a two-hit model similar to the pathogenesis of the many familial cancer predisposition syndromes has been proposed to explain the clinically focal manifestations of the disease (Qian et al., 1996, Cell, 87:979-987; Watnick et al., 1998 Mol. Cell. 2:247-251). Briefly, the model suggests that ADPKD is recessive at the cellular level and that a second somatic mutation or "hit" in a heterozygous PKD defective background would result in the homozygous loss of PKD function in the affected renal tubular epithelial cell. The loss of PKD function is postulated to disrupt the signaling mechanisms required for proper cell differentiation and in turn leads to the abnormal proliferation of the afflicted cell into cystic structures.

Direct sequencing of the PKD-1 gene has revealed the presence of polymorphism in normal individuals and a multitude of different sequence alterations in ADPKD affected individuals. Table 2 shows a sypnosis of the PKD-1 sequence alterations described in the literature to date.

TABLE 2

Published PKD-1 sequence alterations including mutations and polymorphisms*

| Codon Number | Nucleotide Number | Fragment number | Nucleotide Change | Amino Acid Change | Consequence |
|---|---|---|---|---|---|
|  |  | Intron 1-Exon 5 | 3kb del |  |  |
| 5 | 224 | 1 | 13del |  | frameshift |
| 88 | 474 | 2 | GCG-GTG | Ala-Val |  |
| 92 | 487 | 2 | GCG-GCA | Ala—Ala | polymorphism |
| 225 | 885 | 5A + 5B | TCG-TAG | Ser-X | termination |
| 227 | 890 | 5A + 5B | CAG-TAG | Gln-X | termination |
| 230 | 900 | 5A + 5B | TGC-TTC | Cys-Phe |  |
| 324 | 1182 | 5B + 5C | CGC-CTC | Arg-Leu |  |
| 341 | 1234 | 5C | GCC-GCT | Ala—Ala | polymorphism |
| 373 | 1330 | 5C | CTT-CTC | Leu—Leu | polymorphism |
| 403 | 1420 | 6 | CAC-CAT | His—His | polymorphism |
|  |  | 7 | CAG-CAA | splice acceptor | skip exon 7 |
| 570 | 1921 | 8 | CAC-CAT | His—His | polymorphism |
|  |  | 9 | CAG-CAT | splice acceptor | skip exon 9 |
| 695 | 2296 | 10 | C del = ccc-cc^g | Pro—Pro | frameshift |
| 695 | 2296 | 10 | C ins = ccc-cc^c | Pro—Pro | frameshift |
| 705 | 2324 | 11A | CAG-TAG | Gln-X | termination |
| 738 | 2425 | 11A | CCC-CCG | Pro—Pro | polymorphism |
| 749 | 2457 | 11A | TCA-TGA | Ser-X | termination |
| 845 | 2745 | 11B | TTG-TCG | Leu-Ser |  |
| 898 | 2905 | 11B + 11C | GCA-GCC | Ala—Ala | polymorphism |
| 900 | 2911 | 11B + 11C | CCG-CCA | Pro—Pro | polymorphism |
| 910 | 2941 | 11B + 11C | GAC-GAT | Asp—Asp | polymorphism |
| 967 | 3110 | 12 | TGG-CGG | Trp-Arg |  |
| 991 | 3183 | 12 | GTC-GGC | Val—Val | polymorphism |
|  |  | 13 | AGC-TGC | splice acceptor | skip exon 13 |
| 1003 | 3220 | 13 | 4 bp del = agc-ag^g | Ser-Arg | frameshift |
| 1021 | 3274 | 13 | GGT-GGC | Gly—Gly | polymorphism |
| 1037 | 3322 | 13 | CTA-CTG | Leu—Leu | polymorphism |
| 1041 | 3336 | 13 | del g = ggc-g^cg | Gly-Ala | frameshift |
|  |  | 14 | AGG-AAG | splice acceptor | skip exon 14 |
| 1092 | 3486 | 14 | CAT-CAC | His—His | polymorphism |
| 1124 | 3583 | 15A | GCC-GCT | Ala—Ala | polymorphism |
| 1125 | 3586 | 15A | TCC-TCT | Ser—Ser | polymorphism |
| 1166 | 3707 | 15A + 15B | GGC-AGC | Gly-Ser | probable path. |
| 1198 | 3804 | 15B | 7 bp del = agc-a^gg | Ser-Arg | frameshift |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 1288 | 4075 | 15C + 15D | CAC-CAT | His—His | polymorphism |
| 1289 | 4077 | 15C + 15D | t del = gtg-g^gc | Val-Gly | frameshift |
| 1309 | 4137 | 15D | ct del = cct-c^ga | Pro-Arg | frameshift |
| 1346 | 4249 | 15D | ac del = aca-ac^a | Thr—Thr | frameshift |
| 1360 | 4291 | 15D + 15E | g del = gtg-gt^c | Val—Val | frameshift |
| 1399 | 4406 | 15E | TGG-CGG | Trp-Arg | |
| 1525 | 4784 | 15G | g del = gtt-^tta | Val-Leu | frameshift |
| 1537 | 4820 | 15G | GAG-TAG | Glu-X | termination |
| 1545 | 4846 | 15G | AAG-AAA | Lys—Lys | polymorphism |
| 1555 | 4876 | 15G + 15H | GCA-GCC | Ala—Ala | polymorphism |
| 1558 | 4885 | 15G + 15H | ACG-ACA | Thr—Thr | polymorphism |
| 1563 | 4898 | 15O + 15H | t ins = aat-a^ta | Asn-Ile | frameshift |
| 1633 | 5109 | 15I | t ins = gag-gatg | Glu-Asp | frameshift |
| 1653 | 5168 | 15I | CAG-TAG | Gln-X | termination |
| 1672 | 5225 | 15I + 15J | a del = agg-^ggg | Arg-Gly | frameshift |
| 1672 | 5225 | 15I + 15J | ag del = agg-^ggg | Arg-Gly | frameshift |
| 1724 | 5383 | 15J | ACC-ACT | Thr—Thr | polymorphism |
| 1786 | 5566 | 15J + 15K | CCG-CTG | Pro-Leu | |
| 1787 | 5570 | 15J + 15K | CTG-TTG | Leu—Leu | polymorphism |
| 1826 | 5689 | 15K | TGG-TGA | Trp-X | termination |
| 1829 | 5696 | 15K | CTG-TTG | Leu—Leu | polymorphism |
| 1858 | 5783 | 15K | g del = gat-^atg | Asp-Met | frameshift |
| 1874 | 5833 | 15K | TGG-TGA | Trp-X | termination |
| 1887 | 5870 | 15K | 14del = ccatc-cc^gct | Ile-Val | frameshift |
| 1921 | 5974 | 15L | CTG-CTA | Leu—Leu | polymorphism |
| 1922 | 5975 | 15L | CAG-TAG | Gln-X | termination |
| 1938 | 6024 | 15L | 1 bp ins = cac-ca^** | His-** | frameshift |
| 1949 | 6058 | 15L | AGC-AGT | Ser—Ser | polymorphism |
| 1956 | 6078 | 15L | GTG-GAG | Val-Glu | probable path. |
| 1960 | 6089 | 15L | CAG-TAG | Gln-X | termination |
| 1992 | 6187 | 15L | 4 bp del = ttc-tt^ | ** | frameshift |
| 1995 | 6195 | 15L | CGC-CAC | Arg-His | polymorphism |
| 2039 | 6326 | 15M + 15L | CAG-TAG | Gln-X | termination |
| 2075 | 6434 | 15M | 28 bp del | | frameshift |
| 2144 | 6642 | 15M | 27 bp del | | frameshift |
| 2163 | 6698 | 15M | CGA-TGA | Arg-X | termination |
| 2192 | 6785 | 15M + 15N | 7 bp del = acc-^gct | Thr-Ala | frameshift |
| 2220 | 6868 | 15N | 15 bp del = cgg-^gtg | Arg-Val | in frame deletion |
| 2222 | 6876 | 15N | GCG-GTG | Ala-Val | |
| 2229 | 6898 | 15N | TGC-TGA | Cys-X | termination |
| 2242 | 6937 | 15N | ac del = aca-ac^a | Thr—Thr | frameshift |
| 2243 | 6938 | 15N | CAG-TAG | Gln-X | termination |
| 2250 | 6960 | 15N | ACG-ATG | Thr-Met | |
| | | 15 | GGT-GGG | splice donor | |
| | | 16 | CAG-GAG | splice acceptor | skip exon16 |
| 2309 | 7138 | 16 | GGC-GGT | Gly—Gly | polymorphism |
| 2113 | 7147 | 16 | GCG-GCA | Ala—Ala | polymorphism |
| 2323 | 7179 | 16 | 14 bp del = gtc-gt^ | Val-X | termination |
| 2329 | 7196 | 16 | CGG-TGG | Arg-Trp | |
| 2332 | 7205 | 16 | 7del = gct-^tgg | Ala-Trp | frameshift |
| 2334 | 7211 | 16 | 7ins = gtg-^gtg | Val—Val | frameshift |
| 2336 | 7219 | 16 | TAC-TAA | Tyr-X | termination |
| | | 17 | CAG-GAG | splice acceptor | skip exon 17 |
| 2370 | 7321 | 17 | TGT-TGA | Cys-X | termination |
| 2371 | 7324 | 17 | gt del = gtg-gt^c | Val—Val | frameshift |
| 2378 | 7345 | 17 | GTG-GTT | Val—Val | polymorphism |
| 2379 | 7347 | 17 | TAC-TGC | Tyr-Cys | |
| 2389 | 7376 | 17 | TTG-CTG | Leu—Leu | polymorphism |
| 2392 | 7386 | 17 | CGC-CCC | Arg-Pro | |
| 2396 | 7397 | 17 | 11 bp ins = att-^ttg | Ile-Leu | frameshift |
| 2402 | 7415 | 17 | CGA-TGA | Arg-X | termination |
| 2408 | 7433 | 18 | CGT-TGT | Arg-Cys | probable path. |
| 2423 | 7479 | 18 | TCC-TTC | Ser-Phe | |
| 2430 | 7499 | 18 | CGA-TGA | Arg-X | termination |
| 2442 | 7535 | 18 | 3 bp ins = gag-g^gcg | Glu-Gly | probable path. |
| 2471 | 7623 | 18 | CCG-CTG | Pro-Leu | |
| 2481 | 7652 | 18 | CTG-TTG | Leu—Leu | polymorphism |
| 2495 | 7696 | 18 | TGC-TGT | Cys—Cys | polymorphism |
| 2519 | 7767 | 19 | CAG-CTG | Gln-Leu | |
| 2548 | 7853 | 19 | GAG-CAG | Glu-Gln | polymorphism |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 2558 | 7883 | 19 | CAG-TAG | Gln-X | termination |
| 2570 | 7919 | 20 | TTG-CTG | Leu—Leu | polymorphism |
| 2579 | 7945 | 20 | ggc del = ggc-^agc | Gly-Ser | Gly del in frame |
| 2582 | 7956 | 20 | ACG-ATG | Thr-Met | polymorphism |
| 2597 | 8002 | 20 | CCA-CCG | Pro—Pro | polymorphism |
| 2604 | 8021 | 20 | GAT-AAT | Asp-Asn | polymorphism |
| 2607 | 8030 | 20 | 5 bp del = cac-^cat | His—His | frameshift |
| 2612 | 8046 | 20 | gtt del = tcgtt-tc^g | Ser—Ser | Leu del in frame |
| 2638 | 8124 | 21 | CAC-CGC | His-Arg | polymorphism |
| 2639 | 8126 | 21 | CGA-TGA | Arg-X | termination |
| 2639 | 8126 | 21 | 20 ins = cga-c^**** | Arg-** | frameshift |
| 2649 | 8157 | 21 | ACT-ATT | Thr-Ile | |
| 2650 | 8159 | 21 | del ct = ctg-^ggt | Leu-Gly | frameshift |
| 2658 | 8183 | 21 | 8 bp del | Val-X | termination |
| 2674 | 8231 | 22 | CCC-TCC | Pro-Ser | polymorphism |
| 2696 | 8298 | 22 | CTC-CGC | Leu-Arg | |
| 2708 | 8334 | 22 | ACG-ATG | Thr-Met | polymorphism |
| 2734 | 8411 | 23A | CCA-ACA | Pro-Thr | polymorphism |
| 2735 | 8415 | 23A | CAG-CTG | Gln-Leu | polymorphism |
| 2745 | 8446 | 23A | TCT-TCG | Ser—Ser | polymorphism |
| 2760 | 8490 | 23A | ATG-ACG | Met-Thr | |
| 2761 | 8493 | 23A | CGC-CCC | Arg-Pro | |
| 2763 | 8498 | 23A | CTC-GTC | Leu-Val | |
| 2764 | 8502 | 23A | ATG-ACG | Met-Thr | |
| 2765 | 8504 | 23A | CGC-TGC | Arg-Cys | |
| 2766 | 8507 | 23A | 12 bp ins/dup | | polymorphism in frame mutation |
| 2782 | 8556 | 23A | GTG-ATG | Val-Met | polymorphism |
| 2791 | 8583 | 23A + 23B | CGG-CAG | Arg-Gln | |
| 2813 | 8650 | 23A + 23B | AGC-AGT | Ser—Ser | polymorphism |
| 2814 | 8651 | 23A + 23B | GGG-AGG | Gly-Arg | polymorphism |
| 2815 | 8657 | 23A + 23B | c del = gcc-g^cc | Ala—Ala | frameshift |
| 2826 | 8688 | 23B + 23C | ATC-ACC | Ile-Thr | |
| 2888 | 8873 | 23C | CGC-GGC | Arg-Gly | polymorphism |
| 2893 | 8890 | 23C | TCC-TCG | Ser-Ser | polymorphism |
| 2900 | 8909 | 23C | CAG-TAG | Gln-X | termination |
| 2905 | 8924 | 23C | GTC-ATC | Val-Ile | polymorphism |
| 2921 | 8973 | 23C | CAT-CCT | His-Pro | |
| 2966 | 9109 | 24 | GAG-GAC | Glu-Asp | polymorphism |
| 2971 | 9124 | 24 | GCT-GCC | Ala—Ala | polymorphism |
| 2972 | 9125 | 24 | GAC-AAC | Asp-Asn | polymorphism |
| 2978 | 9142 | 24 | ttc del | del of Phe | in frame deletion |
| 2985 | 9164 | 25 | AGA-GGA | Arg-Gly | |
| 2988 | 9175 | 25 | GCG-GCA | Ala—Ala | polymorphism |
| 2993 | 9189 | 25 | CTG-CCG | Leu-Pro | probable path. |
| 3001 | 9213 | 25 | TGG-TAG | Trp-X | termination |
| 3008 | 9233 | 25 | GTG-CTG | Val-Leu | |
| 3012 | 9245 | 25 | 18 bp del | | in frame deletion |
| 3016 | 9258 | 25 | CAG-CGG | Gln-Arg | probable path. |
| 3020 | 9269 | 25 | GAG-TAG | Glu-X | termination |
| 3030 | 9299 | 25 | c del = ctg-^tgc | Leu-Cys | frameshift |
| 2985 | 9326 | 25 | CGC-TCG | Arg-Cys | |
| 3052 | 9367 | 25 | GGC-GGT | Gly—Gly | polymorphism |
| 3064 | 9401 | 25 | TTT-CTT | Phe-Leu | |
| 3065 | 9406 | 25 | GTTT-CCTT | Phe-Leu | polymorphism |
| 3065 | 9406 | 25 | GTG-GTC | Val—Val | polymorphism |
| 3066 | 9407 | 25 | TTT-CTT | Phe-Leu | polymorphism |
| 3090 | 9481 | 26 | GTC-GTT | Val—Val | polymorphism |
| 3110 | 9541 | 26 | CCT-CCC | Pro—Pro | polymorphism |
| 3139 | 9627 | 27 | GGC-TGC | Gly-Cys | |
| 3180 | 9751 | 27 | TGG-TGA | Trp-X | termination |
| 3193 | 9789 | 28 | CCT-CTT | Pro-Leu | |
| 3206 | 9827 | 28 | CAG-TAG | Gln-X | termination |
| 3219 | 9867 | 28 | t del = ctt-c^tt | Leu-Leu | frameshift |
| 3223 | 9880 | 28 | ACG-ACA | Thr—Thr | polymorphism |
| 3285 | 10064 | 29 | GTT-ATT | Val-Ile | |
| 3311 | 10143 | 30 | CAT-CGT | His-Arg | |
| 3341 | 10234 | 30 | CTT-CTC | Leu—Leu | polymorphism |
| 3348 | 10255 | 30 | CGG-CGT | Arg—Arg | polymorphism |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 3350 | 10262 | 31–34 | 2kb del | | frameshift after 3350 |
| 3375 | 10334 | 31 | GTG-ATG | Val-Met | |
| | | IVS31 + 25del19 | | | frameshift after 3389 |
| 3394 | 10391 | 32 | CAG-TAG | Gln-X | termination |
| | | 34-3'UTR | 5.5kb del | | |
| 3474 | 10631 | 34 | CAG-TAG | Gln-X | termination |
| 3509 | 10737 | 35 | ACG-ATG | Thr-Met | polymorphism |
| 3510 | 10739 | 35 | CTG-GTG | Leu-Val | probable path. |
| 3511 | 10743 | 35 | GCG-GTG | Ala-Val | |
| 3513 | 10748 | 35 | CAG-TAG | Gln-X | termination |
| 3561 | 10893 | 36 | AGC-AAC | Ser-Asn | probable poly. |
| 3579 | 10947 | 36 | t ins = ttc-tt^t | Phe—Phe | frameshift |
| 3589 | 10976 | 36 | CTG-TTG | Leu—Leu | polymorphism |
| | IVS37-10C-A | intron 37 | | | unknown poly |
| 3631 | 11104 | 37 | GAG-GAC | Glu-Asp | |
| 3677 | 11241 | 38 | ATG-ACG | Met-Thr | |
| 3692 | 11284 | 38 | t ins = ggc-gg^t | Gly—Gly | frameshift |
| 3692 | 11285 | 38 | c ins = tca-^ctc | Ser-Leu | frameshift |
| 3711 | 11342 | 38 | CGG-GGG | Arg-Gly | frameshift |
| 3747 | 11449 | 39 | 15 bp del = cgg-^cgg | Arg—Arg | in frame deletion |
| 3749 | 11457 | 39 | 15 bp del = gcg-^cag | Arg-Gln | in frame deletion |
| 3752 | 11466 | 39 | CGG-CAG | Arg-Gln | |
| | | IVS39 + 1G-C | Ggt-Gct | splice donor | |
| | | 139E40 − 25 to 139E40 + 47 | 72 bp del | | |
| 3370 | 11521 | 40 | TCG-TCA | Ser—Ser | polymorphism |
| 3780 | 11549 | 40 | 10 bp ins = tac-t^ac | Tyr—Tyr | frameshift |
| 3781 | 11554 | 40 | GAC-GAT | Asp—Asp | polymorphism |
| 3791 | 11584 | 40 | TCG-TCC | Ser—Ser | polymorphism |
| 3794 | 11592 | 40 | TGG-TAG | Trp-X | termination |
| | IVS41-11C-T | intron 41 | | | unknown poly |
| 3818 | 11665 | 41 | TAC-TAA | Tyr-X | termination |
| 3820 | 11669 | 41 | CAG-TAG | Gln-X | termination |
| 3837 | 11720 | 41 | CAG-TAG | Gln-X | termination |
| 3971 | 12124 | 43 | CGC-CGT | Arg—Arg | polymorphism |
| 3984 | 12163 | 43 | TCC-TCG | Ser—Ser | polymorphism |
| 3985 | 12165 | 43 | GCA-GGA | Ala-Glu | |
| 3985 | 12168 | 43 | GCC-GGG | Ala-Gly | probable poly. |
| 3991 | 12184 | 43 | GCC-GCG | Ala—Ala | polymorphism |
| | 12187 | 43 | 9 bp ins | | in frame |
| | | IVS43 + 14del20 | | | complex splicing |
| | | IVS43 + 17del18 | | | complex splicing |
| | | 44 | CAG-CAC | splice acceptor | skip exon 44 |
| 4010 | 12239 | 44 | CAG-TAG | Gln-X | termination |
| 4011 | 12244 | 44 | TGG-TGA | Trp-X | termination |
| 4014 | 12252 | 44 | tt del = ttt-t^gg | Phe-Trp | frameshift |
| 4017 | 12262 | 44 | at del = aca-ac^t | Thr—Thr | frameshift |
| 4020 | 12269 | 44 | CGA-TGA | Arg-X | termination |
| 4024 | 12281 | 44 | GAG-TAG | Glu-X | termination |
| 4027 | 12290 | 44 | g ins = ggg-gg^g | Gly—Gly | frameshift |
| 4031 | 12303 | 44 | GGC-GAC | Gly-Asp | |
| 4032 | 12307 | 44 | CTG-CTC | Leu—Leu | polymorphism |
| 4039 | 12328 | 44 | TAC-TAA | Tyr-X | termination |
| 4041 | 12332 | 44 | CAG-TAG | Gln-X | termination |
| 4044 | 12341 | 44 | ATC-GTC | Ile-Val | probable poly. |
| | | 44 | GGT-GCT | splice donor | del of 4001-4045 |
| | | 45 | CAG-CAA | splice acceptor | skip exon 45 |
| 4058 | 12384 | 45 | GCC-GTC | Ala-Val | probable poly. |
| 4059 | 12386 | 45 | CAG-TAG | Gln-X | termination |
| 4069 | 12416 | 45 | 20 bp ins = ggg-g^**** | Gly-** | frameshift |
| 4075 | 12438 | 45 | 20 bp ins = gcc-gc^g | Ala—Ala | frameshift |
| 4086 | 12469 | 45 | TGT-TGA | Cys-X | termination |
| 4091 | 12483 | 45 | GCA-GCG | Ala—Ala | polymorphism |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 4101 | 12511 | 45 | g ins = -ggg-gg^g | Gly—Gly | frameshift |
| 4124 | 12581 | 45 | CAG-TAG | Gln-X | termination |
| 4126 | 12589 | 45 | TAC-TAG | Tyr-X | termination |
| 4131 | 12601 | 45 | gtt del = gagtt-ga^gtt | Leu-Phe | frameshift |
| 4135 | 12614 | 45 | AGG-GGG | Arg-Gly | |
| 4136 | 12617 | 45 | CTG-TTG | Leu—Leu | polymorphism |
| 4136 | 12617 | 45 | c del = ctg-^tgc | Leu-Cys | frameshift |
| 4139 | 12628 | 45 | TGG-TGA | Trp-X | termination |
| 4145 | 12644 | 45 | GTC-ATC | Val-Ile | probable poly. |
| | IVS45+17i nsG | intron 45 | | | unknown poly |
| 4153 | 12668 | 46 | CGC-TGC | Arg-Cys | |
| 4168 | 12714 | 46 | duplication of 23 bp | | frameshift |
| 4176 | 12739 | 46 | a del = cca-cc^c | Pro—Pro | frameshift |
| 4189 | 12777 | 46 | TCC-TTC | Ser-Phe | polymorphism |
| 4198 | 12801 | 46 | del 28 | | frameshift |
| 4209 | 12838 | 46 | CCT-CCC | Pro—Pro | polymorphism |
| 4224 | 12882 | 46 | CAG-CCG | Gln-Pro | probable path. |
| 4227 | 12890 | 46 | CGA-TGA | Arg-X | termination |
| 4236 | 12919 | 46 | TAC-TAa/g | Tyr-X | termination |
| 4254 | 12973 | 46 | CCC-CCT | Pro—Pro | polymorphism |
| 4275 | 13034 | 46 | CGG-TGG | Arg-Trp | probable path. |

*Updated March 2001.
**is an unidentified base or amino acid.

III. Identification of Unique Sites within PKD Genes

Due to the fact that 70% of the PKD-1 gene is replicated as non-functional homologues with more than 95% sequence identity to PKD-1, the identification of PKD-1 unique sites are critical for the development of a genetic testing method. With the successful decoding of human genome sequences, the unique sites within the PKD genes may be identified by comparing genomic DNA sequences comprising a PKD gene with genomic DNA sequences comprising a PKD homologue. Useful databases and computer programs are known in the art (e.g., databases available through NCBI at www.ncbi.nlm.nih.gov; and computer programs available at http://www.ncbi.nlm.nih.gov/BLAST and DNAStar, www.dnastar.com). A unique site refers to a stretch of sequence within a PKD gene which shares less than or equal to 80% (e.g., less than or equal to 70%, or 60%, or 50% or 40% or 30% or 20% or 10%) sequence identity to a PKD homologue or other sequences.

Several unique sites (e.g., single copy site) have been described in Rossetti et al., 2000, Am. J. Hum. Genet. 68:46-63, the entirety of which hereby incorporated by reference. A novel unique site (5' AGG TCC AGG GCG ACT CGC TGG 3', or 5' CAG GGC CAC ACG CGC TGG GCG 3', or their complement thereof) is identified for PKD-1 by Applicants of the present application. Other unique sites may be found in, for example, in U.S. Pat. Nos. 6,228,591 and 6,031,088, each of which is incorporated herein by its entirety.

The identified Imique sites can be used for designing PKD-specific primers for the amplification of authentic PKD genes. The length of a unique site may vary from several nucleotides to thousands of nucleotides. Most of unique site identified comprises less than or equal to 100 nucleotides, e.g., less than or equal to 50 nucleotides, or less than or equal to 30 nucleotides. Amplification using PKD-specific primers would increase the specificity of the amplification reaction and reduce the amount by-products amplified from PKD homologues. The specifically amplified product of authentic PKD genes may be subsequently used for sequencing to identify allele variant, e.g., a mutant PKD gene, in an individual or for cloning and/or expression for other analysis.

IV. PKD-Specific Primers Useful for the Invention

Samples to be analyzed for the presence or absence of mutations often contain amounts of material too small to detect. The first step in mutation detection assays is, therefore, sample amplification. A preferred amplification reaction of the invention is PCR. PCR amplification comprises steps such as primer design, choice of DNA polymerase enzyme, the number of amplification cycles and concentration of reagents. Each of these steps, as well as other steps involved in the PCR process affects the purity of the amplified product. Although the PCR process and the factors which affect fidelity of replication and product purity are well known in the PCR art, these factors have not been addressed, heretofore, in relation to mutation detection of PKD genes using the separating method of the invention, e.g., DHPLC.

Any primer which anneals, under specific stringent conditions, to a sequence within an authentic PKD gene, but not to a PKD homologue or other sequences is a useful PKD-specific primer according to the invention. Sequences of the identified unique sites serve as the basis for designing PKD-specific primers useful according to the invention. The primers, according to the subject invention, may be incorporated into a convenient kit for identifying a PKD patient.

A. Criteria for Selecting Primers

A PKD species-specific primers preferably comprise a sequence complementary to a sequence located within a unique site of a PKD gene. The PKD-specific primer may be complementary to a unique site of a normal or a mutant PKD gene, so long as the primer preferably anneals to an authentic PKD gene other than a PKD homologue.

PKD species-specific primers may be selected manually by analyzing sequences of the unique sites identified for a PKD gene. When the sequence of a DNA fragment to be amplified by PCR is known, commercially available software can be used to design primers which will produce either the whole fragment, or any sequence within the fragment. The melting map of a fragment can be constructed using software such as MacMelt® (BioRad Laboratories, Hercules, Calif.), MELT (Lerman et al. Meth. Enzymol. 155:482 (1987)), or Win-Melt™ (BioRad Laboratories).

It is known in the art that primers that are about 18-25 bases long and with 50% G-C content will work well at annealing temperature at about 52-58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures. A convenient, simplified formula for obtaining a rough estimate of the melting temperature of a primer 17-25 bases long is as follows:

Melting temperature ($Tm$ in ° C.)=4×(# of $G$+# of $C$)+2×(# of $A$+# of $T$)

The overall design process design consists of both long range (i.e., for the first round PCR) and short range primer (i.e., for the nested PCR) design. In long range primer design, the objective is to design primers that produce good quality PCR products. "Good quality" PCR products are defined herein to mean PCR products produced in high yield and having low amounts of impurities such as primer dimers and PCR induced mutations. Good quality PCR can also be affected by other reaction parameters, such as the enzyme used, the number of PCR cycles, the concentration and type of buffer used, temperature thermal cycling procedures and the quality of the genomic template. Methods for producing good quality PCR products are discussed by Eckert et al. (*PCR: A Practical Approach*, McPherson, Quirke, and Taylor eds., IRL Press, Oxford, Vol. 1, pp. 225-244, 1991). This reference and the references therein are incorporated herein in their entireties.

Short range primer design should fulfill two requirements. First, it should fulfill all the requirements of long range primer design and give good quality PCR products. In addition, it must produce fragments that allow the DHPLC method to detect a mutation or polymorphism regardless of the location of the mutation or polymorphism within the amplified fragment. For example, large DNA fragments, having up to several thousand base pairs, can be amplified by PCR. If the only goal of the amplification is to replicate the desired fragment, then there is a large latitude in the design of primers which can be used for this purpose. However, if the purpose of a PCR amplification is to produce a DNA fragment for mutation detection analysis by DHPLC, then primers must be designed such that the fragment produced in the PCR process is capable of being detected, and will produce a signal, when analyzed by DHPLC. In a preferred embodiment of the invention, the length of an amplified product is 150-600 bps. In a more preferred embodiment, the fragment length for DHPLC mutation detection analysis is 150-400 bp.

There are two goals of designing short range primers. One goal for primer design is if the analysis is used as a "mutation analysis" test. Another goal is in analysis for research or diagnostic purposes, e.g., for identifying a PKD patient. "Mutation analysis" is defined herein as the study or analysis of DNA fragments to determine if the fragments contain variations (i.e., mutations or polymorphisms) in a population and correlate that variation to disease. It is to be understood that, within the context of this invention, the term "mutation" does not include a polymorphism (e.g., normal) which is silent for the disease. When DHPLC is used as a mutation analysis technique, then an important aspect of the present invention is a method for designing primers to produce a fragment in which a putative mutation can be detected, regardless of where the mutation site is located within the fragment. If the mutation is known, on the other hand, then the primer design can be further refined so that the analysis is optimized, i.e., the resolution of the homoduplex and the heteroduplex peaks in DHPLC is maximized. By improving the resolution for the analysis of known mutations, accuracy of analysis can be performed. Improved resolution is required for diagnostic mutation applications. Furthermore, with improved resolution, automatic identification of the positive presence of mutation can be more easily implemented with appropriate software and an algorithm that overlays and comparatively measures the peaks of the normal and mutant DNA samples.

Another method of primer design for mutation analysis applications is to design the primers so that the region of interest is at a lower melting domain within the fragment. In this case the primers are preferred to be designed so that the fragment being measured will overlap the regions of interest as the analysis is performed traveling down the exon. In these cases, the temperature difference between the higher melting domain and the lower melting domain is preferred to be greater than 5° C. and most preferred to be greater than 10° C.

Once the mutation of interest is identified, primers can be redesigned for diagnostic or clinical applications. In these cases, the mutation is preferably located within 25% or 25 bases of the end whichever is closer to the end. The other end of the fragment contains a higher melting domain of preferably 5° C., more preferably 10° C. higher, and most preferably 15° C. higher than the lower domain where the mutation is located. If the primer selection does not result in a high melting domain on the opposite end of the fragment, then a G-C clamp can be applied to increase the melting temperature at the desired end (e.g., an A-T rich end) (Myers et al., 1985, Nucleic Acids Res. 13:3111). G-C clamping is a technique in which additional G or C bases are included on the 5' end of one or both of the primers. The polymerase enzyme will extend over these additional bases incorporating them into the amplified fragment thereby raising the melting temperature of the end(s) of the fragment relative to that in the vicinity of the mutation. For example, in cases where the mutation is in the center of the amplified fragment and the length is less than 100 bp and the melting profile is flat, or in cases where the mutation in a high melting region of the fragment and a higher melting region is in effect a G-C rich region, a G-C clamp may be necessary. In these cases, proper primer selection will result in a fragment in which the mutation can be detected. The size of the G-C clamp can be up to 40 bp and as little as 4 or 5 bp. The most preferred G-C clamp for mutation detection by DHPLC is 10 to 20 bp.

If it is not possible to design primers which will produce, upon PCR amplification, domains having a constant melting range or domains within a fragment which are sufficiently close in Tm, then it may be necessary to lower the Tm of a domain of interest for successful mutation detection by DHPLC. This can be done, for example, by substituting dGTP with the analog 7-deaza-2'-dGTP which is known to effectively lower the melting temperature of G-C base pairs (Dierick et al., 1993, Nucl. Acids Res. 21:4427). If it is necessary to raise the Tm of the domain, then 2, 6-aminopurine can be used in place of dGTP in the PCR amplification.

In a most preferred embodiment, the primers are selected so that the mutation is located in a "lower melting" domain of the fragment. However, a mutation can also be detected by DHPLC in a high melting domain of the fragment either if the high melting domain does not have a melting temperature that is too different from other domains in the fragment or if a higher column temperature is used that is optimized for the higher melting domain of the fragment.

The long range primer design described above can be further refined by local primer design in which several other factors should be considered. For example, primers with non-template tails, such as universal sequencing primers or T7 promoters, may need to be avoided. The preferred primer has a Tm of about 56° C. The difference in Tm between the forward and reverse primers is preferably about 1° C. The difference in Tm between primer and template is preferably 25° C. The 3'-pentomer of each primer is preferably be more stable than $\Delta G°=-6$ kcal/mol (i.e., more negative). Any possible primer dimers are preferably be less stable than the 3'-pentomer by at least 5 kcal/mol (i.e., 5 kcal more positive). Any primer self annealing loops are preferably to have a Tm of less than 12° C. Primers are preferably be of high purity without failure sequences. To avoid degradation, storage in Tris-HCl (pH 8.0) buffer is preferable to pure water.

In some embodiments, it is more convenient to directly separate a long fragment, e.g., an exon, of up to 5 kb (e.g., up to 4 kb, or up to 3 kb, or up to 2 kb, or up to 1 kb) for mutations. Such long fragments generally contain multiple melting temperature domains. Double-stranded DNA fragments melt in a series of discontinuous steps as different regions with differing thermal stabilities which denature in response to increasing temperature. These different regions of thermal stability are referred to as "domains", and each domain is approximately 50-300 bp in length. Each domain has its own respective Tm and will exhibit thermodynamic behavior which is related to its respective Tm. The presence of a base mismatch within a domain will destabilize it, resulting in a decrease in the Tm of that domain in the heteroduplex relative to its fully hydrogen-bonded counterpart found in the homoduplex. Generally the presence of a base mismatch will lower the Tm by approximately 1-2° C.

In accordance with the preferred embodiments, optimal results have been obtained using primers which are 18-51 in length and DNA sequence to the primers with SEQ ID NOs. 3-49 (Table 3 and Table 4). However, one skilled in the art will recognize that the length of the primers used may vary. For example, it is envisioned that shorter primers containing at least 15, and preferably at least 17, consecutive bases of the nucleotide sequences of these primers SEQ ID NOs. 3-49 may be suitable. The exact upper limit of the length of the primers is not critical. However, typically the primers will be less than or equal to approximately 60 bases, preferably less than or equal to 50 bases. Further still, the bases included in the primers may be modified as is conventional in the art, including but not limited to, incorporating detectable labels such as biotin, or fluorescent labels.

TABLE 3

Examples of useful PKD-1 specific primers*

| SEQ ID NO. | Primer Name | Primer Sequence |
|---|---|---|
| | 1X1F | 5' CGT CGC TCA GCA GCA GGT CG 3' |
| | 1X1R | 5' CGT CCT GCT TCC CGT CCC G 3' |
| | 1X2F | 5' GCG CCC CGC CGC CCC CGC CGT TGG GGA TGC TGG CAA TGT GTG 3' |
| | 1X2R | 5' GGG ATT CGG CAA AGC TGA TG 3' |
| | 1X3F | 5' TTC CAT CAG CTT TGC CGA AT 3' |
| | 1X3R | 5' ATC TGG TCT CAA GCC TGG AAG 3' |
| | 1X4F | 5' GCC CCG CGC CCG TCC CGC CGC CCC CGC CGA GAC CCT TCC CAC CAG ACC T 3' |
| | 1X4R | 5' CGC CCC CGC CCG TGA GCC CTG CCC AGT GTC T 3' |
| | 1X5AF | 5' GCG CCC CGC CGC CCC CGC CGG AGC CAG GAG GAG CAG AAC CC 3' |
| | 1X5AR | 5' CAG AGG GAC AGG CAG GCA AAG G 3' |
| | 1X5BF | 5' GCC CCC GCC GCC CAG CCC TCC AGT GCC T 3' |
| | 1X5BR | 5' ATC GCT ATG TGC TGC CTG GG 3' |
| | 1X5CF | 5' CCG AGG TGG ATG CCG CTG 3' |
| | 1X5CR | 5' GAA GGG GAG TGG GCA GCA GAC 3' |
| | 1X6F | 5' CAC TGA CCG TTG ACA CCC TCG 3' |
| | 1X6R | 5' TGC CCC AGT GCT TCA GAG ATC 3' |
| | 1X7F | 5' GGA GTG CCC TGA GCC CCC T 3' |
| | 1X7R | 5' CCC CTA ACC ACA GCC AGC G 3' |
| | 1X8F | 5' TCT GTT CGT CCT GGT GTC CTG 3' |
| | 1X8R | 5' GCA GGA GGG CAG GTT GTA GAA 3' |

TABLE 3-continued

Examples of useful PKD-1 specific primers*

| SEQ ID NO. | Primer Name | Primer Sequence |
|---|---|---|
| | 1X9F | 5' GCG GCC CGC CGC CCC CGC CGG GTA GGG GGA GTC TGG GCT T 3' |
| | 1X9R | 5' GAG GCC ACC CCG AGT CC 3' |
| | 1X10F | 5' GTT GGG CAT CTC TGA CGG TG 3' |
| | 1X10R | 5' CGC CGC CCC CGC CCG GAA GGT GGC CT GAG GAG AT 3' |
| | 1X11AF | 5' GCG GCC CGC CGC CCC CGC CGG GGG TCC ACG GGC CAT G 3' |
| | 1X11AR | 5' AAG CCC AGC AGC ACG GTG AG 3' |
| | 1X11BF | 5' CCG CCG CCC CCG CCG CTG CCC TGC CTG TGC CCT G 3' |
| | 1X11BR | 5' GCC CCG CGC CCG TCC CGC CGC CCC CGC CCG TTC CAC CAC CAC GTC CAC CAC 3' |
| | 1X11CF | 5' GTG GTG GAC GTG GTG GTG GAA 3' |
| | 1X11CR | 5' GGC TGC TGC CCT CAC TGG GAA 3' |
| | 1X12F | 5' TAA GGG CAG AGT CCT CCA CAG 3' |
| | 1X12R | 5' CCA CCC CCG CCC ACC TAC TGA G 3' |
| | 1X13F | 5' GCG GCC CGC CGC CCC CGC CGT GGA GGG AGG GAC GCC AAT C 3' |
| | 1X13R | 5' GAG GCT GGG GCT GGG ACA A 3' |
| | 1X14F | 5' CCC GGT TCA CTC ACT GCG 3' |
| | 1X14R | 5' CCC CCG CCC GCC GTG CTC AGA GCC TGA AAG 3' |
| | 1X15AF | 5' GGC GGG GGG CTT CTG CCG AGC GGG TGG GGA GCA GGT GG 3' |
| | 1X15AR | 5' CGC CGC CCC CGC CCG GCT CTG GGT CAG GAC AGG GGA 3' |
| | 1X15BF | 5' CGC CTG GGG GTG TTC TTT 3' |
| | 1X15BR | 5' ACG TGA TGT TGT CGC CCG 3' |
| | 1X15CF | 5' GCC CCC GCC GGG GCG CCC CCG TGG TGG TCA GC 3' |
| | 1X15CR | 5' CAG GCT GCG TGG GGA TGC 3' |
| | 1X15DF | 5' CTG GAG GTG CTG CGC GTT 3' |
| | 1X15DR | 5' CGC CCC GCC CCG CTG GCT CCA CGC AGA TGC 3' |
| | 1X15EF | 5' CGT GAA CAG GGC GCA TTA 3' |
| | 1X15ER | 5' CCC CCG CCC GGC AGC AGA GAT GTT GTT GGA C 3' |
| | 1X15FF | 5' CCG CCG CCC CCG CCG CCA GGC TCC TAT CTT GTG ACA 3' |
| | 1X15FR | 5' TGA AGT CAC CTG TGC TGT TGT 3' |
| | 1X15GF | 5' CTA CCT GTG GGA TCT GGG G 3' |
| | 1X15GR | 5' TGC TGA AGC TCA CGC TCC 3' |
| | 1X15HF | 5' GGG CTC GTC GTC AAT GCA AG 3' |

TABLE 3-continued

Examples of useful PKD-1 specific primers*

| SEQ ID NO. | Primer Name | Primer Sequence |
|---|---|---|
| | 1X15HR | 5' CGC CGC CCC CGC CCG CCG CCC ACC ACC TGC AGC CCC TCT A 3' |
| | 1X15IF | 5' GCG GCC CGC CGC CCC CGC CGC CGC CCA GGA CAG CAT CTT C 3' |
| | 1X15IR | 5' CGC TGC CCA GCA TGT TGG 3' |
| | 1X15JF | 5' GGC CGG CAG CGG CAA AGG CTT CTC 3' |
| | 1X15JR | 5' GCC CAG CAC CAG CTC ACA T 3' |
| | 1X15KF | 5' CGA GCC ATT TAC CAC CCA TAG 3' |
| | 1X15KR | 5' GGC AGC CAG CAG GAT CTG AA 3' |
| | 1X15LF | 5' CTG TGG GCC AGC AGC AAG GTG 3' |
| | 1X15LR | 5' CCT GAA CCT CCA GCA CCA GCG 3' |
| | 1X15MF | 5' AGG TCC AGG GCG ACT CGC TGG 3' |
| | 1X15MR | 5' CAG GGC CAC ACG CGC TGG GCG 3' |
| | 1X15NF | 5' TTG GAG GCC CAC GTT GAC CTG 3' |
| | 1X15NR | 5' CCC CCG CCC GCA TGG GTG TGG ACG GGT GAG G 3' |
| | 1X16F | 5' TAA AAC TGG ATG GGG CTC TC 3' |
| | 1X16R | 5' GGC CTC CAC CAG CAC TAA 3' |
| | 1X17F | 5' GGG TCC CCC AGT CCT TCC AG 3' |
| | 1X17R | 5' TCC CCA GCC CGC CCA CA 3' |
| | 1X18F | 5' GCC CCC TCA CCA CCC CTT CT 3' |
| | 1X18R | 5' TCC CGC TGC TCC CCC CAC GCA 3' |
| | 1X19F | 5' GAT GCC GTG GGG ACC GTC 3' |
| | 1X19R | 5' GTG AGC AGG TGG CAG TCT CG 3' |
| | 1X20F | 5' CCA CCC CCT CTG CTC GTA GGT 3' |
| | 1X20R | 5' GGT CCC AAG CAC GCA TGC A 3' |
| | 1X21F | 5' TGC CGG CCT CCT GCG CTG CTG A 3' |
| | 1X21R | 5' GCG GGC AGG GTG AGC AGG TGG GGC CAT CC 3' |
| | 1X22F | 5' GAG GCT GTG GGG GTC CAG TCA AGT GG 3' |
| | 1X22R | 5' AGG GAG GCA GAG GAA AGG GCC GAA C 3' |
| | 1X23AF | 5' CGT CCC GCC TGC ACT GAC CTC ACG CAT GT 3' |
| | 1X23AR | 5' CGG CCC GCC GCC CCC GCC CGG CCA AAG GGA AAG GGA TTG GA 3' |
| | 1X23BF | 5' CCG CGG AGC CTG CTG TGC TAT 3' |
| | 1X23BR | 5' CCG CCG CCC CCG CCC GCT GGT GG AGA CGG TGT AGT GC 3' |
| | 1X23CF | 5' TCC AAT CCC TTT CCC TTT GGC 3' |
| | 1X23CR | 5' CAG CAG CCC ATG AAA CAG AAA G 3' |
| | 1X24F | 5' TAT GCT TTC AGG CCC GTG GCA 3' |

TABLE 3-continued

Examples of useful PKD-1 specific primers*

| SEQ ID NO. | Primer Name | Primer Sequence |
|---|---|---|
| | 1X24R | 5' AGA GCC CAT ACC CGG TCC AGT CC 3' |
| | 1X25F | 5' GGA CTG GAC CGG GTA TGG GCT CT 3' |
| | 1X25R | 5' CCC CCG CCC GCA CCC AGG CCC TCC TCG ACT C 3' |
| | 1X26F | 5' CCC CCG CCG CTG GGT GGG CTC GGC TCT ATC 3' |
| | 1X26R | 5' TGG TAG CGA TGC TCA CGT CAC TT 3' |
| | 1X27F | 5' CAG GCC AAA GCT GAG ATG ACT TG 3' |
| | 1X27R | 5' AGA GGC GCA GGA GGG AGG TC 3' |
| | 1X28F | 5' CCC TCT GCC CCC GCA TTG 3' |
| | 1X28R | 5' AAG CGC AAA AGG GCT GCG TCG 3' |
| | 1X29F | 5' GGC CCT CCC TGC CTT CTA GGC G 3 |
| | 1X29R | 5' CCG TGC TGT GTG GAG GAG AG 3' |
| | 1X30F | 5' CCT CTT CCT GCC CAG CCC TTC 3' |
| | 1X30R | 5' CTT CCC GAG CAG CCT TTG GTG 3' |
| | 1X31F | 5' CTG AGC TGC CGC CCG CTG AC 3' |
| | 1X31R | 5' AGG ACC CCC AGC CCA GCC CA 3' |
| | 1X32F | 5' CTT GGC GCA GCT TGG ACT 3' |
| | 1X32R | 5' ACA CCC AGC AAG GAC ACG CA 3' |
| | 1X33F | 5' TGT GAC ACA TCC CCT GGT AC 3' |
| | 1X33R | 5' GCA AGG GTG AGC TTC AGA GC 3' |
| | 1X34F | 5' GCC CCG CGC CCG TCC CGC CGC CCC CGC CCG ACC CTA TGC CTC CTG TAC CTC 3' |
| | 1X34R | 5' CCC CTC CTC TGG CAA TCC 3' |
| 3 | 1X35F | 5' TGG CTG CAA CTG CCT CCT GG 3' |
| 4 | 1X35R | 5' AAG CAG AGA CAG ACC TGT GAG AG 3' |
| 5 | 1X36F | 5' GCC CCC GCC GCT CTC ACA GGT CTG TCT CTG CTT C 3' |
| 6 | 1X36R | 5' GGC CTG TAG CCT ACC CCT GG 3' |
| 7 | 1X37F | 5' GGA CCC CTC TGA AGC CAC C 3' |
| 8 | 1X37R | 5' GGG AGG TGG GAG ACA AGA GAC 3' |
| 9 | 1X38F | 5' AAA GCC CTG CTG TCA CTG TGG 3' |
| 10 | 1X38R | 5' AAC TAA AGC CCA GAA GAC AGA CC 3' |
| 11 | 1X39F | 5' AAC TGT CTG CCC CAG AAC ATC 3' |
| 12 | 1X39R | 5' CTA AAG GCT GCT CTC TCA ACA AG 3' |
| 13 | 1X40F | 5' ACT CCT GTT GGG TTT TGA TGA G 3' |
| 14 | 1X40R | 5' GAG AAC TAC TCC CTT GTC CTT GG 3' |
| 15 | 1X41F | 5' ACG CCA AGG ACA AGG GAG TAG TTC 3' |
| 16 | 1X41R | 5' TGG GCT CCT GGC TGG TGA CTG C 3' |
| 17 | 1X42F | 5' GCG GCC CGC CGC CCC CGC CGC TAC TGA CCC GCA |

TABLE 3-continued

Examples of useful PKD-1 specific primers*

| SEQ ID NO. | Primer Name | Primer Sequence |
|---|---|---|
|  |  | CCC TCT G 3' |
| 18 | 1X42R | 5' GCT GCG AGG GGT GAG ACG 3' |
| 19 | 1X43F | 5' GCG GCC CGC CGC CCC CGC CGC GTC CCT CCC GCC CTC CTG ACC 3' |
| 20 | 1X43R | 5' GCC CCC GCC GCT GCG GAC GAG AAA TCT GTC TGC TTG 3' |
| 21 | 1X44F | 5' CAG GGC TGC AAG CAG ACA GA 3' |
| 22 | 1X44R | 5' CTG AGC TAA GAC GCC CTC CC 3' |
| 23 | 1X45F | 5' CTG TAC GCC CTC ACT GGT GTC 3' |
| 24 | 1X45R | 5' GGC ACA GGG GCT CAG TCA GTC 3' |
| 25 | 1X46AF | 5' GGA CTG ACT GAG CCC CTG TGC 3' |
| 26 | 1X46AR | 5' AGT CGG TCA AAC TGG GTG AG 3' |
| 27 | 1X46BF | 5' CAA GGT GTG AGC CTG AGC CC 3' |
| 28 | 1X46BR | 5' CGG TGT CCA CTC CGA CTC CAC 3' |

*All primer sequences are denoted in the 5'-3' direction. The first number in the name denotes the PKD gene number (1X15AF). The Letter 'X' signifies the word exon (1X15AF). The third number after the 'X' denotes the exon number (1X15AF). The character after the exon number represents the identity of the exon fragment (1X15AF). The last letter indicates the direction of the primer as either forward or reverse (1X15AF).

TABLE 4

Examples of useful PKD-2 specific primers*

| SEQ ID NO. | Primer Name | Primer Sequence |
|---|---|---|
| 29 | 2X1AF | 5' CCG CCC CCG CCG CGC GCC GGA CGC CAG TGA CC 3' |
|  | 2X1AR | 5' CCT GCC GGG AGC ACG ACG AG 3' |
| 30 | 2X1BF | 5' GCC CCC GCC GCC GCG GCC TCC CCT TCT CCT 3' |
|  | 2XIBR | 5' CTG GGC TGG GGC ACG GCG GG 3' |
|  | 2X1CF | 5' GGG GGC TAC CAC GGC GCG GGC 3' |
| 31 | 2X1CR | 5' CGG CCC GCC GCC CCC GCC CGC GGC CGT TCT GGT TCG TGC ATC TG 3' |
| 32 | 2X2F | 5' GCC CCC GCC GAA ATG ATA TCT TTT CTT TTC TTC A 3' |
| 33 | 2X2R | 5' CCC CCG CCC GAA CTT TCC CAT TAG TGC AAG 3' |
|  | 2X3F | 5' TTG GGG CGT TCA TTT GGA TC 3' |
| 34 | 2X3R | 5' CGC CGC CCC CGC CCG TGT GAT AGA GAG GTA CTT TCA 3' |
| 35 | 2X4F | 5' CCG CCG CCC CCG CCG CTT TTT CAA AGA TGT TTC CTT TGC 3' |
| 36 | 2X4R | 5' TAT CAC CGA GTG CCA ATG AG 3' |
| 37 | 2X5F | 5' CCG CCG CCC CCG CCG GCC TCA AGT GTT CCA CTG AT 3' |

TABLE 4-continued

Examples of useful PKD-2 specific primers*

| SEQ ID NO. | Primer Name | Primer Sequence |
|---|---|---|
|  | 2X5R | 5' ACC ACA CAG AAA TAG GAG GG 3' |
|  | 2X6F | 5' TTG TTA TTG TTT TAA TTG TTC TTA 3' |
| 38 | 2X6R | 5' CCC CCG CCC GTT GTA GAA TAG AAT AGG AAA TTT GG 3' |
| 39 | 2X7F | 5' GCC CCC GCC GTT GGT GAA GAA AAA TAT ACT AGT CA 3' |
| 40 | 2X7R | 5' CGC CGC CCC CGC CCG TGG AAC TCA TTT TTT TTA AAG A 3' |
| 41 | 2X8F | 5' GCG GGG GCG GCG GGC CGT TTT ATT ATA CAC AGT CAC ACC 3' |
|  | 2X8R | 5' CTA CTC TGA CTA AAT TTT TCT TCT T 3' |
|  | 2X9F | 5' TTT GGT TTT GTA TTG TGG TG 3' |
|  | 2X9R | 5' AAG GAT TTA CGA AGT TTA AAT TG 3' |
| 42 | 2X10F | 5' GCC CCC GCC GCT TCC TTT AAT TTT TGC CCT CC 3' |
| 43 | 2X10R | 5' CGC CGC CCC CGC CCG GAA ACA ATG CTC ATT TTA TGT CAG 3' |
| 44 | 2X11F | 5' CCG CCG CCC CCG CCG AAA CCA AGT CTT TTA TTT TTT CTC 3' |
|  | 2X11R | 5' AGA ACC TCA GGA AGC ATG ATT 3' |
| 45 | 2X12F | 5' CCG CCG CCC CCG CCG GAT GAA TGT TAT C TAT CCT CTC 3' |
|  | 2X12R | 5' TAG GTA CCA AAT CAA ATC CG 3' |
|  | 2X13F | 5' GTC TCA GTG TTC TGC TCC TC 3' |
| 46 | 2X13R | 5' CGC CGC CCC CGC CCG GCA AAT TCT GCC AAT TCC TTT A 3' |
| 47 | 2X14F | 5' GCC CCC GCC GTT TGT CCC TCT GTA CTG TGT 3' |
|  | 2X14R | 5' AAA TAC AAC TGT CAG CAA CAT A 3' |
| 48 | 2X15F | 5' CCG CCC CCG CCG TGA CCC CCA ACA CCA GTT TC 3' |
| 49 | 2X15R | 5' CGG CCC GCC GCC CCC GCC CGG GAC AGC CAC TTC CTC ACT T 3' |

*All primer sequences are denoted in the 5'-3' direction. The first number in the name denotes the PKD gene number (2X15R). The Letter 'X' signifies the word exon (2X15R). The third number after the 'X' denotes the exon number (2X15R). The last letter indicates the direction of the primer as either forward or reverse (2X15R).

B. Primer Combinations Useful for PKD-specific Amplification

The specifically amplified product can be generated by using one or more PKD-specific primers. Preferably, both primers used to generate one amplified product are PKD-specific primers. However, one PKD-specific primer can be used in combination with another non PKD-specific primer which is not complementary to a unique site of a PKD gene. The non PKD-specific primer is preferably designed according to the same criteria described above herein for the PKD-specific primers and is preferably to be completely complementary to a sequence other. then a unique sequence in a PKD gene. A non PKD-specific primer may also be used as a control primer included in the amplification reaction to generate a control product.

Optimal results may be obtained by using one forward and one reverse primer listed in Table 4 and Table 5, although other combinations may also be used. In a preferred embodiment, a primer pair is selected so that the length of an amplified product is 150-600 bps. In the most preferred embodiment, a primer pair is selected so that the amplified fragment length for DHPLC mutation detection analysis is 150-400 bp.

C. Primer Synthesis

Methods for synthesizing primers are available in the art. The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). Also see particularly Sambrook et al. (1989), Molecular Cloning: A Laboratory Manual (2d ed.; Cold Spring Harbor Laboratory: Plainview, N.Y.), herein incorporated by reference.

V. Preparing Template for Amplification Reaction

Any sample comprising a nucleic acid comprising the entire or a portion of SEQ ID NO. 1 or 2 or their variants (e.g., polymorphism forms or mutant forms) may be used to as template for amplification reaction of the present invention. Useful templates, according to the invention, include, but are not limited to, genomic DNA preparation, total RNA preparation, crude cell lysate and tissue sample.

It's preferred to use genomic DNA as template for PKD-specific amplification of the subject invention. While it is envisioned that crude cell lysate or tissue sample may be used, one skilled in the art will recognize that any non-DNA material present in the sample may interfere with the polymerase reaction or subsequent analysis.

Genomic DNA can be isolated from tissue samples or cells. Preferably, the genomic DNA used as template for the invention is isolated under conditions which preclude degradation and contamination. Tissue samples or cells may be digested with a protease so that there is likely to be little or no DNAase activity. The digest is extracted with a DNA solvent. The extracted genomic DNA may be purified by, for example, dialysis or chromatography. Suitable genomic DNA isolation techniques are known in the art, for example, as described in Current Protocols in Molecular Biology, Ausubel et al., John Weley & Sons, Inc., 1997.

Preferably, genomic DNA or cDNA is extracted from cell lysate of tissue samples taken from an individual and used as template for PKD amplification. Collecting a tissue sample also includes in vitro harvest of cultured human cells derived from an individual's tissue or any means of in vivo sampling directly from a subject, for example, by blood draw, spinal tap, tissue smear or tissue biopsy. Optionally, tissue samples are stored before analysis by well known storage means that will preserve a sample's nucleic acids in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis. In some embodiments, the sample contains DNA, tissue or cells from two or more different individuals.

Any human tissue containing nucleic acids can be sampled and collected for the purpose of practicing the methods of the present invention. A most preferred and convenient tissue for collecting is blood. No patient preparation is necessary prior to blood draw. No medications are known to interfere with sample collection or testing. Usual aseptic techniques and avoidance of contamination are necessary.

Preferably, DNAs are extracted from blood on the day it was drawn. Blood is preferred to stored at room temperature (72° F. or 25° C.) before use. However, whole blood may be stored for short periods at 4° C. but room temperature is recommended. Whole blood specimens may be stable for 48 hrs. After this time hemolysis may compromise DNA recovery and integrity. The optimal amount of blood for DNA extraction for the PCR assay is preferred to be more than 5 ml, e.g., more than 10.0 ml.

VI. PCR Amplification Using PKD-Specific Primers

The subject invention provides a method of mutation analysis of a target nucleic acid comprising SEQ ID NO. 1 or 2 or their variants by amplifying the DNA from a sample comprising the target nucleic acid in a polymerase chain reaction and detecting in a specifically amplified product the presence or absence of a mutation in the target nucleic acid.

Amplification may be carried out by means well known in the art, for example, polymerase chain reaction (PCR), transcription based amplification (reverse transcription), strand displacement amplification (see Current Protocol in Molecular Biology). Preferably, the amplification is carried out by PCR, such as described by Mullis (U.S. Pat. No. 4,683,202), the contents of which are incorporated by reference herein.

PCR makes possible the amplification (replication) of minute samples of DNA or other nucleic acids of any base pair length (size) by taking advantage of highly selective enzymes called DNA polymerases, to extend small DNA strands called "primers" along a "template". The minute DNA sample serves as the template. PCR reproduces the complementary sequence of deoxynucteotide triphosphate (dNTP) bases present in the template or any chosen portion thereof. The PCR is commonly used in conjunction with diagnostic techniques where, for example, a DNA sample having a concentration below the limit of detection is amplified by the PCR process, and the larger amount so obtained is subsequently analyzed.

Apparatus for performing PCR amplifications, e.g. Air Thermo Cycler (Idaho Technologies) and reagents are commercially available from numerous sources, e.g. Perkin-Elmer Catalog "PCR Systems, Reagents and Consumables" (Perkin-Elmer Applied Biosystems, Foster City, Calif.).

PCR is typically run in a buffer at pH 5-8. The buffer contains a double stranded DNA sample to be amplified, a forward primer, a reverse primer, magnesium (e.g., as $MgCl_2$), and the four deoxynucleotide triphosphates (dATP, dTTP, dCTP, and dGTP) generally referred to as "dNTPs", the building blocks of DNA. The reaction mixture is heated to a temperature (e.g., >90° C.) sufficient to denature the DNA sample, thereby separating its two complimentary nucleic acid strands. Alternatively, the DNA may be denatured enzymatically at ambient temperature using a helicase enzyme. If denaturing is effected by heat and a thermostable DNA polymerase is used, the DNA polymerase is added before the reaction is started other denaturing conditions are well known to those skilled in the art and are described in U.S. Pat. No. 5,698,400. DNA polymerases are commercially available from a variety of sources, e.g. Perkin-Elmer Applied Biosystems, (Foster City, Calif.) and Stratagene (La Jolla, Calif.).

The primer sequence is designed to be complimentary to an identified portion of the denatured DNA strands to be replicated by PCR. Upon cooling the reaction to an appropriate annealing temperature, each of the primers anneals to its complimentary base sequence in each strand of the denatured DNA sample to be replicated. Heated to about 70° C. in the presence of the DNA polymerase, the 4 dNTPs and $Mg^{2+}$, replication extends the primers from their 3'-ends by adding complimentary dNTPs along the length of the strand. dNTPs are commercially available from a variety of sources, e.g. Pharmacia (Piscataway, N.J.). By repeating this process numerous times, a geometric increase in the number of desired DNA strands is achieved in the initial stages of the process or as long as a sufficient excess of reagents are present in the reaction medium. Thus, the amount of the original DNA sample is amplified.

The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. Preferably, a DNA polymerase with proof-reading activity is used.

The amount of each primer must be in substantial excess of the amount of target DNA to be amplified. The amount of primer needed for the reaction mixture can be estimated by one skilled in the art in terms of the ultimate number of amplified fragments desired at the conclusion of the reaction.

To prevent false positive results, one skilled in the art will recognize that the assays should include negative controls as is conventional in the art. For instance, suitable negative controls may contain no primer or no DNA (i.e. "water controls"). To prevent false negative results, positive controls are provided by the control primers (see below).

A. Optimization of PCR Conditions

Successful specific amplification, e.g., an amplification which produces maximal amount of specifically amplified products and minimal amount of non-specifically amplified products, according to the invention, depends in great measure on the specific annealing of the PKD-specific primers to the corresponding matched template. If the primer anneals non-specifically to many different sequences in the reaction mixture, the amplification process will not be specific. Although it is unlikely in most of the embodiments to avoid any non-specific annealing or non-specific amplification, it is desirable to optimize the PCR amplification reaction condition so to reduce the non-specific amplification while increase the specific amplification.

In addition, PCR induced mutations, wherein a non-complimentary base is added to a template, are often formed during sample amplification. Such PCR induced mutations make mutation detection results ambiguous, since it may not be clear if a detected mutation was present in the sample or was produced during the PCR process. Applicants have recognized the importance of optimizing PCR sample amplification in order to minimize the formation of PCR induced mutations and ensure an accurate and unambiguous analysis of putative mutation containing samples.

B. Controlling the Specificity of PKD-specific Annealing of PKD-Specific Primers.

The degree of fidelity of replication of DNA fragments by PCR depends on many factors which have long been recognized in the art. Some of these factors are interrelated in the sense that a change in the PCR product profile caused by an increase or decrease in the quantity or concentration of one factor can be offset, or even reversed by a change in a different factor. For example, an increase in the enzyme concentration may reduce the fidelity of replication, while a decrease in the reaction temperature may increase the replication fidelity. An increase in magnesium ion concentration or dNTP concentration may result in an increased rate of reaction which may have the effect of reducing PCR fidelity. A detailed discussion of the factors contributing to PCR fidelity is presented by Eckert et al., (in *PCR: A Practical Approach*, 1991, McPherson, Quirke, and Taylor eds., In Press, Oxford, Vol. 1, pp. 225-244); and Andre, et. al., (1977, *GENOME RESEARCH*, Cold Spring Harbor Laboratory Press, pp. 843-852). These references and the references cited therein are incorporated in their entirety herein. Thus, availability of a product profile of the PCR process, makes possible the optimization of PCR conditions to improve results in a highly efficient manner.

In PCR amplification, the specificity of the annealing is most important in the first few cycles. The remaining cycles only serve to expend the pool of template which is amplified in the first few cycles. The specificity of primer annealing to template is controlled by the ionic strength (primarily the $K^+$ concentration) of the buffer, the $Mg^{2+}$ concentration (which is bound to dNTPs and therefore affected by the amount of dNTPs), and the annealing temperature of each cycle of the amplification. In preferred embodiments, the dNTP concentrations are 50 nM, preferably 100 nM, more preferably 200 nM.

Conditions for specific annealing of primers to particular template targets must be determined empirically, usually by varying the annealing temperature in several degree increments and comparing the specificity and sensitivity of the amplification process by agarose gel electrophoresis (See *Current Protocol in Molecular Biology*, supra).

Because a unique region to which a PKD-specific primer complement to may differ from a homologue sequence only by a few nucleotides, sometimes by only one nucleotide, the specificity of the amplification reaction needs to be tested for each PKD-specific primer used in the reaction.

The formula for calculating primer annealing temperature provided above is only a rough guide, successive trials at different annealing temperatures is the usual way to optimize this important parameter in the PKD-specific amplification reaction. Apparatus are available for simultaneous testing of different annealing temperatures of particular primer-template pairs, which enables the optimal annealing temperature to be determined rapidly and reliably (e.g., Robocycler Gradient Temperature Cycler, Cat # 400864, Stratagene; Eppendorf mastercycler gradient, Cat # 5331 000.045, Brinkmann Instruments, Inc. Westbury, N.Y.).

In some embodiments, the target sequences are amplified at an annealing and extending temperature that is between 1° C. and 10° C. higher than the Tm for the primer pair. Although amplification at this temperature is inefficient, any primer extension that occurs is target specific. Consequently, during the high temperature cycle(s), the sample is enriched for the particular target sequence and any number of cycles, i.e., 1-15 enhances product specificity. The annealing temperature may be then decreased to increase amplification efficiency and provide a detectable amount of PCR product. Or a nested amplification reaction may be performed using the amplified product from the first PCR reaction as template (see below).

Alternatively, one can simultaneously run a set of reactions at a constant temperature but vary the concentration of KCl or $MgCl_2$ or add variable amounts of a denaturant such as formamide (e.g., 0, 2, 4, 6%), DMSO (1-10%) to define the optimum conditions for generating a high yield of specific product with a minimum of nonspecific products.

In one embodiment, a pair of primers comprising at least one selected from the group consisting of SEQ ID NOs. 3-49 is used in the amplification reaction mixture. The orientation of the two primers is opposite to allow the generation of one or more specifically amplified product.

In some embodiments of the invention, when primers used for PKD-specific amplification are selected from SEQ ID NOs. 3-49, AmpliTaq Gold DNA polymerase with GeneAmp PCR buffer II and $MgCl_2$ solution and rTth DNA polymerase XL & XL buffer II pack from. Perkin Elmer, and TagPlus Precision PCR system from Stratagene were used. PFU-Turbo™ is another high fidelity DNA polymerase having greater proof reading provided by Stratagene.

In other embodiments, an annealing temperature of above 65° C. (e.g., 68-72° C.) is used for PKD-specific amplification using primers selected from SEQ ID NOs. 3-49.

In general, it is preferred but not essential that the DNA polymerase is added to the amplification reaction mixture after both the primer and template are added. Alternatively, for example, the enzyme and primer are added last or the reaction buffer or template plus buffer are added last. It is generally desirable that at least one component that is essential for polymerization not be present until such time as the primer and template are both present, and the enzyme can bind to and extend the desired primer/template substrate. This method, termed "hot start," minimizes the formation of "primer-dimer" and improves specificity of the amplification.

The degree of specificity of DNA polymerases varies with the reaction conditions employed as well as with the type of enzyme used. No enzyme affords completely error free extension of a primer. Therefore, a non-complimentary base may be introduced from time to time. Such enzyme related errors produce double stranded DNA products which are not exact copies of the original DNA sample, but contain PCR induced mutations. Other PCR process features, such as reaction temperature, primer annealing temperature, enzyme concentration, dNTP concentration, $Mg^{2+}$ concentration, and combinations thereof, all have the potential to contribute to the degradation of the accuracy or fidelity of DNA replication by the PCR process, as described above herein.

C. Sensitivity of PKD-specific Amplification

The sensitivity of the PKD-specific amplification of the subject invention depends on the template and primers used in an amplification reaction, as well as ionic strength and annealing temperature of each cycle of the amplification.

When genomic DNA is used as template, as few as one or two copies of the template (about 3-5 pg) can be used for successful PCR amplification if the reaction condition has been optimized. However, it's known in the art that a higher template concentration may increase the specificity and efficiency of the amplification.

Shorter fragments are amplified more efficiently than longer fragments. Preferably, primers which generate an amplified product of less than 1 kb, more preferably less than 600 bp, or less than 450 bp in length are used to increase sensitivity of the amplification assay.

Preferably, the sensitivity of the amplification assay is less than 100 ng genomic DNA template. More preferably, the sensitivity of the assay is less than 10 ng genomic DNA template. More preferably, the sensitivity of the assay is less than 1 ng genomic DNA template. More preferably, the sensitivity of the assay is less than 0.1 ng genomic DNA template. Even more preferably, the sensitivity of the assay is less than 0.01 ng genomic DNA template.

D. Nested Amplification

In some embodiments of the invention, a nested amplification is performed using amplified products in a preceding amplification reaction as templates. Preferably, the nested amplification reaction is a nested PCR using PCR amplified products from a preceding PCR reaction as templates. In addition to optimizing the annealing temperature of the primers, "nested" amplification can be used to increase the specificity and sensitivity of the PKD-specific amplification assay.

For example, a method comprising a nested PCR involves two sequential PCR reactions. After multiple cycles of PCR (e.g., 10 to 40, or 10 to 30 or 10 to 20 cycles) with the first pair of primers comprising at least one PKD-specific primer (e.g., a PKD-specific primer and a control primer or two PKD-specific primers), a small amount aliquot of the first reaction (e.g., 1 µl of a 50 µl reaction) serves as the template for a second multiple cycles of PCR reaction (e.g., 10 to 40, or 10 to 30 or 10 to 20 cycles) with a new set of primers comprising at least one PKD-specific primer (e.g., a PKD-specific primer and a control primer or two PKD-specific primers) that anneal to sequences internal to, or nested between, the first pair.

Methods for designing nested primers and for performing nested PCR are known in the art (see *Current Protocol in Molecular Biology*, supra). The general criteria for selecting primers as described above also applies to the design of nested primers. Both nested primers need to anneal to sequences internal to (e.g., within) the first pair of primers and at least one of the nested primers, however, according to the subject invention, needs to be PKD-specific.

Using the nested PCR procedure, the template that is successfully amplified is selected twice for PKD-specificity. The use of nested PCR can also greatly enhance the yield of the species-specific product, therefore the sensitivity of the assay, when a single primer pair fails by itself.

A sample comprising genomic DNA or cDNA may be used to provide DNA template for the amplification reaction. Preferably, genomic DNA is used as template. When a sample comprising genomic DNA is used in the reaction mixture, a pair of primers comprising at least one selected from the group consisting of SEQ ID NOs. 3-49 generate at least two specifically amplified product, one from each PKD allele in the genomic DNA sample.

E. Amplification Controls

Control primers can be used to serve as positive control for the PKD-specific amplification. The control primers may be added to the same reaction mixture for PKD-specific amplification, or it may be added to a control reaction which is run in the same PCR apparatus under the same parameters. A control primer may comprise a sequence complementary to any identical sequence between a PKD gene and a PKD homologue. Preferably, the control primers generate a single amplified product whose size is distinguishable from that amplified by a pair of primers comprising at least one PKD-specific primers. The size of the amplified product by the control primers may be greater or smaller than the size of the amplified products generated by the pair of primers comprising at least one PKD-specific primers. Preferably, the control primers are chosen to generate a control product which has at least 100 bp, more preferably at least 500 bp, more preferably at least 1000 bp difference in size compared to the amplified product generated in the same amplification reaction by the pair of primers comprising at least one PKD-specific primers.

A control amplification is especially important when analyzing a PKD allele with deletions at the location where a PKD-specific primer anneals. The lack of a specific amplification in the presence of an amplified control product may indicate the presence of the deletion at a specific location of a PKD gene. In some embodiments, more than one pair of control primers is used in the reaction mixture.

See Example 2 for various controls that might be used for the genetic testing method of the invention.

Amplified products may be purified to get rid of free primers used in the amplification by methods known in the art (e.g., Current Protocols in Molecular Biology, supra). In a preferred embodiment, the PCR products are purified using the Quickstep™ 96 well PCR Purification Kit from Edge Biosystems.

VII. Detecting the Presence of PCR Amplified Products

The cycle of DNA denaturation, primer annealing and synthesis of the DNA segment defined by the 5' ends of the primers is repeated as many times as is necessary to amplify the template target until a sufficient amount of either a species-specific or a universal product is available for detection.

At the conclusion of the amplification reaction, the presence of amplified products may be detected using techniques conventional in the art.

The primers may be labeled for facilitating the detection. The primers can be labeled with a directly detectable tag, for example a radioactive label such as $^{32}P$, $^{35}S$, $^{14}C$ or $^{125}I$, a fluorescent compound such as fluorescein or rhodamine derivatives, an enzyme such as a peroxidase or alkaline phosphatase, or avidin or biotin. The PKD-specific primers used to generate the PKD-specific product and the control primers used only to generate the control product may have the same or different labels.

In a preferred embodiment, the amplification products are conveniently analyzed by gel electrophoresis.

Electrophoresis is conducted under conditions which effect a desired degree of resolution of fragments. A degree of resolution that separates fragments that differ in size by as little as about 500 bp is usually sufficient. Preferably, the resolution is at about 100 bp. More preferably, the resolution is at about 10 bp. Size markers may also be run on the gel to permit estimation of the size of fragments. Preliminary analysis of the size of specifically amplified products may indicate insertions or deletions within a PKD gene, and the information obtained can be interpreted together with results obtained from subsequent DHPLC and sequence analysis.

The amplification product pattern may be visualized. Where an amplification primer has been labeled, this label may be revealed. A substrate carrying the separated labeled DNA fragments is contacted with a reagent which detects the presence of the label. For example, an amplified product generated from a radioactively labeled primer may be detected by radioautography. Where the amplification primers are not labeled, the substrate bearing the PCR product may be contacted with ethidium bromide and the DNA fragments visualized under ultraviolet light.

VIII. Separating PCR Amplified Products

Under the most stringent condition which only allows the annealing of completely complementary sequences but not sequences comprising one or more non-complementary nucleotides, a PKD-specific primer will only anneal to an authentic PKD gene template, but not a PKD homologue. Therefore, under the most stringent condition, a PKD-specific primer, in combination with a primer with opposite orientation, being PKD-specific or not, will only produce amplified product from an authentic PKD template, but not from a PKD homologue. However, during a typical PCR amplification reaction, a PKD-specific may anneal to a template comprising an authentic PKD gene and a PKD homologue, especially due to the temperature cycling required by a PCR reaction. Therefore, both specifically amplified products and non-specifically amplified products may be produced, although the amount of non-specifically amplified products may be reduced by the use of at least one PKD-specific primer.

A. Formation of Homoduplex and Heteroduplex

In one embodiment of the invention, a mixture of homoduplexes and heteroduplexes is formed prior to the DHPLC analysis. A standard nucleic acid homoduplex (e.g., amplified product from a normal PKD allele) may be added to the sample and the mixture is subjected to denaturation, e.g. by heating the mixture to about 90° C. or about 95° C. The denatured single stranded nucleic acids formed during the denaturation process are then annealed by slowly cooling the mixture to ambient temperature. A new mixture of homoduplexes and heteroduplexes is formed if the sample contains a mutation. If the sample does not contain a mutation, only a homoduplex of the standard nucleic acid will be formed. In the preferred embodiment, the standard nucleic acid is the "normal" nucleic acid.

In most cases, a PKD patient individual is heterozygous at the loci comprising a PKD gene. That is, the carrier has only one PKD allele and a mutant form and has the other allele as a normal form (e.g., wild type). Since most of the PKD mutations result in a dominant phenotype, one mutant allele is sufficient to predispose a risk for ADPKD development. Another heterozygous situation is when both alleles are mutated but each carries one or more different mutations. For a heterozygous PKD patient, a PCR amplification using a primer pair comprising at least one PKD-specific primer, including a nested PCR amplification, would result in at least two specifically amplified PKD products, one from each allele. The two specifically amplified PKD products may or may not be of the same length (e.g., different length if the mutation on one allele comprises a deletion or an insertion) and would differ in at least one nucleotide from each other.

The amplified products may be denatured and re-annealed with each other to form duplexes. When a specifically amplified product from a normal allele or a specifically amplified product from a mutant allele anneals to another specifically amplified product from the same allele, they will form homoduplex. However, if a specifically amplified product from a normal allele anneals to a specifically amplified product from a mutant allele, they form a heteroduplex.

In rare cases, a mutation is in homozygous form, that is, both alleles in an individual (e.g., a PKD patient) comprise the same mutations. If a sample is taken from a homozygous PKD patient, the PCR amplification will not generate specifically amplified products which can form heteroduplex upon denaturing and re-annealing. In some embodiments of the invention, a sample comprising a normal (e.g., a wide type) PKD gene is added to the PCR reaction mixture so that amplification using a primer pair comprising at least one PKD-specific primer will produce specifically amplified products from the normal PKD gene, therefore ensuring the formation of a heteroduplex during the denaturation and re-annealing process following PCR amplification.

Homoduplexes formed in the denaturation and re-annealing process may also include those formed by non-specifically amplified products. If in very rare cases, a sequence in a template allele (e.g., a PKD homologue sequence) which give rise to non-specifically amplified products also comprises one or more mutation, a heteroduplex may also form. The heteroduplex formed between non-specifically amplified products will also be subjected to further separating the identification process.

B. Separating and Identifying Heteroduplex

The presence of a heteroduplex formed by PKD-specifically amplified products indicates the presence of a mutation in a PKD gene. By separating for heteroduplexes, one can identify whether a mutant allele present in the sample, e.g., taken from an individual. This separating process gets rid of most of the non-specifically amplified products and specifically amplified products from normal alleles, therefore improves the efficiency and specificity of identifying a mutant allele and a PKD patient.

It is well known in the DNA art that a heteroduplex strand will denature selectively at the site of base pair mismatch, creating a "bubble", at a lower temperature than is necessary to denature the remainder of the heteroduplex strand, i.e., those portions of the heteroduplex strand which contain complimentary base pairs. This phenomenon, generally referred to as partial denaturation, occurs because the hydrogen bonds between mismatched bases are weaker than the hydrogen bonds between complimentary bases. Therefore, less energy is required to denature the heteroduplex at the mutation site, hence the lower temperature required to partially denature the heteroduplex at the site of base pair mismatch than in the remainder of the strand.

Since at least one base pair in a heteroduplex is not complimentary, it takes less energy to separate the bases at that site compared to its fully complimentary base pair analog in a homoduplex. This results in the lower melting temperature of a heteroduplex compared to a homoduplex. The local denaturation creates, what is generally called, a "bubble" at the site of base pair mismatch. The bubble distorts the structure of a DNA fragment compared to a fully complimentary homoduplex of the same base pair length. This structural distortion under partially denaturing conditions has serves as the basis for DHPLC to separate heteroduplexes and homoduplexes.

A separation process called "Denaturing HPLC" (DHPLC) has been used to detect mutations by separating a heteroduplex (resulting from the presence of a mutation) and a homoduplex having the same bp length. DHPLC has been applied to mutation detection (e.g., see Underhill, et al., 1997, Genome Research 7:996; Liu, et al., 1998, Nucleic Acid Res., 26; 1396). This separation is based on the fact that a heteroduplex has a lower melting temperature (Tm) than a homoduplex. When DHPLC is carried out at a partially denaturing temperature, i.e., a temperature sufficient to denature a heteroduplex at the site of base pair mismatch, homoduplexes can be separated from heteroduplexes having the same base pair length (Hayward-Lester, et al., 1995, Genome Research, 5:494; Underhill, et al., 1996, Proc. Natl. Acad. Sci. USA 93:193; Doris, et al., 1997, DHPLC Workshop, Stanford University). These references and the references contained therein are incorporated herein in their entireties. Thus, the use of DHPLC was applied to mutation detection (Underhill, et al., 1997, Genome Research 7:996; Liu, et al., 1998, Nucleic Acid Res., 26:1396). DHPLC can separate heteroduplexes that differ by as little as one base pair under certain conditions. The references cited above and the references contained therein are incorporated in their entireties herein.

The change in the structure of DNA from an orderly helix to a disordered, unstacked structure without base pairs is called the helix-random chain transition, or melting. Statistical-mechanical analysis of equilibria representing this change as a function of temperature for double-stranded molecules of natural sequence has been presented by Wartell and Montroll (1972, Adv. Chem. Phys. 22: 129). The theory assumes that each base pair can exist in only two possible states-either stacked, helical, and hydrogen bonded, or disordered. It permits calculation of the probability that each individual base pair is either helical or melted at any temperature, given only the base sequence and a very small number of empirically calibrated parameters. The statistical-mechanical theories take into account the differing intrinsic stabilities of each base pair or cluster of neighboring base pairs, the influence of adjacent helical structure on the probability that a neighboring base pair is helical or melted (the coopertivity), and the restrictions on the conformational liberty of a disordered region if it is bounded at both ends by helical regions.

Iteration of the probability calculation at a closely spaced series of temperature steps and interpolation permit determination of the midpoint temperature at which each base pair is at 50/50 equilibrium between the helical and melted states. The MELT program provides the midpoint temperature and some other functions. A plot of midpoint temperature as a function of position along the molecule is called a melting map. It clearly shows that the melting of nearby base pairs is closely coupled over substantial lengths of the molecule despite their individual differences in stability. The existence of fairly long regions, 30-300 bp, termed domains, in which all bases melt at very nearly the same temperature, is typical. The melting map directly delineates the lowest melting domains in the molecules.

At a partially denaturing temperature, a heteroduplex having a base pair mismatch within a sample sequence will denature at the site of the mismatch, while the rest of the sample sequence will remain intact. The partially denatured heteroduplex can be separated and detected using DHPLC.

When HPLC is used under partially denaturing conditions (e.g., DHPLC) to separate a mixture of homoduplexes and heteroduplexes, the heteroduplexes usually elute ahead of the homoduplexes.

In particular embodiment of the invention, a heteroduplex is separated and identified from a homoduplex by DHPLC, and the presence of heteroduplex indicates the presence of at least one mutation in the PKD gene, e.g., a substitution of one or more nucleotides (or insertion or deletion of one or more nucleotides) present in the mutant allele.

In another particular embodiment, DHPLC gradient is determined by Wavemaker™ 4.0 software from Transgenomic, Inc. (San Jose, Calif.).

Separating applications require that the mutation can be detected regardless of where the mutation might be located on the fragment. In this situation, the mutation might be located in the middle of the fragment or in a higher melting domain, both cases where it is more difficult to detect. It is preferred than the range of melting variation of the fragment is no greater than 10° C. and most preferred is the range of variation is no greater than 5° C.

In some mutation analyses, only two peaks or a partially resolved peak(s) are observed in DHPLC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

If a sample contained homozygous DNA fragments of the same length, then hybridization and analysis by DHPLC would only produce a single peak at any temperature since no heteroduplexes could be formed. In the operation of the present method, the determination of a mutation can be made by hybridizing the homozygous sample with the known wild type fragment and performing a DHPLC analysis at a partially denaturing temperature. If the sample contained only normal allele then a single peak would be seen in the DHPLC analysis since no heteroduplexes could be formed. If the sample contained heterozygous mutant alleles, then analysis by DHPLC would show the separation of linmnduplexec and beterndliplexec.

The temperature at which 50% of a constant melting domain is denatured may also be determined experimentally by plotting the UV (UV) absorbance of a DNA sample against temperature. The absorbance increases with temperature and the resulting plot is called a melting profile (Breslauer et al., 1986, Proc. Natl. Acad. Sci. USA 83:3746; Breslauer, 1987, *Calculating Thermodynamic Data for Transitions of any Molecularity*, p. 221, Marky et al. eds., J. Wiley and Sons). The midpoint of the absorbance axis on the melting profile represents the melting temperature (Tm), i.e. the temperature at which 50% of the DNA strands in the duplex are denatured. In one embodiment of the present invention, this observed Tm is used as a starting temperature for performing DHPLC for mutation detection. The temperature may be then adjusted according to the patterns observed using different controls (see below). In one embodiment, a consistent Tm is used to analyze the same amplicons (i.e., produced by the same pair of primers) from different samples.

In another embodiment of the present invention, software such as MELT (Lerman, et al., 1987, Meth. Enzymol. 155: 482) or WinMelt™, version 2.0, is used to obtain a calculated Tm which is used as a starting temperature for performing DHPLC for mutation detection. These software programs show that despite individual differences in base pair stability, the melting temperature of nearby base pairs is closely coupled, i.e., there is a cooperative effect. Thus, there are long regions of 30 to 300 base pairs, called "domains", in which the melting temperature is fairly constant. In a similar manner, the software MELTSCAN (Brossette, et al., 1994, Nucleic Acid Res. 22:4321) calculates melting domains in a DNA fragment and their corresponding melting temperatures. The concept of a constant temperature melting domain is important since it makes possible the detection of a mutation in any portion of the domain at a single heteromutant site selective temperature.

Another particular method for separating and identifying heteroduplex is Matched Ion Nucleic acid Chromatography (MIPC). MIPC was introduced to effectively separate mixtures of double stranded nucleic acids, in general and DNA, in particular, wherein the separations are based on base pair length (U.S. Pat. Nos. 5,585,236 and 6,287,822; Huber et al., 1993, Chromatographia 37:653; Huber et al., 1993, Anal. Biochem. 212:351). These references and the references contained therein are incorporated herein in their entireties. MIPC separations are complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and column inlet areas.

Although DHPLC and MICP are the described methods for separating and identifying heteroduplex, it is understood that other methods known in the art may also be used for identifying heteroduplex. For example, heteroduplex analysis on high resolution gel matrices are also able to detect even single nucleotide polymorphisms. (Hauser et al., 1998, Plant. J. 16:117-25). The PCR/OLA procedure can be used for analyzing amplification products to detect SNPs in the 3' end of the human PKD gene (Glick and Pasternak, 1994, *Molecular Biotechnology: Principles and Applications of Recombinant DNA*, ASM Press, Washington, D.C., pp. 197-200). Conformation-sensitive gel electrophoresis of amplification products may also be employed as a means of analysis by the skilled artisan in practicing the methods of the present invention. (Markoff et al., 1998, Eur. J. Genet. 6:145-50). This can also be achieved by techniques such as PCR-restriction fragment-SSCP, which can detect single base substitutions, deletions or insertions (Tawata et al., 1996, Genet. Anal. 12(3-4): 125-27; Lee et al., 1992, Anal. Biochem. 205:289-93). Electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence (Keparnik et al., 1998, Electrophoresis 19:249-55; Inoue et al. 1998, J. Chromatogr. A. 802:179-84; Dovichi, 1997, 18:2393-99; Arakawa et al., 1997, J. Pharm. Biomed. Anal. 15:1537-44; Baba, 1996, J. Chromatgr B. Biomed. Appl. 687:271-302; Chan et al., 1997, J. Chromatogr B. Biomed. Sci. Appl. 695:13-15). Any of diverse fluorescent dyes can optionally be used to label primers of the present invention or amplification products for ease of analysis, including but not limited to, SYBR Green I, Y10-PRO-1, thiazole orange, Hex (i.e., 6-carboxy-2',4',7',4, 7-hexachlorofluoroscein), pico green, edans, fluorescein, FAM (i.e., 6-carboxyfluorescein), or TET (i.e., 4,7,2',7'-tetrachloro-6-carboxyfluoroscein) (e.g., Skeidsvoll and Ueland, 1995, Anal. Biochem. 231:359-65; Iwahana et al., 1996, Biotechniques 21:510-14, 516-19).

In using the invention in its preferred embodiment to effect a separation of homoduplexes and heteroduplexes for the purpose of mutation detection, a DNA sample is hybridized with a normal DNA fragment by denaturing and annealing the mixture as described herein above. The DNA sample can be hybridized with normal DNA directly. The DNA sample can also be amplified by PCR and then hybridized with the normal DNA. Alternatively, a normal fragment may be added to the sample prior to PCR amplification. The amplified mixture can then be hybridized following amplification. In each of these three hybridization scenarios, a mixture of homoduplexes and heteroduplexes is produced if a mutation is present in the sample. The sample, so prepared, is analyzed by DHPLC under partially denaturing conditions, preferably at 56 to 58° C., for the presence of a mutation using the method of the invention.

When the method of the invention is used for separating a large number of samples for the presence of a mutation, the throughput of samples may be increased significantly by speeding up the analysis for each sample using a steeper gradient for the fragment bracketing range.

In all embodiments and aspects of the invention, the nucleic acid fragments are detected as they are separated and eluted from the DHPLC column. Any detector capable of detecting nucleic acids can be used in the DHPLC mutation detection method. The preferred detector is an online UV detector. If the DNA fragments are tagged with fluorescent or radioactive tags, then a fluorescence detector or radioactivity detector can be employed, respectively. Following detection, the separated fragments are displayed on a video display separate or printed by a printer. The fragments so displayed appear either as peaks or as bands in a lane.

C. Quality Controls Helpful for Evaluating DHPLC for PKD-2 and PKD-1 Unique Region The chemical principles which permit DHPLC to distinguish between heteroduplex-homoduplex mixtures and homoduplexes alone also make the methodology quite sensitive to (1) buffer composition, (2) oven temperature at the time of analysis, (3) column condition, and (4) system condition at the time a sample is injected. Fluctuation in elution patterns is normal, and varies depending on the size and sequence of the amplicon, and the specific DHPLC conditions under which it is analyzed. One skilled in the art would have the knowledge in interpreting the elution patterns produced, for example, by following the protocol provided by the manufacture of the DHPLC equipment. However, limits on the extent of fluctuation are appropriate to help ensure that conditions are within a range that would be expected to effectively separate for DNA variants. The following quality control requirements are useful examples established for each analytical condition to ensure consistent assay performance.

1. No DNA Control

This control demonstrates that reagents and materials are free of non-specific signal that could interfere with patient analysis. In some embodiment, the control must show minimal signal (<10% of normal control peak height) in a no-DNA sample treated identically to a sample comprising a DNA, e.g., extracted from a tissue. Because all of the analytical system's hardware is re-used for each sample analysis, and because the DHPLC analysis is the separating component, up to 10% peak height of the normal control is permitted. Actual contamination with a different sequence might cause a false positive DHPLC pattern difference which would trigger reflexing to sequencing which would not be expected to detect a 10% contaminant. In the event that a sequence difference is detected, the fragment would be repeated from the point of PCR to confirm the result. Similarly contamination of an actual positive with 10% of a normal sequence would not be expected to significantly alter the pattern since 50% of the DNA present is already normal. Rare cases where a very subtle pattern change might be obscured by 10% extra normal DNA in the injection are accounted for in the sensitivity estimates of 78-96%. However, persistent no DNA signal each time the amplicon is analyzed indicates the need to alter analytical conditions to minimize or eliminate a systematic and persistent no DNA signal.

2. Normal Control

In one embodiment, the normal control pattern must be consistent with historic patterns. Consistency with established patterns indicates acceptable amplification, retention times, peak height, and peak shape. Therefore, PCR and DHPLC conditions (machine and buffers, etc.) are performed as specified in the Examples. Homologues, or other non-specific amplification signals are absent as indicated by comparison with the established normal control pattern.

3. Positive Control

The positive controls are "DHPLC analytical condition controls" used to demonstrate that the established DHPLC analytical conditions (which detect the positive control heteroduplex) are in effect at the time of analysis. A positive control pattern distinct from normal control and consistent with historic patterns indicates acceptable retention time, peak height(s), peak shape and pattern. Heteroduplex detection indicates that the specific DHPLC analysis conditions optimal for the individual fragment were in effect during patient analysis. It is important to note that these controls are not necessarily PKD positive signals. Specific PKD positive samples for each of the 83 PKD fragments are not available. In their absence, another heteroduplex (positive and normal control) is used as the positive indicator demonstrating appropriate analytical conditions at the time of analysis.

4. Additional Positive Controls

Additional positive controls provide pattern(s) consistent with historic patterns for this specific mutation and may be used to separate out very common polymorphisms. Generally, a specific DNA variant will generate a unique signature heteroduplex pattern that is highly reproducible from sample to sample. A pattern consistent with the established pattern indicates acceptable retention time, peak height(s), peak shape and pattern. The specific heteroduplex pattern demonstrates that specific DHPLC analysis conditions optimal for this DNA variant were in effect during patient analysis and, therefore, patient patterns matching this can be considered to possess the common polymorphism. This optional separating method for common polymorphisms is highly specific to the unique amplicon and variant and is dependent upon appropriate validation studies unique to the variant.

D. Analyzing DHPLC Results

Since DHPLC is a separating process, any specimen (e.g., DNA, or cell lysate or tissue sample) with a signal that differs from the normal control should be considered a potential positive and treated by one of several options available depending on the circumstances. For some embodiments, a signal that is too week to interpret (less than 25% of the normal control peak height) could be caused by PCR failure, Wave injection failure, or some other sporadic instrumentation problem unique to the sample. Options include repeat from the point of PCR, repeat the Wave injection (with all controls), or report the wave result as inconclusive and proceed to sequencing. A signal that differs from the normal control in pattern should be considered positive, scored as "P", and sequenced. A signal that differs very slightly front the normal control pattern should be scored as "B" and sequenced. A signal that is much stronger than the normal control signal should be scored as "P" and sequenced. Note that no patient specimens will be resulted based on these results alone. The specific options utilized will vary with the amplicon and its DHPLC performance history, and the specific circumstances for the specimen.

In some embodiments, the only results released from the DHPLC results will be those scored as "normal" by Wave analysis. In order to be scored as normal, the specimen's DHPLC pattern must be consistent with the normal control by the following QC criteria: (a) peak number, (b) peak height, (c) peak pattern, (d) retention time, (e) baseline shape. In other words, the pattern for the individual specimen must look like the normal control, within a reasonable expected range of variation. Consult with the validation data reference patterns if necessary. The sensitivity of DHPLC separating was assessed by counting patterns that differ substantially from the normal control. When a pattern genuinely appears to differ from the normal control, there should be no doubt—it is scored as positive and sent on for sequencing. Only those that meet the requirements for that specific amplicon and have a pattern consistent with the normal control should be scored and released as normal.

Specific numerical criteria used for judging "consistent with" include, but are not limited to, (a) number of peaks where a peak represents a local maximum in the signal intensity, (b) peak heights, or maximum signal intensities, which are usually between 0.5 and 2.0 times the height of the normal control, (c) retention time of peaks, which must be +/−60 seconds compared to the corresponding normal controls. Peak pattern is judged by relative correspondence of each slope change within a peak, and relative intensities and retention times of individual peaks within a complex pattern. Baseline patterns are usually smooth and consistent in all samples. A relatively low baseline change may represent a heteroduplex that elutes and perhaps melts at considerably different retention times from the homoduplex peak(s). The retention time and peak height criteria for each amplicon are specified in the attached tables in the Examples.

In one embodiment, the peak pattern assessment is a combination of (1) the sample signal satisfying the same run control criteria as the normal control, and (2) the sample signal pattern consistent with the normal control based on the relative comparison for that nun. Normal control patterns are expected to vary slightly from run to run, and still be acceptable, so individual samples scored as normal are a combination of satisfying (1) the same run control criteria as the normal control, (2) the relative control criteria inherent in the comparison of the normal control to each patient sample, described above. It seems clear that subtle changes in the pattern of the patient sample might be consistent with the absolute run criteria for the normal control, yet be clearly distinct using relative comparison of normal and patient within a run. The relative comparison within a run always supersedes historic patterns, assuming the normal control has passed control criteria and the run is accepted.

IX. Verification of Heteroduplex

Optionally, the identified heteroduplex may be verified by means of digesting the amplification products with one or more restriction enzymes. The restriction enzymes useful for this purpose are selected by comparing the sequences of authentic PKD genes and PKD homologues, or by comparing PKD polymorphisms. Useful restriction enzymes according to the invention generate distinguishable fragment profiles for an authentic PKD gene and a PKD homologue. Examples of such restriction enzymes include, but are not limited to, Pst I, Stu I, Xma I, Mlu I, Pvu II, BssHII, Fsp I, Msc I, and Bln I. Useful restriction enzymes may also generate distinguishable fragment profile for a normal PKD gene and a mutant PKD gene. It is understood that more restriction enzymes may be identified by simply comparing the sequence of a PKD gene and a PKD homologue gene or a normal PKD allele and a mutant PKD allele. A restriction enzyme with its recognition site or cleavage site in one sequence altered so as to abolish or create a cleavage site but not in the other sequence may be considered a useful restriction enzyme for the subject invention. Restriction of nucleic acids is followed by separation of the resulting fragments and analysis of fragment length or differential fragment migration in denaturing high-performance liquid chromatography (DHPLC) or gel electrophoresis, as above, including restriction-capillary electrophoresis.

X. Sequencing of Heteroduplexes Identified by DHPLC

Heteroduplex indicating the presence of one or more mutation, identified by DHPLC, may be cloned, amplified, and/or sequenced. Any known sequencing method known in the art can be used to sequence the heteroduplex. In some embodiments, the heteroduplex identified was used as template for PCR amplification and amplified products are sequenced by Sequetech Corporation (Mountain View, Calif.). In a preferred embodiment, sequencing is carried out by using one of the primers with SEQ ID NOs. 3-49.

In some embodiments, the identified heteroduplex is amplified and cloned into a plasmid (e.g., Zero Blunt TOPO PCR cloning kit, Invitrogen, Carlsbad, Calif., Cat #4560-01) before sequencing. The plasmid containing the PCR fragment is then propagated by well known methods in the art before subject to sequencing.

XI. DNA Alterations Identified According to the Methods of the Present Invention A number of nucleotide and amino acid alterations have been identified in individuals diagnosed with ADPKD. FIG. 14A-14CC summarizes a list of non-limiting examples of alterations identified in PKD-1 and PKD-2 nucleotide and amino acid sequences from ADPKD patients according to one embodiment of the invention. The sequence positions indicated in FIG. 14A-14CC correspond to the nucleotide or amino acid positions as disclosed in FIGS. 15A-15T and 16A-16D, for PKD-1 and PKD-2 (without introns) respectively.

The nucleotide and amino acid alterations listed in FIG. 14 include both known alterations in the art and novel alterations identified the first time by applicants of the present invention. Both known and novel alterations are identified in the present invention as to be associated with an individual diagnosed with ADPKD, therefore, both known and novel alterations disclosed in FIG. 14A-14CC may be used as markers for diagnosing PKD-caused ADPKD or for any other clinical use as described below. Primers which can be used to identify each nucleotide sequence alteration are indicated in FIG. 14A-14CC as well, e.g., as PKD1X1, PKD1X36, etc. The sequences of the primers are disclosed in Table 3 herein above.

In one embodiment, the invention provides a primer selected from the group consisting of SEQ ID NOs. 3-49.

In one embodiment, the invention provides an isolated PKD-1 or PKD-2 polynucleotide comprising one or more nucleotide sequence alterations as disclosed in FIG. 14A-14CC.

In another embodiment, the invention provides an isolated PKD-1 or PKD-2 polynucleotide comprising one or more novel nucleotide sequence alterations as disclosed in FIG. 14A-14CC (indicated by bold text).

In another embodiment, the invention provides a purified PKD-1 or PKD-2 polypeptide comprising one or more amino acid sequence alterations as disclosed in 14A-14CC.

In another embodiment, the invention provides a purified PKD-1 or PKD-2 polypeptide comprising one or more novel amino acid sequence alterations as disclosed in 14A-14CC (indicated by bold text).

Preferably, the PKD-1 or PKD-2 polynucleotide or polypeptide comprising one or more sequence alterations is used as a marker for ADPKD.

XII. Clinical Use of the Subject Method and Identified Alterations

The genetic testing method described in this application is targeted toward identifying DNA alterations in the coding region of the PKD-1 or PKD-2 gene, including the splice junction acceptor/donor sequences, which have been reported to cause ADPKD. The method can be performed to assists physicians to:

A. Diagnose PKD-caused ADPKD in symptomatic individuals.

B. Follow up on ultrasound results indicating the presence of one or two cysts in an individual at or near the age of onset.

C. Diagnose between different variants of ADPKD (type 1 and 2), which may or may not be feasible to determine from family history, ultrasound and other clinical data.

In one embodiment, the invention provides a method for diagnosing ADPKD in an individual, comprising identifying nucleotide sequence of PKD-1 or PKD-2 gene of the individual, where the existence of one or more nucleotide sequence alterations in the nucleotide sequence of PKD-1 or PKD-2 gene as disclosed in FIG. 14 is indicative of ADPKD in the individual.

D. Determine and provide genetic counseling for other at-risk family members once an ADPKD proband has been identified in a family.

E. Determine the suitability of a living related donor in transplantation cases.

The invention provides methods for detecting the presence of absence of mutant PKD genes, and the presence or absence of ADPKD.

In one embodiment, the present invention provides a method for determining in an individual the presence or absence of a mutant PKD gene, comprising the steps of a) identifying the nucleotide sequence of a PKD-1 or PKD-2 gene of the individual; b) comparing the nucleotide sequence of step a) to the nucleotide sequence alteration in the nucleotide sequence of a PKD-1 or PKD-2 gene as disclosed in FIG. 14A-14CC; and c) detecting the presence of one or more of the nucleotide sequence alterations disclosed in FIG. 14A-14CC; wherein the presence of at least one of the nucleotide sequence alterations is indicative of ADPKD in the individual; and wherein the absence of any of said nucleotide sequence alterations indicates the absence of a mutant PKD-1 and/or PKD-2 gene.

XIII. Kits

The invention also provides kits for performing the mutation analysis method and the PKD patient identification method of the invention. The invention provides for kits for detecting the presence of absence of mutant PKD genes, and the presence or absence of ADPKD.

Embodiments of the subject kits, in accordance with the methods of the invention, include at least one isolated first nucleic acid selected from the group of SEQ ID NOs. 3-49 and/or their complementary sequences. The kit may further comprise at least one isolated second nucleic acid which has an opposite orientation from the first nucleic acid, and where the first and second nucleic acids amplify a fragment of a template nucleic acid comprising a sequence of SEQ ID NO. 1 or 2, and packaging materials therefore. The kit of the invention may further comprise at least one component selected from the group consisting of: a DNA polymerase, a template nucleic acid, a restriction enzyme, a control oligonucleotide primer, ddNTPs, a PCR reaction buffer and the combination thereof. Kits of the invention, in addition to the reagents, preferably include written instructions for performing the subject methods. Kits are preferably packaged in a unit container and may contain the reagents in pre-measured amounts designed to operate with each other so as to produce the desired result.

EXAMPLES

The invention is illustrated by the following non-limiting examples wherein the following materials and methods are employed.

Example 1

Reagents, Special Supplies and Equipment

A. Chemicals

The following is a listed of chemicals used for PKD-1 amplification and DHPLC (WAVE) analysis.

1% Agarose, 1×TBE, 54 Well Gel with Ethidium Bromide (Embitec, Catalog Number GE 4580)

2% Agarose, 1×TBE, 54 Well Gel with Ethidium Bromide (Embitec, Catalog Number GE 4582)

96 Well Gel Filtration Block (Edge Biosystems, Catalog Number 91751)

Quickstep™ 96 Well PCR Purification Kit (Edge Biosystems, Catalog Number 99605)

AmpliTaq Gold with GeneAmp PCR Buffer II & MgCl$_2$ Solution (Perkin Elmer, Catalog Number N808-0241)

rTth DNA Polymerase, XL & XL Buffer II Pack (Perkin Elmer, Catalog Number N808-00193)

TapPlus Precision PCR System (Stratagene, Catalog Number 600211)

Dimethyl Sulphoxide (DMSO) (Sigma, Catalog Number D-2650)

Ready-Load 100 bp DNA Ladder or Equivalent (Gibco BRL, Catalog Number 10380-012)

Ready-Load 1 kb DNA Ladder or Equivalent (Gibco BRL, 1800-828-6686, Catalog Number 10381-010)

Big Dye Terminator Ready Reaction Kit (Perkin Elmer, Catalog Number 4303150)

Gel Filtration Cartridge (Edge Biosystems, Catalog Number 42453)

Long Ranger Singel™ packs (FMC BioProducts, Catalog Number 50691 or 50693).

Oligonucleotides (Operon Technologies, Inc.)

WAVE Mutation Standard (209 bp), Catalog Number 560077 (180 ul)

Acetonitrile-HPLC Grade (VWR, Catalog Number BJO15-1)

HPLC Grade Water (VWR, Catalog Number BJ365-4)

Triethylammonium Acetate (TEAA) (Transgenomic, Catalog Number SP5890)

B. Reagents and Solutions

10 μM oligonucleotide primers: 10 μM working aliquots of PCR primers dissolved in TE buffer should be stored at 4° C. in Pre-PCR refrigerator; sequencing primer working aliquots should be stored at 4° C. in Post-PCR refrigerator.

Solution X-127: Upgrade Blue Dextran in 50 mM EDTA (pH=8.0)

Combine 0.5 ml 50 mM EDTA pH=8.0 (Solution X-35), 500 mg Blue Dextran AND 9.5 ml AUTOCLAVED, STERILE FILTERED DiH$_2$O in a sterile 15 ml conical centrifuge tube. Thoroughly mix the solution by vortexing.

Solution X-126: Upgrade Gel Loading Buffer: Combine 200 μl deionized Formamide and 40 μl Upgrade Blue Dextran in 50 mM EDTA (Solution X-127) in a 1.5 ml sterile microcentrifuge tube. Vortex thoroughly.

WAVE Solution A: Solution A (0.025% ACN)

Preparation of 2 L: 100 ml Ion Pairing Agent (TEAA)
   500 μl Acetonitrile (ACN)
   Top to 2 L with HPLC grade water WAVE Solution B: Solution B (25% ACN)

Preparation of 2 L: 100 ml Ion Pairing Agent (TEAA)
   500 ml Acetonitrile (ACN)
   Top to 2 L with HPLC grade water WAVE Syringe Wash Solution: Syringe Wash (8% ACN)

Preparation of 2 L: 160 ml Acetonitrile (ACN)
   Top to 2 L with HPLC grade water WAVE Solution D: Solution D (75% ACN)

Preparation of 2 L: 500 ml HPLC grade water
   Top to 2 L with Acetonitrile (ACN)

C. Equipment and Special Supplies

TABLE 5

| | |
|---|---|
| Perkin Elmer<br>761 Main Avenue<br>Norwalk, CT 06859 | ABI Prism ™ 377 DNA Sequencer |
| VWR Scientific Products<br>P.O. Box 232<br>Boston, MA 02101 | 1. Beckman Allegra ™ 21 Centrifuge<br>2. Eppendorf Microcentrifuge 5415C<br>3. Multichannel pipet<br>4. Sterile reservoirs<br>5. DURX 670 wipers<br>6. VWR Model 1300U Oven |
| Transgenomic, Inc.<br>12325 Emmet Street<br>Omaha, NE 68164 | WAVE Nucleic Acid Fragment Analysis System |

Example 2

Procedure

Stage I: Preparation of DNA and/or RNA from Patient Specimens

DNA is extracted from whole blood or lymphocytes using the Puregene® DNA extraction kit. DNA extracted using these reagents should be successfully PCR amplified under the conditions specific to the assay. This is tested by performing the assay as specified in the protocol and comparing the results obtained with the positive DNA control that has been previously validated.

Extracted DNA is quantitated and the 260/280 ratio is 1.4 or greater. Samples with lower ratios indicate that the quality of DNA is poor and may not meet PCR standards. If end results of the assay are not interpretable the sample should be re-extracted.

Stage II: Amplification of DNA by PCR

PCR reaction mixtures and cycling parameters (e.g., for exon 1 of PKD-1 gene) were set up as illustrated in Table 5. PCR conditions were set up similarly, but optimized for specific and efficient amplification of other exons.

TABLE 6

PCR Reaction Master Mix Component Concentrations and Thermal Cycling Conditions For First round PCR Products 1-8 (L1-L8)
LOWER MASTER MIX:

| Component: | Reaction Concentration | Volume/reaction |
|---|---|---|
| Water | — | 13.0 ul |
| 10× Buffer | 1X | 2.0 ul |
| Mg(Oac)$_2$ | 0.9 mM | None |
| dNTP mix | 200 uM | 1.0 ul |
| Primer 1 | 0.25 uM | 1.25 ul |
| Primer 2 | 0.25 uM | 1.25 ul |
| DMSO | 7.5% | 1.5 ul |
| TOTAL VOLUME | | 20 ul |

One wax bead was added to each well and incubated in a thermal cycler @ 80° C. for 5 minutes to melt the wax and incubated at 25° C. for an additional 5 minutes before placed on ice for further handling.

Upper Master Mix:

| Component: | Reaction Concentration | Volume/reaction |
|---|---|---|
| Water | — | 23.15 ul |
| 10× Buffer | 1X | 3.0 ul |
| TaqPlus Precision Polymerase mixture | 5 U/rxn | 1.0 ul |
| DMSO | 7.5% | 2.25 ul |
| TOTAL VOLUME | | 29.4 ul |
| Genomic DNA @ 500 ng/ul | | 0.6 ul |

| Cycling Parameters | | | |
|---|---|---|---|
| Melting the Wax | Amplification | | |
| 80° C. 5 min  1 cycle | 94° C. | 3 min | 1 cycle |
| 25° C. forever | 96° C. | 30 sec | |
| *Add Upper Master Mix and DNA before proceeding to next cycling step. | 68° C. | 20 sec | 35 cycles |
| | 72° C. | 3 min + 4 sec/cycle | |
| | 72° C. | 10 min | 1 cycle |

TABLE 7

Example of nested PCR reaction setup

| REAGENT | STOCK CONCENTRATION | VOLUME PER REACTION | REACTION CONCENTRATION |
|---|---|---|---|
| Water | — | 31.0 μl | — |
| Buffer II | 10X | 5.0 μl | 1X |
| MgCl$_2$ | 25 mM | 2.0 μl | 1.0 mM |
| DNTP mix | 10 mM each | 1.0 μl | 200 μM each |
| CAD-18-PF1 (primer) | 10 μM | 3.0 μl | 0.6 μM |
| CAD-18-PR1 (primer) | 10 μM | 3.0 μl | 0.6 μM |
| DMSO | 100% | 2.5 μl | 5% |
| Amplitaq Gold | 5 U/μl | 0.5 μl | 2.5 U |
| TOTAL | | 48.0 μl | |

TABLE 8

Summary of Amplification Conditions For Exons

| CYCLE NUMBER | TEMPERATURE | TIME | DESCRIPTION |
|---|---|---|---|
| 1 cycle | 94° C. | 10 min | AmpliTaq Gold activation |
| | 92° C. | 1 min | Denaturing |
| 35 cycles | 55° C. | 1 min | Annealing |
| | 72° C. | 1 min | Extension |
| 1 cycle | 72° C. | 10 min | Final extension |
| (hold) | 4° C. | forever | |

PCR amplified fragments may be compared in size, signal intensity and migration pattern with positive control DNA control that has been previously validated. The size of the PCR amplified fragments is determined by comparison to the Molecular weight marker (DNA MASS™ Ladder-Gibco BRL) on the gel. The low range DNA Mass Ladder gives 6 bands of double stranded (100-2000 bp) DNA on staining the gel with ethidium bromide.

Stage III: DHPLC Analysis of PCR Products

Heteroduplexes formed by PCR amplified products are analyzed using WAVE nucleic acid fragment analysis system from Transgenomic, Inc. (Omaha, Nebr. 68164).

Stage IV: Cycle Sequencing

Tables 9 and 10 provide examples of sequencing conditions used in one embodiment of the invention.

TABLE 9

Sequencing Reaction Master Mix Component

| REAGENT | STOCK CONCENTRATION | VOLUME PER REACTION | REACTION CONCENTRATION |
|---|---|---|---|
| Water | — | 14.0 μl | — |
| Big Dye Terminator Ready Reaction Mix | 2.5X | 4.0 μl | 0.5X |
| Primer | 10 μM | 1.0 μl | 0.5 μM |
| FINAL VOLUME | | 19.0 μl | |

TABLE 10

Cycle Sequencing Conditions

| CYCLE NUMBER | TEMPERATURE | TIME | DESCRIPTION |
|---|---|---|---|
|  | 94° C. | 10 sec | Denaturing |
| 30 cycles | 55° C. | 5 sec | Annealing |
|  | 60° C. | 4 min | Extension |
| (hold) | 4° C. | forever |  |

Example 3

Summary of Results

Figure 4:
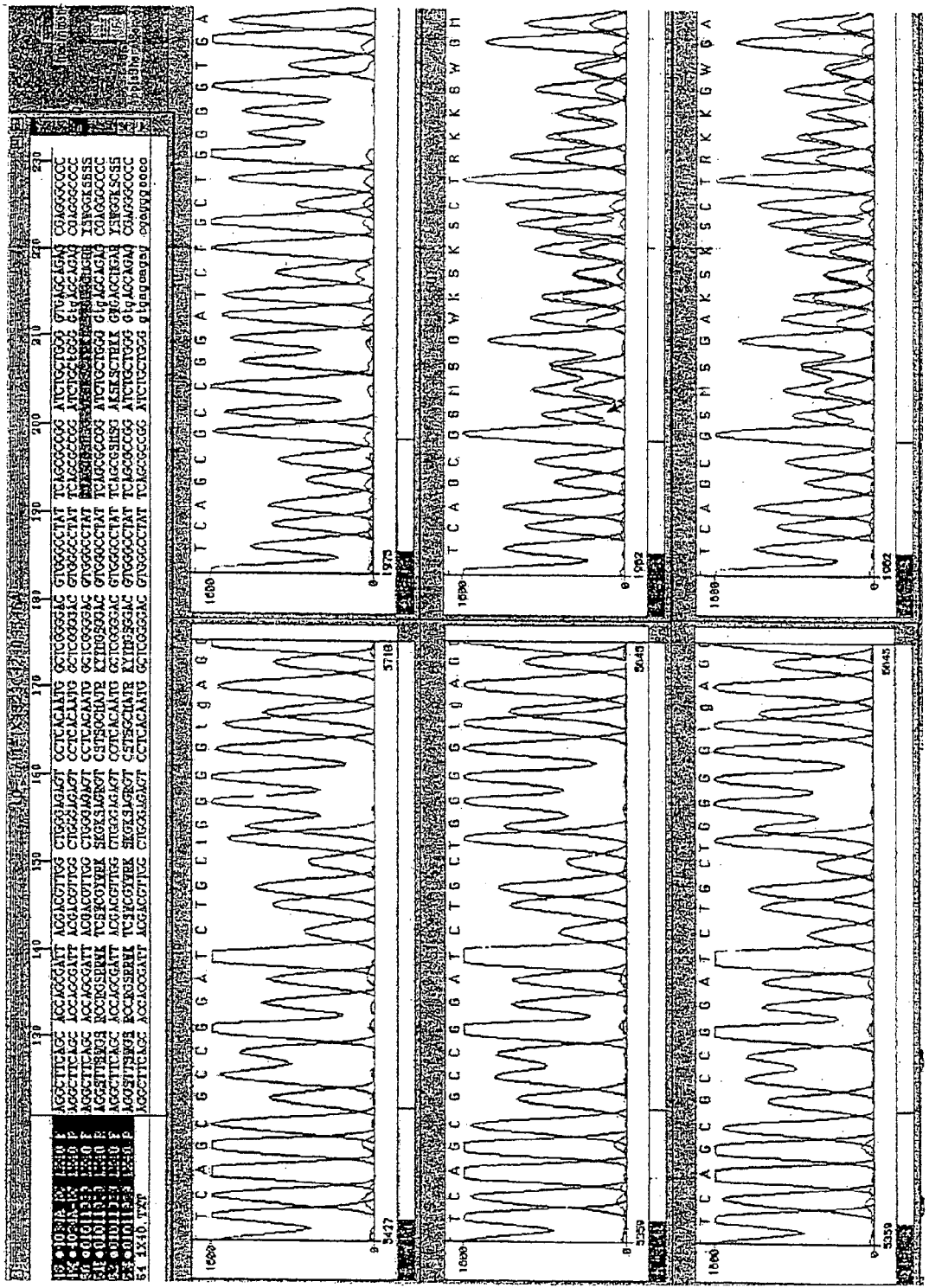
FIG. 4 is a graph showing PKD1 exon 40 sequences of the normal control and a sequence with a 19 bp insertion (duplication) at nucleotide 11606, codon 3799 according to one embodiment.
Figure 5:
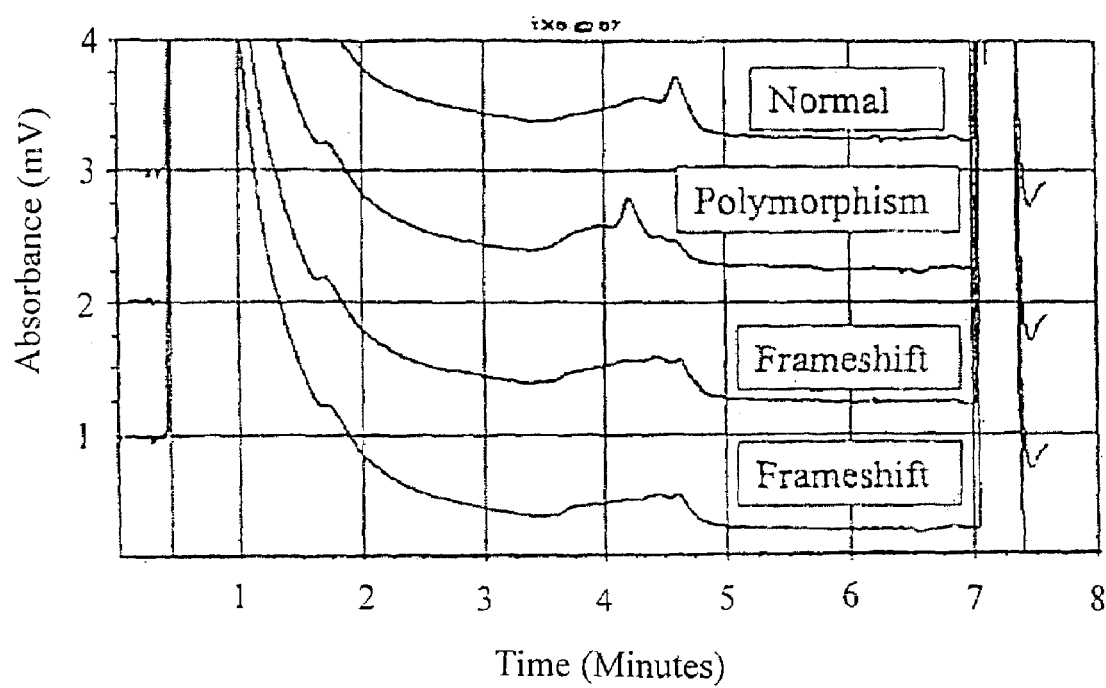
FIG. 5 is a graph showing PKD1 exon 6 DHPLC patterns of an intron 5 probable polymorphism (IVS5-9 G->A) and a frameshift at nucleotide 1502 (insert G) in two related patients according to one embodiment.
Figure 6:
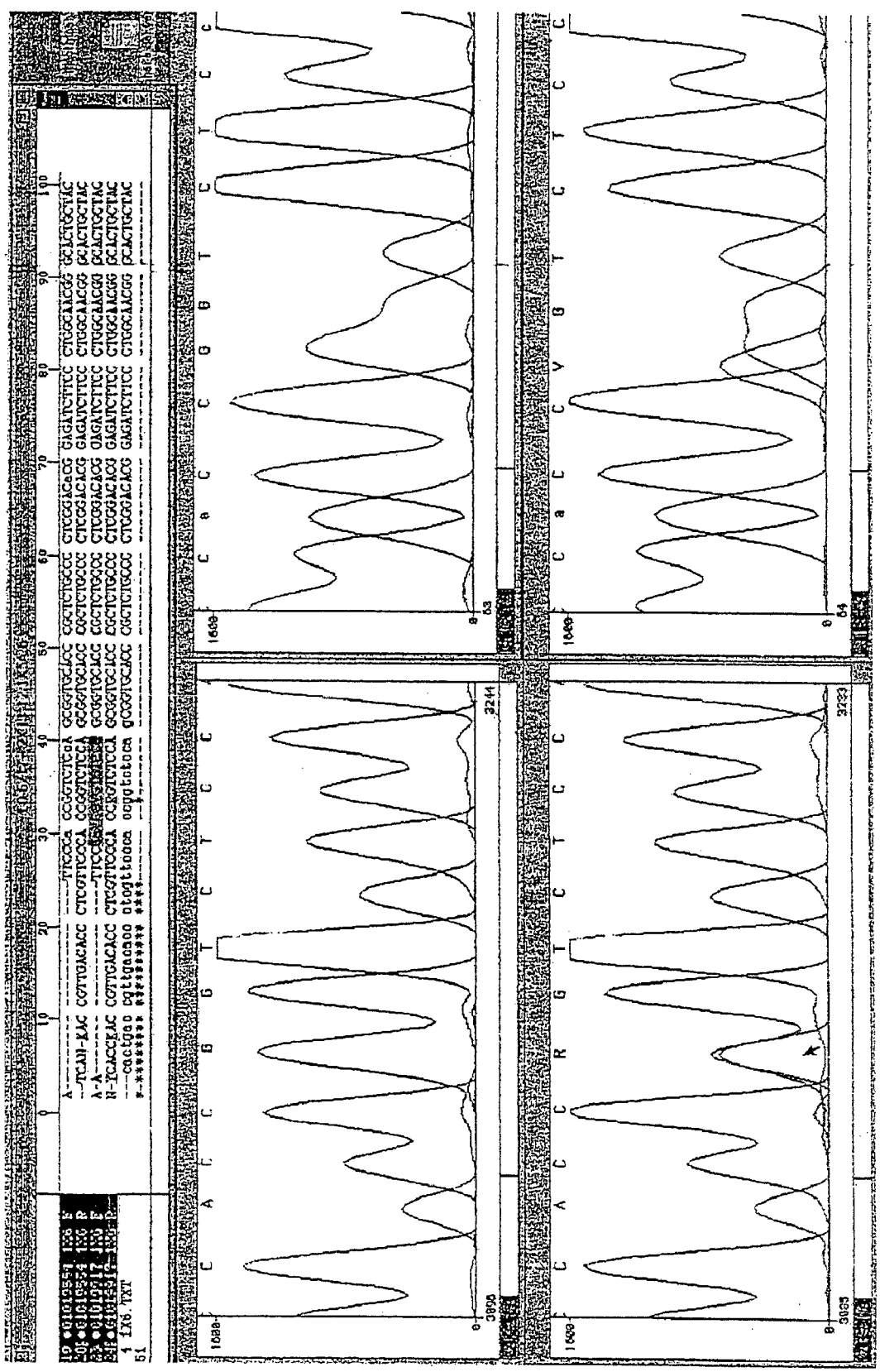
FIG. 6 is a graph showing PKD1 exon 6 sequences of the normal control and a sequence with intron 5 probable polymorphism (IVS5-9 G->A) according to one embodiment.
Figure 7:
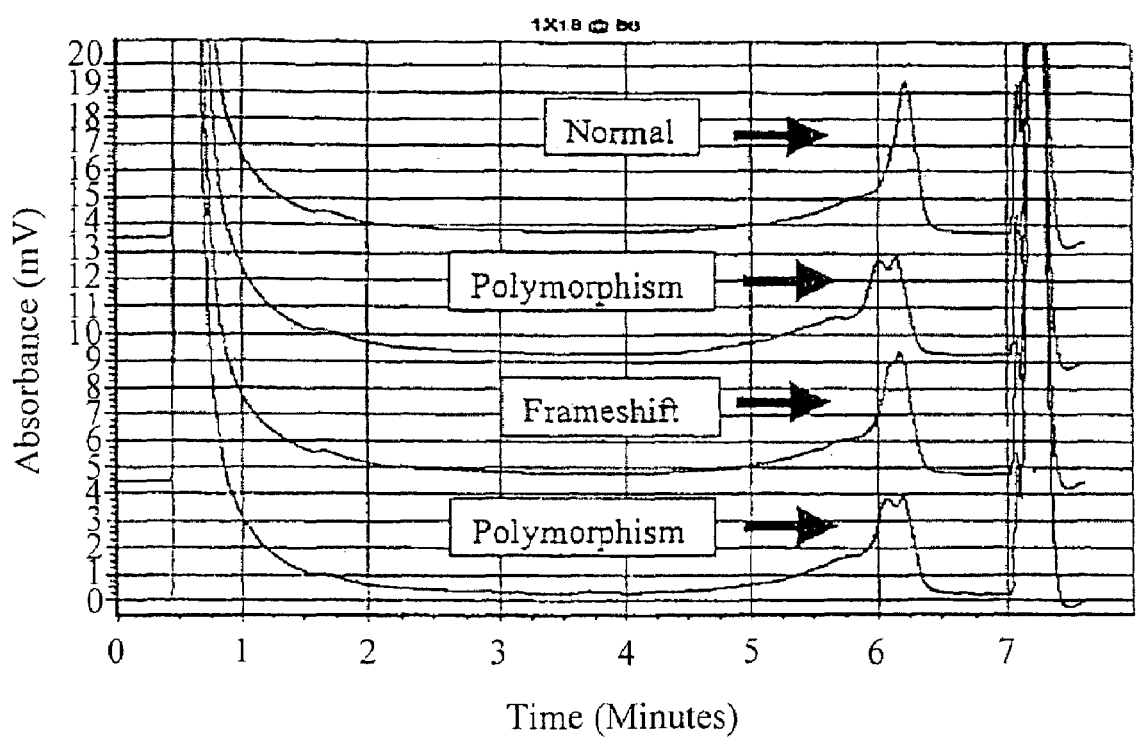
FIG. 7 is a graph showing PKD1 exon 18 DHPLC patterns of a frameshift at nucleotide 7518, codon 2436 (insert C), and a common polymorphism C7652T according to one embodiment.
Figure 8:
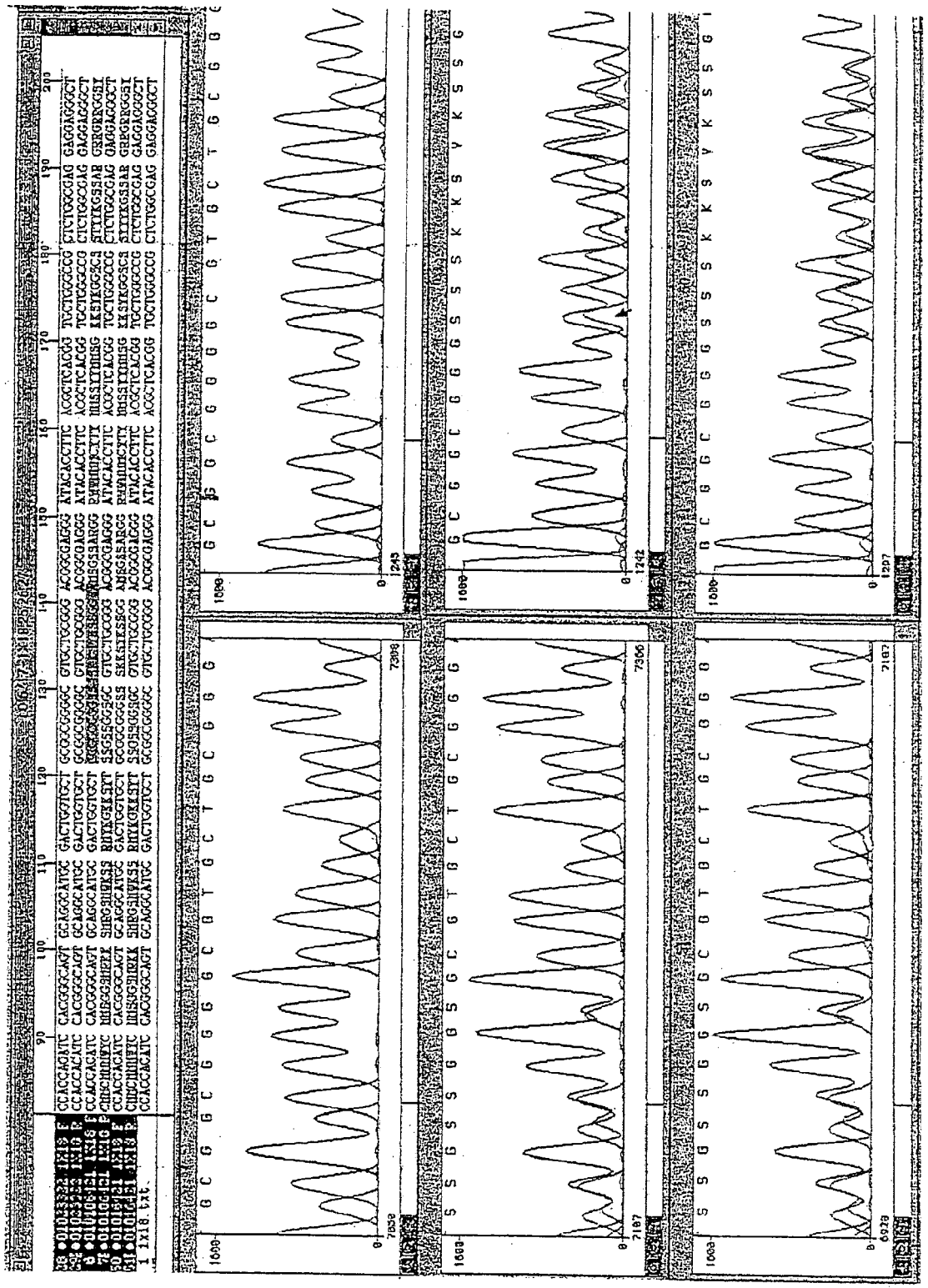
FIG. 8 is a graph showing PKD1 exon 18 sequences of the normal control and a sequence with frameshift at nucleotide 7518, codon 2436 (insert C) according to one embodiment.
Figure 9:
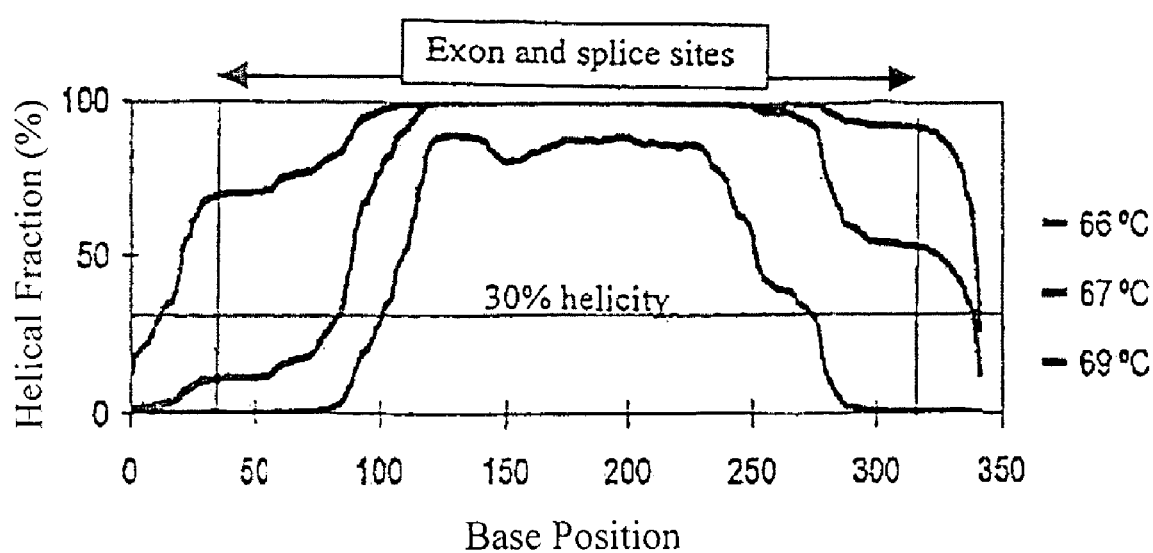
FIG. 9 is a graph showing an example of a software-predicted melt profile and the need for multiple temperatures to establish partial melting near the ends of an exon according to one embodiment.
Figure 10A:
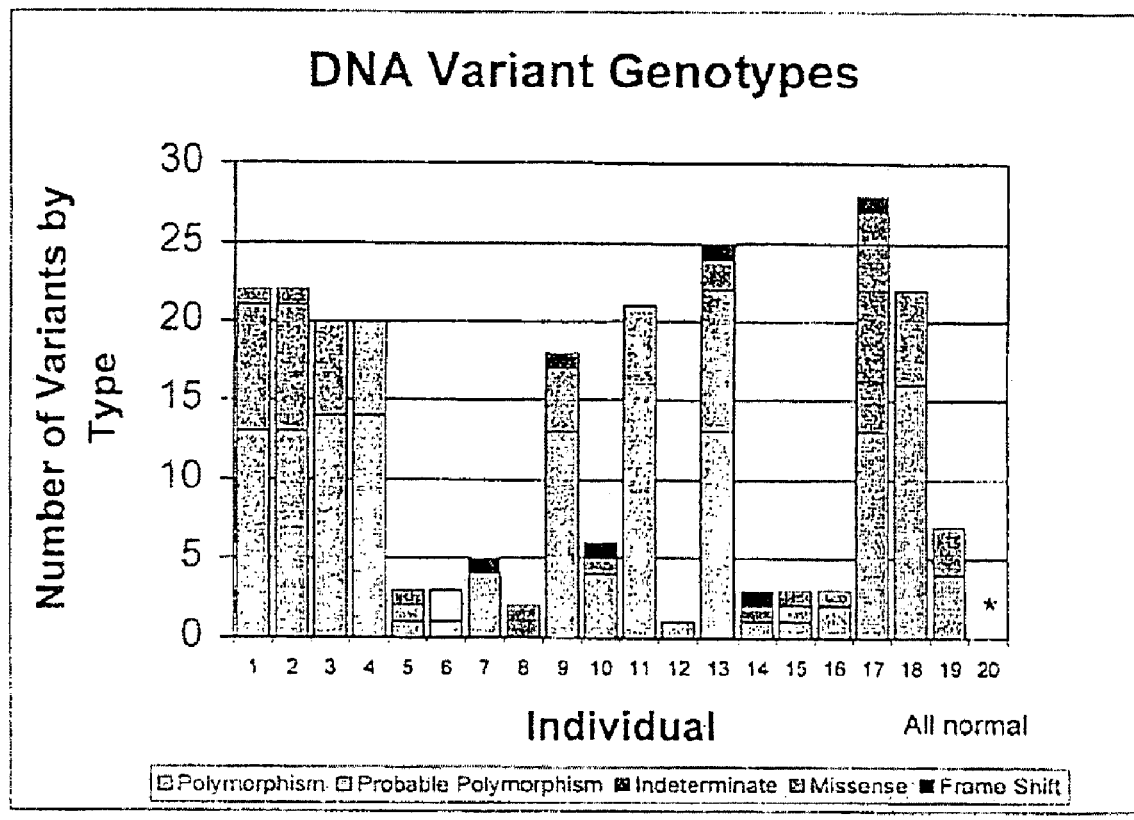
FIG. 10A is a chart showing patient DNA variant genotypes determined in one embodiment of the invention.
Figure 13:
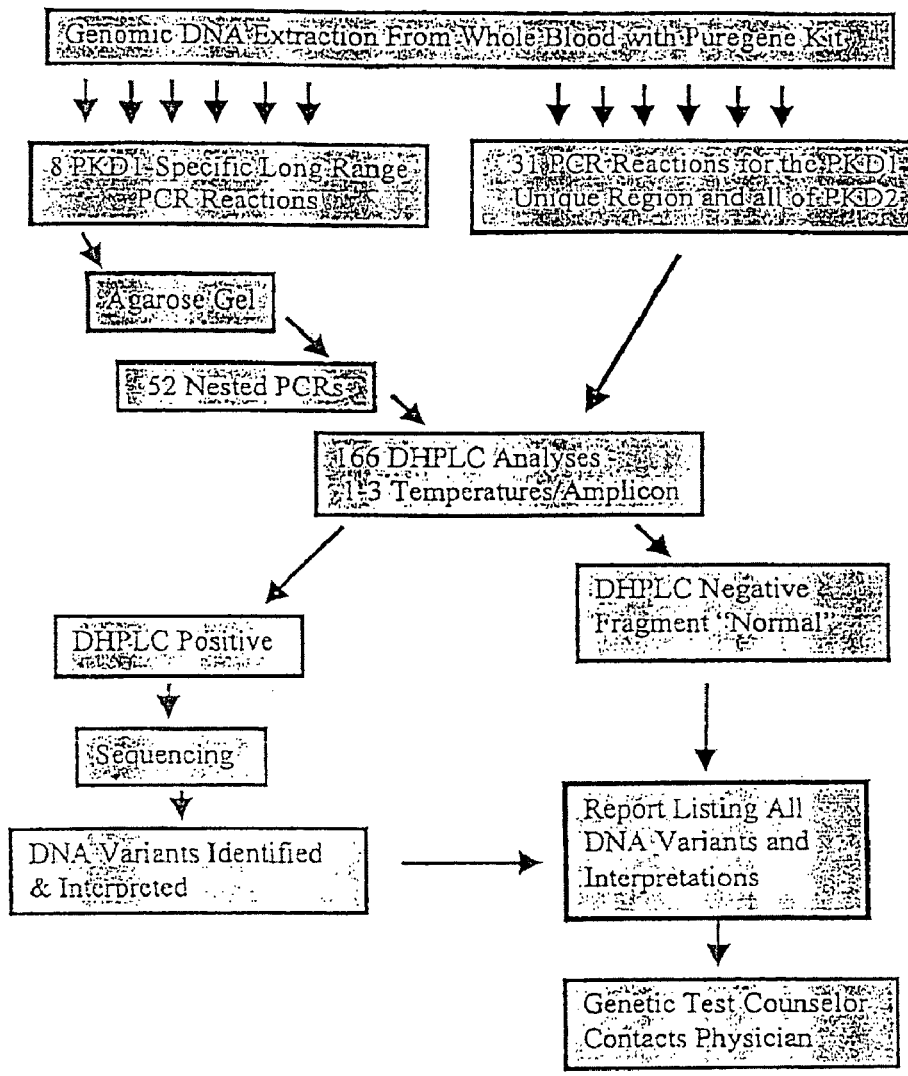
FIG. 13 is a schematic diagram showing patient specimen processing steps in one embodiment of the invention.

In one experiment, detection of mutations in exons 1-34 of the PKD-1 gene was achieved by using eight sets of oligonucleotide primers in eight separate first round PCR reaction to amplify DNA fragments of the following sizes: a) LR1 was 2.2 kb and contains exon 1. b) LR2 was 4.6 kb and contains exons 2-7. c) LR3 was 4.2 kb and contains exons 8-12. d) LR4 was 4.4 kb and contains exons 13-15. e) LR5 was 3.4 kb and contains exons 15 (3'-end) through 21. f) LR6 was 0.3 kb and consists of exon 22. g) LR7 was 4.2 kb and contains exons 23-28. h) LR8 was 5.8 kb and contained exons 29-34 of the duplicated region of the gene. The amplified product from the first round of amplification were then serially diluted to 1:10$^4$ or 1:10$^5$ to remove genomic contamination and subsequently used as template in a second round of nested PCR. The nested PCR products were heteroduplexed and screened for sequence alterations by DHPLC. Each fragment was analyzed against a normal and positive control using a temperature and acetonitrile gradient specific to the amplicon. Any samples testing positive by DHPLC analysis were subsequently purified and sequenced. Cycle sequenced products were then separated on an ABI 377 automated sequencer and the results were analyzed using an assortment of sequencing software. Tables 11-12 and FIGS. 1 to 13 illustrate the results and procedures of some embodiments of the invention.

TABLE 11

Numbers of products analyzed for each PKD gene

| Analysis: | PKD-1 | PKD-2 | Total |
|---|---|---|---|
| First Round PCRs | 8 | — | 8 |
| Amplicons | 66 | 17 | 83 |
| DHPLC analyses | 133 | 33 | 166 |
| Base Pairs evaluated | 13,830 | 3204 | 17,034 |

TABLE 12

Variant detection rates

| Source of Variant | Naturally occurring - Independent Sequence confirmed | Naturally occurring - SSCP Separated | Mutagenesis Sequence confirmed | Gene Total |
|---|---|---|---|---|
| PKD-1 | 14/18 | 15/17 | 45/47 | 74/82 |
|  | 78% | 88% | 96% | 90% |
| PKD-2 | 20/21 | 0/0 | 22/23 | 42/44 |
|  | 95% |  | 96% | 95% |
| Type total | 34/39 | 15/17 | 67/70 | 116/126 |
|  | 87% | 88% | 96% | 92% |

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only and that in general numerous equivalent methods and techniques may be employed to achieve the same result. All applications, patents and literature referred to in the specification are hereby incorporated by reference, in their entirety, including figures and tables.

What is claimed is:

1. A method of detecting autosomal dominant polycystic kidney disease (ADPKD) in an individual comprising detecting the presence of one or more nucleotide sequence alterations selected from the group consisting of:
   a) PKD1X10 (transition C>T at nucleotide 2300, codon 697 of PKD1 gene),
   b) PKD1X15J (1 base pair deletion T at nucleotide 5352, codon 1714 of PKD1 gene),
   c) PKD1X40 (19 base pair insertion at nucleotide 11606, codon 3799 of PKD1 gene),
   d) PKD1X40 (1 base pair insertion at nucleotide 11558, codon 3783 of PKD1 gene),
   e) PKD1X31 (1 base pair deletion of C at nucleotide 10287, codon 3359 of PKD1 gene),
   f) PKD2X1A (52 base pair insertion at nucleotides 139-190, codons 25-42 of PKD2 gene),
   g) PKD1X36 (13 base pair insertion at nucleotide 10884, codon 3558 of PKD1 gene),
   h) PKD2X4 (transition of C>T at nucleotide 1147, codon 361 of PKD2 gene),
   i) PKD2X1C (4 base pair insertion of CGCC at nucleotide 596, codon 177 of PKD2 gene), j PKD1X13 (1 base pair deletion of C at nucleotide 3310, codon 1033 of PKD1 gene),
k PKD1X1 (1 base pair deletion of C at nucleotide 364, codon 51 of PKD1 gene),
l PKD1X15A (transition G>A at nucleotide 3694, codon 1161 of PKD1 gene),
m PKD2X1B (1 base pair deletion of G at nucleotide 405, codon 113 of PKD2 gene),
n PKD1X24 (1 base pair insertion of T at nucleotide 9134, codon 2975 of PKD1 gene),
o PKD1X35 (2 base pair deletion of GA at nucleotides 10735-10736, codons 3508-3509 of PKD1 gene),
p PKD1X42 (1 base pair deletion at nucleotide 11836, codon 3875 of PKD1 gene),
q PKD1X14 (transition C>T at nucleotide 3395, codon 1062 of PKD1 gene), and
r PKD1X46B (transversion G>T at nucleotide 12926, codon 4239) in the nucleotide sequence of a PKD-1 or PKD-2 gene in a nucleic acid sample obtained from said individual, wherein the presence of said one or more nucleotide sequence alterations indicates that the individual has ADPKD.

2. The method of claim 1 further comprising:
amplifying the nucleic acid sequence of the PKD-1 or PDK-2 gene prior to detection.

3. The method of claim 2, wherein the presence or absence of said one or more nucleotide sequence alterations in said nucleic acid sequence is detected by a method selected from the group consisting of ligase chain reaction, sequencing, hybridization with one or more nucleic acid probes and denaturing high performance liquid chromatography.

4. The method of claim 2, wherein said amplification is performed using an isolated nucleic acid comprising a sequence selected from the group consisting of SEQ ID NOs. 3-49 and complementary sequences thereof.

5. The method of claim 1 wherein the nucleotide sequence of said PKD-1 gene comprises SEQ ID NO:1 and the nucleotide sequence of said PKD-2 gene comprises SEQ ID NO:2.

6. A method for detecting in an individual the presence or absence of a mutant PKD gene comprising:
(a) obtaining a nucleic acid sample from said individual; and
(b) detecting the presence or absence of one or more mutations in a PKD-1 or PKD-2 gene of said individual, wherein the mutation or deletion is selected from the group consisting of:
a PKD1X10 (transition C>T at nucleotide 2300, codon 697 of PKD1 gene),
b PKD1X15J (1 base pair deletion T at nucleotide 5352, codon 1714 of PKD1 gene),
c PKD1X40 (19 base pair insertion at nucleotide 11606, codon 3799 of PKD1 gene),
d PKD1X40 (1 base pair insertion at nucleotide 11558, codon 3783 of PKD1 gene),
e PKD1X31 (1 base pair deletion of C at nucleotide 10287, codon 3359 of PKD1 gene),
f PKD2X1A (52 base pair insertion at nucleotides 139-190, codons 25-42 of PKD2 gene),
g PKD1X36 (13 base pair insertion at nucleotide 10884, codon 3558 of PKD1 gene),
h PKD2X4 (transition of C>T at nucleotide 1147, codon 361 of PKD2 gene),
i PKD2X1C (4 base pair insertion of CGCC at nucleotide 596, codon 177 of PKD2 gene),
j PKD1X13 (1 base pair deletion of C at nucleotide 3310, codon 1033 of PKD1 gene),
k PKD1X1 (1 base pair deletion of C at nucleotide 364, codon 51 of PKD1 gene),
l PKD1X15A (transition G>A at nucleotide 3694, codon 1161 of PKD1 gene),
m PKD2X1B (1 base pair deletion of G at nucleotide 405, codon 113 of PKD2 gene),
n PKD1X24 (1 base pair insertion of T at nucleotide 9134, codon 2975 of PKD1 gene),
o PKD1X35 (2 base pair deletion of GA at nucleotides 10735-10736, codons 3508-3509 of PKD1 gene),
p PKD1X42 (1 base pair deletion at nucleotide 11836, codon 3875 of PKD1 gene),
q PKD1X14 (transition C>at nucleotide 3395, codon 1062 of PKD1 gene), and
r PKD1X46B (transversion G>T at nucleotide 12926, codon 4239).

7. The method of claim 6 wherein the presence of one or more mutations or deletion in said PKD-1 or PKD-2 gene of said individual indicates that the individual has autosomal dominant polycystic kidney disease (ADPKD).

8. The method of claim 7 wherein the nucleic acid sample is amplified and presence or absence of said one or more mutations in said nucleic acid sequence is detected by at least one method selected from the group consisting of ligase chain reaction, sequencing, hybridization with one or more nucleic acid probes and denaturing high performance liquid chromatography.

9. The method of claim 8, wherein said amplification is performed using an isolated nucleic acid comprising a sequence selected from the group consisting of SEQ ID NOs. 3-49 and complementary sequences thereof.

10. The method of claim 6 wherein the nucleotide sequence of said PKD-1 gene comprises SEQ ID NO:1 and the nucleotide sequence of said PKD-2 gene comprises SEQ ID NO:2.

11. A method for detecting the presence or absence of one or more mutations in a nucleic acid encoding a PKD-1 protein, a PKD-2 protein or PKD-1 protein and a PKD-2 protein comprising:
(a) analyzing a test sample containing a nucleic acid sequence encoding a PKD-1 protein comprising SEQ ID NO. 171 or a PKD-2 protein comprising SEQ ID NO. 172 for one or more mutations or deletions in said nucleic acid sequence selected from the group consisting of:
a PKD1X10 (transition C>T at nucleotide 2300, codon 697 of PKD1 gene),
b PKD1X15J (1 base pair deletion T at nucleotide 5352, codon 1714 of PKD1 gene),
c PKD1X40 (19 base pair insertion at nucleotide 11606, codon 3799 of PKD1 gene),
d PKD1X40 (1 base pair insertion at nucleotide 11558, codon 3783 of PKD1 gene),
e PKD1X31 (1 base pair deletion of C at nucleotide 10287, codon 3359 of PKD1 gene),
f PKD2X1A (52 base pair insertion at nucleotides 139-190, codons 25-42 of PKD2 gene),
g PKD1X36 (13 base pair insertion at nucleotide 10884, codon 3558 of PKD1 gene),
h PKD2X4 (transition of C>T at nucleotide 1147, codon 361 of PKD2 gene),
i PKD2X1C (4 base pair insertion of CGCC at nucleotide 596, codon 177 of PKD2 gene),
j PKD1X13 (1 base pair deletion of C at nucleotide 3310, codon 1033 of PKD1 gene),
k PKD1X1 (1 base pair deletion of C at nucleotide 364, codon 51 of PKD1 gene), l PKD1X15A (transition G>A at nucleotide 3694, codon 1161 of PKD1 gene),
m PKD2X1B (1 base pair deletion of G at nucleotide 405, codon 113 of PKD2 gene),
n PKD1X24 (1 base pair insertion of T at nucleotide 9134, codon 2975 of PKD1 gene),
o PKD1X35 (2 base pair deletion of GA at nucleotides 10735-10736, codons 3508-3509 of PKD1 gene),
p PKD1X42(1 base pair deletion at nucleotide 11836, codon 3875 of PKD1 gene),
q PKD1X14 (transition C>T at nucleotide 3395, codon 1062 of PKD1 gene), and
r PKD1X46B (transversion G>T at nucleotide 12926, codon 4239); and
(b) comparing the results of the analysis of the test sample with the results of analysis of a control sample,
wherein the control sample comprises the nucleic acid sequence encoding a PKD-1 protein of SEQ ID NO. 171, a PKD-2 protein of SEQ ID NO. 172 or a PKD-1 protein of SEQ ID NO. 171 and a PKD-2 protein of SEQ ID NO. 172 without a mutation.

12. The method of claim 11 further comprising amplifying the nucleic acid sequence prior to analysis.

13. The method of claim 12 wherein the presence or absence of said one or more mutations in said nucleic acid sequence is detected by at least one method selected from the group consisting of ligase chain reaction, sequencing, one or more nucleic acid probes and denaturing high performance liquid chromatography.

14. The method of claim 12, wherein said amplification is performed using an isolated nucleic acid comprising a sequence selected from the group consisting of SEQ ID NOs. 3-49 and complementary sequences thereof.

* * * * *

SEQUENCE LISTING

<160> NUMBER OF SEQ ID NOS: 172

<210> SEQ ID NO 1
<211> LENGTH: 14136
<212> TYPE: DNA
<213> ORGANISM: Homo sapiens

<400> SEQUENCE: 1

| | | | | | |
|---|---|---|---|---|---|
| gcactgcagc | gccagcgtcc | gagcgggcgg | ccgagctccc | ggagcggcct | ggccccgagc | 60 |
| cccgagcggg | cgtcgctcag | cagcaggtcg | cggccgcgca | gccccatcca | gccccgcgcc | 120 |
| cgccatgccg | tccgcgggcc | ccgcctgagc | tgcggtctcc | gcgcgcgggc | gggcctgggg | 180 |
| acggcggggc | catgcgcgcg | ctgccctaac | gatgccgccc | gccgcgcccg | cccgcctggc | 240 |
| gctggccctg | ggcctgggcc | tgtggctcgg | ggcgctggcg | ggggccccg | ggcgcggctg | 300 |
| cgggccctgc | gagccccct | gcctctgcgg | cccagcgccc | ggcgccgcct | gccgcgtcaa | 360 |
| ctgctcgggc | gcgggctgc | ggacgctcgg | tcccgcgctg | cgcatccccg | cggacgccac | 420 |
| agcgctagac | gtctcccaca | acctgctccg | ggcgctggac | gttgggctcc | tggcgaacct | 480 |
| ctcggcgctg | gcagagctgg | atataagcaa | caacaagatt | tctacgttag | aagaaggaat | 540 |
| atttgctaat | ttatttaatt | taagtgaaat | aaacctgagt | gggaacccgt | ttgagtgtga | 600 |
| ctgtggcctg | gcgtggctgc | cgcgatgggc | ggaggagcag | caggtgcggg | tggtgcagcc | 660 |
| cgaggcagcc | acgtgtgctg | ggcctggctc | cctggctggc | cagcctctgc | ttggcatccc | 720 |
| cttgctggac | agtggctgtg | gtgaggagta | tgtcgcctgc | ctccctgaca | acagctcagg | 780 |
| caccgtggca | gcagtgtcct | tttcagctgc | ccacgaaggc | ctgcttcagc | cagaggcctg | 840 |
| cagcgccttc | tgcttctcca | ccggccaggg | cctcgcagcc | ctctcggagc | agggctggtg | 900 |
| cctgtgtggg | gcgccccagc | cctccagtgc | ctcctttgcc | tgcctgtccc | tctgctccgg | 960 |
| ccccccgcca | cctcctgccc | ccacctgtag | ggccccacc | ctcctccagc | acgtcttccc | 1020 |
| tgcctcccca | ggggccaccc | tggtggggcc | ccacggacct | ctggcctctg | gccagctagc | 1080 |
| agccttccac | atcgctgccc | cgctccctgt | cactgccaca | cgctgggact | tcggagacgg | 1140 |
| ctccgccgag | gtggatgccg | ctgggccggc | tgcctcgcat | cgctatgtgc | tgcctgggcg | 1200 |
| ctatcacgtg | acggccgtgc | tggccctggg | ggccggctca | gccctgctgg | ggacagacgt | 1260 |
| gcaggtggaa | gcggcacctg | ccgccctgga | gctcgtgtgc | ccgtcctcgg | tgcagagtga | 1320 |
| cgagagcctt | gacctcagca | tccagaaccg | cggtggttca | ggcctggagg | ccgcctacag | 1380 |
| catcgtggcc | ctgggcgagg | agccggcccg | agcggtgcac | ccgctctgcc | cctcggacac | 1440 |
| ggagatcttc | cctggcaacg | ggcactgcta | ccgcctggtg | gtggagaagg | cggcctggct | 1500 |
| gcaggcgcag | gagcagtgtc | aggcctgggc | cggggccgcc | ctggcaatgg | tggacagtcc | 1560 |
| cgccgtgcag | cgcttcctgg | tctcccgggt | caccaggagc | ctagacgtgt | ggatcggctt | 1620 |
| ctcgactgtg | caggggtgg | aggtgggccc | agcgccgcag | ggcgaggcct | tcagcctgga | 1680 |
| gagctgccag | aactggctgc | ccggggagcc | acacccagcc | acagccgagc | actgcgtccg | 1740 |
| gctcgggccc | accgggtggt | gtaacaccga | cctgtgctca | gcgccgcaca | gctacgtctg | 1800 |
| cgagctgcag | cccggaggcc | cagtgcagga | tgccgagaac | ctcctcgtgg | gagcgcccag | 1860 |
| tggggacctg | cagggacccc | tgacgcctct | ggcacagcag | gacggcctct | cagcccgca | 1920 |
| cgagcccgtg | gaggtcatgg | tattcccggg | cctgcgtctg | agccgtgaag | ccttcctcac | 1980 |
| cacggccgaa | tttgggaccc | aggagctccg | gcggcccgcc | cagctgcggc | tgcaggtgta | 2040 |

```
ccggctcctc agcacagcag ggaccccgga gaacggcagc gagcctgaga gcaggtcccc    2100
ggacaacagg acccagctgg cccccgcgtg catgccaggg ggacgctggt gccctggagc    2160
caacatctgc ttgccgctgg acgcctcttg ccaccccag gcctgcgcca atggctgcac     2220
gtcagggcca gggctacccg ggcccccta tgcgctatgg agagagttcc tcttctccgt     2280
tgccgcgggg cccccgcgc agtactcggt caccctccac ggccaggatg tcctcatgct     2340
ccctggtgac ctcgttggct tgcagcacga cgctggccct ggcgccctcc tgcactgctc    2400
gccggctccc ggccaccctg gtccccaggc ccgtacctc tccgccaacg cctcgtcatg     2460
gctgccccac ttgccagccc agctggaggg cacttgggcc tgccctgcct gtgccctgcg    2520
gctgcttgca gccacggaac agctcaccgt gctgctgggc ttgaggccca accctggact    2580
gcggatgcct gggcgctatg aggtccgggc agaggtgggc aatggcgtgt ccaggcacaa    2640
cctctcctgc agctttgacg tggtctcccc agtggctggg ctgcgggtca tctaccctgc    2700
cccccgcgac ggccgcctct acgtgcccac caacggctca gccttggtgc tccaggtgga    2760
ctctggtgcc aacgccacgg ccacggctcg ctggcctggg ggcagtgtca gcgcccgctt    2820
tgagaatgtc tgccctgccc tggtggccac cttcgtgccc ggctgccct gggagaccaa     2880 cgatacctg ttctcagtgg tagcactgcc gtggctcagt gaggggagc acgtggtgga     2940 cgtggtggtg gaaaacagcg ccagccgggc caacctcagc ctgcgggtga cggcggagga    3000
gcccatctgt ggcctccgcg ccacgcccag cccgaggcc cgtgtactgc agggagtcct     3060
agtgaggtac agccccgtgg tggaggccgg ctcggacatg gtcttccggt ggaccatcaa    3120
cgacaagcag tccctgacct tccagaacgt ggtcttcaat gtcatttatc agagcgcggc    3180
ggtcttcaag ctctcactga cggcctccaa ccacgtgagc aacgtcaccg tgaactacaa    3240
cgtaaccgtg gagcggatga acaggatgca gggtctgcag gtctccacag tgccggccgt    3300
gctgtccccc aatgccacgc tagcactgac ggcgggcgtg ctggtggact cggccgtgga    3360
ggtggccttc ctgtggaact ttggggatgg ggagcaggcc ctccaccagt tccagcctcc    3420
gtacaacgag tccttcccgg ttccagaccc ctcggtggcc caggtgctgg tggagcacaa    3480
tgtcatgcac acctacgctg ccccaggtga gtacctcctg accgtgctgg catctaatgc    3540
cttcgagaac ctgacgcagc aggtgcctgt gagcgtgcgc gcctccctgc cctccgtggc    3600
tgtgggtgtg agtgacggcg tcctggtggc cggccggccc gtcaccttct acccgcaccc    3660
gctgccctcg cctggggtg ttctttacac gtgggacttc ggggacggct cccctgtcct     3720
gacccagagc cagccggctg ccaaccacac ctatgcctcg aggggcacct accacgtgcg    3780
cctggaggtc aacaacacgg tgagcggtgc ggcggcccag gcggatgtgc gcgtctttga    3840
ggagctccgc ggactcagcg tggacatgag cctggccgtg gagcagggcg ccccgtggt    3900 ggtcagcgcc gcggtgcaga cgggcgacaa catcacgtgg accttcgaca tggggacgg    3960 caccgtgctg tcgggcccgg aggcaacagt ggagcatgtg tacctgcggg cacagaactg    4020
cacagtgacc gtgggtgcgg ccagcccgc cggccacctg gcccggagcc tgcacgtgct     4080
ggtcttcgtc ctggaggtgc tgcgcgttga acccgccgcc tgcatcccca cgcagcctga    4140
cgcgcggctc acggcctacg tcaccgggaa cccggcccac tacctcttcg actgggacct    4200
cggggatggc tcctccaaca cgaccgtgcg ggggtgcccg acggtgacac acaacttcac    4260
gcggagcggc acgttccccc tggcgctggt gctgtccagc cgcgtgaaca gggcgcatta    4320
cttcaccagc atctgcgtgg agccagaggt gggcaacgtc accctgcagc cagagaggca    4380
```

```
gtttgtgcag ctcggggacg aggcctggct ggtggcatgt gcctggcccc cgttcccta      4440
ccgctacacc tgggactttg gcaccgagga agccgccccc acccgtgcca ggggccctga      4500
ggtgacgttc atctaccgag acccaggctc ctatcttgtg acagtcaccg cgtccaacaa      4560
catctctgct gccaatgact cagccctggt ggaggtgcag gagcccgtgc tggtcaccag      4620
catcaaggtc aatggctccc ttgggctgga gctgcagcag ccgtacctgt tctctgctgt      4680
gggccgtggg cgccccgcca gctacctgtg ggatctgggg gacggtgggt ggctcgaggg      4740
tccggaggtc acccacgctt acaacagcac aggtgacttc accgttaggg tggccggctg      4800
gaatgaggtg agccgcagcg aggcctggct caatgtgacg gtgaagcggc gcgtgcgggg      4860
gctcgtcgtc aatgcaagcc gcacggtggt gcccctgaat gggagcgtga gcttcagcac      4920
gtcgctggag gccggcagtg atgtgcgcta ttcctgggtg ctctgtgacc gctgcacgcc      4980
catccctggg ggtcctacca tctcttacac cttccgctcc gtgggcacct tcaatatcat      5040
cgtcacggct gagaacgagg tgggctccgc ccaggacagc atcttcgtct atgtcctgca      5100
gctcatagag gggctgcagg tggtgggcgg tggccgctac ttccccacca accacacggt      5160
acagctgcag gccgtggtta gggatggcac caacgtctcc tacagctgga ctgcctggag      5220
ggacagggc ccggccctgg ccggcagcgg caaaggcttc tcgctcaccg tgctcgaggc      5280
cggcacctac catgtgcagc tgcgggccac caacatgctg ggcagcgcct gggccgactg      5340
caccatggac ttcgtggagc ctgtggggtg gctgatggtg accgcctccc cgaacccagc      5400
tgccgtcaac acaagcgtca ccctcagtgc cgagctggct ggtggcagtg gtgtcgtata      5460
cacttggtcc ttggaggagg ggctgagctg ggagacctcc gagccattta ccacccatag      5520
cttccccaca cccggcctgc acttggtcac catgacggca gggaacccgc tgggctcagc      5580
caacgccacc gtggaagtgg atgtgcaggt gcctgtgagt ggcctcagca tcagggccag      5640
cgagcccgga ggcagcttcg tggcggccgg gtcctctgtg ccctttggg ggcagctggc      5700
cacgggcacc aatgtgagct ggtgctgggc tgtgcccggc ggcagcagca agcgtggccc      5760
tcatgtcacc atggtcttcc cggatgctgg caccttctcc atccggctca atgcctccaa      5820
cgcagtcagc tgggtctcag ccacgtacaa cctcacggcg gaggagccca tcgtgggcct      5880
ggtgctgtgg gccagcagca aggtggtggc gcccgggcag ctggtccatt ttcagatcct      5940
gctggctgcc ggctcagctg tcaccttccg cctgcaggtc ggcggggcca accccgaggt      6000
gctccccggg ccccgtttct cccacagctt cccccgcgtc ggagaccacg tggtgagcgt      6060
gcggggcaaa aaccacgtga gctgggccca ggcgcaggtg cgcatcgtgg tgctggaggc      6120
cgtgagtggg ctgcagatgc ccaactgctg cgagcctggc atcgccacgg gcactgagag      6180
gaacttcaca gcccgcgtgc agcgcggctc tcgggtcgcc tacgcctggt acttctcgct      6240
gcagaaggtc cagggcgact cgctggtcat cctgtcgggc cgcgacgtca cctacacgcc      6300
cgtggccgcg ggctgttgg agatccaggt gcgcgccttc aacgcctggg cagtgagaa      6360
ccgcacgctg gtgctggagg ttcaggacgc cgtccagtat gtggccctgc agagcggccc      6420
ctgcttcacc aaccgctcgg cgcagtttga ggccgccacc agcccagcc ccggcgtgt      6480
ggcctaccac tgggactttg ggatgggtc gccagggcag gacacagatg agcccagggc      6540
cgagcactcc tacctgaggc ctgggggacta ccgcgtgcag gtgaacgcct ccaacctggt      6600
gagcttcttc gtggcgcagg ccacggtgac cgtccaggtg ctggcctgcc gggagccgga      6660
ggtgacgtg gtcctgcccc tgcaggtgct gatgcggcga tcacagcgca actacttgga      6720
ggcccacgtt gacctgcgcg actgcgtcac ctaccagact gagtaccgct gggaggtgta      6780
```

```
tcgcaccgcc agctgccagc ggccggggcg cccagcgcgt gtggccctgc ccggcgtgga      6840
cgtgagccgg cctcggctgg tgctgccgcg gctggcgctg cctgtggggc actactgctt      6900
tgtgtttgtc gtgtcatttg gggacacgcc actgacacag agcatccagg ccaatgtgac      6960
ggtggccccc gagcgcctgg tgcccatcat tgagggtggc tcataccgcg tgtggtcaga      7020
cacacgggac ctggtgctgg atgggagcga gtcctacgac cccaacctgg aggacgcgca      7080
ccagacgccg ctcagtttcc actgggcctg tgtggcttcg acacagaggg aggctggcgg      7140
gtgtgcgctg aactttgggc cccgcgggag cagcacggtc accattccac gggagcggct      7200
ggcggctggc gtggagtaca ccttcagcct gaccgtgtgg aaggccggcc gcaaggagga      7260
ggccaccaac cagacggtgc tgatccggag tggccgggtg cccattgtgt ccttggagtg      7320
tgtgtcctgc aaggcacagg ccgtgtacga agtgagccgc agctcctacg tgtacttgga      7380
gggccgctgc tcaattgca gcagcggctc caagcgaggg cggtgggctg cacgtacgtt      7440
cagcaacaag acgctggtgc tggatgagac caccacatcc acgggcagtg caggcatgcg      7500
actggtgctg cggcggggcg tgctgcggga cggcgaggga tacaccttca cgctcacggt      7560
gctgggccgc tctggcgagg aggagggctg cgcctccatc cgcctgtccc ccaaccgccc      7620
gccgctgggg ggctcttgcc gcctcttccc actgggcgct gtgcacgccc tcaccaccaa      7680
ggtgcacttc gaatgcacgg gctggcatga cgcggaggat gctggcgccc cgctggtgta      7740
cgccctgctg ctgcggcgct gtcgccaggg ccactgcgag gagttctgtg tctacaaggg      7800
cagcctctcc agctacggag ccgtgctgcc cccgggtttc aggccacact cgaggtgggg      7860
cctggccgtg gtggtgcagg accagctggg agccgctgtg gtcgccctca acaggtcttt      7920
ggccatcacc ctcccagagc ccaacggcag cgcaacgggg ctcacagtct ggctgcacgg      7980
gctcaccgct agtgtgctcc cagggctgct gcggcaggcc gatcccagc acgtcatcga      8040 gtactcgttg gccctggtca ccgtgctgaa cgagtacgag cgggccctgg acgtggcggc      8100
agagcccaag cacgagcggc agcaccgagc ccagatacgc aagaacatca cggagactct      8160
ggtgtccctg agggtccaca ctgtggatga catccagcag atcgctgctg cgctggccca      8220
gtgcatgggg cccagcaggg agctcgtatg ccgctcgtgc ctgaagcaga cgctgcacaa      8280
gctggaggcc atgatgctca tcctgcaggc agagaccacc gcgggcaccg tgacgcccac      8340
cgccatcgga cacagcatcc tcaacatcac aggagacctc atccacctgg ccagctcgga      8400
cgtgcgggca ccacagccct cagagctggg agccgagtca ccatctcgga tggtggcgtc      8460
ccaggcctac aacctgacct ctgccctcat gcgcatcctc atgcgctccc gcgtgctcaa      8520
cgaggagccc ctgacgctgg cgggcgagga gatcgtggcc cagggcaagc gctcggaccc      8580
gcggagcctg ctgtgctatg gcggcgcccc agggcctggc tgccacttct ccatccccga      8640
ggctttcagc ggggccctgg ccaacctcag tgacgtggtg cagctcatct ttctggtgga      8700
ctccaatccc tttcccttg gctatatcag caactacacc gtctccacca aggtggcctc      8760
gatggcattc cagacacagg ccggcgccca gatccccatc gagcggctgg cctcagagcg      8820
cgccatcacc gtgaaggtgc ccaacaactc ggactgggct gccggggcc accgcagctc      8880 cgccaactcc gccaactccg ttgtggtcca gccccaggcc tccgtcggtg ctgtggtcac      8940
cctggacagc agcaaccctg cggccgggct gcatctgcag ctcaactata cgctgctgga      9000
cggccactac ctgtctgagg aacctgagcc ctacctggca gtctacctac actcggagcc      9060
ccggcccaat gagcacaact gctcggctag caggaggatc cgcccagagt cactccaggg      9120
```

```
tgctgaccac cggccctaca ccttcttcat tccccgggg agcagagacc cagcggggag    9180
ttaccatctg aacctctcca gccacttccg ctggtcggcg ctgcaggtgt ccgtgggcct    9240
gtacacgtcc ctgtgccagt acttcagcga ggaggacatg gtgtggcgga cagagggct    9300
gctgccctg gaggagacct cgccccgcca ggccgtctgc ctcacccgcc acctcaccgc    9360
cttcggcgcc agcctcttcg tgccccaag ccatgtccgc tttgtgtttc ctgagccgac    9420
agcggatgta aactacatcg tcatgctgac atgtgctgtg tgcctggtga cctacatggt    9480
catggccgcc atcctgcaca agctggacca gttggatgcc agccggggcc gcgccatccc    9540
tttctgtggg cagcggggcc gcttcaagta cgagatcctc gtcaagacag ctggggccg    9600
gggctcaggt accacggccc acgtgggcat catgctgtat ggggtggaca gccgagcgg    9660
ccaccggcac ctggacggcg acagagcctt ccaccgcaac agcctggaca tcttccggat    9720
cgccaccccg cacagcctgg gtagcgtgtg aagatccga gtgtggcacg acaacaaagg    9780
gctcagccct gcctggttcc tgcagcacgt catcgtcagg gacctgcaga cggcacgcag    9840
cgccttcttc ctggtcaatg actggctttc ggtggagacg gaggccaacg ggggcctggt    9900
ggagaaggag gtgctggccg cgagcgacgc agcccttttg cgcttccggc gcctgctggt    9960
ggctgagctg cagcgtggct tctttgacaa gcacatctgg ctctccatat gggaccggcc   10020
gcctcgtagc cgtttcactc gcatccagag ggccacctgc tgcgttctcc tcatctgcct   10080
cttcctgggc gccaacgccg tgtggtacgg ggctgttggc gactctgcct acagcacggg   10140
gcatgtgtcc aggctgagcc cgctgagcgt cgacacagtc gctgttggcc tggtgtccag   10200
cgtggttgtc tatcccgtct acctggccat ccttttttctc ttccggatgt cccggagcaa   10260
ggtggctggg agcccgagcc ccacacctgc cgggcagcag gtgctggaca tcgacagctg   10320
cctggactcg tccgtgctgg acagctcctt cctcacgttc tcaggcctcc acgctgaggc   10380
ctttgttgga cagatgaaga gtgacttgtt tctggatgat tctaagagtc tggtgtgctg   10440
gccctccggc gagggaacgc tcagttggcc ggacctgctc agtgacccgt ccattgtggg   10500
tagcaatctg cggcagctgg cacggggcca ggcgggccat gggctgggcc cagaggagga   10560
cggcttctcc ctggccagcc cctactcgcc tgccaaatcc ttctcagcat cagatgaaga   10620
cctgatccag caggtccttg ccgagggggt cagcagccca gcccctaccc aagcacccca   10680
catggaaacg gacctgctca gcagcctgtc cagcactcct ggggagaaga cagagacgct   10740
ggcgctgcag aggctggggg agctgggcc acccagccca ggcctgaact gggaacagcc   10800
ccaggcagcg aggctgtcca ggacaggact ggtggagggt ctgcggaagc gcctgctgcc   10860
ggcctggtgt gcctccctgg cccacgggct cagcctgctc ctggtggctg tggctgtggc   10920
tgtctcaggg tgggtgggtg cgagcttccc ccgggcgtg agtgttgcgt ggctcctgtc   10980
cagcagcgcc agcttcctgg cctcattcct cggctgggag ccactgaagg tcttgctgga   11040
agccctgtac ttctcactgg tggccaagcg gctgcacccg gatgaagatg acaccctggt   11100
agagagcccg gctgtgacgc ctgtgagcgc acgtgtgccc cgcgtacggc cacccacgg   11160
ctttgcactc ttcctggcca aggaagaagc ccgcaaggtc aagaggctac atggcatgct   11220
gcggagcctc ctggtgtaca tgcttttttct gctggtgacc ctgctggcca gctatgggga   11280
tgcctcatgc catgggcacg cctacgtctc gcaaagcgcc atcaagcagg agctgcacag   11340
ccggggcctt ctggccatca cgcggtctga ggagctctgg ccatggatgg cccacgtgct   11400
gctgccctac gtccacggga accagtccag cccagagctg ggccccccac ggctgcggca   11460
ggtgcggctg caggaagcac tctacccaga ccctcccggc cccaggtgtcc acacgtgctc   11520
```

```
ggccgcagga ggcttcagca ccagcgatta cgacgttggc tgggagagtc ctcacaatgg    11580
ctcggggacg tgggcctatt cagcgccgga tctgctgggg gcatggtcct ggggctcctg    11640
tgccgtgtat gacagcgggg gctacgtgca ggagctgggc ctgagcctgg aggagagccg    11700
cgaccggctg cgcttcctgc agctgcacaa ctggctggac aacaggagcc gcgctgtgtt    11760
cctggagctc acgcgctaca gcccggccgt ggggctgcac gccgccgtca cgctgcgcct    11820
cgagttcccg gcggccggcc gcgccctggc cgccctcagc gtccgcccct ttgcgctgcg    11880
ccgcctcagc gcgggcctct cgctgcctct gctcacctcg gtgtgcctgc tgctgttcgc    11940
cgtgcacttc gccgtggccg aggcccgtac ttggcacagg gaagggcgct ggcgcgtgct    12000
gcggctcgga gcctgggcgc ggtggctgct ggtggcgctg acggcggcca cggcactggt    12060
acgcctcgcc cagctgggtg ccgctgaccg ccagtggacc cgtttcgtgc gcggccgccc    12120
gcgccgcttc actagcttcg accaggtggc gcagctgagc tccgcagccc gtggcctggc    12180
ggcctcgctg ctcttcctgc ttttggtcaa ggctgcccag cagctacgct tcgtgcgcca    12240
gtggtccgtc tttggcaaga cattatgccg agctctgcca gagctcctgg gggtcacctt    12300
gggcctggtg gtgctcgggg tagcctacgc ccagctggcc atcctgctcg tgtcttcctg    12360
tgtggactcc ctctggagcg tgcccaggc cctgttggtg ctgtgccctg ggactgggct    12420
ctctaccctg tgtcctgccg agtcctgcca cctgtcaccc ctgctgtgtg tggggctctg    12480
ggcactgcgg ctgtggggcg ccctacggct gggggctgtt attctccgct ggcgctacca    12540
cgccttgcgt ggagagctgt accggccggc ctgggagccc caggactacg agatggtgga    12600
gttgttcctg cgcaggctgc gcctctggat gggcctcagc aaggtcaagg agttccgcca    12660
caaagtccgc tttgaaggga tggagccgct gccctctcgc tcctccaggg gctccaaggt    12720
atccccggat gtgcccccac ccagcgctgg ctccgatgcc tcgcacccct ccacctcctc    12780
cagccagctg gatgggctga gcgtgagcct gggccggctg gggacaaggt gtgagcctga    12840
gccctcccgc ctccaagccg tgttcgaggc cctgctcacc cagtttgacc gactcaacca    12900
ggccacagag gacgtctacc agctggagca gcagctgcac agcctgcaag gccgcaggag    12960
cagccgggcg cccgccggat cttcccgtgg cccatccccg ggcctgcggc cagcactgcc    13020
cagccgcctt gcccggggcca gtcggggtgt ggacctggcc actggccccca gcaggacacc    13080 ccttcgggcc aagaacaagg tccaccccag cagcacttag tcctccttcc tggcggggt    13140 gggccgtgga gtcggagtgg acaccgctca gtattacttt ctgccgctgt caaggccgag    13200
ggccaggcag aatggctgca cgtaggttcc ccagagagca ggcaggggca tctgtctgtc    13260
tgtgggcttc agcactttaa agaggctgtg tggccaacca ggacccaggg tcccctcccc    13320
agctcccttg ggaaggacac agcagtattg gacggtttct agcctctgag atgctaattt    13380
atttccccga gtcctcaggt acagcgggct gtgcccggcc ccacccctg gcagatgtc    13440 ccccactgct aaggctgctg gcttcaggga gggttagcct gcaccgccgc caccctgccc    13500
ctaagttatt acctctccag ttcctaccgt actccctgca ccgtctcact gtgtgtctcg    13560
tgtcagtaat ttatatggtg ttaaaatgtg tatattttg tatgtcacta ttttcactag    13620
ggctgagggg cctgcgccca gagctggcct ccccaacac ctgctgcgct tggtaggtgt    13680
ggtggcgtta tggcagcccg gctgctgctt ggatgcgagc ttggccttgg gccggtgctg    13740
ggggcacagc tgtctgccag gcactctcat caccccagag gccttgtcat cctcccttgc    13800
cccaggccag gtagcaagag agcagcgccc aggcctgctg gcatcaggtc tgggcaagta    13860
```

-continued

```
gcaggactag gcatgtcaga ggaccccagg gtggttagag gaaaagactc ctcctggggg      13920
ctggctccca gggtggagga aggtgactgt gtgtgtgtgt gtgtgcgcgc gcgacgcgcg      13980
agtgtgctgt atggcccagg cagcctcaag gccctcggag ctggctgtgc ctgcttctgt      14040
gtaccacttc tgtgggcatg gccgcttcta gagcctcgac accccccaa cccccgcacc       14100 aagcagacaa agtcaataaa agagctgtct gactgc                                14136
```

<210> SEQ ID NO 2
<211> LENGTH: 6749
<212> TYPE: DNA
<213> ORGANISM: Homo sapiens
<220> FEATURE:
<221> NAME/KEY: misc_feature
<222> LOCATION: (1)..(6749)
<223> OTHER INFORMATION: "n" at position 719, 1277, 1278, 1279, 1280, 1288, 1289, 1638, 1967, 2248, 2251, 2254, 2283, 2585, 2586, 2625, 2932, 2949, 2972, 2978, 3406, is any of A, T, G, and C.
<223> OTHER INFORMATION: "n" at position 3419, 3604, 3675, 3849, 4132, 4337, 4367, 4368, 4369, 4396, 4404, 5700, 5701, 5702, 6611, 6628, 6637, 6700, 6733 is any of A, T, G, and C.

<400> SEQUENCE: 2

```
ggctcctgag gcgcacagcg ccgagcgcgg cgccgcgcac ccgcgcgccg gacgccagtg        60
accgcgatgg tgaactccag tcgcgtgcag cctcagcagc ccggggacgc caagcggccg       120
cccgcgcccc gcgcgccgga cccgggccgg ctgatggctg gctgcgcggc cgtgggcgcc       180
agcctcgccg ccccgggccg cctctgcgag cagcggggcc tggagatcga gatgcagcgc       240
atccggcagg cggccgcgcg ggaccccccg gccggagccg cggcctcccc ttctcctccg       300
ctctcgtcgt gctcccggca ggcgtggagc cgcgataacc ccggcttcga ggccgaggag       360
gaggaggagg aggtggaagg ggaagaaggc ggaatggtgg tggagatgga cgtagagtgg       420
cgcccgggca gccggaggtc ggccgcctcc tcggccgtga gctccgtggg gcgcgcggagc      480 cggggggcttg ggggctacca cggcgcgggc caccccgagcg ggaggcggcg ccggcgagag     540
gaccagggcc cgccgtgccc cagcccagtc ggcggcgggg accgctgca tcgccacctc       600 cccctggaag ggcagccgcc ccgagtggcc tgggcggaga ggctggttcg cgggctgcga       660
ggtgtaagag cgcgcgaccc gcagcggcag atgcacgaac cagaacggcc ggcgccggng       720
gcttcttaaa taaatgata tcttttcttt tcttcattat tatttaaag gtctctgggg         780 aacaagactc atggaggaaa gcagcactaa ccgagagaaa taccttaaaa gtgttttacg       840
ggaactggtc atacctcc ttttttctcat agtcttgtgc atctgtaagt agaatatttc        900
cttgcactaa tgggaaagtt ttgaaacgat gtgaatttgt ccaaaatgtt tatccacagg       960
aacaatccct ttgtgaaggc tgctggtatg tggatgtgtg ccggttccct tggggcgttc      1020
atttggatct ttctgtgttc cagtgaccta cggcatgatg agctccaatg tgtactacta      1080
cacccggatg atgtcacagc tcttcctaga caccccgtg tccaaaacgg agaaaactaa       1140
ctttaaaact ctgtcttcca tggaagactt ctggaaggta tttggaaata actttgaaag      1200
tacctctcta tcacaagcca atgcttggtt atgcaacgat gcaggcaggg caaagcagcg      1260
gcatgagctt gaacttnnnn agatgttnnc tttcttttag ttcacagaag gctccttatt      1320
ggatgggctg tactgaaga tgcagcccag caaccagact gaagctgaca accgaagttt       1380
catcttctat gagaacctgc tgttagggggt tccacgaata cggcaactcc gagtcagaaa      1440
tggatcctgc tctatccccc aggacttgag agatgaaatt aaagagtgct atgatgtcta      1500
ctctgtcagt agtgaagata gggctcccctt tgggcccgga aatggaaccg cgtaagtgtc     1560
```

```
tgtgactcat tggcactcgg tgatattcat ccttgtaatt gcctcaagtg ttccactgat   1620
tgtaactgtt tgtttttngg ttttgttttt aatcagttgg atctacacaa gtgaaaaaga   1680
cttgaatggt agtagccact ggggaatcat tgcaacttat agtggagctg gctattatct   1740
ggatttgtca agaacaagag aggaaacagc tgcacaagtt gctagcctca agaaaaatgt   1800
ctggctggac cgaggaacca gggcaacttt tattgacttc tcagtgtaca acgccaacat   1860
taacctgttc tgtgtggtca ggtgtgtgac tgaggacatg catccctcct atttctgtgt   1920
ggttgtacat acatcctatt ctagggttac ccagaaaaac cttttntgc aggttgttat    1980 tgttttaatt gttcttattt acatgcaggt tattggttga attcccagca acaggtggtg   2040
tgattccatc ttggcaattt cagccttaa agctgatccg atatgtcaca acttttgatt    2100
tcttcctggc agcctgtgag attatctttt gtttctttat cttttactat gtggtggaag   2160
agatattgga aattcgcatt cacaaactac actatttcag gagtttctgg aattgtctgg   2220
atgttgtgat cgttgtggta ggtccganca ncancaccaa atttcctatt ctattctaca   2280
agnatgttaa caattaatac attggtgaag aaaaatatac tagtcatatt aaggtaagtt   2340
tcatattctt aaaacactgt aataaaatat aaatattttg cttttcagct gtcagtggta   2400
gctataggaa ttaacatata cagaacatca aatgtggagg tgctactaca gtttctggaa   2460
gatcaaaata ctttcccccaa ctttgagcat ctggcatatt ggcagataca gttcaacaat   2520
atagctgctg tcacagtatt ttttgtctgg attaaggtaa tttataaatt tcatgttcta   2580
cattnnaaat aatattttct ttaaaaaaaa tgagttccac aaaancatgc gaaacaatgt   2640
tttattatac acagtcacac catttggttt atccattcat ctattgatgt cttctctctc   2700
ttacagctct tcaaattcat caattttaac aggaccatga gccagctctc gacaaccatg   2760
tctcgatgtg ccaaagacct gtttggcttt gctattatgt tcttcattat tttcctagcg   2820
tatgctcagt tggcatacct tgtctttggc actcaggtcg atgacttcag tactttccaa   2880
gagtgtatgt aagtatatat gaaattaaga agaaaaattt agtcagagta gncactgttg   2940
cgtggacant ctttggtttt gtattgtggt gntttgtntt attttatag cttcactcaa    3000 ttccgtatca ttttgggcga tatcaacttt gcagagatta aggaagctaa tcgagttttg   3060
ggaccaattt atttcactac atttgtgttc tttatgttct tcattctttt ggtatgtaca   3120
tttatattta tagtggaggt tcaatttaaa cttcgtaaat ccttgtcttc tcttttttga   3180
ttgataattc caaattatgt ttcttccttt aattttttgcc ctcctttcat ttacaaacag   3240
aatatgtttt tggctatcat caatgatact tactctgaag tgaaatctga cttggcacag   3300
cagaaagctg aaatggaact ctcagatctt atcagaaagg taggaaaaac cttaattctc   3360
aaaaattctt ctgtttctga cataaaatga gcattgtttc acccanattt tagaatacnc   3420
taaaccaagt cttttatttt ttctctctct gatagggcta ccataaagct ttggtcaaac   3480
taaaactgaa aaaaaatacc gtggatgaca tttcagagag tctgcggcaa ggaggaggca   3540
agttaaactt tgacgaactt cgacaagatc tcaaagggtg agaatcatgc ttcctgaggt   3600
tctnaaaaat tcctgcttct aaagataaat tcctggtgat aagagtattt ctagcccaag   3660
ggctcatggg aacanaggat gaatgttatc tgtatcctct ctctaatttc aggaagggcc   3720
atactgatgc agagattgag gcaatattca caaagtacga ccaagatgga gaccaagaac   3780
tgaccgaaca tgaacatcag cagatgagag acgacttgga gaaagagagg gtgggtctgg   3840
tttaggagna accggatttg atttggtacc tacaacacca cacttctgtg gggtctcagt   3900
gttctgctcc tcactcagtg acccccttgtt cttcaggagg acctggattt ggatcacagt   3960
```

```
tctttaccac gtcccatgag cagccgaagt ttccctcgaa gcctggatga ctctgaggag    4020
gatgacgatg aagatagcgg acatagctcc agaaggaggg gaagcatttc tagtggcgtt    4080
tcttacgaag agtttcaagt gtaagtataa aggaattggc agaatttgcg tngacaattt    4140
gtccctctgt actgtgtttt ccttgcagcc tggtgagacg agtggaccgg atggagcatt    4200
ccatcggcag catagtgtcc aagattgacg ccgtgatcgt gaagctagag attatggagc    4260
gagccaaact gaagaggagg gaggtgctgg gaaggctgtt ggatggggtg gccgaggtca    4320
gtagtcatga gctgaanaca ccgctgctga gcatggtgtt attaatnnna atatatgttg    4380
ctgacagttg tatttnaagt attnactgac ccccaacacc agtttctttt tccctttta    4440
ggatgaaagg ctgggtcgtg acagtgaaat ccatagggaa cagatggaac ggctagtacg    4500
tgaagagttg gaacgctggg aatccgatga tgcagcttcc cagatcagtc atggtttagg    4560
cacgccagtg ggactaaatg gtcaacctcg ccccagaagc tcccgcccat cttcctccca    4620
atctacagaa ggcatggaag gtgcaggtgg aaatgggagt tctaatgtcc acgtatgata    4680
tgtgtgtttc agtatgtgtg tttctaataa gtgaggaagt ggctgcctg aattgctgta    4740
acaagcacac tatttatatg ccctgaccac cataggatgc tagtctttgt gaccgattgc    4800
taatcttctg cactttaatt tattttatat aaactttacc catggttcaa agattttttt    4860
ttcttttttct catataagaa atctaggtgt aaatattgag tacagaaaaa aaatcttcat    4920
gatgtgtatt gagcggtacg cccagttgcc accatgactg agtcttctca gttgacaatg    4980
aagtagcctt ttaaagctag aaaactgtca aagggcttct gagtttcatt tccagtcaca    5040
aaaatcagta ttgttatttt tttccaagag tgtgaaggaa aatggggcaa ttcctttcca    5100
ctctggcata gttcatgagc ttaatacata gctttctttt aagaaggag cctttttttt    5160
caactagctt cctggggtaa acttttctaa aagataaaat gggaaggaac tccaaactat    5220
gatagaatct gtgtgaatgg ttaagatgaa tgttaaatac tatgcttttt tgtaagttga    5280
tcgtatctga tgtctgtggg actaactgta tcacttaatt tttaccttat tttggctcta    5340
atttgaataa gctgagtaaa accaccaaag atcagttata ggataaaatg gcatctctaa    5400
ccataacaca ggagaattgg aaggagccct aagttgtcac tcagtttaat ttcttttaat    5460
ggttagttta gcctaaagat ttatctgcat attctttttc ccatgtggct ctactcattt    5520
gcaactgaat ttaatgttat aactcatcta gtgagaccaa cttactaaat ttttagtatg    5580
cactgaaagt ttttatccaa caattatgtt cattttaagc aaaattttaa gaaagttttg    5640
aaattcataa agcatttggt tttaaactat tttaagaata tagtactcgg tcaggtatgn    5700
nncacgcctg taatcccagc actttgggag gccgaaacag gcgaatcact tgagcccagg    5760
agttcaagac caacatgggc aatgtggcga aactccatct ctacaaaaaa tgcaaaaata    5820
aaaaatatag tactcaagta ttcttgatcc tgtgtttcaa aactagaatt tgtaatgcaa    5880
atggagctca gtctaataaa aaagaggttt tggtattaaa agttcataca ttagacagta    5940
tcagccaaaa tttgagttag caacactgtt tctttacga gagggtctca cccaaattta    6000
tggggagaaa tctatttctc aaaaaaaaaa aatcttcttt tacagaaatg ttgagtaagg    6060
tgacattttg agcgctaata agcaaaagag catgcagtgc tgttgaataa ccctcacttg    6120
gagaaccaag agaatcctgt cgtttaatgc tatatttaa tttcacaagt tgttcattta    6180
actggtagaa tgtcagtcca atctccaatg agaacatgag caaatagacc tttccaggtt    6240
gaaagtgaaa catactgggt ttctgtaagt ttttcctcat ggcttcatct ctatctttac    6300
```

```
tttctcttga atatgctaca caaagttctt tattactaca tactaaagtt tgcattccag    6360
ggatattgac tgtacatatt tatgtatatg taccatgttg ttacatgtaa acaaacttca    6420
atttgaagtg cagctattat gtggtatcca tgtgtatcga ccatgtgcca tatatcaatt    6480
atggtcacta gaaagtctct ttatgatact ttttattgta ctgttttca tttcacttgc     6540 aaaattttgc agaattcctc ctttctaccc ataaattaca tataatttt cttctttagt     6600 catggagaac ncccccccat catctcancc ctattanctt tcccatgtgt actggtatta    6660
ttaaaaagac atttacatac gcaagttttt cactgacaan caagaatgtt attaatgtgt    6720
aatactgagc acntttactt cttaataaa                                     6749

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 3
tggctgcaac tgcctcctgg                                                 20

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 4
aagcagagac agacctgtga gag                                             23

<210> SEQ ID NO 5
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 5
gcccccgccg ctctcacagg tctgtctctg cttc                                 34

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 6
ggcctgtagc ctaccccctgg                                                20

<210> SEQ ID NO 7
<211> LENGTH: 19
<212> TYPE: DNA
<213> ORGANISM: Artificial Sequence
<220> FEATURE:
<221> NAME/KEY: misc_feature
```

```
<222> LOCATION: (1)..(19)
<223> OTHER INFORMATION: Synthetic primer

<400> SEQUENCE: 7
ggacccctct gaagccacc                                                    19

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 8
gggaggtggg agacaagaga c                                                 21

<210> SEQ ID NO 9
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 9
aaagccctgc tgtcactgtg g                                                 21

<210> SEQ ID NO 10
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 10
aactaaagcc cagaagacag acc                                               23

<210> SEQ ID NO 11
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 11
aactgtctgc cccagaacat c                                                 21

<210> SEQ ID NO 12
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 12
ctaaaggctg ctctctcaac aag                                               23

<210> SEQ ID NO 13
```

```
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 13
actcctgttg ggttttgatg ag                                              22

<210> SEQ ID NO 14
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 14
gagaactact cccttgtcct tgg                                             23

<210> SEQ ID NO 15
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 15
acgccaagga caagggagta gttc                                            24

<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 16
tgggctcctg gctggtgact gc                                              22

<210> SEQ ID NO 17
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 17
gcggcccgcc gcccccgccg ctactgaccc gcaccctctg                           40

<210> SEQ ID NO 18
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 18
```

-continued gctgcgaggg gtgagacg                                                    18

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer

<400> SEQUENCE: 19
gcggcccgcc gccccgccg cgtccctccc gccctcctga cc                          42

<210> SEQ ID NO 20
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 20
gcccccgccg ctgcggacga gaaatctgtc tgcttg                                36

<210> SEQ ID NO 21
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 21
cagggctgca agcagacaga                                                  20

<210> SEQ ID NO 22
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 22
ctgagctaag acgccctccc                                                  20

<210> SEQ ID NO 23
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 23
ctgtacgccc tcactggtgt c                                                21

<210> SEQ ID NO 24
<211> LENGTH: 21
<212> TYPE: DNA
<213> ORGANISM: Artificial Sequence
<220> FEATURE:

```
<221> NAME/KEY: misc_feature
<222> LOCATION: (1)..(21)
<223> OTHER INFORMATION: Synthetic primer

<400> SEQUENCE: 24
ggcacagggg ctcagtcagt c                                                   21

<210> SEQ ID NO 25
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 25
ggactgactg agcccctgtg c                                                   21

<210> SEQ ID NO 26
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 26
agtcggtcaa actgggtgag                                                     20

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 27
caaggtgtga gcctgagccc                                                     20

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 28
cggtgtccac tccgactcca c                                                   21

<210> SEQ ID NO 29
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 29
ccgcccccgc cgcgcgccgg acgccagtga cc                                       32
```

```
<210> SEQ ID NO 30
<211> LENGTH: 30
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 30
gcccccgccg ccgcggcctc cccttctcct                                    30

<210> SEQ ID NO 31
<211> LENGTH: 44
<212> TYPE: DNA
<213> ORGANISM: Artificial Sequence
<220> FEATURE:
<221> NAME/KEY: misc_feature
<222> LOCATION: (1)..(44)
<223> OTHER INFORMATION: Synthetic primer

<400> SEQUENCE: 31
cggcccgccg ccccgcccg cggccgttct ggttcgtgca tctg                     44

<210> SEQ ID NO 32
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 32
gcccccgccg aaatgatatc ttttcttttc ttca                               34

<210> SEQ ID NO 33
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 33 ccccgcccg aactttccca ttagtgcaag                                     30

<210> SEQ ID NO 34
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 34
cgccgccccc gcccgtgtga tagagaggta ctttca                             36

<210> SEQ ID NO 35
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer
```

```
<400> SEQUENCE: 35
ccgccgcccc cgccgctttt tcaaagatgt ttcctttgc                                39

<210> SEQ ID NO 36
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 36
tatcaccgag tgccaatgag                                                    20

<210> SEQ ID NO 37
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 37
ccgccgcccc cgccggcctc aagtgttcca ctgat                                   35

<210> SEQ ID NO 38
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 38
cccccgcccg ttgtagaata gaataggaaa tttgg                                   35

<210> SEQ ID NO 39
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 39
gcccccgccg ttggtgaaga aaatatact agtca                                    35

<210> SEQ ID NO 40
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 40
cgccgccccc gcccgtggaa ctcatttttt ttaaaga                                 37

<210> SEQ ID NO 41
<211> LENGTH: 39
<212> TYPE: DNA
<213> ORGANISM: Artificial Sequence
```

```
<220> FEATURE:
<221> NAME/KEY: misc_feature
<222> LOCATION: (1)..(39)
<223> OTHER INFORMATION: Synthetic primer

<400> SEQUENCE: 41 gcggggcgg cgggccgttt tattatacac agtcacacc                              39

<210> SEQ ID NO 42
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 42
gcccccgccg cttcctttaa tttttgccct cc                                    32

<210> SEQ ID NO 43
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 43 cgccgcccc gcccggaaac aatgctcatt ttatgtcag                              39

<210> SEQ ID NO 44
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 44
ccgccgcccc cgccgaaacc aagtctttta ttttttctc                             39

<210> SEQ ID NO 45
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 45
ccgccgcccc cgccggatga atgttatctg tatcctctc                             39

<210> SEQ ID NO 46
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 46
cgccgccccc gcccggcaaa ttctgccaat tccttta                               37
```

```
<210> SEQ ID NO 47
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 47
gcccccgccg tttgtccctc tgtactgtgt tt                                  32

<210> SEQ ID NO 48
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 48 ccgccccgc cgtgacccccc aacaccagtt tc                                  32

<210> SEQ ID NO 49
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 49
cggcccgccg ccccgcccg ggacagccac ttcctcactt                           40

<210> SEQ ID NO 50
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 50
cgtcgctcag cagcaggtcg                                                20

<210> SEQ ID NO 51
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 51
cgtcctgctt cccgtcccg                                                 19

<210> SEQ ID NO 52
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer
```

```
<400> SEQUENCE: 52
gcggcccgcc gccccgccg ttggggatgc tggcaatgtg tg                              42

<210> SEQ ID NO 53
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 53
gggattcggc aaagctgatg                                                     20

<210> SEQ ID NO 54
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 54
ttccatcagc tttgccgaat                                                     20

<210> SEQ ID NO 55
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 55
atctggtctc aagcctggaa g                                                   21

<210> SEQ ID NO 56
<211> LENGTH: 49
<212> TYPE: DNA
<213> ORGANISM: Artificial Sequence
<220> FEATURE:
<221> NAME/KEY: misc_feature
<222> LOCATION: (1)..(49)
<223> OTHER INFORMATION: Synthetic primer

<400> SEQUENCE: 56
gccccgcgcc cgtcccgccg ccccgccga gaccttccc accagacct                       49

<210> SEQ ID NO 57
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 57
cgcccccgcc cgtgagccct gcccagtgtc t                                        31

<210> SEQ ID NO 58
<211> LENGTH: 41
<212> TYPE: DNA
```

```
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 58
gcggcccgcc gccccccgccg agccaggag gagcagaacc c                          41

<210> SEQ ID NO 59
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 59
cagagggaca ggcaggcaaa gg                                               22

<210> SEQ ID NO 60
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: Synthetic primer

<400> SEQUENCE: 60
gcccccgccg cccagccctc cagtgcct                                         28

<210> SEQ ID NO 61
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 61
atcgctatgt gctgcctggg                                                  20

<210> SEQ ID NO 62
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 62
ccgaggtgga tgccgctg                                                    18

<210> SEQ ID NO 63
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 63
gaaggggagt gggcagcaga c                                                21
```

```
<210> SEQ ID NO 64
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 64
cactgaccgt tgacaccctc g                                              21

<210> SEQ ID NO 65
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 65
tgccccagtg cttcagagat c                                              21

<210> SEQ ID NO 66
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 66
ggagtgccct gagccccct                                                 19

<210> SEQ ID NO 67
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 67
cccctaacca cagccagcg                                                 19

<210> SEQ ID NO 68
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 68
tctgttcgtc ctggtgtcct g                                              21

<210> SEQ ID NO 69
<211> LENGTH: 21
<212> TYPE: DNA
<213> ORGANISM: Artificial Sequence
<220> FEATURE:
<221> NAME/KEY: misc_feature
<222> LOCATION: (1)..(21)
```

<223> OTHER INFORMATION: Synthetic primer

<400> SEQUENCE: 69
gcaggagggc aggttgtaga a                                    21

<210> SEQ ID NO 70
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 70
gcggcccgcc gcccccgccg ggtaggggga gtctgggctt                40

<210> SEQ ID NO 71
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic primer

<400> SEQUENCE: 71
gaggccaccc cgagtcc                                         17

<210> SEQ ID NO 72
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 72
gttgggcatc tctgacggtg                                      20

<210> SEQ ID NO 73
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 73
cgccgccccc gcccgggaag gtggcctgag gagat                     35

<210> SEQ ID NO 74
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 74
gcggcccgcc gcccccgccg ggggtccacg ggccatg                   37

<210> SEQ ID NO 75
<211> LENGTH: 20

```
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 75
aagcccagca gcacggtgag                                              20

<210> SEQ ID NO 76
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 76
ccgccgcccc cgccgctgcc ctgcctgtgc cctg                              34

<210> SEQ ID NO 77
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 77
gccccgcgcc cgtcccgccg ccccccgcccg ttccaccacc acgtccacca c          51

<210> SEQ ID NO 78
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 78
gtggtggacg tggtggtgga a                                            21

<210> SEQ ID NO 79
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 79
ggctgctgcc ctcactggga a                                            21

<210> SEQ ID NO 80
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 80
```

-continued taagggcaga gtcctccaca g                                    21

<210> SEQ ID NO 81
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 81 ccaccccgc ccacctactg ag                                    22

<210> SEQ ID NO 82
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 82
gcggcccgcc gccccgccg tggagggagg gacgccaatc                 40

<210> SEQ ID NO 83
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 83
gaggctgggg ctgggacaa                                       19

<210> SEQ ID NO 84
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 84
cccggttcac tcactgcg                                        18

<210> SEQ ID NO 85
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 85
cccccgcccg ccgtgctcag agcctgaaag                           30

<210> SEQ ID NO 86
<211> LENGTH: 38
<212> TYPE: DNA
<213> ORGANISM: Artificial Sequence
<220> FEATURE:
<221> NAME/KEY: misc_feature

```
<222> LOCATION: (1)..(38)
<223> OTHER INFORMATION: Synthetic primer

<400> SEQUENCE: 86 ggcgggggc ttctgccgag cgggtgggga gcaggtgg                              38

<210> SEQ ID NO 87
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 87
cgccgccccc gcccggctct gggtcaggac agggga                               36

<210> SEQ ID NO 88
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 88
cgcctggggg tgttcttt                                                   18

<210> SEQ ID NO 89
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 89
acgtgatgtt gtcgcccg                                                   18

<210> SEQ ID NO 90
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 90
gcccccgccg gggcgccccc gtggtggtca gc                                   32

<210> SEQ ID NO 91
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 91
caggctgcgt ggggatgc                                                   18

<210> SEQ ID NO 92
```

<210> SEQ ID NO 92
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 92
ctggaggtgc tgcgcgtt					18

<210> SEQ ID NO 93
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 93
cgcccccgcc cgctggctcc acgcagatgc					30

<210> SEQ ID NO 94
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 94
cgtgaacagg gcgcatta					18

<210> SEQ ID NO 95
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 95
cccccgcccg gcagcagaga tgttgttgga c					31

<210> SEQ ID NO 96
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 96
ccgccgcccc cgccgccagg ctcctatctt gtgaca					36

<210> SEQ ID NO 97
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 97

```
tgaagtcacc tgtgctgttg t                                        21

<210> SEQ ID NO 98
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 98
ctacctgtgg gatctgggg                                           19

<210> SEQ ID NO 99
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 99
tgctgaagct cacgctcc                                            18

<210> SEQ ID NO 100
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 100
gggctcgtcg tcaatgcaag                                          20

<210> SEQ ID NO 101
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 101
cgccgccccc gcccgccgcc caccacctgc agcccctcta                    40

<210> SEQ ID NO 102
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 102
gcggcccgcc gccccgccg ccgcccagga cagcatcttc                     40

<210> SEQ ID NO 103
<211> LENGTH: 18
<212> TYPE: DNA
<213> ORGANISM: Artificial Sequence
<220> FEATURE:
```

```
<221> NAME/KEY: misc_feature
<222> LOCATION: (1)..(18)
<223> OTHER INFORMATION: Synthetic primer

<400> SEQUENCE: 103
cgctgcccag catgttgg                                                      18

<210> SEQ ID NO 104
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 104
ggccggcagc ggcaaaggct tctc                                               24

<210> SEQ ID NO 105
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 105
gcccagcacc agctcacat                                                     19

<210> SEQ ID NO 106
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 106
cgagccattt accacccata g                                                  21

<210> SEQ ID NO 107
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 107
ggcagccagc aggatctgaa                                                    20

<210> SEQ ID NO 108
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 108
ctgtgggcca gcagcaaggt g                                                  21
```

```
<210> SEQ ID NO 109
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 109
cctgaacctc cagcaccagc g                                              21

<210> SEQ ID NO 110
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 110
aggtccaggg cgactcgctg g                                              21

<210> SEQ ID NO 111
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 111
cagggccaca cgcgctgggc g                                              21

<210> SEQ ID NO 112
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 112
ttggaggccc acgttgacct g                                              21

<210> SEQ ID NO 113
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 113
cccccgcccg catgggtgtg gacgggtgag g                                   31

<210> SEQ ID NO 114
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
```

```
<400> SEQUENCE: 114
taaaactgga tggggctctc                                              20

<210> SEQ ID NO 115
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 115
ggcctccacc agcactaa                                                18

<210> SEQ ID NO 116
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 116
gggtccccca gtccttccag                                              20

<210> SEQ ID NO 117
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic primer

<400> SEQUENCE: 117
tccccagccc gcccaca                                                 17

<210> SEQ ID NO 118
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 118 gcccctcac caccccttct                                               20

<210> SEQ ID NO 119
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 119
tcccgctgct ccccccacgc a                                            21

<210> SEQ ID NO 120
<211> LENGTH: 18
<212> TYPE: DNA
<213> ORGANISM: Artificial Sequence
```

```
<220> FEATURE:
<221> NAME/KEY: misc_feature
<222> LOCATION: (1)..(18)
<223> OTHER INFORMATION: Synthetic primer

<400> SEQUENCE: 120
gatgccgtgg ggaccgtc                                                        18

<210> SEQ ID NO 121
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 121
gtgagcaggt ggcagtctcg                                                      20

<210> SEQ ID NO 122
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 122
ccaccccctc tgctcgtagg t                                                    21

<210> SEQ ID NO 123
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 123
ggtcccaagc acgcatgca                                                       19

<210> SEQ ID NO 124
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 124
tgccggcctc ctgcgctgct ga                                                   22

<210> SEQ ID NO 125
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

<400> SEQUENCE: 125
gcgggcaggg tgagcaggtg gggccatcc                                            29
```

```
<210> SEQ ID NO 126
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic primer

<400> SEQUENCE: 126
gaggctgtgg gggtccagtc aagtgg                                        26

<210> SEQ ID NO 127
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic primer

<400> SEQUENCE: 127
agggaggcag aggaaagggc cgaac                                         25

<210> SEQ ID NO 128
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

<400> SEQUENCE: 128
cgtcccgcct gcactgacct cacgcatgt                                     29

<210> SEQ ID NO 129
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 129
cggcccgccg cccccgcccg gccaaaggga aagggattgg a                       41

<210> SEQ ID NO 130
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 130
ccgcggagcc tgctgtgcta t                                             21

<210> SEQ ID NO 131
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer
```

-continued

```
<400> SEQUENCE: 131
ccgccgcccc cgcccgcttg gtggagacgg tgtagttgc                              39

<210> SEQ ID NO 132
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 132
tccaatccct ttccctttgg c                                                 21

<210> SEQ ID NO 133
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 133
cagcagccca tgaaacagaa ag                                                22

<210> SEQ ID NO 134
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 134
tatgctttca ggcccgtggc a                                                 21

<210> SEQ ID NO 135
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 135
agagcccata cccggtccag tcc                                               23

<210> SEQ ID NO 136
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 136
ggactggacc gggtatgggc tct                                               23

<210> SEQ ID NO 137
<211> LENGTH: 31
<212> TYPE: DNA
```

```
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 137
cccccgcccg cacccaggcc ctcctcgact c                                     31

<210> SEQ ID NO 138
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 138
cccccgccgc tgggtgggct cggctctatc                                       30

<210> SEQ ID NO 139
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 139
tggtagcgat gctcacgtca ctt                                              23

<210> SEQ ID NO 140
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 140
caggccaaag ctgagatgac ttg                                              23

<210> SEQ ID NO 141
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 141
agaggcgcag gagggaggtc                                                  20

<210> SEQ ID NO 142
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 142
ccctctgccc ccgcattg                                                    18
```

-continued

<210> SEQ ID NO 143
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 143
aagcgcaaaa gggctgcgtc g                                        21

<210> SEQ ID NO 144
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 144
ggccctccct gccttctagg cg                                       22

<210> SEQ ID NO 145
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 145
ccgtgctgtg tggaggagag                                          20

<210> SEQ ID NO 146
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 146
cctcttcctg cccagccctt c                                        21

<210> SEQ ID NO 147
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 147
cttcccgagc agcctttggt g                                        21

<210> SEQ ID NO 148
<211> LENGTH: 20
<212> TYPE: DNA
<213> ORGANISM: Artificial Sequence
<220> FEATURE:
<221> NAME/KEY: misc_feature
<222> LOCATION: (1)..(20)

<223> OTHER INFORMATION: Synthetic primer

<400> SEQUENCE: 148
ctgagctgcc gcccgctgac                                                   20

<210> SEQ ID NO 149
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 149
aggaccccca gcccagccca                                                   20

<210> SEQ ID NO 150
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 150
cttggcgcag cttggact                                                     18

<210> SEQ ID NO 151
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 151
acacccagca aggacacgca                                                   20

<210> SEQ ID NO 152
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 152
tgtgacacat cccctggtac                                                   20

<210> SEQ ID NO 153
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 153
gcaagggtga gcttcagagc                                                   20

<210> SEQ ID NO 154
<211> LENGTH: 51

```
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 154
gccccgcgcc cgtcccgccg ccccgcccg accctatgcc tcctgtacct c            51

<210> SEQ ID NO 155
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 155
cccctcctct ggcaatcc                                                 18

<210> SEQ ID NO 156
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 156
cctgccggga gcacgacgag                                               20

<210> SEQ ID NO 157
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 157
ctgggctggg gcacggcggg                                               20

<210> SEQ ID NO 158
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 158
gggggctacc acggcgcggg c                                             21

<210> SEQ ID NO 159
<211> LENGTH: 20
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 159
```

```
ttggggcgtt catttggatc                                                      20
```

<210> SEQ ID NO 160
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 160

```
accacacaga aataggaggg                                                      20
```

<210> SEQ ID NO 161
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 161

```
ttgttattgt tttaattgtt ctta                                                 24
```

<210> SEQ ID NO 162
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic primer

<400> SEQUENCE: 162

```
ctactctgac taaatttttc ttctt                                                25
```

<210> SEQ ID NO 163
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 163

```
tttggttttg tattgtggtg                                                      20
```

<210> SEQ ID NO 164
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 164

```
aaggatttac gaagtttaaa ttg                                                  23
```

<210> SEQ ID NO 165
<211> LENGTH: 21
<212> TYPE: DNA
<213> ORGANISM: Artificial Sequence
<220> FEATURE:
<221> NAME/KEY: misc_feature

```
<222> LOCATION: (1)..(21)
<223> OTHER INFORMATION: Synthetic primer

<400> SEQUENCE: 165
agaacctcag gaagcatgat t                                              21

<210> SEQ ID NO 166
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 166
taggtaccaa atcaaatccg                                                20

<210> SEQ ID NO 167
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 167
gtctcagtgt tctgctcctc                                                20

<210> SEQ ID NO 168
<211> LENGTH: 22
<212> TYPE: DNA
<213> ORGANISM: Artificial Sequence Sequence
<220> FEATURE:
<221> NAME/KEY: misc_feature
<222> LOCATION: (1)..(22)
<223> OTHER INFORMATION: Synthetic primer

<400> SEQUENCE: 168
aaatacaact gtcagcaaca ta                                             22

<210> SEQ ID NO 169
<211> LENGTH: 12909
<212> TYPE: DNA
<213> ORGANISM: Homo sapiens

<400> SEQUENCE: 169
atgccgcccg ccgcgcccgc cgcctggcg  ctggccctgg gcctgggcct gtggctcggg      60
gcgctggcgg ggggcccgg  gcgcggctgc gggccctgcg agcccccctg cctctgcggc     120
ccagcgcccg gcgccgcctg ccgcgtcaac tgctcgggcc gcgggctgcg gacgctcggt     180
cccgcgctgc gcatccccgc ggacgccaca gcgctagacg tctcccacaa cctgctccgg     240
gcgctggacg ttgggctcct ggcgaacctc tcggcgctgg cagagctgga tataagcaac     300
aacaagattt ctacgttaga agaaggaata tttgctaatt tatttaattt aagtgaaata     360
aacctgagtg ggaacccgtt tgagtgtgac tgtggcctgg cgtggctgcc gcgatgggcg     420
gaggagcagc aggtgcgggt ggtgcagccc gaggcagcca cgtgtgctgg gcctggctcc     480
ctggctggcc agcctctgct tggcatcccc ttgctggaca gtggctgtgg tgaggagtat     540
gtcgcctgcc tccctgacaa cagctcaggc accgtggcag cagtgtcctt ttcagctgcc     600
cacgaaggcc tgcttcagcc agaggcctgc agcgccttct gcttctccac cggccagggc     660
```

```
ctcgcagccc tctcggagca gggctggtgc ctgtgtgggg cggcccagcc ctccagtgcc    720
tcctttgcct gcctgtccct ctgctccggc ccccgccac ctcctgcccc cacctgtagg     780
ggccccaccc tcctccagca cgtcttccct gcctccccag gggccaccct ggtggggccc    840
cacggacctc tggcctctgg ccagctagca gccttccaca tcgctgcccc gctccctgtc    900
actgccacac gctgggactt cggagacggc tccgccgagg tggatgccgc tgggccggct    960
gcctcgcatc gctatgtgct gcctgggcgc tatcacgtga cggccgtgct ggccctgggg   1020
gccggctcag ccctgctggg gacagacgtg caggtggaag cggcacctgc cgccctggag   1080
ctcgtgtgcc cgtcctcggt gcagagtgac gagagccttg acctcagcat ccagaaccgc   1140
ggtggttcag gcctggaggc cgcctacagc atcgtggccc tgggcgagga gccggcccga   1200
gcggtgcacc cgctctgccc ctcggacacg gagatcttcc ctggcaacgg gcactgctac   1260
cgcctggtgg tggagaaggc ggcctggctg caggcgcagg agcagtgtca ggcctgggcc   1320
ggggccgccc tggcaatggt ggacagtccc gccgtgcagc gcttcctggt ctcccgggtc   1380
accaggagcc tagacgtgtg gatcggcttc tcgactgtgc agggggtgga ggtgggccca   1440
gcgccgcagg gcgaggcctt cagcctggag agctgccaga actggctgcc cggggagcca   1500
cacccagcca cagccgagca ctgcgtccgg ctcgggccca ccgggtggtg taacaccgac   1560
ctgtgctcag cgccgcacag ctacgtctgc gagctgcagc ccgaggcccc agtgcaggat   1620
gccgagaacc tcctcgtggg agcgcccagt ggggacctgc agggaccccct gacgcctctg   1680 gcacagcagg acgcctctc agcccgcac gagcccgtgg aggtcatggt attcccgggc    1740
ctgcgtctga gccgtgaagc cttcctcacc acggccgaat ttgggaccca ggagctccgg   1800
cggcccgccc agctgcggct gcaggtgtac cggctcctca gcacagcagg gaccccggag   1860
aacggcagcg agcctgagag caggtccccg gacaacagga cccagctggc ccccgcgtgc   1920
atgccagggg gacgctggtg ccctggagcc aacatctgct gccgctgga cgcctcttgc   1980 cacccccagg cctgcgccaa tggctgcacg tcagggccag ggctacccgg ggcccctat     2040 gcgctatgga gagagttcct cttctccgtt gccgcggggc ccccgcgca gtactcggtc    2100 accctccacg gccaggatgt cctcatgctc cctggtgacc tcgttggctt gcagcacgac   2160
gctggccctg gcgccctcct gcactgctcg ccggctcccg gccaccctgg tcccaggcc     2220 ccgtacctct ccgccaacgc ctcgtcatgg ctgccccact tgccagccca gctggagggc   2280
acttgggcct gccctgcctg tgccctgcgg ctgcttgcag ccacggaaca gctcaccgtg   2340
ctgctgggct tgaggcccaa ccctggactg cggatgcctg ggcgctatga ggtccgggca   2400
gaggtgggca atggcgtgtc caggcacaac ctctcctgca gctttgacgt ggtctcccca   2460
gtggctgggc tgcgggtcat ctaccctgcc ccccgcgacg gccgcctcta cgtgcccacc   2520
aacggctcag ccttggtgct ccaggtggac tctggtgcca acgccacggc cacggctcgc   2580
tggcctgggg gcagtgtcag cgcccgcttt gagaatgtct gccctgccct ggtggccacc   2640
ttcgtgcccg gctgccctg ggagaccaac gataccctgt tctcagtggt agcactgccg    2700
tggctcagtg aggggagca cgtggtggac gtggtggtga aaaacagcgc cagccgggcc    2760
aacctcagcc tgcgggtgac ggcggaggag cccatctgtg gcctccgcgc cacgcccagc   2820
cccgaggccc gtgtactgca gggagtccta gtgaggtaca gccccgtggt ggaggccggc   2880
tcggacatgg tcttccggtg gaccatcaac gacaagcagt ccctgacctt ccagaacgtg   2940
gtcttcaatg tcatttatca gagcgcgcg gtcttcaagc tctcactgac ggcctccaac    3000
cacgtgagca acgtcaccgt gaactacaac gtaaccgtgg agcggatgaa caggatgcag   3060
```

```
ggtctgcagg tctccacagt gccggccgtg ctgtccccca atgccacgct agcactgacg   3120
gcgggcgtgc tggtggactc ggccgtggag gtggccttcc tgtggaactt tggggatggg   3180
gagcaggcc tccaccagtt ccagcctccg tacaacgagt ccttcccggt tccagacccc   3240
tcggtggccc aggtgctggt ggagcacaat gtcatgcaca cctacgctgc cccaggtgag   3300
tacctcctga ccgtgctggc atctaatgcc ttcgagaacc tgacgcagca ggtgcctgtg   3360
agcgtgcgcg cctccctgcc ctccgtggct gtgggtgtga gtgacggcgt cctggtggcc   3420
ggccggcccg tcaccttcta cccgcacccg ctgccctcgc ctgggggtgt tctttacacg   3480
tgggacttcg gggacggctc ccctgtcctg acccagagcc agccggctgc caaccacacc   3540
tatgcctcga ggggcaccta ccacgtgcgc ctggaggtca acaacacggt gagcggtgcg   3600
gcggcccagg cggatgtgcg cgtctttgag gagctccgcg gactcagcgt ggacatgagc   3660
ctggccgtgg agcagggcgc ccccgtggtg gtcagcgccg cggtgcagac gggcgacaac   3720
atcacgtgga ccttcgacat gggggacggc accgtgctgt cgggcccgga ggcaacagtg   3780
gagcatgtgt acctgcgggc acagaactgc acagtgaccg tgggtgcggc cagccccgcc   3840
ggccacctgg cccggagcct gcacgtgctg gtcttcgtcc tggaggtgct gcgcgttgaa   3900
cccgccgcct gcatccccac gcagcctgac gcgcggctca cggcctacgt caccgggaac   3960
ccggcccact acctcttcga ctggaccttc ggggatggct cctccaacac gaccgtgcgg   4020
gggtgcccga cggtgacaca caacttcacg cggagcggca cgttccccct ggcgctggtg   4080
ctgtccagcc gcgtgaacag ggcgcattac ttcaccagca tctgcgtgga gccagaggtg   4140
ggcaacgtca ccctgcagcc agagaggcag tttgtgcagc tcggggacga ggcctggctg   4200
gtggcatgtg cctggccccc gttcccctac cgctacacct gggactttgg caccgaggaa   4260
gccgccccca cccgtgccag gggccctgag gtgacgttca tctaccgaga cccaggctcc   4320
tatcttgtga cagtcaccgc gtccaacaac atctctgctg ccaatgactc agccctggtg   4380
gaggtgcagg agcccgtgct ggtcaccagc atcaaggtca atggctccct tgggctggag   4440
ctgcagcagc cgtacctgtt ctctgctgtg ggccgtgggc gccccgccag ctacctgtgg   4500
gatctggggg acggtgggtg gctcgagggt ccggaggtca cccacgctta caacagcaca   4560
ggtgacttca ccgttagggt ggccggctgg aatgaggtga ccgcagcga ggcctggctc   4620
aatgtgacgg tgaagcggcg cgtgcggggg ctcgtcgtca atgcaagccg cacggtggtg   4680
cccctgaatg ggagcgtgag cttcagcacg tcgctggagg ccggcagtga tgtgcgctat   4740
tcctgggtgc tctgtgaccg ctgcacgccc atccctgggg gtcctaccat ctcttacacc   4800
ttccgctccg tgggcacctt caatatcatc gtcacggctg agaacgaggt gggctccgcc   4860
caggacagca tcttcgtcta tgtcctgcag ctcatagagg ggctgcaggt ggtgggcggt   4920
ggccgctact tccccaccaa ccacacggta cagctgcagg ccgtggttag ggatggcacc   4980
aacgtctcct acagctggac tgcctggagg gacaggggcc cggccctggc cggcagcggc   5040
aaaggcttct cgctcaccgt gctcgaggcc ggcacctacc atgtgcagct gcgggccacc   5100
aacatgctgg gcagcgcctg gccgactgc accatggact tcgtggagcc tgtggggtgg   5160
ctgatggtga ccgcctcccc gaacccagct gccgtcaaca caagcgtcac cctcagtgcc   5220
gagctggctg gtgcagtgg tgtcgtatac acttggtcct tggaggaggg gctgagctgg   5280
gagacctccg agccatttac cacccatagc ttccccacac ccggcctgca cttggtcacc   5340
atgacggcag ggaacccgct gggctcagcc aacgccaccg tggaagtgga tgtgcaggtg   5400
```

```
cctgtgagtg gcctcagcat cagggccagc gagcccggag gcagcttcgt ggcggccggg    5460
tcctctgtgc cctttgggg gcagctggcc acgggcacca atgtgagctg gtgctgggct    5520
gtgcccggcg gcagcagcaa gcgtggccct catgtcacca tggtcttccc ggatgctggc    5580
accttctcca tccggctcaa tgcctccaac gcagtcagct gggtctcagc cacgtacaac    5640
ctcacggcgg aggagcccat cgtgggcctg tgtctgtggg ccagcagcaa ggtggtggcg    5700
cccgggcagc tggtccattt tcagatcctg ctggctgccg gctcagctgt caccttccgc    5760
ctgcaggtcg gcggggccaa ccccgaggtg ctccccgggc ccgtttctc ccacagcttc    5820
ccccgcgtcg gagaccacgt ggtgagcgtg cggggcaaaa accacgtgag ctgggcccag    5880
gcgcaggtgc gcatcgtggt gctggaggcc gtgagtgggc tgcagatgcc caactgctgc    5940
gagcctggca tcgccacggg cactgagagg aacttcacag cccgcgtgca gcgcggctct    6000
cgggtcgcct acgcctggta cttctcgctg cagaaggtcc agggcgactc gctggtcatc    6060
ctgtcgggcc gcgacgtcac ctacacgccc gtggccgcgg ggctgttgga gatccaggtg    6120
cgcgccttca acgccctggg cagtgagaac cgcacgctgg tgctggaggt tcaggacgcc    6180
gtccagtatg tggccctgca gagcggcccc tgcttcacca accgctcggc gcagtttgag    6240
gccgccacca gccccagccc ccggcgtgtg gcctaccact gggactttgg ggatgggtcg    6300
ccagggcagg acacagatga gcccagggcc gagcactcct acctgaggcc tggggactac    6360
cgcgtgcagg tgaacgcctc caacctggtg agcttcttcg tggcgcaggc cacggtgacc    6420
gtccaggtgc tggcctgccg ggagccggag gtggacgtgg tcctgcccct gcaggtgctg    6480
atgcggcgat cacagcgcaa ctacttggag gcccacgttg acctgcgcga ctgcgtcacc    6540
taccagactg agtaccgctg ggaggtgtat cgcaccgcca gctgccagcg gccggggcgc    6600
ccagcgcgtg tggccctgcc cggcgtggac gtgagccggc ctcggctggt gctgccgcgg    6660
ctggcgctgc ctgtggggca ctactgcttt gtgtttgtcg tgtcatttgg ggacacgcca    6720
ctgacacaga gcatccaggc caatgtgacg gtggcccccg agcgcctggt gcccatcatt    6780
gagggtggct cataccgcgt gtggtcagac acacgggacc tggtgctgga tgggagcgag    6840
tcctacgacc ccaacctgga ggacggcgac cagacgccgc tcagtttcca ctgggcctgt    6900
gtggcttcga cacagaggga ggctggcggg tgtgcgctga actttgggcc ccgcgggagc    6960
agcacggtca ccattccacg ggagcggctg gcggctggcg tggagtacac cttcagcctg    7020
accgtgtgga aggccggccg caaggaggag gccaccaacc agacggtgct gatccggagt    7080
ggccgggtgc ccattgtgtc cttggagtgt gtgtcctgca aggcacaggc cgtgtacgaa    7140
gtgagccgca gctcctacgt gtacttggag ggccgctgcc tcaattgcag cagcggctcc    7200
aagcgagggc ggtgggctgc acgtacgttc agcaacaaga cgctggtgct ggatgagacc    7260
accacatcca cgggcagtgc aggcatgcga ctggtgctgc ggcggggcgt gctgcgggac    7320
ggcgagggat acaccttcac gctcacggtg ctggccgct ctggcgagga ggaggctgc    7380
gcctccatcc gcctgtcccc caaccgcccg ccgctggggg gctcttgccg cctcttccca    7440
ctgggcgctg tgcacgccct caccaccaag gtgcacttcg aatgcacggg ctggcatgac    7500
gcggaggatg ctggcgcccc gctggtgtac gccctgctgc tgcggcgctg tcgccagggc    7560
cactgcgagg agttctgtgt ctacaagggc agcctctcca gctacggagc cgtgctgccc    7620
ccgggtttca ggccacactt cgaggtgggc ctggccgtgg tggtgcagga ccagctggga    7680
gccgctgtgg tcgccctcaa caggtctttg gccatcaccc tcccagagcc caacggcagc    7740
gcaacggggc tcacagtctg gctgcacggg ctcaccgcta gtgtgctccc agggctgctg    7800
```

```
cggcaggccg atccccagca cgtcatcgag tactcgttgg ccctggtcac cgtgctgaac   7860
gagtacgagc gggccctgga cgtggcggca gagcccaagc acgagcggca gcaccgagcc   7920
cagatacgca agaacatcac ggagactctg gtgtccctga gggtccacac tgtggatgac   7980
atccagcaga tcgctgctgc gctggcccag tgcatggggc ccagcaggga gctcgtatgc   8040
cgctcgtgcc tgaagcagac gctgcacaag ctggaggcca tgatgctcat cctgcaggca   8100
gagaccaccg cgggcaccgt gacgcccacc gccatcggag acagcatcct caacatcaca   8160
ggagacctca tccacctggc cagctcggac gtgcgggcac cacagccctc agagctggga   8220
gccgagtcac catctcggat ggtggcgtcc caggcctaca acctgacctc tgccctcatg   8280
cgcatcctca tgcgctcccg cgtgctcaac gaggagcccc tgacgctggc gggcgaggag   8340
atcgtggccc agggcaagcg ctcggacccg cggagcctgc tgtgctatgg cggcgcccca   8400
gggcctggct gccacttctc catccccgag gctttcagcg gggccctggc caacctcagt   8460
gacgtggtgc agctcatctt tctggtggac tccaatccct ttcccttggg ctatatcagc   8520
aactacaccg tctccaccaa ggtggcctcg atggcattcc agacacaggc cggcgcccag   8580
atccccatcg agcggctggc ctcagagcgc gccatcaccg tgaaggtgcc caacaactcg   8640
gactgggctg ccgggggcca ccgcagctcc gccaactccg ccaactccgt tgtggtccag   8700
ccccaggcct ccgtcggtgc tgtggtcacc ctggacagca gcaaccctgc ggccgggctg   8760
catctgcagc tcaactatac gctgctggac ggccactacc tgtctgagga acctgagccc   8820
tacctggcag tctacctaca ctcggagccc cggcccaatg agcacaactg ctcggctagc   8880
aggaggatcc gcccagagtc actccagggt gctgaccacc ggccctacac cttcttcatt   8940
tccccgggga gcagagaccc agcggggagt taccatctga acctctccag ccacttccgc   9000
tggtcggcgc tgcaggtgtc cgtgggcctg tacgtccc tgtgccagta cttcagcgag   9060
gaggacatgg tgtggcggac agaggggctg ctgcccctgg aggagacctc gccccgccag   9120
gccgtctgcc tcacccgcca cctcaccgcc ttcggcgcca gcctcttcgt gcccccaagc   9180
catgtccgct ttgtgtttcc tgagccgaca gcggatgtaa actacatcgt catgctgaca   9240
tgtgctgtgt gcctggtgac ctacatggtc atggccgcca tcctgcacaa gctggaccag   9300
ttggatgcca gccggggccg cgccatccct ttctgtgggc agcggggccg cttcaagtac   9360
gagatcctcg tcaagacagg ctggggccgg ggctcaggta ccacggccca cgtgggcatc   9420
atgctgtatg gggtggacag ccggagcggc caccggcacc tggacggcga cagagccttc   9480
caccgcaaca gcctggacat cttccggatc gccacccgc acagcctggg tagcgtgtgg   9540
aagatccgag tgtggcacga caacaaaggg ctcagccctg cctggttcct gcagcacgtc   9600
atcgtcaggg acctgcagac ggcacgcagc gccttcttcc tggtcaatga ctggctttcg   9660
gtggagacgg aggccaacgg gggcctggtg gagaaggagg tgctggccgc gagcgacgca   9720
gcccttttgc gcttccggcg cctgctggtg gctgagctgc agcgtggctt cttttgacaag   9780
cacatctggc tctccatatg ggaccggccg cctcgtagcc gtttcactcg catccagagg   9840
gccacctgct gcgttctcct catctgcctc ttcctgggcg ccaacgccgt gtggtacggg   9900
gctgttggcg actctgccta cagcacgggg catgtgtcca ggctgagccc gctgagcgtc   9960
gacacagtcg ctgttggcct ggtgtccagc gtggttgtct atcccgtcta cctggccatc  10020
cttttttctct tccggatgtc ccggagcaag gtgctgggga gcccgagccc cacacctgcc  10080
gggcagcagg tgctggacat cgacagctgc ctggactcgt ccgtgctgga cagctccttc  10140
```

```
ctcacgttct caggcctcca cgctgaggcc tttgttggac agatgaagag tgacttgttt    10200
ctggatgatt ctaagagtct ggtgtgctgg ccctccggcg agggaacgct cagttggccg    10260
gacctgctca gtgacccgtc cattgtgggt agcaatctgc ggcagctggc acggggccag    10320
gcgggccatg ggctgggccc agaggaggac ggcttctccc tggccagccc ctactcgcct    10380
gccaaatcct tctcagcatc agatgaagac ctgatccagc aggtccttgc cgaggggtc     10440 agcagcccag cccctaccca agacacccac atggaaacgg acctgctcag cagcctgtcc    10500
agcactcctg gggagaagac agagacgctg gcgctgcaga ggctgggga gctgggcca      10560 cccagcccag gcctgaactg ggaacagccc caggcagcga ggctgtccag gacaggactg    10620
gtggagggtc tgcggaagcg cctgctgccg gcctggtgtg cctccctggc ccacgggctc    10680
agcctgctcc tggtggctgt ggctgtggct gtctcagggt gggtgggtgc gagcttcccc    10740
ccgggcgtga gtgttgcgtg gctcctgtcc agcagcgcca gcttcctggc ctcattcctc    10800
ggctgggagc cactgaaggt cttgctggaa gccctgtact tctcactggt ggccaagcgg    10860
ctgcacccgg atgaagatga caccctggta gagagcccgg ctgtgacgcc tgtgagcgca    10920
cgtgtgcccc gcgtacggcc accccacggc tttgcactct tcctggccaa ggaagaagcc    10980
cgcaaggtca gaggctaca tggcatgctg cggagcctcc tggtgtacat gcttttctg      11040 ctggtgaccc tgctggccag ctatggggat gcctcatgcc atgggcacgc ctaccgtctg    11100
caaagcgcca tcaagcagga gctgcacagc cgggccttcc tggccatcac gcggtctgag    11160
gagctctggc catggatggc ccacgtgctg ctgcccctacg tccacgggaa ccagtccagc    11220
ccagagctgg ggcccccacg gctgcggcag gtgcggctgc aggaagcact ctacccagac    11280
cctcccggcc ccagggtcca cacgtgctcg gccgcaggag gcttcagcac cagcgattac    11340
gacgttggct gggagagtcc tcacaatggc tcggggacgt gggcctattc agcgccggat    11400
ctgctggggg catggtcctg gggctcctgt gccgtgtatg acagcggggg ctacgtgcag    11460
gagctgggcc tgagcctgga ggagagccgc gaccggctgc gcttcctgca gctgcacaac    11520
tggctggaca acaggagccg cgctgtgttc ctggagctca cgcgctacag cccggccgtg    11580
gggctgcacg ccgccgtcac gctgcgcctc gagttcccgg cggccggccg cgccctggcc    11640
gccctcagcg tccgcccctt tgcgctgcgc cgcctcagcg cgggcctctc gctgcctctg    11700
ctcacctcgg tgtgcctgct gctgttcgcc gtgcacttcg ccgtggccga ggcccgtact    11760
tggcacaggg aagggcgctg gcgcgtgctg cggctcggag cctgggcgcg gtggctgctg    11820
gtggcgctga cggcggccac ggcactggta cgcctcgccc agctgggtgc cgctgaccgc    11880
cagtggaccc gtttcgtgcg cggccgcccg cgccgcttca ctagcttcga ccaggtggcg    11940
cagctgagct ccgcagcccg tggcctggcg gcctcgctgc tcttcctgct tttggtcaag    12000
gctgcccagc agctacgctt cgtgcgccag tggtccgtct ttggcaagac attatgccga    12060
gctctgccag agtcctggg ggtcaccttg gcctggtgg tgctcgggt agcctacgcc       12120 cagctggcca tcctgctcgt gtcttcctgt gtggactccc tctggagcgt ggcccaggcc    12180
ctgttggtgc tgtgccctgg gactgggctc tctaccctgt gtcctgccga gtcctggcac    12240
ctgtcacccc tgctgtgtgt ggggctctgg gcactgcggc tgtggggcgc cctacggctg    12300
ggggctgtta ttctccgctg gcgctaccac gccttgcgtg gagagctgta ccggccggcc    12360
tgggagcccc aggactacga gatggtggag ttgttcctgc gcaggctgcg cctctggatg    12420
ggcctcagca aggtcaagga gttccgccac aaagtccgct ttgaagggat ggagccgctg    12480
ccctctcgct cctccagggg ctccaaggta tccccggatg tgcccccacc cagcgctggc    12540
```

| | |
|---|---:|
| tccgatgcct cgcacccctc cacctcctcc agccagctgg atgggctgag cgtgagcctg | 12600 |
| ggccggctgg ggacaaggtg tgagcctgag ccctcccgcc tccaagccgt gttcgaggcc | 12660 |
| ctgctcaccc agtttgaccg actcaaccag gccacagagg acgtctacca gctggagcag | 12720 |
| cagctgcaca gcctgcaagg ccgcaggagc agccgggcgc ccgccggatc ttcccgtggc | 12780 |
| ccatccccgg gcctgcggcc agcactgccc agccgccttg cccgggccag tcggggtgtg | 12840 |
| gacctggcca ctggccccag caggacaccc cttcgggcca agaacaaggt ccaccccagc | 12900 |
| agcacttag | 12909 |

<210> SEQ ID NO 170
<211> LENGTH: 2907
<212> TYPE: DNA
<213> ORGANISM: Homo sapiens

<400> SEQUENCE: 170

| | |
|---|---:|
| atggtgaact ccagtcgcgt gcagcctcag cagcccgggg acgccaagcg gccgcccgcg | 60 |
| ccccgcgcgc cggacccggg ccggctgatg gctggctgcg cggccgtggg cgccagcctc | 120 |
| gccgccccgg gcggcctctg cgagcagcgg ggcctggaga tcgagatgca gcgcatccgg | 180 |
| caggcggccg cgcgggaccc cccggccgga gccgcggcct ccccttctcc tccgctctcg | 240 |
| tcgtgctccc ggcaggcgtg gagccgcgat aaccccggct cgaggccgga ggaggaggag | 300 |
| gaggaggtgg aagggaaga aggcggaatg gtggtggaga tggacgtaga gtggcgcccg | 360 |
| ggcagccgga ggtcggccgc ctcctcggcc gtgagctccg tgggcgcgcg gagccggggg | 420 |
| cttgggggct accacggcgc gggccacccg agcgggaggc ggcgccggcg agaggaccag | 480 |
| ggcccgccgt gccccagccc agtcggcggc ggggaccccg ctgcatcgcc actcccctg | 540 |
| gaagggcagc cgccccgagt ggcctgggcg gagaggctgg ttcgcgggct gcgaggtctc | 600 |
| tggggaacaa gactcatgga ggaaagcagc actaaccgag agaaatacct taaaagtgtt | 660 |
| ttacgggaac tggtcacata cctccttttt ctcatagtct tgtgcatctt gacctacggc | 720 |
| atgatgagct ccaatgtgta ctactacacc cggatgatgt cacagctctt cctagacacc | 780 |
| cccgtgtcca aaacggagaa aactaacttt aaaactctgt cttccatgga agacttctgg | 840 |
| aagttcacag aaggctcctt attggatggg ctgtactgga agatgcagcc cagcaaccag | 900 |
| actgaagctg acaaccgaag tttcatcttc tatgagaacc tgctgttagg ggttccacga | 960 |
| atacggcaac tccgagtcag aaatggatcc tgctctatcc cccaggactt gagagatgaa | 1020 |
| attaaagagt gctatgatgt ctactctgtc agtagtgaag atagggctcc ctttgggccc | 1080 |
| cgaaatggaa ccgcttggat ctacacaagt gaaaaagact gaatggtag tagccactgg | 1140 |
| ggaatcattg caacttatag tggagctggc tattatctgg atttgtcaag aacaagagag | 1200 |
| gaaacagctg cacaagttgc tagcctcaag aaaaatgtct ggctggaccg aggaaccagg | 1260 |
| gcaacttta ttgacttctc agtgtacaac gccaacatta acctgttctg tgtggtcagg | 1320 |
| ttattggttg aattcccagc aacaggtggt gtgattccat cttggcaatt tcagccttta | 1380 |
| aagctgatcc gatatgtcac aacttttgat ttcttcctgg cagcctgtga gattatcttt | 1440 |
| tgtttctta tcttttacta tgtggtggaa gagatattgg aaattcgcat tcacaaacta | 1500 |
| cactatttca ggagtttctg gaattgtctg gatgttgtga tcgttgtgct gtcagtggta | 1560 |
| gctataggaa ttaacatata cagaacatca aatgtggagg tgctactaca gtttctggaa | 1620 |
| gatcaaaata cttccccaa ctttgagcat ctggcatatt ggcagataca gttcaacaat | 1680 |

-continued

```
atagctgctg tcacagtatt ttttgtctgg attaagctct tcaaattcat caattttaac    1740
aggaccatga gccagctctc gacaaccatg tctcgatgtg ccaaagacct gtttggcttt    1800
gctattatgt tcttcattat tttcctagcg tatgctcagt tggcatacct tgtctttggc    1860
actcaggtcg atgacttcag tactttccaa gagtgtatct tcactcaatt ccgtatcatt    1920
ttgggcgata tcaactttgc agagattgag gaagctaatc gagttttggg accaatttat    1980
ttcactacat ttgtgttctt tatgttcttc attcttttga atatgttttt ggctatcatc    2040
aatgatactt actctgaagt gaaatctgac ttggcacagc agaaagctga aatggaactc    2100
tcagatctta tcagaaaggg ctaccataaa gctttggtca aactaaaact gaaaaaaaat    2160
accgtggatg acatttcaga gagtctgcgg caaggaggag gcaagttaaa ctttgacgaa    2220
cttcgacaag atctcaaagg gaagggccat actgatgcag agattgaggc aatattcaca    2280
aagtacgacc aagatggaga ccaagaactg accgaacatg aacatcagca gatgagagac    2340
gacttggaga agagagggga ggacctggat ttggatcaca gttctttacc acgtcccatg    2400
agcagccgaa gtttccctcg aagcctggat gactctgagg aggatgacga tgaagatagc    2460
ggacatagct ccagaaggag gggaagcatt tctagtggcg tttcttacga agagtttcaa    2520
gtcctggtga gacgagtgga ccggatggag cattccatcg gcagcatagt gtccaagatt    2580
gacgccgtga tcgtgaagct agagattatg gagcgagcca aactgaagag gagggaggtg    2640
ctgggaaggc tgttggatgg ggtggccgag gatgaaaggc tgggtcgtga cagtgaaatc    2700
catagggaac agatggaacg gctagtacgt gaagagttgg aacgctggga atccgatgat    2760
gcagcttccc agatcagtca tggtttaggc acgccagtgg gactaaatgg tcaacctcgc    2820
cccagaagct cccgcccatc ttcctcccaa tctacagaag gcatggaagg tgcaggtgga    2880
aatgggagtt ctaatgtcca cgtatga                                        2907
```

<210> SEQ ID NO 171
<211> LENGTH: 4302
<212> TYPE: PRT
<213> ORGANISM: Homo sapiens

<400> SEQUENCE: 171

```
Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Pro Gly Ala Ala Cys Arg
        35                  40                  45

Val Asn Cys Ser Gly Arg Gly Leu Arg Thr Leu Gly Pro Ala Leu Arg
    50                  55                  60

Ile Pro Ala Asp Ala Thr Ala Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
    130                 135                 140

Val Arg Val Val Gln Pro Glu Ala Ala Thr Cys Ala Gly Pro Gly Ser
145                 150                 155                 160
```

-continued

```
Leu Ala Gly Gln Pro Leu Leu Gly Ile Pro Leu Leu Asp Ser Gly Cys
            165                 170                 175
Gly Glu Glu Tyr Val Ala Cys Leu Pro Asp Asn Ser Ser Gly Thr Val
            180                 185                 190
Ala Ala Val Ser Phe Ser Ala Ala His Glu Gly Leu Leu Gln Pro Glu
            195                 200                 205
Ala Cys Ser Ala Phe Cys Phe Ser Thr Gly Gln Gly Leu Ala Ala Leu
            210                 215                 220
Ser Glu Gln Gly Trp Cys Leu Cys Gly Ala Ala Gln Pro Ser Ser Ala
225                 230                 235                 240
Ser Phe Ala Cys Leu Ser Leu Cys Ser Gly Pro Pro Pro Pro Pro Ala
                245                 250                 255
Pro Thr Cys Arg Gly Pro Thr Leu Leu Gln His Val Phe Pro Ala Ser
            260                 265                 270
Pro Gly Ala Thr Leu Val Gly Pro His Gly Pro Leu Ala Ser Gly Gln
            275                 280                 285
Leu Ala Ala Phe His Ile Ala Ala Pro Leu Pro Val Thr Ala Thr Arg
            290                 295                 300
Trp Asp Phe Gly Asp Gly Ser Ala Glu Val Asp Ala Ala Gly Pro Ala
305                 310                 315                 320
Ala Ser His Arg Tyr Val Leu Pro Gly Arg Tyr His Val Thr Ala Val
                325                 330                 335
Leu Ala Leu Gly Ala Gly Ser Ala Leu Leu Gly Thr Asp Val Gln Val
            340                 345                 350
Glu Ala Ala Pro Ala Ala Leu Glu Leu Val Cys Pro Ser Ser Val Gln
            355                 360                 365
Ser Asp Glu Ser Leu Asp Leu Ser Ile Gln Asn Arg Gly Gly Ser Gly
            370                 375                 380
Leu Glu Ala Ala Tyr Ser Ile Val Ala Leu Gly Glu Glu Pro Ala Arg
385                 390                 395                 400
Ala Val His Pro Leu Cys Pro Ser Asp Thr Glu Ile Phe Pro Gly Asn
                405                 410                 415
Gly His Cys Tyr Arg Leu Val Val Glu Lys Ala Ala Trp Leu Gln Ala
                420                 425                 430
Gln Glu Gln Cys Gln Ala Trp Ala Gly Ala Ala Leu Ala Met Val Asp
            435                 440                 445
Ser Pro Ala Val Gln Arg Phe Leu Val Ser Arg Val Thr Arg Ser Leu
450                 455                 460
Asp Val Trp Ile Gly Phe Ser Thr Val Gln Gly Val Glu Val Gly Pro
465                 470                 475                 480
Ala Pro Gln Gly Glu Ala Phe Ser Leu Glu Ser Cys Gln Asn Trp Leu
            485                 490                 495
Pro Gly Glu Pro His Pro Ala Thr Ala Glu His Cys Val Arg Leu Gly
            500                 505                 510
Pro Thr Gly Trp Cys Asn Thr Asp Leu Cys Ser Ala Pro His Ser Tyr
            515                 520                 525
Val Cys Glu Leu Gln Pro Gly Gly Pro Val Gln Asp Ala Glu Asn Leu
            530                 535                 540
Leu Val Gly Ala Pro Ser Gly Asp Leu Gln Gly Pro Leu Thr Pro Leu
545                 550                 555                 560
Ala Gln Gln Asp Gly Leu Ser Ala Pro His Glu Pro Val Glu Val Met
                565                 570                 575
```

```
Val Phe Pro Gly Leu Arg Leu Ser Arg Glu Ala Phe Leu Thr Thr Ala
            580                 585                 590
Glu Phe Gly Thr Gln Glu Leu Arg Arg Pro Ala Gln Leu Arg Leu Gln
            595                 600                 605
Val Tyr Arg Leu Leu Ser Thr Ala Gly Thr Pro Glu Asn Gly Ser Glu
    610                 615                 620
Pro Glu Ser Arg Ser Pro Asp Asn Arg Thr Gln Leu Ala Pro Ala Cys
625                 630                 635                 640
Met Pro Gly Gly Arg Trp Cys Pro Gly Ala Asn Ile Cys Leu Pro Leu
            645                 650                 655
Asp Ala Ser Cys His Pro Gln Ala Cys Ala Asn Gly Cys Thr Ser Gly
            660                 665                 670
Pro Gly Leu Pro Gly Ala Pro Tyr Ala Leu Trp Arg Glu Phe Leu Phe
            675                 680                 685
Ser Val Ala Ala Gly Pro Pro Ala Gln Tyr Ser Val Thr Leu His Gly
            690                 695                 700
Gln Asp Val Leu Met Leu Pro Gly Asp Leu Val Gly Leu Gln His Asp
705                 710                 715                 720
Ala Gly Pro Gly Ala Leu Leu His Cys Ser Pro Ala Pro Gly His Pro
            725                 730                 735
Gly Pro Gln Ala Pro Tyr Leu Ser Ala Asn Ala Ser Ser Trp Leu Pro
            740                 745                 750
His Leu Pro Ala Gln Leu Glu Gly Thr Trp Ala Cys Pro Ala Cys Ala
            755                 760                 765
Leu Arg Leu Leu Ala Ala Thr Glu Gln Leu Thr Val Leu Leu Gly Leu
            770                 775                 780
Arg Pro Asn Pro Gly Leu Arg Met Pro Gly Arg Tyr Glu Val Arg Ala
785                 790                 795                 800
Glu Val Gly Asn Gly Val Ser Arg His Asn Leu Ser Cys Ser Phe Asp
            805                 810                 815
Val Val Ser Pro Val Ala Gly Leu Arg Val Ile Tyr Pro Ala Pro Arg
            820                 825                 830
Asp Gly Arg Leu Tyr Val Pro Thr Asn Gly Ser Ala Leu Val Leu Gln
            835                 840                 845
Val Asp Ser Gly Ala Asn Ala Thr Ala Thr Ala Arg Trp Pro Gly Gly
            850                 855                 860
Ser Val Ser Ala Arg Phe Glu Asn Val Cys Pro Ala Leu Val Ala Thr
865                 870                 875                 880
Phe Val Pro Gly Cys Pro Trp Glu Thr Asn Asp Thr Leu Phe Ser Val
            885                 890                 895
Val Ala Leu Pro Trp Leu Ser Glu Gly Glu His Val Val Asp Val Val
            900                 905                 910
Val Glu Asn Ser Ala Ser Arg Ala Asn Leu Ser Leu Arg Val Thr Ala
            915                 920                 925
Glu Glu Pro Ile Cys Gly Leu Arg Ala Thr Pro Ser Pro Glu Ala Arg
            930                 935                 940
Val Leu Gln Gly Val Leu Val Arg Tyr Ser Pro Val Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
            980                 985                 990
Lys Leu Ser Leu Thr Ala Ser Asn  His Val Ser Asn Val  Thr Val Asn
```

-continued

```
             995                  1000                1005
Tyr Asn Val Thr Val Glu Arg Met Asn Arg Met Gln Gly Leu Gln
        1010                1015                1020

Val Ser Thr Val Pro Ala Val Leu Ser Pro Asn Ala Thr Leu Ala
        1025                1030                1035

Leu Thr Ala Gly Val Leu Val Asp Ser Ala Val Glu Val Ala Phe
        1040                1045                1050

Leu Trp Asn Phe Gly Asp Gly Glu Gln Ala Leu His Gln Phe Gln
        1055                1060                1065

Pro Pro Tyr Asn Glu Ser Phe Pro Val Pro Asp Pro Ser Val Ala
        1070                1075                1080

Gln Val Leu Val Glu His Asn Val Met His Thr Tyr Ala Ala Pro
        1085                1090                1095

Gly Glu Tyr Leu Leu Thr Val Leu Ala Ser Asn Ala Phe Glu Asn
        1100                1105                1110

Leu Thr Gln Gln Val Pro Val Ser Val Arg Ala Ser Leu Pro Ser
        1115                1120                1125

Val Ala Val Gly Val Ser Asp Gly Val Leu Val Ala Gly Arg Pro
        1130                1135                1140

Val Thr Phe Tyr Pro His Pro Leu Pro Ser Pro Gly Gly Val Leu
        1145                1150                1155

Tyr Thr Trp Asp Phe Gly Asp Gly Ser Pro Val Leu Thr Gln Ser
        1160                1165                1170

Gln Pro Ala Ala Asn His Thr Tyr Ala Ser Arg Gly Thr Tyr His
        1175                1180                1185

Val Arg Leu Glu Val Asn Asn Thr Val Ser Gly Ala Ala Ala Gln
        1190                1195                1200

Ala Asp Val Arg Val Phe Glu Glu Leu Arg Gly Leu Ser Val Asp
        1205                1210                1215

Met Ser Leu Ala Val Glu Gln Gly Ala Pro Val Val Val Ser Ala
        1220                1225                1230

Ala Val Gln Thr Gly Asp Asn Ile Thr Trp Thr Phe Asp Met Gly
        1235                1240                1245

Asp Gly Thr Val Leu Ser Gly Pro Glu Ala Thr Val Glu His Val
        1250                1255                1260

Tyr Leu Arg Ala Gln Asn Cys Thr Val Thr Val Gly Ala Ala Ser
        1265                1270                1275

Pro Ala Gly His Leu Ala Arg Ser Leu His Val Leu Val Phe Val
        1280                1285                1290

Leu Glu Val Leu Arg Val Glu Pro Ala Ala Cys Ile Pro Thr Gln
        1295                1300                1305

Pro Asp Ala Arg Leu Thr Ala Tyr Val Thr Gly Asn Pro Ala His
        1310                1315                1320

Tyr Leu Phe Asp Trp Thr Phe Gly Asp Gly Ser Ser Asn Thr Thr
        1325                1330                1335

Val Arg Gly Cys Pro Thr Val Thr His Asn Phe Thr Arg Ser Gly
        1340                1345                1350

Thr Phe Pro Leu Ala Leu Val Leu Ser Ser Arg Val Asn Arg Ala
        1355                1360                1365

His Tyr Phe Thr Ser Ile Cys Val Glu Pro Glu Val Gly Asn Val
        1370                1375                1380

Thr Leu Gln Pro Glu Arg Gln Phe Val Gln Leu Gly Asp Glu Ala
        1385                1390                1395
```

-continued

```
Trp Leu Val Ala Cys Ala Trp Pro Pro Phe Pro Tyr Arg Tyr Thr
1400                1405                1410

Trp Asp Phe Gly Thr Glu Glu Ala Ala Pro Thr Arg Ala Arg Gly
1415                1420                1425

Pro Glu Val Thr Phe Ile Tyr Arg Asp Pro Gly Ser Tyr Leu Val
1430                1435                1440

Thr Val Thr Ala Ser Asn Asn Ile Ser Ala Ala Asn Asp Ser Ala
1445                1450                1455

Leu Val Glu Val Gln Glu Pro Val Leu Val Thr Ser Ile Lys Val
1460                1465                1470

Asn Gly Ser Leu Gly Leu Glu Leu Gln Gln Pro Tyr Leu Phe Ser
1475                1480                1485

Ala Val Gly Arg Gly Arg Pro Ala Ser Tyr Leu Trp Asp Leu Gly
1490                1495                1500

Asp Gly Gly Trp Leu Glu Gly Pro Glu Val Thr His Ala Tyr Asn
1505                1510                1515

Ser Thr Gly Asp Phe Thr Val Arg Val Ala Gly Trp Asn Glu Val
1520                1525                1530

Ser Arg Ser Glu Ala Trp Leu Asn Val Thr Val Lys Arg Arg Val
1535                1540                1545

Arg Gly Leu Val Val Asn Ala Ser Arg Thr Val Val Pro Leu Asn
1550                1555                1560

Gly Ser Val Ser Phe Ser Thr Ser Leu Glu Ala Gly Ser Asp Val
1565                1570                1575

Arg Tyr Ser Trp Val Leu Cys Asp Arg Cys Thr Pro Ile Pro Gly
1580                1585                1590

Gly Pro Thr Ile Ser Tyr Thr Phe Arg Ser Val Gly Thr Phe Asn
1595                1600                1605

Ile Ile Val Thr Ala Glu Asn Glu Val Gly Ser Ala Gln Asp Ser
1610                1615                1620

Ile Phe Val Tyr Val Leu Gln Leu Ile Glu Gly Leu Gln Val Val
1625                1630                1635

Gly Gly Gly Arg Tyr Phe Pro Thr Asn His Thr Val Gln Leu Gln
1640                1645                1650

Ala Val Val Arg Asp Gly Thr Asn Val Ser Tyr Ser Trp Thr Ala
1655                1660                1665

Trp Arg Asp Arg Gly Pro Ala Leu Ala Gly Ser Gly Lys Gly Phe
1670                1675                1680

Ser Leu Thr Val Leu Glu Ala Gly Thr Tyr His Val Gln Leu Arg
1685                1690                1695

Ala Thr Asn Met Leu Gly Ser Ala Trp Ala Asp Cys Thr Met Asp
1700                1705                1710

Phe Val Glu Pro Val Gly Trp Leu Met Val Thr Ala Ser Pro Asn
1715                1720                1725

Pro Ala Ala Val Asn Thr Ser Val Thr Leu Ser Ala Glu Leu Ala
1730                1735                1740

Gly Gly Ser Gly Val Val Tyr Thr Trp Ser Leu Glu Glu Gly Leu
1745                1750                1755

Ser Trp Glu Thr Ser Glu Pro Phe Thr Thr His Ser Phe Pro Thr
1760                1765                1770

Pro Gly Leu His Leu Val Thr Met Thr Ala Gly Asn Pro Leu Gly
1775                1780                1785
```

-continued

```
Ser Ala Asn Ala Thr Val Glu Val Asp Val Gln Val Pro Val Ser
    1790            1795                1800

Gly Leu Ser Ile Arg Ala Ser Glu Pro Gly Gly Ser Phe Val Ala
    1805            1810                1815

Ala Gly Ser Ser Val Pro Phe Trp Gly Gln Leu Ala Thr Gly Thr
    1820            1825                1830

Asn Val Ser Trp Cys Trp Ala Val Pro Gly Gly Ser Ser Lys Arg
    1835            1840                1845

Gly Pro His Val Thr Met Val Phe Pro Asp Ala Gly Thr Phe Ser
    1850            1855                1860

Ile Arg Leu Asn Ala Ser Asn Ala Val Ser Trp Val Ser Ala Thr
    1865            1870                1875

Tyr Asn Leu Thr Ala Glu Glu Pro Ile Val Gly Leu Val Leu Trp
    1880            1885                1890

Ala Ser Ser Lys Val Val Ala Pro Gly Gln Leu Val His Phe Gln
    1895            1900                1905

Ile Leu Leu Ala Ala Gly Ser Ala Val Thr Phe Arg Leu Gln Val
    1910            1915                1920

Gly Gly Ala Asn Pro Glu Val Leu Pro Gly Pro Arg Phe Ser His
    1925            1930                1935

Ser Phe Pro Arg Val Gly Asp His Val Val Ser Val Arg Gly Lys
    1940            1945                1950

Asn His Val Ser Trp Ala Gln Ala Gln Val Arg Ile Val Val Leu
    1955            1960                1965

Glu Ala Val Ser Gly Leu Gln Met Pro Asn Cys Cys Glu Pro Gly
    1970            1975                1980

Ile Ala Thr Gly Thr Glu Arg Asn Phe Thr Ala Arg Val Gln Arg
    1985            1990                1995

Gly Ser Arg Val Ala Tyr Ala Trp Tyr Phe Ser Leu Gln Lys Val
    2000            2005                2010

Gln Gly Asp Ser Leu Val Ile Leu Ser Gly Arg Asp Val Thr Tyr
    2015            2020                2025

Thr Pro Val Ala Ala Gly Leu Leu Glu Ile Gln Val Arg Ala Phe
    2030            2035                2040

Asn Ala Leu Gly Ser Glu Asn Arg Thr Leu Val Leu Glu Val Gln
    2045            2050                2055

Asp Ala Val Gln Tyr Val Ala Leu Gln Ser Gly Pro Cys Phe Thr
    2060            2065                2070

Asn Arg Ser Ala Gln Phe Glu Ala Ala Thr Ser Pro Ser Pro Arg
    2075            2080                2085

Arg Val Ala Tyr His Trp Asp Phe Gly Asp Gly Ser Pro Gly Gln
    2090            2095                2100

Asp Thr Asp Glu Pro Arg Ala Glu His Ser Tyr Leu Arg Pro Gly
    2105            2110                2115

Asp Tyr Arg Val Gln Val Asn Ala Ser Asn Leu Val Ser Phe Phe
    2120            2125                2130

Val Ala Gln Ala Thr Val Thr Val Gln Val Leu Ala Cys Arg Glu
    2135            2140                2145

Pro Glu Val Asp Val Val Leu Pro Leu Gln Val Leu Met Arg Arg
    2150            2155                2160

Ser Gln Arg Asn Tyr Leu Glu Ala His Val Asp Leu Arg Asp Cys
    2165            2170                2175

Val Thr Tyr Gln Thr Glu Tyr Arg Trp Glu Val Tyr Arg Thr Ala
```

-continued

```
                2180                2185                2190

Ser Cys Gln Arg Pro Gly Arg Pro Ala Arg Val Ala Leu Pro Gly
    2195                2200                2205

Val Asp Val Ser Arg Pro Arg Leu Val Leu Pro Arg Leu Ala Leu
    2210                2215                2220

Pro Val Gly His Tyr Cys Phe Val Phe Val Ser Phe Gly Asp
    2225                2230                2235

Thr Pro Leu Thr Gln Ser Ile Gln Ala Asn Val Thr Val Ala Pro
    2240                2245                2250

Glu Arg Leu Val Pro Ile Ile Glu Gly Gly Ser Tyr Arg Val Trp
    2255                2260                2265

Ser Asp Thr Arg Asp Leu Val Leu Asp Gly Ser Glu Ser Tyr Asp
    2270                2275                2280

Pro Asn Leu Glu Asp Gly Asp Gln Thr Pro Leu Ser Phe His Trp
    2285                2290                2295

Ala Cys Val Ala Ser Thr Gln Arg Glu Ala Gly Gly Cys Ala Leu
    2300                2305                2310

Asn Phe Gly Pro Arg Gly Ser Ser Thr Val Thr Ile Pro Arg Glu
    2315                2320                2325

Arg Leu Ala Ala Gly Val Glu Tyr Thr Phe Ser Leu Thr Val Trp
    2330                2335                2340

Lys Ala Gly Arg Lys Glu Glu Ala Thr Asn Gln Thr Val Leu Ile
    2345                2350                2355

Arg Ser Gly Arg Val Pro Ile Val Ser Leu Glu Cys Val Ser Cys
    2360                2365                2370

Lys Ala Gln Ala Val Tyr Glu Val Ser Arg Ser Ser Tyr Val Tyr
    2375                2380                2385

Leu Glu Gly Arg Cys Leu Asn Cys Ser Ser Gly Ser Lys Arg Gly
    2390                2395                2400

Arg Trp Ala Ala Arg Thr Phe Ser Asn Lys Thr Leu Val Leu Asp
    2405                2410                2415

Glu Thr Thr Thr Ser Thr Gly Ser Ala Gly Met Arg Leu Val Leu
    2420                2425                2430

Arg Arg Gly Val Leu Arg Asp Gly Glu Gly Tyr Thr Phe Thr Leu
    2435                2440                2445

Thr Val Leu Gly Arg Ser Gly Glu Glu Glu Gly Cys Ala Ser Ile
    2450                2455                2460

Arg Leu Ser Pro Asn Arg Pro Pro Leu Gly Gly Ser Cys Arg Leu
    2465                2470                2475

Phe Pro Leu Gly Ala Val His Ala Leu Thr Thr Lys Val His Phe
    2480                2485                2490

Glu Cys Thr Gly Trp His Asp Ala Glu Asp Ala Gly Ala Pro Leu
    2495                2500                2505

Val Tyr Ala Leu Leu Leu Arg Arg Cys Arg Gln Gly His Cys Glu
    2510                2515                2520

Glu Phe Cys Val Tyr Lys Gly Ser Leu Ser Ser Tyr Gly Ala Val
    2525                2530                2535

Leu Pro Pro Gly Phe Arg Pro His Phe Glu Val Gly Leu Ala Val
    2540                2545                2550

Val Val Gln Asp Gln Leu Gly Ala Ala Val Val Ala Leu Asn Arg
    2555                2560                2565

Ser Leu Ala Ile Thr Leu Pro Glu Pro Asn Gly Ser Ala Thr Gly
    2570                2575                2580
```

-continued

```
Leu Thr Val Trp Leu His Gly Leu Thr Ala Ser Val Leu Pro Gly
    2585                2590                2595

Leu Leu Arg Gln Ala Asp Pro Gln His Val Ile Glu Tyr Ser Leu
    2600                2605                2610

Ala Leu Val Thr Val Leu Asn Glu Tyr Glu Arg Ala Leu Asp Val
    2615                2620                2625

Ala Ala Glu Pro Lys His Glu Arg Gln His Arg Ala Gln Ile Arg
    2630                2635                2640

Lys Asn Ile Thr Glu Thr Leu Val Ser Leu Arg Val His Thr Val
    2645                2650                2655

Asp Asp Ile Gln Gln Ile Ala Ala Ala Leu Ala Gln Cys Met Gly
    2660                2665                2670

Pro Ser Arg Glu Leu Val Cys Arg Ser Cys Leu Lys Gln Thr Leu
    2675                2680                2685

His Lys Leu Glu Ala Met Met Leu Ile Leu Gln Ala Glu Thr Thr
    2690                2695                2700

Ala Gly Thr Val Thr Pro Thr Ala Ile Gly Asp Ser Ile Leu Asn
    2705                2710                2715

Ile Thr Gly Asp Leu Ile His Leu Ala Ser Ser Asp Val Arg Ala
    2720                2725                2730

Pro Gln Pro Ser Glu Leu Gly Ala Glu Ser Pro Ser Arg Met Val
    2735                2740                2745

Ala Ser Gln Ala Tyr Asn Leu Thr Ser Ala Leu Met Arg Ile Leu
    2750                2755                2760

Met Arg Ser Arg Val Leu Asn Glu Glu Pro Leu Thr Leu Ala Gly
    2765                2770                2775

Glu Glu Ile Val Ala Gln Gly Lys Arg Ser Asp Pro Arg Ser Leu
    2780                2785                2790

Leu Cys Tyr Gly Gly Ala Pro Gly Pro Gly Cys His Phe Ser Ile
    2795                2800                2805

Pro Glu Ala Phe Ser Gly Ala Leu Ala Asn Leu Ser Asp Val Val
    2810                2815                2820

Gln Leu Ile Phe Leu Val Asp Ser Asn Pro Phe Pro Phe Gly Tyr
    2825                2830                2835

Ile Ser Asn Tyr Thr Val Ser Thr Lys Val Ala Ser Met Ala Phe
    2840                2845                2850

Gln Thr Gln Ala Gly Ala Gln Ile Pro Ile Glu Arg Leu Ala Ser
    2855                2860                2865

Glu Arg Ala Ile Thr Val Lys Val Pro Asn Asn Ser Asp Trp Ala
    2870                2875                2880

Ala Arg Gly His Arg Ser Ser Ala Asn Ser Ala Asn Ser Val Val
    2885                2890                2895

Val Gln Pro Gln Ala Ser Val Gly Ala Val Val Thr Leu Asp Ser
    2900                2905                2910

Ser Asn Pro Ala Ala Gly Leu His Leu Gln Leu Asn Tyr Thr Leu
    2915                2920                2925

Leu Asp Gly His Tyr Leu Ser Glu Glu Pro Glu Pro Tyr Leu Ala
    2930                2935                2940

Val Tyr Leu His Ser Glu Pro Arg Pro Asn Glu His Asn Cys Ser
    2945                2950                2955

Ala Ser Arg Arg Ile Arg Pro Glu Ser Leu Gln Gly Ala Asp His
    2960                2965                2970
```

-continued

```
Arg Pro Tyr Thr Phe Phe Ile Ser Pro Gly Ser Arg Asp Pro Ala
    2975                2980                2985

Gly Ser Tyr His Leu Asn Leu Ser Ser His Phe Arg Trp Ser Ala
    2990                2995                3000

Leu Gln Val Ser Val Gly Leu Tyr Thr Ser Leu Cys Gln Tyr Phe
    3005                3010                3015

Ser Glu Glu Asp Met Val Trp Arg Thr Glu Gly Leu Leu Pro Leu
    3020                3025                3030

Glu Glu Thr Ser Pro Arg Gln Ala Val Cys Leu Thr Arg His Leu
    3035                3040                3045

Thr Ala Phe Gly Ala Ser Leu Phe Val Pro Pro Ser His Val Arg
    3050                3055                3060

Phe Val Phe Pro Glu Pro Thr Ala Asp Val Asn Tyr Ile Val Met
    3065                3070                3075

Leu Thr Cys Ala Val Cys Leu Val Thr Tyr Met Val Met Ala Ala
    3080                3085                3090

Ile Leu His Lys Leu Asp Gln Leu Asp Ala Ser Arg Gly Arg Ala
    3095                3100                3105

Ile Pro Phe Cys Gly Gln Arg Gly Arg Phe Lys Tyr Glu Ile Leu
    3110                3115                3120

Val Lys Thr Gly Trp Gly Arg Gly Ser Gly Thr Thr Ala His Val
    3125                3130                3135

Gly Ile Met Leu Tyr Gly Val Asp Ser Arg Ser Gly His Arg His
    3140                3145                3150

Leu Asp Gly Asp Arg Ala Phe His Arg Asn Ser Leu Asp Ile Phe
    3155                3160                3165

Arg Ile Ala Thr Pro His Ser Leu Gly Ser Val Trp Lys Ile Arg
    3170                3175                3180

Val Trp His Asp Asn Lys Gly Leu Ser Pro Ala Trp Phe Leu Gln
    3185                3190                3195

His Val Ile Val Arg Asp Leu Gln Thr Ala Arg Ser Ala Phe Phe
    3200                3205                3210

Leu Val Asn Asp Trp Leu Ser Val Glu Thr Glu Ala Asn Gly Gly
    3215                3220                3225

Leu Val Glu Lys Glu Val Leu Ala Ala Ser Asp Ala Ala Leu Leu
    3230                3235                3240

Arg Phe Arg Arg Leu Leu Val Ala Glu Leu Gln Arg Gly Phe Phe
    3245                3250                3255

Asp Lys His Ile Trp Leu Ser Ile Trp Asp Arg Pro Pro Arg Ser
    3260                3265                3270

Arg Phe Thr Arg Ile Gln Arg Ala Thr Cys Cys Val Leu Leu Ile
    3275                3280                3285

Cys Leu Phe Leu Gly Ala Asn Ala Val Trp Tyr Gly Ala Val Gly
    3290                3295                3300

Asp Ser Ala Tyr Ser Thr Gly His Val Ser Arg Leu Ser Pro Leu
    3305                3310                3315

Ser Val Asp Thr Val Ala Val Gly Leu Val Ser Ser Val Val Val
    3320                3325                3330

Tyr Pro Val Tyr Leu Ala Ile Leu Phe Leu Phe Arg Met Ser Arg
    3335                3340                3345

Ser Lys Val Ala Gly Ser Pro Ser Pro Thr Pro Ala Gly Gln Gln
    3350                3355                3360

Val Leu Asp Ile Asp Ser Cys Leu Asp Ser Ser Val Leu Asp Ser
```

-continued

```
         3365                3370               3375

Ser Phe Leu Thr Phe Ser Gly Leu His Ala Glu Ala Phe Val Gly
    3380                3385               3390

Gln Met Lys Ser Asp Leu Phe Leu Asp Asp Ser Lys Ser Leu Val
    3395                3400               3405

Cys Trp Pro Ser Gly Glu Gly Thr Leu Ser Trp Pro Asp Leu Leu
    3410                3415               3420

Ser Asp Pro Ser Ile Val Gly Ser Asn Leu Arg Gln Leu Ala Arg
    3425                3430               3435

Gly Gln Ala Gly His Gly Leu Gly Pro Glu Glu Asp Gly Phe Ser
    3440                3445               3450

Leu Ala Ser Pro Tyr Ser Pro Ala Lys Ser Phe Ser Ala Ser Asp
    3455                3460               3465

Glu Asp Leu Ile Gln Gln Val Leu Ala Glu Gly Val Ser Ser Pro
    3470                3475               3480

Ala Pro Thr Gln Asp Thr His Met Glu Thr Asp Leu Leu Ser Ser
    3485                3490               3495

Leu Ser Ser Thr Pro Gly Glu Lys Thr Glu Thr Leu Ala Leu Gln
    3500                3505               3510

Arg Leu Gly Glu Leu Gly Pro Pro Ser Pro Gly Leu Asn Trp Glu
    3515                3520               3525

Gln Pro Gln Ala Ala Arg Leu Ser Arg Thr Gly Leu Val Glu Gly
    3530                3535               3540

Leu Arg Lys Arg Leu Leu Pro Ala Trp Cys Ala Ser Leu Ala His
    3545                3550               3555

Gly Leu Ser Leu Leu Val Ala Val Ala Val Ala Val Ser Gly
    3560                3565               3570

Trp Val Gly Ala Ser Phe Pro Pro Gly Val Ser Val Ala Trp Leu
    3575                3580               3585

Leu Ser Ser Ser Ala Ser Phe Leu Ala Ser Phe Leu Gly Trp Glu
    3590                3595               3600

Pro Leu Lys Val Leu Leu Glu Ala Leu Tyr Phe Ser Leu Val Ala
    3605                3610               3615

Lys Arg Leu His Pro Asp Glu Asp Asp Thr Leu Val Glu Ser Pro
    3620                3625               3630

Ala Val Thr Pro Val Ser Ala Arg Val Pro Arg Val Arg Pro Pro
    3635                3640               3645

His Gly Phe Ala Leu Phe Leu Ala Lys Glu Glu Ala Arg Lys Val
    3650                3655               3660

Lys Arg Leu His Gly Met Leu Arg Ser Leu Leu Val Tyr Met Leu
    3665                3670               3675

Phe Leu Leu Val Thr Leu Leu Ala Ser Tyr Gly Asp Ala Ser Cys
    3680                3685               3690

His Gly His Ala Tyr Arg Leu Gln Ser Ala Ile Lys Gln Glu Leu
    3695                3700               3705

His Ser Arg Ala Phe Leu Ala Ile Thr Arg Ser Glu Glu Leu Trp
    3710                3715               3720

Pro Trp Met Ala His Val Leu Leu Pro Tyr Val His Gly Asn Gln
    3725                3730               3735

Ser Ser Pro Glu Leu Gly Pro Pro Arg Leu Arg Gln Val Arg Leu
    3740                3745               3750

Gln Glu Ala Leu Tyr Pro Asp Pro Pro Gly Pro Arg Val His Thr
    3755                3760               3765
```

-continued

```
Cys Ser Ala Ala Gly Gly Phe Ser Thr Ser Asp Tyr Asp Val Gly
3770            3775                3780

Trp Glu Ser Pro His Asn Gly Ser Gly Thr Trp Ala Tyr Ser Ala
3785            3790                3795

Pro Asp Leu Leu Gly Ala Trp Ser Trp Gly Ser Cys Ala Val Tyr
3800            3805                3810

Asp Ser Gly Gly Tyr Val Gln Glu Leu Gly Leu Ser Leu Glu Glu
3815            3820                3825

Ser Arg Asp Arg Leu Arg Phe Leu Gln Leu His Asn Trp Leu Asp
3830            3835                3840

Asn Arg Ser Arg Ala Val Phe Leu Glu Leu Thr Arg Tyr Ser Pro
3845            3850                3855

Ala Val Gly Leu His Ala Ala Val Thr Leu Arg Leu Glu Phe Pro
3860            3865                3870

Ala Ala Gly Arg Ala Leu Ala Ala Leu Ser Val Arg Pro Phe Ala
3875            3880                3885

Leu Arg Arg Leu Ser Ala Gly Leu Ser Leu Pro Leu Leu Thr Ser
3890            3895                3900

Val Cys Leu Leu Leu Phe Ala Val His Phe Ala Val Ala Glu Ala
3905            3910                3915

Arg Thr Trp His Arg Glu Gly Arg Trp Arg Val Leu Arg Leu Gly
3920            3925                3930

Ala Trp Ala Arg Trp Leu Leu Val Ala Leu Thr Ala Ala Thr Ala
3935            3940                3945

Leu Val Arg Leu Ala Gln Leu Gly Ala Ala Asp Arg Gln Trp Thr
3950            3955                3960

Arg Phe Val Arg Gly Arg Pro Arg Arg Phe Thr Ser Phe Asp Gln
3965            3970                3975

Val Ala Gln Leu Ser Ser Ala Ala Arg Gly Leu Ala Ala Ser Leu
3980            3985                3990

Leu Phe Leu Leu Leu Val Lys Ala Ala Gln Gln Leu Arg Phe Val
3995            4000                4005

Arg Gln Trp Ser Val Phe Gly Lys Thr Leu Cys Arg Ala Leu Pro
4010            4015                4020

Glu Leu Leu Gly Val Thr Leu Gly Leu Val Val Leu Gly Val Ala
4025            4030                4035

Tyr Ala Gln Leu Ala Ile Leu Leu Val Ser Ser Cys Val Asp Ser
4040            4045                4050

Leu Trp Ser Val Ala Gln Ala Leu Leu Val Leu Cys Pro Gly Thr
4055            4060                4065

Gly Leu Ser Thr Leu Cys Pro Ala Glu Ser Trp His Leu Ser Pro
4070            4075                4080

Leu Leu Cys Val Gly Leu Trp Ala Leu Arg Leu Trp Gly Ala Leu
4085            4090                4095

Arg Leu Gly Ala Val Ile Leu Arg Trp Arg Tyr His Ala Leu Arg
4100            4105                4110

Gly Glu Leu Tyr Arg Pro Ala Trp Glu Pro Gln Asp Tyr Glu Met
4115            4120                4125

Val Glu Leu Phe Leu Arg Arg Leu Arg Leu Trp Met Gly Leu Ser
4130            4135                4140

Lys Val Lys Glu Phe Arg His Lys Val Arg Phe Glu Gly Met Glu
4145            4150                4155
```

```
Pro Leu Pro Ser Arg Ser Ser Arg Gly Ser Lys Val Ser Pro Asp
    4160                4165                4170

Val Pro Pro Pro Ser Ala Gly Ser Asp Ala Ser His Pro Ser Thr
    4175                4180                4185

Ser Ser Ser Gln Leu Asp Gly Leu Ser Val Ser Leu Gly Arg Leu
    4190                4195                4200

Gly Thr Arg Cys Glu Pro Glu Pro Ser Arg Leu Gln Ala Val Phe
    4205                4210                4215

Glu Ala Leu Leu Thr Gln Phe Asp Arg Leu Asn Gln Ala Thr Glu
    4220                4225                4230

Asp Val Tyr Gln Leu Glu Gln Gln Leu His Ser Leu Gln Gly Arg
    4235                4240                4245

Arg Ser Ser Arg Ala Pro Ala Gly Ser Ser Arg Gly Pro Ser Pro
    4250                4255                4260

Gly Leu Arg Pro Ala Leu Pro Ser Arg Leu Ala Arg Ala Ser Arg
    4265                4270                4275

Gly Val Asp Leu Ala Thr Gly Pro Ser Arg Thr Pro Leu Arg Ala
    4280                4285                4290

Lys Asn Lys Val His Pro Ser Ser Thr
    4295                4300

<210> SEQ ID NO 172
<211> LENGTH: 968
<212> TYPE: PRT
<213> ORGANISM: Homo sapiens

<400> SEQUENCE: 172

Met Val Asn Ser Ser Arg Val Gln Pro Gln Gln Pro Gly Asp Ala Lys
1               5                   10                  15

Arg Pro Pro Ala Pro Arg Ala Pro Asp Pro Gly Arg Leu Met Ala Gly
                20                  25                  30

Cys Ala Ala Val Gly Ala Ser Leu Ala Ala Pro Gly Gly Leu Cys Glu
            35                  40                  45

Gln Arg Gly Leu Glu Ile Glu Met Gln Arg Ile Arg Gln Ala Ala Ala
        50                  55                  60

Arg Asp Pro Pro Ala Gly Ala Ala Ser Pro Ser Pro Pro Leu Ser
65                  70                  75                  80

Ser Cys Ser Arg Gln Ala Trp Ser Arg Asp Asn Pro Gly Phe Glu Ala
                85                  90                  95

Glu Glu Glu Glu Glu Val Glu Gly Glu Gly Gly Met Val Val
            100                 105                 110

Glu Met Asp Val Glu Trp Arg Pro Gly Ser Arg Arg Ser Ala Ala Ser
        115                 120                 125

Ser Ala Val Ser Ser Val Gly Ala Arg Ser Arg Gly Leu Gly Gly Tyr
    130                 135                 140

His Gly Ala Gly His Pro Ser Gly Arg Arg Arg Arg Glu Asp Gln
145                 150                 155                 160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
            180                 185                 190

Leu Val Arg Gly Leu Arg Gly Leu Trp Gly Thr Arg Leu Met Glu Glu
        195                 200                 205

Ser Ser Thr Asn Arg Glu Lys Tyr Leu Lys Ser Val Leu Arg Glu Leu
    210                 215                 220
```

```
Val Thr Tyr Leu Leu Phe Leu Ile Val Leu Cys Ile Leu Thr Tyr Gly
225                 230                 235                 240

Met Met Ser Ser Asn Val Tyr Tyr Thr Arg Met Met Ser Gln Leu
            245                 250                 255

Phe Leu Asp Thr Pro Val Ser Lys Thr Glu Lys Thr Asn Phe Lys Thr
                260                 265                 270

Leu Ser Ser Met Glu Asp Phe Trp Lys Phe Thr Glu Gly Ser Leu Leu
            275                 280                 285

Asp Gly Leu Tyr Trp Lys Met Gln Pro Ser Asn Gln Thr Glu Ala Asp
    290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
                325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
            355                 360                 365

Thr Ser Glu Lys Asp Leu Asn Gly Ser Ser His Trp Gly Ile Ile Ala
370                 375                 380

Thr Tyr Ser Gly Ala Gly Tyr Tyr Leu Asp Leu Ser Arg Thr Arg Glu
385                 390                 395                 400

Glu Thr Ala Ala Gln Val Ala Ser Leu Lys Lys Asn Val Trp Leu Asp
                405                 410                 415

Arg Gly Thr Arg Ala Thr Phe Ile Asp Phe Ser Val Tyr Asn Ala Asn
            420                 425                 430

Ile Asn Leu Phe Cys Val Val Arg Leu Leu Val Glu Phe Pro Ala Thr
            435                 440                 445

Gly Gly Val Ile Pro Ser Trp Gln Phe Gln Pro Leu Lys Leu Ile Arg
450                 455                 460

Tyr Val Thr Thr Phe Asp Phe Leu Ala Ala Cys Glu Ile Ile Phe
465                 470                 475                 480

Cys Phe Phe Ile Phe Tyr Tyr Val Val Glu Glu Ile Leu Glu Ile Arg
                485                 490                 495

Ile His Lys Leu His Tyr Phe Arg Ser Phe Trp Asn Cys Leu Asp Val
            500                 505                 510

Val Ile Val Val Leu Ser Val Val Ala Ile Gly Ile Asn Ile Tyr Arg
            515                 520                 525

Thr Ser Asn Val Glu Val Leu Leu Gln Phe Leu Glu Asp Gln Asn Thr
530                 535                 540

Phe Pro Asn Phe Glu His Leu Ala Tyr Trp Gln Ile Gln Phe Asn Asn
545                 550                 555                 560

Ile Ala Ala Val Thr Val Phe Phe Val Trp Ile Lys Leu Phe Lys Phe
                565                 570                 575

Ile Asn Phe Asn Arg Thr Met Ser Gln Leu Ser Thr Thr Met Ser Arg
            580                 585                 590

Cys Ala Lys Asp Leu Phe Gly Phe Ala Ile Met Phe Phe Ile Ile Phe
            595                 600                 605

Leu Ala Tyr Ala Gln Leu Ala Tyr Leu Val Phe Gly Thr Gln Val Asp
            610                 615                 620

Asp Phe Ser Thr Phe Gln Glu Cys Ile Phe Thr Gln Phe Arg Ile Ile
625                 630                 635                 640
```

```
                                              -continued
Leu Gly Asp Ile Asn Phe Ala Glu Ile Glu Glu Ala Asn Arg Val Leu
                645                 650                 655

Gly Pro Ile Tyr Phe Thr Thr Phe Val Phe Met Phe Phe Ile Leu
                660                 665                 670

Leu Asn Met Phe Leu Ala Ile Ile Asn Asp Thr Tyr Ser Glu Val Lys
                675                 680                 685

Ser Asp Leu Ala Gln Gln Lys Ala Glu Met Glu Leu Ser Asp Leu Ile
690                 695                 700

Arg Lys Gly Tyr His Lys Ala Leu Val Lys Leu Lys Leu Lys Lys Asn
705                 710                 715                 720

Thr Val Asp Asp Ile Ser Glu Ser Leu Arg Gln Gly Gly Lys Leu
                725                 730                 735

Asn Phe Asp Glu Leu Arg Gln Asp Leu Lys Gly Lys Gly His Thr Asp
                740                 745                 750

Ala Glu Ile Glu Ala Ile Phe Thr Lys Tyr Asp Gln Asp Gly Asp Gln
                755                 760                 765

Glu Leu Thr Glu His Glu His Gln Gln Met Arg Asp Asp Leu Glu Lys
770                 775                 780

Glu Arg Glu Asp Leu Asp Leu Asp His Ser Ser Leu Pro Arg Pro Met
785                 790                 795                 800

Ser Ser Arg Ser Phe Pro Arg Ser Leu Asp Asp Ser Glu Glu Asp Asp
                805                 810                 815

Asp Glu Asp Ser Gly His Ser Ser Arg Arg Arg Gly Ser Ile Ser Ser
                820                 825                 830

Gly Val Ser Tyr Glu Glu Phe Gln Val Leu Val Arg Arg Val Asp Arg
                835                 840                 845

Met Glu His Ser Ile Gly Ser Ile Val Ser Lys Ile Asp Ala Val Ile
850                 855                 860

Val Lys Leu Glu Ile Met Glu Arg Ala Lys Leu Lys Arg Arg Glu Val
865                 870                 875                 880

Leu Gly Arg Leu Leu Asp Gly Val Ala Glu Asp Glu Arg Leu Gly Arg
                885                 890                 895

Asp Ser Glu Ile His Arg Glu Gln Met Glu Arg Leu Val Arg Glu Glu
                900                 905                 910

Leu Glu Arg Trp Glu Ser Asp Asp Ala Ala Ser Gln Ile Ser His Gly
                915                 920                 925

Leu Gly Thr Pro Val Gly Leu Asn Gly Gln Pro Arg Pro Arg Ser Ser
930                 935                 940

Arg Pro Ser Ser Ser Gln Ser Thr Glu Gly Met Glu Gly Ala Gly Gly
945                 950                 955                 960

Asn Gly Ser Ser Asn Val His Val
                965
```